(12) United States Patent
Shimizu et al.

(10) Patent No.: US 7,348,587 B2
(45) Date of Patent: Mar. 25, 2008

(54) METHOD FOR PRODUCING BIOCHEMICAL ANALYSIS DATA AND APPARATUS USED THEREFOR

(75) Inventors: Hitoshi Shimizu, Kanagawa (JP); Nobuhiko Ogura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 10/175,425

(22) Filed: Jun. 20, 2002

(65) Prior Publication Data

US 2003/0001122 A1 Jan. 2, 2003

(30) Foreign Application Priority Data

| Jun. 28, 2001 | (JP) | ............................. 2001-196199 |
| Jul. 30, 2001 | (JP) | ............................. 2001-229065 |
| Jan. 31, 2002 | (JP) | ............................. 2002-023986 |

(51) Int. Cl.
*G03B 42/08* (2006.01)

(52) U.S. Cl. ...................................... 250/584; 250/583

(58) Field of Classification Search ................ 250/584, 250/583

See application file for complete search history.

(56) References Cited

U.S. PATENT DOCUMENTS

| 4,922,092 | A | | 5/1990 | Rushbrooke et al. |
| 5,528,050 | A | * | 6/1996 | Miller et al. .................. 250/585 |
| 5,589,351 | A | | 12/1996 | Harootunian |
| 5,998,802 | A | | 12/1999 | Struye et al. |
| 6,043,506 | A | * | 3/2000 | Heffelfinger et al. ........ 250/584 |
| 6,071,748 | A | * | 6/2000 | Modlin et al. ............... 436/174 |
| 2001/0021504 | A1 | * | 9/2001 | Makino et al. ................. 435/6 |

FOREIGN PATENT DOCUMENTS

| EP | 0 725 278 | A1 | | 8/1996 |
| EP | 1037071 | A2 | * | 9/2000 |
| GB | 2 315 130 | B1 | | 1/1998 |
| JP | 1-60784 | | | 5/1984 |
| JP | 1-60782 | | | 1/1985 |
| JP | 4-3952 | | | 4/1985 |
| JP | 2-28543 | A | | 1/1990 |
| JP | 09-072843 | | | 3/1997 |
| JP | 10-281994 | A | | 10/1998 |
| JP | 11-173987 | | | 7/1999 |
| JP | 11-271227 | B1 | | 10/1999 |
| JP | 2001-33456 | A | | 2/2001 |
| JP | 2001-083090 | | | 3/2001 |
| JP | 2001-147297 | A | | 5/2001 |
| JP | 2001-183372 | | | 7/2001 |
| JP | 2002-514739 | A | | 5/2002 |
| JP | 2003-004637 | A | | 1/2003 |

* cited by examiner

*Primary Examiner*—David Porta
*Assistant Examiner*—Shun Lee
(74) *Attorney, Agent, or Firm*—Sughrue Mion, PLLC

(57) ABSTRACT

A method for producing biochemical analysis data includes the steps of collecting light selectively released from a plurality of light releasable regions two-dimensionally formed to be spaced apart from each other in a sample placed on a sample stage by a plurality of light guide member each of which is disposed to face one of the plurality of light releasable regions, leading the thus collected light to a light detector and photoelectrically detecting the light by the light detector. According to this method, it is possible to produce biochemical analysis data having high quantitative characteristics by photoelectrically detecting light emitted from a plurality of light releasable regions even in the case where the plurality of light releasable regions labeled with a labeling substance are formed in a sample at a high density.

33 Claims, 28 Drawing Sheets

METHOD FOR PRODUCING BIOCHEMICAL ANALYSIS DATA AND APPARATUS USED THEREFOR

BACKGROUND OF THE INVENTION

The present invention relates to a method for producing biochemical analysis data and an apparatus used therefor and, particularly, to a method for producing biochemical analysis data and an apparatus used therefor which can produce biochemical analysis data having high quantitative characteristics by photoelectrically detecting light emitted from a plurality of spot-like regions even in the case where the plurality of spot-like regions labeled with a labeling substance are formed in a biochemical analysis unit at a high density.

DESCRIPTION OF THE PRIOR ART

An autoradiographic analyzing system using as a detecting material for detecting radiation a stimulable phosphor which can absorb, store and record the energy of radiation when it is irradiated with radiation and which, when it is then stimulated by an electromagnetic wave having a specified wavelength, can release stimulated emission whose light amount corresponds to the amount of radiation with which it was irradiated is known, which comprises the steps of introducing a radioactively labeled substance into an organism, using the organism or a part of the tissue of the organism as a specimen, superposing the specimen and a stimulable phosphor sheet formed with a stimulable phosphor layer for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

There is further known chemiluminescence analysis system comprising the steps of employing, as a detecting material for light, a stimulable phosphor which can absorb and store the energy of light upon being irradiated therewith and release a stimulated emission whose amount is proportional to that of the received light upon being stimulated with an electromagnetic wave having a specific wavelength range, selectively labeling a fixed high molecular substance such as a protein or a nucleic acid sequence with a labeling substance which generates chemiluminescence emission when it contacts a chemiluminescent substance, contacting the high molecular substance selectively labeled with the labeling substance and the chemiluminescent substance, storing and recording the chemiluminescence emission in the wavelength of visible light generated by the contact of the chemiluminescent substance and the labeling substance in the stimulable phosphor contained in a stimulable phosphor layer formed on a stimulable phosphor sheet, scanning the stimulable phosphor layer with an electromagnetic wave to excite the stimulable phosphor, photoelectrically detecting the stimulated emission released from the stimulable phosphor to produce digital signals, effecting data processing on the obtained digital signals, and reproducing data on displaying means such as a CRT or a recording material such as a photographic film (see for example, U.S. Pat. No. 5,028,793, UK Patent Application 2,246,197 A and the like).

Unlike the system using a photographic film, according to these systems using the stimulable phosphor as a detecting material, development, which is chemical processing, becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence analyzing system using a fluorescent substance as a labeling substance instead of a radioactive labeling substance in the autoradiographic analyzing system is known. According to this system, it is possible to study a genetic sequence, study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescence emission, detecting the released fluorescence emission to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescence emission, detecting the released fluorescence emission to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescence emission releasing property, exciting the thus produced fluorescent substance by a stimulating ray to release fluorescence emission, detecting the fluorescence emission to produce an image and detecting the distribution of the target DNA on the transfer support. This fluorescence detecting system is advantageous in that a genetic sequence or the like can be easily detected without using a radioactive substance.

Similarly, there is known a chemiluminescence detecting system comprising the steps of fixing a substance derived from a living organism such as a protein or a nucleic acid sequence on a support, selectively labeling the substance derived from a living organism with a labeling substance which generates chemiluminescence emission when it contacts a chemiluminescent substrate, contacting the substance derived from a living organism and selectively labeled with the labeling substance and the chemiluminescent substrate, photoelectrically detecting the chemiluminescence emission in the wavelength of visible light generated by the contact of the chemiluminescent substrate and the labeling substance to produce digital image signals, effecting image processing thereon, and reproducing a chemiluminescent image on a display means such as a CRT or a recording material such as a photographic film, thereby obtaining information relating to the high molecular substance such as genetic information Further, a micro-array analyzing system has been recently developed, which comprises the steps of using a spotting device to drop at different positions on the surface of a carrier such as a slide glass plate, a membrane filter or the like specific binding substances, which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substances using a hybridization method or the like with a substance derived from a living organism such as a cell, virus, hormone, tumor marker, enzyme, antibody, antigen, abzyme, other protein, a nuclear acid, cDNA, DNA or mRNA by extraction, isolation or the like and optionally further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as fluorescence emission released from a labeling substance such as a fluorescent substance, dye or the like, and analyzing the substance derived from a living organism. This micro-array analyzing system is advantageous in that a substance derived from a living organism can be analyzed in a short time period by forming a number of spots of specific binding substances at different positions of the surface of a carrier such as a slide glass plate at a high density and hybridizing them with a substance derived from a living organism and labeled with a labeling substance.

In addition, a macro-array analyzing system using a radioactive labeling substance as a labeling substance has been further developed, which comprises the steps of using a spotting device to drop at different positions on the surface of a carrier such as a membrane filter or the like specific binding substances, which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substance using a hybridization method or the like with a substance derived from a living organism such as a cell, virus, hormone, tumor marker, enzyme, antibody, antigen, abzyme, other protein, a nuclear acid, cDNA, DNA or mRNA by extraction, isolation or the like and optionally further subjected to chemical processing, chemical modification or the like and which is labeled with a radioactive labeling substance, thereby forming a macro-array, superposing the macro-array and a stimulable phosphor sheet formed with a stimulable phosphor layer, exposing the stimulable phosphor layer to a radioactive labeling substance, irradiating the stimulable phosphor layer with a stimulating ray to excite the stimulable phosphor, photoelectrically detecting the stimulated emission released from the stimulable phosphor to produce biochemical analysis data, and analyzing the substance derived from a living organism.

However, in the macro-array analyzing system using a radioactive labeling substance as a labeling substance, when the stimulable phosphor layer is exposed to a radioactive labeling substance, since the radiation energy of the radioactive labeling substance contained in spot-like regions formed on the surface of a carrier such as a membrane filter is very large, electron beams ($\beta$ rays) released from the radioactive labeling substance contained in the individual spot-like regions are scattered in the carrier such as a membrane filter, thereby impinging on regions of the stimulable phosphor layer that should be exposed only to the radioactive labeling substance contained in neighboring spot-like regions, or electron beams released from the radioactive labeling substance adhering to the surface of the carrier such as a membrane filter between neighboring spot-like regions impinge on the stimulable phosphor layer, to generate noise in biochemical analysis data produced by photoelectrically detecting stimulated emission, thus making data of neighboring spot-like regions hard to separate and lowering resolution, and to lower the accuracy of biochemical analysis when a substance derived from a living organism is analyzed by quantifying the radiation amount of each spot. The degradation of the resolution and accuracy of biochemical analysis is particularly pronounced when spots are formed close to each other at a high density.

In order to solve these problems by preventing noise caused by the scattering of electron beams released from radioactive labeling substance contained in neighboring spot-like regions, it is inevitably required to increase the distance between neighboring spot-like regions and this makes the density of the spot-like regions lower and the test efficiency lower.

Furthermore, in the field of biochemical analysis, it is often required to analyze a substance derived from a living organism by forming at different positions on the surface of a carrier such as a membrane filter or the like a plurality of spot-like regions containing specific binding substances which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, specifically binding, using a hybridization method or the like, the specific binding substances contained in the plurality of spot-like regions with a substance derived from a living organism labeled with a labeling substance which generates chemiluminescence emission when it contacts a chemiluminescent substrate, thereby selectively labeling the plurality of spot-like regions, causing the plurality of spot-like regions to come into contact with a chemiluminescent substrate, exposing the stimulable phosphor layer of a stimulable phosphor sheet to chemiluminescence emission in the wavelength of visible light generated by the contact of the chemiluminescent substance and the labeling substance, thereby storing the energy of chemiluminescence emission in the stimulable phosphor layer, irradiating the stimulable phosphor layer with a stimulating ray, and photoelectrically detecting stimulated emission released from the stimulable phosphor layer, thereby effecting biochemical analysis. In this case, chemiluminescence emission released from any particular spot-like region is scattered in the carrier such as a membrane filter, thereby impinging on regions of the stimulable phosphor layer that should be exposed only to the chemiluminescence emission released from neighboring spot-like regions to generate noise in biochemical analysis data produced by photoelectrically detecting stimulated emission, thus making data of neighboring spot-like regions hard to separate and lowering resolution, and to lower the quantitative characteristics of biochemical analysis data.

Further, in the field of biochemical analysis, it is often required to analyze a substance derived from a living organism by forming a plurality of spot-like regions containing specific binding substances spot-like formed at different positions on the surface of a carrier such as a membrane filter or the like, which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, specifically binding, using a hybridization method or the like, the specific binding substances contained in the plurality of spot-like regions with a substance derived from a living organism labeled with a labeling substance which generates chemiluminescence emission when it contacts a chemiluminescent substrate and/or a fluorescent substance, thereby selectively labeling the plurality of spot-like regions, and causing it to contact a chemiluminescent substrate, thereby photoelectrically detecting the chemiluminescence emission in the wavelength of visible light, or irradiating it with a stimulating ray, thereby photoelectrically detecting fluorescence emission released from a fluorescent substance. In these cases, chemiluminescence emission or fluorescence emission released from the plurality of spot-like regions is scattered in the carrier such as a membrane filter or chemiluminescence emission or fluorescence emission released from any particular spot-like region is scattered and mixed with chemiluminescence emission or fluorescence emission released from neighboring spot-like regions, thereby generating noise in biochemical analysis data produced by photoelectrically detecting chemiluminescence emission and/or fluorescence emission.

SUMMARY OF THE INVENTION

It is therefore an object of the present invention to provide a method for producing biochemical analysis data and an apparatus used therefor which can produce biochemical analysis data having high quantitative characteristics by photoelectrically detecting light emitted from a plurality of spot-like regions even in the case where the plurality of spot-like regions labeled with a labeling substance are formed in a biochemical analysis unit at a high density.

The above other objects of the present invention can be accomplished by a method for producing biochemical analysis data comprising the steps of collecting light selectively released from a plurality of light releasable regions two-dimensionally formed to be spaced apart from each other in a sample placed on a sample stage by a plurality of light guide member each of which is disposed to face one of the plurality of light releasable regions, leading the thus collected light to a light detector and photoelectrically detecting the light by the light detector.

According to one application of the present invention, even in the case where a plurality of spot-like regions selectively labeled with a radioactive labeling substance are formed in a biochemical analysis unit such as a membrane filter at a high density, biochemical analysis data having high quantitative characteristics can be produced with high resolution by superposing a stimulable phosphor sheet formed with a plurality of stimulable phosphor layer regions in the same pattern as that of the plurality of spot-like regions formed in the biochemical analysis unit on the biochemical analysis unit in such a manner that each of the stimulable phosphor layer regions of the stimulable phosphor sheet faces the corresponding absorptive region of the biochemical analysis unit, exposing the plurality of stimulable phosphor layer regions of the stimulable phosphor sheet to a radioactive labeling substance contained in the plurality of spot-like regions while preventing electron beams (β rays) released from the radioactive labeling substance contained in any particular spot-like region from entering stimulable phosphor layer regions other than that to be exposed to electron beams (β rays) released from the radioactive labeling substance contained in the spot-like region, thereby storing radiation energy therein, placing the stimulable phosphor sheet on the sample stage, irradiating the plurality of stimulable phosphor layer regions of the stimulable phosphor sheet placed on the sample stage with a stimulating ray to excite stimulable phosphor contained in the stimulable phosphor layer regions, collecting stimulated emission released from the stimulable phosphor layer regions by the light guide member each of which is disposed to face one of the plurality of stimulable phosphor layer regions, leading stimulated emission through the light guide members to the light detector, photoelectrically detecting the stimulated emission by the light detector and reading radiation data stored in the plurality of stimulable phosphor layer regions of the stimulable phosphor sheet.

More specifically, according to this application of the present invention, when biochemical analysis data are to be produced by irradiating the plurality of stimulable phosphor layer regions two-dimensionally formed to be spaced apart from each other in the stimulable phosphor sheet with the stimulating ray to excite stimulable phosphor contained in the stimulable phosphor layer regions, photoelectrically detecting stimulated emission released from the stimulable phosphor layer regions and reading radiation data, since stimulated emission released from the plurality of stimulable phosphor layer regions is collected by the plurality of light guide members each of which is disposed to face one of the plurality of stimulable phosphor layer regions to lead it to the light detector and the stimulated emission is photoelectrically detected by the light detector thereby reading radiation data recorded in the plurality of stimulable phosphor layer regions of the stimulable phosphor sheet, it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector and to read radiation data recorded in the plurality of stimulable phosphor layer regions of the stimulable phosphor sheet, thereby producing biochemical analysis data. Therefore, biochemical analysis data having high quantitative characteristics can be produced with high resolution.

According to another application of the present invention, even in the case where a plurality of spot-like regions selectively labeled with a labeling substance which generates chemiluminescence emission when it contacts a chemiluminescent substrate are formed in a biochemical analysis unit such as a membrane filter at a high density, biochemical analysis data having high quantitative characteristics can be produced with high resolution by bringing the plurality of spot-like regions of the biochemical analysis unit into contact with a chemiluminescent substrate, thereby causing the spot-like regions to selectively release chemiluminescence emission, superposing a stimulable phosphor sheet formed with a plurality of stimulable phosphor layer regions in the same pattern as that of the plurality of spot-like regions formed in the biochemical analysis unit on the biochemical analysis unit in such a manner that each of the stimulable phosphor layer regions of the stimulable phosphor sheet faces the corresponding absorptive region of the biochemical analysis unit, exposing the plurality of stimulable phosphor layer regions of the stimulable phosphor sheet to chemiluminescence emission selectively released from the spot-like regions of the biochemical analysis unit while preventing chemiluminescence emission released from any particular spot-like region of the biochemical analysis unit from entering stimulable phosphor layer regions other than that to be exposed to chemiluminescence emission released from the spot-like region, thereby storing the energy of chemiluminescence emission therein, placing the stimulable phosphor sheet on the sample stage, irradiating the plurality of stimulable phosphor layer regions of the stimulable phosphor sheet placed on the sample stage with a stimulating ray to excite stimulable phosphor contained in the stimulable phosphor layer regions, collecting stimulated emission released from the stimulable phosphor layer regions by the light guide member each of which is disposed to face one of the plurality of stimulable phosphor layer regions, leading stimulated emission through the light guide members to the light detector, photoelectrically detecting the stimulated emission by the light detector and reading chemiluminescence data stored in the plurality of stimulable phosphor layer regions of the stimulable phosphor sheet.

More specifically, according to this application of the present invention, when biochemical analysis data are to be produced by irradiating the plurality of stimulable phosphor layer regions two-dimensionally formed to be spaced apart from each other in the stimulable phosphor sheet with the stimulating ray to excite stimulable phosphor contained in the stimulable phosphor layer regions, photoelectrically detecting stimulated emission released from the stimulable phosphor layer regions and reading chemiluminescence data, since stimulated emission released from the plurality of stimulable phosphor layer regions is collected by the plurality of light guide members each of which is disposed to face one of the plurality of stimulable phosphor layer regions to lead it to the light detector and the stimulated emission is photoelectrically detected by the light detector, it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, to photoelectrically detect the stimulated emission by the light detector and to read chemiluminescence data recorded in the plurality of stimulable phosphor layer regions of the stimulable phosphor sheet, thereby producing biochemical analysis data. Therefore, biochemical analysis data having high quantitative characteristics can be produced with high resolution.

According to a further application of the present invention, even in the case where a plurality of spot-like regions selectively labeled with a fluorescent substance such as a fluorescent dye are formed in a biochemical analysis unit such as a membrane filter at a high density, biochemical analysis data having high quantitative characteristics can be produced with high resolution by placing the biochemical analysis unit on the sample stage, irradiating the plurality of spot-like regions of the biochemical analysis unit with a stimulating ray to excite a fluorescent substance contained the plurality of spot-like regions of the biochemical analysis unit, collecting fluorescence emission released from the spot-like regions by the plurality of light guide members each of which is disposed to face one of the plurality of spot-like regions, leading fluorescence emission through the light guide members to the light detector, photoelectrically detecting the fluorescence emission by the light detector and reading fluorescence data stored in the plurality of spot-like regions of the biochemical analysis unit.

More specifically, according to this application of the present invention, when biochemical analysis data are to be produced by irradiating the plurality of spot-like regions two-dimensionally formed to be spaced apart from each other in the biochemical analysis unit with the stimulating ray to excite fluorescent substance contained in the spot-like regions, photoelectrically detecting fluorescence emission released from the spot-like regions and reading fluorescence data recorded in the plurality of spot-like regions of the biochemical analysis unit, since fluorescence emission released from the plurality of spot-like regions is collected by the plurality of light guide members each of which is disposed to face one of the plurality of spot-like regions to lead it to the light detector and the fluorescence emission is photoelectrically detected by the light detector, thereby reading fluorescence data recorded in the number of spot-like regions of the biochemical analysis unit, it is possible to effectively prevent fluorescence emission released from neighboring spot-like regions formed in the biochemical analysis unit from being mixed with each other and to lead only fluorescence emission released from the spot-like region through the corresponding light guide member to the light detector, to photoelectrically detect the fluorescence emission by the light detector and to read fluorescence data recorded in the plurality of spot-like regions of the biochemical analysis unit, thereby producing biochemical analysis data. Therefore, biochemical analysis data having high quantitative characteristics can be produced with high resolution.

According to a further application of the present invention, even in the case where a plurality of spot-like regions selectively labeled with a labeling substance which generates chemiluminescence emission when it contacts a chemiluminescent substrate are formed in a biochemical analysis unit such as a membrane filter at a high density, biochemical analysis data having high quantitative characteristics can be produced with high resolution by bringing the plurality of spot-like regions of the biochemical analysis unit into contact with a chemiluminescent substrate, thereby causing the spot-like regions to selectively release chemiluminescence emission, placing the biochemical analysis unit on the sample stage, collecting chemiluminescence emission released from the plurality of spot-like regions of the biochemical analysis unit placed on the sample stage by the light guide members each of which is disposed to face one of the plurality of spot-like regions, leading chemiluminescence emission through the light guide members to the light detector, photoelectrically detecting the chemiluminescence emission by the light detector and reading chemiluminescence data stored in the plurality of spot-like regions of the biochemical analysis unit.

More specifically, according to this application of the present invention, when biochemical analysis data are to be produced by photoelectrically detecting chemiluminescence emission released from the spot-like regions of the biochemical analysis unit and reading chemiluminescence data, since chemiluminescence emission released from the plurality of spot-like regions is collected by the plurality of light guide members each of which is disposed to face one of the plurality of spot-like regions to lead it to the light detector and the chemiluminescence emission is photoelectrically detected by the light detector, thereby reading chemiluminescence data recorded in the plurality of spot-like-regions of the biochemical analysis unit, it is possible to effectively prevent chemiluminescence emission released from neighboring spot-like regions formed in the biochemical analysis unit from being mixed with each other and to lead only chemiluminescence emission released from the spot-like region through the corresponding light guide member to the light detector, to photoelectrically detect the chemiluminescence emission by the light detector and to read chemiluminescence data recorded in the plurality of spot-like regions of the biochemical analysis unit, thereby producing biochemical analysis data. Therefore, biochemical analysis data having high quantitative characteristics can be produced with high resolution.

In a preferred aspect of the present invention, each of the plurality of light guide members includes a light collecting end portion capable of collecting light and the light collecting end portion of each of the plurality of light guide members is disposed to face one of the plurality of light releasable regions formed in the sample placed on the sample stage.

According to one application of this preferred aspect of the present invention, when biochemical analysis data are to be produced by irradiating the plurality of stimulable phosphor layer regions two-dimensionally formed to be spaced apart from each other in the stimulable phosphor sheet and containing recorded radiation data with the stimulating ray to excite stimulable phosphor contained in the stimulable phosphor layer regions, photoelectrically detecting stimulated emission released from the stimulable phosphor layer regions and reading radiation data recorded in the plurality of stimulable phosphor layer regions of the stimulable phosphor sheet, it is possible for each of the light collecting end portions of the light guide members to effectively collect only stimulated emission released from the corresponding stimulable phosphor layer region by disposing the plurality of light guide members so that each of the light collecting end portions of the light guide members is located sufficiently close to one of the stimulable phosphor layer regions of the stimulable phosphor sheet placed on the sample stage. Therefore, since it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector and to read radiation data recorded in the plurality of stimulable phosphor layer regions of the stimulable phosphor sheet, thereby producing biochemical analysis data, biochemical analysis data having high quantitative characteristics can be produced with high resolution.

According to another application of this preferred aspect of the present invention, when biochemical analysis data are to be produced by irradiating the plurality of stimulable phosphor layer regions two-dimensionally formed to be spaced apart from each other in the stimulable phosphor sheet and containing recorded chemiluminescence data with the stimulating ray to excite stimulable phosphor contained in the stimulable phosphor layer regions, photoelectrically detecting stimulated emission released from the stimulable phosphor layer regions and reading chemiluminescence data recorded in the plurality of stimulable phosphor layer regions of the stimulable phosphor sheet, it is possible for each of the light collecting end portions of the light guide members to effectively collect only stimulated emission released from the corresponding stimulable phosphor layer region by disposing the plurality of light guide members so that each of the light collecting end portions of the light guide members is located sufficiently close to one of the stimulable phosphor layer regions of the stimulable phosphor sheet placed on the sample stage. Therefore, since it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector and to read chemiluminescence data recorded in the plurality of stimulable phosphor layer regions of the stimulable phosphor sheet, thereby producing biochemical analysis data, biochemical analysis data having high quantitative characteristics can be produced with high resolution.

According to a further application of this preferred aspect of the present invention, when biochemical analysis data are to be produced by irradiating the plurality of spot-like regions two-dimensionally formed to be spaced apart from each other in the biochemical analysis unit and containing recorded fluorescence data with the stimulating ray to excite fluorescent substance contained in the spot-like regions, photoelectrically detecting fluorescence emission released from the spot-like regions and reading fluorescence data recorded in the plurality of spot-like regions of the biochemical analysis unit, it is possible for each of the light collecting end portions of the light guide members to effectively collect only fluorescence emission released from the corresponding spot-like region by disposing the plurality of light guide members so that each of the light collecting end portions of the light guide members is located sufficiently close to one of the spot-like regions of the biochemical analysis unit placed on the sample stage. Therefore, since it is possible to effectively prevent fluorescence emission released from neighboring spot-like regions formed in the biochemical analysis unit from being mixed with each other and to lead only fluorescence emission released from the spot-like region through the corresponding light guide member to the light detector, to photoelectrically detect the fluorescence emission by the light detector and to read fluorescence data recorded in the plurality of spot-like regions of the biochemical analysis unit, thereby producing biochemical analysis data, biochemical analysis data having high quantitative characteristics can be produced with high resolution.

According to a further application of this preferred aspect of the present invention, when biochemical analysis data are to be produced by photoelectrically detecting chemiluminescence emission released from the spot-like regions of the biochemical analysis unit and reading chemiluminescence data recorded in the plurality of spot-like regions of the biochemical analysis unit, it is possible for each of the light collecting end portions of the light guide members to effectively collect only chemiluminescence emission released from the corresponding spot-like region by disposing the plurality of light guide members so that each of the light collecting end portions of the light guide members is located sufficiently close to one of the spot-like regions of the biochemical analysis unit placed on the sample stage. Therefore, since it is possible to effectively prevent chemiluminescence emission released from neighboring spot-like regions formed in the biochemical analysis unit from being mixed with each other and to lead only chemiluminescence emission released from the spot-like region through the corresponding light guide member to the light detector, to photoelectrically detect the chemiluminescence emission by the light detector and to read chemiluminescence data recorded in the plurality of spot-like regions of the biochemical analysis unit, thereby producing biochemical analysis data, biochemical analysis data having high quantitative characteristics can be produced with high resolution.

In a preferred aspect of the present invention, each of the plurality of light guide members is formed of at least one optical fiber.

In another preferred aspect of the present invention, each of the plurality of light guide members is formed of an optical fiber bundle constituted by a plurality of optical fibers.

In a preferred aspect of the present invention, the plurality of light guide members are disposed in such a manner that each of the plurality of light releasable regions formed in the sample faces one of the light collecting end portions of the plurality of light guide members.

In another preferred aspect of the present invention, the plurality of light guide members are disposed in such a manner that at least some of the plurality of light releasable regions formed in the sample face two or more light collecting end portions of the plurality of light guide members.

According to this preferred aspect of the present invention, since it is not necessary to accurately position the light collecting end portions of the plurality of light guide members and the plurality of light releasable regions formed in the sample, it is possible to markedly lower the cost of manufacturing an apparatus for producing biochemical analysis data.

In a preferred aspect of the present invention, the plurality of light guide members are gathered in the vicinity of end portions opposite to the light collecting end portions.

According to this preferred aspect of the present invention, since the plurality of light guide members are gathered in the vicinity of end portions opposite to the light collecting end portions, in the case where light released from the plurality of light releasable regions of the sample and led through the plurality of light guide members is photoelectrically detected by a two-dimensional sensor, it is possible to employ a two-dimensional sensor having a small light detecting surface, thereby enabling an apparatus for producing biochemical analysis data to be smaller and lowering cost for manufacturing it.

In a preferred aspect of the present invention, the plurality of light guide members are mounted on a fixing head in the vicinity of the light collecting end portions so that each of the light collecting end portions of the plurality of light guide members is disposed to face one of the light releasable regions of the sample placed on the sample stage.

In a preferred aspect of the present invention, the sample is constituted by a stimulable phosphor sheet including a support two-dimensionally formed with a plurality of through-holes to be spaced apart from each other and the plurality of light releasable regions are constituted by a plurality of stimulable phosphor layer regions formed by charging stimulable phosphor in the plurality of through-holes formed in the support and selectively storing radiation energy in the stimulable phosphor regions by exposing them to a radioactive labeling substance.

According to this preferred aspect of the present invention, when biochemical analysis data are to be produced by irradiating the plurality of stimulable phosphor layer regions two-dimensionally formed to be spaced apart from each other in the support of the stimulable phosphor sheet and selectively containing stored radiation energy with the stimulating ray to excite stimulable phosphor contained in the stimulable phosphor layer regions, photoelectrically detecting stimulated emission released from the stimulable phosphor layer regions and reading radiation data recorded in the plurality of stimulable phosphor layer regions of the stimulable phosphor sheet, it is possible for each of the light collecting end portions of the light guide members to effectively collect only stimulated emission released from the corresponding stimulable phosphor layer region by disposing the plurality of light guide members so that each of the light collecting end portions of the light guide members is located sufficiently close to one of the stimulable phosphor layer regions of the stimulable phosphor sheet placed on the sample stage. Therefore, since it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector and to read radiation data recorded in the plurality of stimulable phosphor layer regions of the stimulable phosphor sheet, thereby producing biochemical analysis data, biochemical analysis data having high quantitative characteristics can be produced with high resolution.

In another preferred aspect of the present invention, the sample is constituted by a stimulable phosphor sheet including a support two-dimensionally formed with a plurality of through-holes to be spaced apart from each other and the plurality of light releasable regions are constituted by a plurality of stimulable phosphor layer regions formed by charging stimulable phosphor in the plurality of through-holes formed in the support and selectively storing the energy of chemiluminescence in the stimulable phosphor regions by exposing them to chemiluminescence emission.

According to this preferred aspect of the present invention, when biochemical analysis data are to be produced by irradiating the plurality of stimulable phosphor layer regions two-dimensionally formed to be spaced apart from each other in the support of the stimulable phosphor sheet and selectively containing stored energy of chemiluminescence emission with the stimulating ray to excite stimulable phosphor contained in the stimulable phosphor layer regions, photoelectrically detecting stimulated emission released from the stimulable phosphor layer regions and reading chemiluminescence data recorded in the plurality of stimulable phosphor layer regions of the stimulable phosphor sheet, it is possible for each of the light collecting end portions of the light guide members to effectively collect only stimulated emission released from the corresponding stimulable phosphor layer region by disposing the plurality of light guide members so that each of the light collecting end portions of the light guide members is located sufficiently close to one of the stimulable phosphor layer regions of the stimulable phosphor sheet placed on the sample stage. Therefore, since it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector and to read chemiluminescence data recorded in the plurality of stimulable phosphor layer regions of the stimulable phosphor sheet, thereby producing biochemical analysis data, biochemical analysis data having high quantitative characteristics can be produced with high resolution.

In a further preferred aspect of the present invention, the method for producing biochemical analysis data comprises the steps of simultaneously irradiating the plurality of stimulable phosphor layer regions formed in the support of the stimulable phosphor sheet with a stimulating ray emitted from a stimulating ray source for a predetermined time from a side of the stimulable phosphor sheet opposite to the side facing the light collecting end portion of the plurality of light guide members, exciting stimulable contained in the plurality of stimulable phosphor layer regions, collecting stimulated emission released from the plurality of stimulable phosphor layer regions by the light collecting end portions of the plurality of light guide members, leading the thus collected stimulated emission through the plurality of light guide members to a stimulating ray cutting filter having a property of cutting light having a wavelength of that of the stimulating ray and transmitting light having a wavelength of that of stimulated emission, thereby cutting the stimulating ray, further leading stimulated emission transmitted through the stimulating ray cutting filter to a two-dimensional solid state sensor, and photoelectrically detecting stimulated emission by the two-dimensional solid state sensor to produce biochemical analysis data.

According to this preferred aspect of the present invention, when biochemical analysis data are to be produced by simultaneously irradiating the plurality of stimulable phosphor layer regions formed in the support of the stimulable phosphor sheet placed on the sample stage with the stimulating ray, exciting stimulable phosphor contained in the plurality of stimulable phosphor layer regions and photoelectrically detecting stimulated emission released from the plurality of stimulable phosphor layer regions, it is possible for each of the light collecting end portions of the light guide members to collect stimulated emission released from the plurality of stimulable phosphor layer regions with high efficiency by positioning the plurality of light guide members so that each of the light collecting end portions thereof is located sufficiently close to one of the plurality of stimulable phosphor layer regions formed in the support of the stimulable phosphor sheet placed on the sample stage and, therefore, biochemical analysis data having an excellent quantitative characteristic can be produced with high resolution by photoelectrically detecting stimulated emission led through the plurality of light collecting members to the two-dimensional solid state sensor.

Further, according to this preferred aspect of the present invention, since the stimulating ray is simultaneously projected onto the plurality of stimulable phosphor layer regions formed in the support of the stimulable phosphor sheet from the side opposite to the plurality of light guide members for leading stimulated emission for a predetermined time, thereby exciting stimulable phosphor contained in the plurality of stimulable phosphor layer regions, unlike the case where the surface of a stimulable phosphor layer of a stimulable phosphor sheet is scanned with the stimulating ray at a high density, it is possible to prevent neighboring stimulable phosphor layer regions from being irradiated with the stimulating ray, thereby exciting stimulable phosphor contained therein and being caused to release radiation energy or the energy of chemiluminescence emission stored therein in the form of stimulated emission. Instead, since each of the stimulable phosphor layer regions can be irradiated with the stimulating ray for a sufficiently long time to excite stimulable phosphor contained therein and almost all radiation energy or the energy of chemiluminescence emission stored therein can be released in the form of stimulated emission, biochemical analysis data can be produced with sufficiently high sensitivity by leading stimulated emission through the plurality of light guide members via the stimulating ray cutting filter to the two-dimensional solid state sensor and photoelectrically detecting the stimulated emission.

In a further preferred aspect of the present invention, the method for producing biochemical analysis data comprises the steps of producing position data by detecting what region on a photo-electric detecting surface of the two-dimensional solid state sensor will receive stimulated emission to be released from the plurality of stimulable phosphor layer regions formed in the support of the stimulable phosphor sheet and producing biochemical analysis data based on the thus produced position data by photoelectrically detecting stimulated emission released from the plurality of stimulable phosphor layer regions formed in the support of the stimulable phosphor sheet with the two-dimensional solid state sensor.

According to this preferred aspect of the present invention, since it is not necessary to accurately dispose end portions of the plurality of light guide members opposite to the light collecting end portions with respect to the photoelectric detecting surface of the two-dimensional solid state sensor, it is possible to markedly lower the cost of manufacturing an apparatus for producing biochemical analysis data.

In a further preferred aspect of the present invention, the position data are produced by using a position data producing unit including a substrate formed with a plurality of through-holes in the same pattern as that of the plurality of stimulable phosphor layer regions formed in the support of the stimulable phosphor sheet, leading light transmitted through the plurality of through-holes through the plurality of light guide members to the two-dimensional solid state sensor, and photoelectrically detecting the light.

In a further preferred aspect of the present invention, the two-dimensional solid state sensor is constituted by a cooled CCD area sensor.

According to this preferred aspect of the present invention, since the two-dimensional solid state sensor is constituted by a cooled CCD area sensor, it is possible to irradiate the plurality of stimulable phosphor layer regions formed in the support of the stimulable phosphor sheet with the stimulating ray for a long time, thereby exciting stimulable phosphor contained therein and to cause the plurality of stimulable phosphor layer regions to release radiation energy or the energy of chemiluminescence emission stored therein in the form of stimulated emission, biochemical analysis data can be produced with sufficiently high sensitivity by leading stimulated emission through the plurality of light guide members. Therefore, biochemical analysis data can be produced by collecting stimulated emission by photoelectrically detecting stimulated emission collected by the plurality of light guide members and led thereby to the cooled CCD area sensor with sufficiently high sensitivity by the cooled CCD area sensor.

In a further preferred aspect of the present invention, two or more two-dimensional solid state sensors are used.

In another preferred aspect of the present invention, the method for producing biochemical analysis data comprises the steps of sequentially irradiating the plurality of stimulable phosphor layer regions formed in the support of the stimulable phosphor sheet placed on the sample stage with a stimulating ray emitted from a stimulating ray source from a side of the stimulable phosphor sheet opposite to the side facing the light collecting end portion of the plurality of light guide members, exciting stimulable phosphor contained in the plurality of stimulable phosphor layer regions, collecting stimulated emission released from each of the plurality of stimulable phosphor layer regions by the light collecting end portion of the corresponding light guide member among the plurality of light guide members, leading stimulated emission collected by the corresponding light guide member to a stimulating ray cutting filter having a property of cutting light having a wavelength of that of the stimulating ray and transmitting light having a wavelength of that of stimulated emission, thereby cutting the stimulating ray, further leading stimulated emission transmitted through the stimulating ray cutting filter to a zero-dimensional sensor, and photoelectrically detecting stimulated emission by the zero-dimensional sensor to produce biochemical analysis data.

In the present invention, a zero-dimensional sensor as termed herein means a sensor whose pixel is not divided.

According to this preferred aspect of the present invention, when biochemical analysis data are to be produced by sequentially irradiating the plurality of stimulable phosphor layer regions formed in the support of the stimulable phosphor sheet placed on the sample stage with the stimulating ray, exciting stimulable phosphor contained in each of the plurality of stimulable phosphor layer regions and photoelectrically detecting stimulated emission released from each of the plurality of stimulable phosphor layer regions, it is possible for each of the light collecting end portions of the light guide members to collect stimulated emission released from one of the plurality of stimulable phosphor layer regions with high efficiency by positioning the plurality of light guide members so that each of the light collecting end portions thereof is located sufficiently close to one of the plurality of stimulable phosphor layer regions formed in the support of the stimulable phosphor sheet placed on the sample stage and, therefore, biochemical analysis data having an excellent quantitative characteristic can be produced with high resolution by photoelectrically detecting stimulated emission led through the plurality of light collecting members to the zero-dimensional sensor.

In a further preferred aspect of the present invention, the stimulating ray emitted from the stimulating ray source is intermittently moved by a pitch equal to a distance between neighboring stimulable phosphor layer regions formed in the support of the stimulable phosphor, thereby scanning the plurality of stimulable phosphor layer regions formed in the support of the stimulable phosphor sheet placed on the sample stage with the stimulating ray.

In a further preferred aspect of the present invention, the zero-dimensional sensor is constituted as a photomultiplier.

In a further preferred aspect of the present invention, the support of the stimulable phosphor sheet has a property of attenuating light energy.

According to this preferred aspect of the present invention, since the support of the stimulable phosphor sheet has a property of attenuating light energy, stimulated emission released from the plurality of stimulable phosphor layer region of the stimulable phosphor sheet in response to the excitation of stimulable phosphor contained therein with the stimulating ray can be effectively prevented from scattering in the support of the stimulable phosphor sheet and stimulated emission released from neighboring stimulable phosphor layer regions can be effectively prevented from being mixed with each other. Therefore, biochemical analysis data having an excellent quantitative characteristic can be produced with high resolution by scanning the plurality of stimulable phosphor layer regions selectively exposed to a radioactive labeling substance or chemiluminescence emission and photoelectrically detecting stimulated emission released from the plurality of stimulable phosphor layer regions.

In a preferred aspect of the present invention, the support of the stimulable phosphor sheet has a property of reducing the energy of light to $1/5$ or less when the light travels in the support by a distance equal to that between neighboring stimulable phosphor layer regions.

In a further preferred aspect of the present invention, the support of the stimulable phosphor sheet has a property of reducing the energy of light to $1/10$ or less when the light travels in the support by a distance equal to that between neighboring stimulable phosphor layer regions.

In a further preferred aspect of the present invention, the support of the stimulable phosphor sheet has a property of reducing the energy of light to $1/50$ or less when the light travels in the support by a distance equal to that between neighboring stimulable phosphor layer regions.

In a further preferred aspect of the present invention, the support of the stimulable phosphor sheet has a property of reducing the energy of light to $1/100$ or less when the light travels in the support by a distance equal to that between neighboring stimulable phosphor layer regions.

In a further preferred aspect of the present invention, the support of the stimulable phosphor sheet has a property of reducing the energy of light to $1/500$ or less when the light travels in the support by a distance equal to that between neighboring stimulable phosphor layer regions.

In a further preferred aspect of the present invention, the support of the stimulable phosphor sheet has a property of reducing the energy of light to $1/1,000$ or less when the light travels in the support by a distance equal to that between neighboring stimulable phosphor layer regions.

In a preferred aspect of the present invention, the support of the stimulable phosphor sheet has a property of attenuating radiation energy.

According to this preferred aspect of the present invention, since the support of the stimulable phosphor sheet has a property of attenuating radiation energy, when the stimulable phosphor sheet is superposed on the biochemical analysis unit so that the plurality of stimulable phosphor layer regions formed in the stimulable phosphor sheet are exposed to a radioactive labeling substance selectively contained in the plurality of spot-like regions of the biochemical analysis unit, electron beams ($\beta$ rays) released from the radioactive labeling substance contained in the individual spot-like regions can be effectively prevented from scattering in the support of the stimulable phosphor sheet and entering stimulable phosphor layer regions other than that to be exposed to electron beams ($\beta$ rays) released from the radioactive labeling substance contained in the spot-like region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

In a preferred aspect of the present invention, the support of the stimulable phosphor sheet has a property of reducing the radiation energy to $\frac{1}{5}$ or less when the radiation travels in the support by a distance equal to that between neighboring stimulable phosphor layer regions.

In a further preferred aspect of the present invention, the support of the stimulable phosphor sheet has a property of reducing the radiation energy to $\frac{1}{10}$ or less when the radiation travels in the support by a distance equal to that between neighboring stimulable phosphor layer regions.

In a further preferred aspect of the present invention, the support of the stimulable phosphor sheet has a property of reducing the radiation energy to $\frac{1}{50}$ or less when the radiation travels in the support by a distance equal to that between neighboring stimulable phosphor layer regions.

In a further preferred aspect of the present invention, the support of the stimulable phosphor sheet has a property of reducing the radiation energy to $\frac{1}{100}$ or less when the radiation travels in the support by a distance equal to that between neighboring stimulable phosphor layer regions.

In a further preferred aspect of the present invention, the support of the stimulable phosphor sheet has a property of reducing the radiation energy to $\frac{1}{500}$ or less when the radiation travels in the support by a distance equal to that between neighboring stimulable phosphor layer regions.

In a further preferred aspect of the present invention, the support of the stimulable phosphor sheet has a property of reducing the radiation energy to $\frac{1}{1,000}$ or less when the radiation travels in the support by a distance equal to that between neighboring stimulable phosphor layer regions.

In the present invention, the material for forming the support of the stimulable phosphor sheet is preferably capable of attenuating light energy and is more preferably capable of attenuating radiation energy but is not particularly limited. The material for forming the support of the stimulable phosphor sheet may be any type of inorganic compound material or organic compound material and the support of the stimulable phosphor sheet can preferably be formed of a metal material, a ceramic material or a plastic material.

Illustrative examples of inorganic compound materials preferably usable for forming the support of the stimulable phosphor sheet in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound can preferably be used as an organic compound material preferably usable for forming the support of the stimulable phosphor sheet. Illustrative examples of high molecular compounds preferably usable for forming the support of the stimulable phosphor sheet in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene; butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating light energy generally increases as scattering and/or absorption of light increases, the support of the stimulable phosphor sheet preferably has absorbance of 0.3 per cm (thickness) or more and more preferably has absorbance of 1 per cm (thickness) or more. The absorbance can be determined by placing an integrating sphere immediately behind a plate-like member having a thickness of T cm, measuring an amount A of transmitted light at a wavelength of probe light or emission light used for measurement by a spectrophotometer, and calculating A/T. In the present invention, a light scattering substance or a light absorbing substance may be added to the support of the stimulable phosphor sheet in order to improve the capability of attenuating light energy. Particles of a material different from a material forming the support of the stimulable phosphor sheet may be preferably used as a light scattering substance and a pigment or dye may be preferably used as a light absorbing substance.

Since the capability of attenuating radiation energy generally increases as specific gravity increases, the support of the stimulable phosphor sheet is preferably formed of a compound material or a composite material having specific gravity of 1.0 $g/cm^3$ or more and more preferably formed of a compound material or a composite material having specific gravity of 1.5 $g/cm^3$ to 23 $g/cm^3$.

In a preferred aspect of the present invention, the support of the stimulable phosphor sheet is formed with 10 or more stimulable phosphor layer regions.

In a further preferred aspect of the present invention, the support of the stimulable phosphor sheet is formed with 50 or more stimulable phosphor layer regions.

In a further preferred aspect of the present invention, the support of the stimulable phosphor sheet is formed with 100 or more stimulable phosphor layer regions.

In a further preferred aspect of the present invention, the support of the stimulable phosphor sheet is formed with 500 or more stimulable phosphor layer regions.

In a further preferred aspect of the present invention, the support of the stimulable phosphor sheet is formed with 1,000 or more stimulable phosphor layer regions.

In a further preferred aspect of the present invention, the support of the stimulable phosphor sheet is formed with 5,000 or more stimulable phosphor layer regions.

In a further preferred aspect of the present invention, the support of the stimulable phosphor sheet is formed with 10,000 or more stimulable phosphor layer regions.

In a further preferred aspect of the present invention, the support of the stimulable phosphor sheet is formed with 50,000 or more stimulable phosphor layer regions.

In a further preferred aspect of the present invention, the support of the stimulable phosphor sheet is formed with 10,0000 or more stimulable phosphor layer regions.

In a preferred aspect of the present invention, each of the plurality of stimulable phosphor layer regions is formed in the stimulable phosphor sheet to have a size of less than 5 mm².

In a further preferred aspect of the present invention, each of the plurality of stimulable phosphor layer regions is formed in the stimulable phosphor sheet to have a size of less than 1 mm².

In a further preferred aspect of the present invention, each of the plurality of stimulable phosphor layer regions is formed in the stimulable phosphor sheet to have a size of less than 0.5 mm².

In a further preferred aspect of the present invention, each of the plurality of stimulable phosphor layer regions is formed in the stimulable phosphor sheet to have a size of less than 0.1 mm².

In a further preferred aspect of the present invention, each of the plurality of stimulable phosphor layer regions is formed in the stimulable phosphor sheet to have a size of less than 0.05 mm².

In a further preferred aspect of the present invention, each of the plurality of stimulable phosphor layer regions is formed in the stimulable phosphor sheet to have a size of less than 0.01 mm².

In the present invention, the density of the stimulable phosphor layer regions formed in the support of the stimulable phosphor sheet can be determined based upon the material of the support, the kind of electron beam released from the radioactive labeling substance and the like.

In a preferred aspect of the present invention, the plurality of stimulable phosphor layer regions are formed in the support of the stimulable phosphor sheet at a density of 10 or more per cm².

In a further preferred aspect of the present invention, the plurality of stimulable phosphor layer regions are formed in the support of the stimulable phosphor sheet at a density of 50 or more per cm².

In a further preferred aspect of the present invention, the plurality of stimulable phosphor layer regions are formed in the support of the stimulable phosphor sheet at a density of 100 or more per cm².

In a further preferred aspect of the present invention, the plurality of stimulable phosphor layer regions are formed in the support of the stimulable phosphor sheet at a density of 500 or more per cm².

In a further preferred aspect of the present invention, the plurality of stimulable phosphor layer regions are formed in the support of the stimulable phosphor sheet at a density of 1,000 or more per cm².

In a further preferred aspect of the present invention, the plurality of stimulable phosphor layer regions are formed in the support of the stimulable phosphor sheet at a density of 5,000 or more per cm².

In a further preferred aspect of the present invention, the plurality of stimulable phosphor layer regions are formed in the support of the stimulable phosphor sheet at a density of 10,000 or more per cm².

In a preferred aspect of the present invention, each of the stimulable phosphor layer regions is formed substantially circular in the support of the stimulable phosphor sheet.

In another preferred aspect of the present invention, each of the stimulable phosphor layer regions is formed substantially rectangular in the support of the stimulable phosphor sheet.

In the present invention, the stimulable phosphor usable for storing radiation energy may be of any type insofar as it can store radiation energy or electron beam energy and can be stimulated by an electromagnetic wave to release the radiation energy or the electron beam energy stored therein in the form of light. More specifically, preferably employed stimulable phosphors include alkaline earth metal fluorohalide phosphors $(Ba_{1-x}, M^{2+}_x)FX:yA$ (where $M^{2+}$ is at least one alkaline earth metal selected from the group consisting of Mg, Ca, Sr, Zn and Cd; X is at least one element selected from the group consisting of Cl, Br and I, A is at least one element selected from the group consisting of Eu, Tb, Ce, Tm, Dy, Pr, Ho, Nd, Yb and Er; x is equal to or greater than 0 and equal to or less than 0.6 and y is equal to or greater than 0 and equal to or less than 0.2) disclosed in U.S. Pat. No. 4,239,968, alkaline earth metal fluorohalide phosphors SrFX:Z (where X is at least one halogen selected from the group consisting of Cl, Br and I; Z is at least one of Eu and Ce) disclosed in Japanese Patent Application Laid Open No. 2-276997, europium activated complex halide phosphors BaFXxNaX':aEu²⁺ (where each of X or X' is at least one halogen selected from the group consisting of Cl, Br and I; x is greater than 0 and equal to or less than 2; and y is greater than 0 and equal to or less than 0.2) disclosed in Japanese Patent Application Laid Open No. 59-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1) disclosed in Japanese Patent Application laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br and I; and x is greater than 0 and equal to or less than 0.1) disclosed in U.S. Pat. No. 4,539,137, and europium activated complex halide phosphors $M^{II}FXaM^{I'}X'bM^{II'}X''_2cM^{III'}X'''_3xA:yEu^{2+}$ (where $M^{II}$ is at least one alkaline earth metal selected from the group consisting of Ba, Sr and Ca; $M^I$ is at least one alkaline metal selected from the group consisting of Li, Na, K, Rb and Cs; $M^{III}$ is at least one divalent metal selected from the group consisting of Be and Mg; $M^{III}$ is at least one trivalent metal selected from the group consisting of Al, Ga, In and Ti; A is at least one metal oxide; X is at least one halogen selected from the group consisting of Cl, Br and I; each of X', X" and X''' is at least one halogen selected from the group consisting of F, Cl, Br and I; a is equal to or greater than 0 and equal to or less than 2; b is equal to or greater than 0 and equal to or less than $10^{-2}$; C is equal to or greater than 0 and equal to or less than $10^{-2}$; a+b+c is equal to or greater than $10^{-2}$; x is greater than 0 and equal to or less than 0.5; and y is greater than 0 and equal to or less than 0.2) disclosed in U.S. Pat. No. 4,962,047.

In the present invention, the stimulable phosphor usable for storing the energy of chemiluminescence emission may be of any type insofar as it can store the energy of light in the wavelength band of visible light and can be stimulated by an electromagnetic wave to release in the form of light the energy of light in the wavelength band of visible light stored therein. More specifically, preferably employed stimulable phosphors include at least one selected from the group consisting of metal halophosphates, rare-earth-activated sulfide-host phosphors, aluminate-host phosphors, silicate-host phosphors, fluoride-host phosphors and mixtures of two, three or more of these phosphors. Among them, rare-earth-activated sulfide-host phosphors are more preferable and, particularly, rare-earth-activated alkaline earth metal sulfide-host phosphors disclosed in U.S. Pat. Nos.

5,029,253 and 4,983,834, zinc germanate such as $Zn_2GeO_4$: Mn, V; $Zn_2GeO_4$:Mn disclosed in Japanese Patent Application Laid Open No. 2001-131545, alkaline-earth aluminate such as $Sr_4Al_{14}O_{25}$:Ln (wherein Ln is a rare-earth element) disclosed in Japanese Patent Application Laid Open No. 2001-123162, $Y_{0.8}Lu_{1.2}SiO_5$:Ce, Zr; GdOCl:Ce disclosed in Japanese Patent Publication No. 6-31904 and the like are most preferable.

In a preferred aspect of the present invention, the sample is constituted by a biochemical analysis unit including a substrate two-dimensionally formed with a plurality of through-holes to be spaced apart from each other and the plurality of light releasable regions are constituted by a plurality of absorptive regions formed by charging an absorptive material in the plurality of through-holes formed in the substrate of the biochemical analysis unit and selectively labeled with a fluorescent substance.

In the present invention, the case where a plurality of absorptive regions are selectively labeled with a fluorescent substance as termed herein includes the case where a plurality of absorptive regions are selectively labeled with a fluorescent substance by selectively binding a substance derived from a living organism and labeled with a fluorescent substance with specific binding substances contained in the plurality of absorptive regions and the case where a plurality of absorptive regions are selectively labeled with a fluorescent substance by selectively binding a substance derived from a living organism and labeled with a hapten with specific binding substances contained in the plurality of absorptive regions, and binding an antibody for the hapten labeled with an enzyme which generates fluorescence emission when it contacts a fluorescent substrate with the hapten by an antigen-antibody reaction.

In the present invention, illustrative examples of the combination of hapten and antibody include digoxigenin and anti-digoxigenin antibody, theophylline and anti-theophylline antibody, fluorosein and anti-fluorosein antibody, and the like. Further, the combination of biotin and avidin, antigen and antibody may be utilized instead of the combination of hapten and antibody.

According to a further application of this preferred aspect of the present invention, when biochemical analysis data are to be produced by irradiating the plurality of absorptive regions two-dimensionally formed to be spaced apart from each other in the substrate of the biochemical analysis unit and selectively labeled with a fluorescent substance with the stimulating ray to excite fluorescent substance contained in the absorptive regions, photoelectrically detecting fluorescence emission released from the plurality of absorptive regions and reading fluorescence data recorded in the plurality of absorptive regions formed in the substrate of the biochemical analysis unit, since fluorescence emission released from the plurality of absorptive regions is collected by the plurality of light guide members each of which is disposed to face one of the plurality of absorptive regions to lead it to the light detector and the fluorescence emission is photoelectrically detected by the light detector, thereby reading fluorescence data recorded in the number of absorptive regions formed in the substrate of the biochemical analysis unit, it is possible to effectively prevent fluorescence emission released from neighboring absorptive regions formed in the substrate of the biochemical analysis unit from being mixed with each other and to lead only fluorescence emission released from the absorptive region through the corresponding light guide member to the light detector, to photoelectrically detect the fluorescence emission by the light detector and to read fluorescence data recorded in the plurality of absorptive regions formed in the substrate of the biochemical analysis unit, thereby producing biochemical analysis data. Therefore, biochemical analysis data having high quantitative characteristics can be produced with high resolution.

In a preferred aspect of the present invention, each of the plurality of light guide members includes a light collecting end portion capable of collecting light and the light collecting end portion of each of the plurality of light guide members is disposed to face one of the plurality of absorptive regions formed in the substrate of the biochemical analysis unit placed on the sample stage.

According to a further application of this preferred aspect of the present invention, when biochemical analysis data are to be produced by irradiating the plurality of absorptive regions two-dimensionally formed to be spaced apart from each other in the substrate of the biochemical analysis unit and selectively labeled with a fluorescent substance with the stimulating ray to excite fluorescent substance contained in the absorptive regions, photoelectrically detecting fluorescence emission released from the absorptive regions and reading fluorescence data recorded in the plurality of absorptive regions formed in the substrate of the biochemical analysis unit, it is possible for each of the light collecting end portions of the light guide members to effectively collect only fluorescence emission released from the corresponding absorptive region by disposing the plurality of light guide members so that each of the light collecting end portions of the light guide members is located sufficiently close to one of the absorptive regions formed in the substrate of the biochemical analysis unit placed on the sample stage. Therefore, since it is possible to effectively prevent fluorescence emission released from neighboring absorptive regions formed in the substrate of the biochemical analysis unit from being mixed with each other and to lead only fluorescence emission released from the absorptive region through the corresponding light guide member to the light detector, to photoelectrically detect the fluorescence emission by the light detector and to read fluorescence data recorded in the plurality of absorptive regions formed in the substrate of the biochemical analysis unit, thereby producing biochemical analysis data, biochemical analysis data having high quantitative characteristics can be produced with high resolution.

In a preferred aspect of the present invention, each of the plurality of light guide members is formed of at least one optical fiber.

In another preferred aspect of the present invention, each of the plurality of light guide members is formed of an optical fiber bundle constituted by a plurality of optical fibers.

In a preferred aspect of the present invention, the plurality of light guide members are disposed in such a manner that each of the plurality of absorptive regions formed in the substrate of the biochemical analysis unit faces one of the light collecting end portions of the plurality of light guide members.

In another preferred aspect of the present invention, the plurality of light guide members are disposed in such a manner that at least some of the plurality of absorptive regions formed in the substrate of the biochemical analysis unit face the two or more light collecting end portions of the plurality of light guide members.

According to this preferred aspect of the present invention, since it is not necessary to accurately position the light collecting end portions of the plurality of light guide members and the plurality of absorptive regions formed in the substrate of the biochemical analysis unit, it is possible to markedly lower the cost of manufacturing an apparatus for producing biochemical analysis data.

In a preferred aspect of the present invention, the plurality of light guide members are gathered in the vicinity of end portions opposite to the light collecting end portions.

According to this preferred aspect of the present invention, since the plurality of light guide members are gathered in the vicinity of end portions opposite to the light collecting end portions, in the case where fluorescence emission released from the plurality of absorptive regions formed in the substrate of the biochemical analysis unit and led through the plurality of light guide members is photoelectrically detected by a two-dimensional sensor, it is possible to employ a two-dimensional sensor having a small light detecting surface, thereby enabling an apparatus for producing biochemical analysis data to be smaller and lowering cost for manufacturing it.

In a preferred aspect of the present invention, the plurality of light guide members are mounted on a fixing head in the vicinity of the light collecting end portions so that each of the light collecting end portions of the plurality of light guide members are disposed to face one of the absorptive regions formed in the substrate of the biochemical analysis unit placed on the sample stage.

In a preferred aspect of the present invention, the method for producing biochemical analysis data comprises the steps of simultaneously irradiating the plurality of absorptive regions formed in the substrate of the biochemical analysis unit with a stimulating ray emitted from a stimulating ray source for a predetermined time from a side of the biochemical analysis unit opposite to the side facing the light collecting end portion of the plurality of light guide members, exciting a fluorescent substance contained in the plurality of absorptive regions, collecting fluorescence emission released from the plurality of absorptive regions by the light collecting end portion of the plurality of light guide members, leading the thus collected fluorescence emission through the plurality of light guide members to a stimulating ray cutting filter having a property of cutting light having a wavelength of that of the stimulating ray and transmitting light having a wavelength longer than that of stimulating ray, thereby cutting the stimulating ray, further leading fluorescence emission transmitted through the stimulating ray cutting filter to a two-dimensional solid state sensor, and photoelectrically detecting fluorescence emission by the two-dimensional solid state sensor to produce biochemical analysis data.

According to this preferred aspect of the present invention, when biochemical analysis data are to be produced by simultaneously irradiating the plurality of absorptive regions formed in the substrate of the biochemical analysis unit placed on the sample stage with the stimulating ray, exciting a fluorescent substance contained in the plurality of absorptive regions and photoelectrically detecting fluorescence emission released from the plurality of absorptive regions, it is possible for each of the light collecting end portions of the light guide members to collect fluorescence emission released from the plurality of absorptive regions with high efficiency by positioning the plurality of light guide members so that each of the light collecting end portions thereof is located sufficiently close to one of the plurality of absorptive regions formed in the substrate of the biochemical analysis unit placed on the sample stage and, therefore, biochemical analysis data having an excellent quantitative characteristic can be produced with high resolution by photoelectrically detecting fluorescence emission led through the plurality of light collecting members to the two-dimensional solid state sensor.

Further, according to this preferred aspect of the present invention, since the stimulating ray is simultaneously projected onto the plurality of absorptive regions formed in the substrate of the biochemical analysis unit from the side opposite to the plurality of light guide members for leading fluorescence emission for a predetermined time, thereby exciting a fluorescent substance contained in the plurality of absorptive regions and fluorescence emission released from the plurality of absorptive regions is collected by the plurality of light guide member, it is possible to irradiate the plurality of absorptive regions with the stimulating ray for a sufficiently long time, thereby exciting a fluorescent substance contained in the plurality of absorptive regions and cause the plurality of absorptive regions to release a sufficiently large amount of fluorescence emission. Therefore, since a sufficiently large amount of fluorescence emission can be led via the stimulating ray cutting filter to a two-dimensional solid state sensor, biochemical analysis data having an excellent quantitative characteristic can be produced by photoelectrically detecting fluorescence emission with high sensitivity.

In a further preferred aspect of the present invention, the method for producing biochemical analysis data comprises the steps of producing position data by detecting what region on a photo-electric detecting surface of the two-dimensional solid state sensor will receive fluorescence emission to be released from the plurality of absorptive regions formed in the substrate of the biochemical analysis unit and producing biochemical analysis data based on the thus produced position data by photoelectrically detecting fluorescence emission released from the plurality of absorptive regions formed in the substrate of the biochemical analysis unit with the two-dimensional solid state sensor.

According to this preferred aspect of the present invention, since it is not necessary to accurately dispose end portions of the plurality of light guide members opposite to the light collecting end portions with respect to the photoelectric detecting surface of the two-dimensional solid state sensor, it is possible to markedly lower the cost of manufacturing an apparatus for producing biochemical analysis data.

In a further preferred aspect of the present invention, the position data are produced by using a position data producing unit including a substrate formed with a plurality of through-holes in the same pattern as that of the plurality of absorptive regions formed in the substrate of the biochemical analysis unit, leading light transmitted through the plurality of through-holes through the plurality of light guide members to the two-dimensional solid state sensor, and photoelectrically detecting the light.

In a further preferred aspect of the present invention, two or more two-dimensional solid state sensors are used.

In a preferred aspect of the present invention, each of the plurality of light guiding members is constituted as a condenser lens disposed so as to face one of the plurality of absorptive regions formed in the substrate of the biochemical analysis unit placed on the sample stage so that fluorescence emission released from the plurality of absorptive regions can be led through the plurality of condenser lens to a two-dimensional solid state sensor.

According to this preferred aspect of the present invention, when biochemical analysis data are to be produced by irradiating the plurality of absorptive regions two-dimensionally formed to be spaced apart from each other in the substrate of the biochemical analysis unit and selectively labeled with a fluorescent substance with the stimulating ray to excite fluorescent substance contained in the plurality of absorptive regions, photoelectrically detecting fluorescence emission released from the absorptive regions and reading fluorescence data recorded in the plurality of absorptive regions formed in the substrate of the biochemical analysis unit, it is possible to collect fluorescence emission released from the plurality of absorptive regions by the plurality of condenser lens with high light collecting efficiency and lead it to the two-dimensional solid state sensor. Therefore, since it is possible to effectively prevent fluorescence emission released from neighboring absorptive regions formed in the substrate of the biochemical analysis unit and to effectively prevent noise caused by the scattering of fluorescence emission from being generated in biochemical analysis data, biochemical analysis data having an excellent quantitative characteristic can be produced.

Further, according to this preferred aspect of the present invention, unlike the case where fluorescence emission released from the plurality of absorptive regions is led through a single condenser lens to the two-dimensional solid state sensor, since generation of stray light in the condenser lens can be prevented by decreasing a view angle from each of the plurality of absorptive regions into the condenser lens, fluorescence emission released from the plurality of absorptive regions can be detected by the two-dimensional solid state sensor with high sensitivity and data, biochemical analysis data having an excellent quantitative characteristic can be produced.

In a further preferred aspect of the present invention, each of the plurality of condenser lenses is constituted as a lens having a great numerical aperture.

In a further preferred aspect of the present invention, the plurality of condenser lenses are mounted on a lens array so that a pitch between neighboring condenser lenses is equal to a distance between neighboring absorptive regions formed in the substrate of the biochemical analysis unit.

In a further preferred aspect of the present invention, the two-dimensional solid state sensor is constituted by a cooled CCD area sensor.

According to this preferred aspect of the present invention, since the two-dimensional solid state sensor is constituted by a cooled CCD area sensor, it is possible to irradiate the plurality of absorptive regions formed in the substrate of the biochemical analysis unit with the stimulating ray for a long time, thereby exciting a fluorescent substance contained therein and to detect fluorescence emission released from the plurality of absorptive regions, biochemical analysis data can be produced with sufficiently high sensitivity by photoelectrically detecting fluorescence emission by the cooled CCD area sensor.

In another preferred aspect of the present invention, the method for producing biochemical analysis data comprises the steps of sequentially irradiating the plurality of absorptive regions formed in the substrate of the biochemical analysis unit placed on the sample stage with a stimulating ray emitted from a stimulating ray source from a side of the biochemical analysis unit opposite to the side facing the light collecting end portion of the plurality of light guide members, exciting a fluorescent substance contained in the plurality of absorptive regions, collecting fluorescence emission released from each of the plurality of absorptive regions by the light collecting end portion of the corresponding light guide member among the plurality of light guide members, leading fluorescence emission collected by the corresponding light guide member to a stimulating ray cutting filter having a property of cutting light having a wavelength of that of the stimulating ray and transmitting light having a wavelength longer than that of stimulating ray, thereby cutting the stimulating ray, further leading fluorescence emission transmitted through the stimulating ray cutting filter to a zero-dimensional sensor, and photoelectrically detecting fluorescence emission by the zero-dimensional sensor to produce biochemical analysis data.

According to this preferred aspect of the present invention, when biochemical analysis data are to be produced by sequentially irradiating the plurality of absorptive regions formed in the substrate of the biochemical analysis unit placed on the sample stage with a stimulating ray, exciting a fluorescent substance contained in each of the plurality of absorptive regions and photoelectrically detecting fluorescence emission released from each of the plurality of absorptive regions, it is possible for each of the light collecting end portions of the light guide members to collect fluorescence emission released from one of the plurality of absorptive regions with high efficiency by positioning the plurality of light guide members so that each of the light collecting end portions thereof is located sufficiently close to one of the plurality of absorptive regions formed in the substrate of the biochemical analysis unit placed on the sample stage and, therefore, biochemical analysis data having an excellent quantitative characteristic can be produced with high resolution by photoelectrically detecting fluorescence emission led through the plurality of light collecting members to the zero-dimensional sensor.

In a further preferred aspect of the present invention, the stimulating ray emitted from the stimulating ray source is intermittently moved by a pitch equal to a distance between neighboring absorptive regions formed in the substrate of the biochemical analysis unit, thereby scanning the plurality of absorptive regions formed in the substrate of the biochemical analysis unit placed on the sample stage are scanned with the stimulating ray.

In a further preferred aspect of the present invention, the zero-dimensional sensor is constituted as a photomultiplier.

In a further preferred aspect of the present invention, the plurality of absorptive regions formed in the substrate of the biochemical analysis unit are selectively labeled with a fluorescent substance by spotting a solution containing specific binding substances which can specifically bind with a substance derived from a living organism and whose sequence, base length, composition and the like are known into the plurality of absorptive regions and specifically binding a substance derived from a living body and labeled with a fluorescent substance with the specific binding substances contained in the plurality of absorptive regions.

In a preferred aspect of the present invention, the sample is constituted by a biochemical analysis unit including a substrate two-dimensionally formed with a plurality of through-holes to be spaced apart from each other and the plurality of light releasable regions are constituted by a plurality of absorptive regions formed by charging an absorptive material in the plurality of through-holes formed in the substrate of the biochemical analysis unit and selectively labeled with a labeling substance which generates chemiluminescence emission when it contacts a chemiluminescent substrate.

In the present invention, the case where a plurality of light releasable regions are selectively labeled with a labeling substance which generates chemiluminescent emission when it contacts a chemiluminescent substrate as termed herein includes the case where a plurality of light releasable regions are selectively labeled with a labeling substance which generates chemiluminescent emission when it contacts a chemiluminescent substrate by selectively binding a substance derived from a living organism and labeled with a labeling substance which generates chemiluminescent emission when it contacts a chemiluminescent substrate with specific binding substances contained in the plurality of light releasable regions and the case where a plurality of light releasable regions are selectively labeled with a labeling substance which generates chemiluminescent emission when it contacts a chemiluminescent substrate by selectively binding a substance derived from a living organism and labeled with a hapten with specific binding substances contained in the plurality of light releasable, and binding an antibody for the hapten labeled with an enzyme which generates chemiluminescent emission when it contacts a chemiluminescent substrate with the hapten by an antigen-antibody reaction.

According to a further application of this preferred aspect of the present invention, when biochemical analysis data are to be produced by bringing the plurality of absorptive regions two-dimensionally formed to be spaced apart from each other in the substrate of the biochemical analysis unit and selectively labeled with a labeling substance which generates chemiluminescence emission when it contacts a chemiluminescent substrate into contact with a chemiluminescent substrate, thereby causing the plurality of absorptive regions to release chemiluminescence emission, photoelectrically detecting chemiluminescence emission released from the plurality of absorptive regions and reading chemiluminescence data recorded in the plurality of absorptive regions formed in the substrate of the biochemical analysis unit, since chemiluminescence emission released from the plurality of absorptive regions is collected by the plurality of light guide members each of which is disposed to face one of the plurality of absorptive regions to lead it to the light detector and the chemiluminescence emission is photoelectrically detected by the light detector, thereby reading chemiluminescence data recorded in the number of absorptive regions formed in the substrate of the biochemical analysis unit, it is possible to effectively prevent chemiluminescence emission released from neighboring absorptive regions formed in the substrate of the biochemical analysis unit from being mixed with each other and to lead only chemiluminescence emission released from the absorptive region through the corresponding light guide member to the light detector, to photoelectrically detect the chemiluminescence emission by the light detector and to read chemiluminescence data recorded in the plurality of absorptive regions formed in the substrate of the biochemical analysis unit, thereby producing biochemical analysis data. Therefore, biochemical analysis data having high quantitative characteristics can be produced with high resolution.

In a preferred aspect of the present invention, each of the plurality of light guide members includes a light collecting end portion capable of collecting light and the light collecting end portion of each of the plurality of light guide members is disposed to face one of the plurality of absorptive regions formed in the substrate of the biochemical analysis unit placed on the sample stage.

According to this preferred aspect of the present invention, when biochemical analysis data are to be produced by bringing the plurality of absorptive regions two-dimensionally formed to be spaced apart from each other in the substrate of the biochemical analysis unit and selectively labeled with a labeling substance which generates chemiluminescence emission when it contacts a chemiluminescent substrate into contact with a chemiluminescent substrate, thereby causing the plurality of absorptive regions to release chemiluminescence emission, photoelectrically detecting chemiluminescence emission released from the plurality of absorptive regions and reading chemiluminescence data recorded in the plurality of absorptive regions formed in the substrate of the biochemical analysis unit, it is possible for each of the light collecting end portions of the light guide members to effectively collect only chemiluminescence emission released from the corresponding absorptive region by disposing the plurality of light guide members so that each of the light collecting end portions of the light guide members is located sufficiently close to one of the absorptive regions formed in the substrate of the biochemical analysis unit placed on the sample stage. Therefore, since it is possible to effectively prevent chemiluminescence emission released from neighboring absorptive regions formed in the substrate of the biochemical analysis unit from being mixed with each other and to lead only chemiluminescence emission released from the absorptive region through the corresponding light guide member to the light detector, to photoelectrically detect the chemiluminescence emission by the light detector and to read chemiluminescence data recorded in the plurality of absorptive regions formed in the substrate of the biochemical analysis unit, thereby producing biochemical analysis data, biochemical analysis data having high quantitative characteristics can be produced with high resolution.

In a preferred aspect of the present invention, each of the plurality of light guide members is formed of at least one optical fiber.

In another preferred aspect of the present invention, each of the plurality of light guide members is formed of an optical fiber bundle constituted by a plurality of optical fibers.

In a preferred aspect of the present invention, the plurality of light guide members are disposed in such a manner that each of the plurality of absorptive regions formed in the substrate of the biochemical analysis unit faces one of the light collecting end portions of the plurality of light guide members.

In another preferred aspect of the present invention, the plurality of light guide members are disposed in such a manner that at least some of the plurality of absorptive regions formed in the substrate of the biochemical analysis unit face the two or more light collecting end portions of the plurality of light guide members.

According to this preferred aspect of the present invention, since it is not necessary to accurately position the light collecting end portions of the plurality of light guide members and the plurality of absorptive regions formed in the substrate of the biochemical analysis unit, it is possible to markedly lower the cost of manufacturing an apparatus for producing biochemical analysis data.

In a preferred aspect of the present invention, the plurality of light guide members are gathered in the vicinity of end portions opposite to the light collecting end portions.

According to this preferred aspect of the present invention, since the plurality of light guide members are gathered in the vicinity of end portions opposite to the light collecting end portions, in the case where chemiluminescence emission released from the plurality of absorptive regions formed in the substrate of the biochemical analysis unit and led through the plurality of light guide members is photoelectrically detected by a two-dimensional sensor, it is possible to employ a two-dimensional sensor having a small light detecting surface, thereby enabling an apparatus for producing biochemical analysis data to be smaller and lowering cost for manufacturing it.

In a preferred aspect of the present invention, the plurality of light guide members are mounted on a fixing head in the vicinity of the light collecting end portions so that each of the light collecting end portions of the plurality of light guide members are disposed to face one of the absorptive regions formed in the substrate of the biochemical analysis unit placed on the sample stage.

In a preferred aspect of the present invention, the method for producing biochemical analysis data comprises the steps of collecting fluorescence emission released from the plurality of absorptive regions by the light collecting end portion of the plurality of light guide members, leading the thus collected fluorescence emission through the plurality of light guide members to a two-dimensional solid state sensor, and photoelectrically detecting fluorescence emission by the two-dimensional solid state sensor to produce biochemical analysis data.

According to this preferred aspect of the present invention, when biochemical analysis data are to be produced by photoelectrically detecting chemiluminescence emission released from the plurality of absorptive regions formed in the substrate of the biochemical analysis unit placed on the sample stage, it is possible for each of the light collecting end portions of the light guide members to collect chemiluminescence emission released from the plurality of absorptive regions with high efficiency by positioning the plurality of light guide members so that each of the light collecting end portions thereof is located sufficiently close to one of the plurality of absorptive regions formed in the substrate of the biochemical analysis unit placed on the sample stage and, therefore, biochemical analysis data having an excellent quantitative characteristic can be produced with high resolution by photoelectrically detecting chemiluminescence emission led through the plurality of light collecting members to the two-dimensional solid state sensor.

In a further preferred aspect of the present invention, the method for producing biochemical analysis data comprises the steps of producing position data by detecting what region on a photo-electric detecting surface of the two-dimensional solid state sensor will receive chemiluminescence emission to be released from the plurality of absorptive regions formed in the substrate of the biochemical analysis unit and producing biochemical analysis data based on the thus produced position data by photoelectrically detecting chemiluminescence emission released from the plurality of absorptive regions formed in the substrate of the biochemical analysis unit with the two-dimensional solid state sensor.

According to this preferred aspect of the present invention, since it is not necessary to accurately dispose end portions of the plurality of light guide members opposite to the light collecting end portions with respect to the photo-electric detecting surface of the two-dimensional solid state sensor, it is possible to markedly lower the cost of manufacturing an apparatus for producing biochemical analysis data.

In a further preferred aspect of the present invention, the position data are produced by using a position data producing unit including a substrate formed with a plurality of through-holes in the same pattern as that of the plurality of absorptive regions formed in the substrate of the biochemical analysis unit, leading light transmitted through the plurality of through-holes through the plurality of light guide members to the two-dimensional solid state sensor, and photoelectrically detecting the light.

In a further preferred aspect of the present invention, two or more two-dimensional solid state sensors are used.

In a preferred aspect of the present invention, each of the plurality of light guiding members is constituted as a condenser lens disposed so as to face one of the plurality of absorptive regions formed in the substrate of the biochemical analysis unit placed on the sample stage so that chemiluminescence emission released from the plurality of absorptive regions can be led through the plurality of condenser lens to a two-dimensional solid state sensor.

According to this preferred aspect of the present invention, when biochemical analysis data are to be produced by bringing the plurality of absorptive regions two-dimensionally formed to be spaced apart from each other in the substrate of the biochemical analysis unit and selectively labeled with a labeling substance which generates chemiluminescence emission when it contacts a chemiluminescent substrate into contact with a chemiluminescent substrate, thereby causing the plurality of absorptive regions to release chemiluminescence emission, photoelectrically detecting chemiluminescence emission released from the absorptive regions and reading chemiluminescence data recorded in the plurality of absorptive regions formed in the substrate of the biochemical analysis unit, it is possible to collect chemiluminescence emission released from the plurality of absorptive regions by the plurality of condenser lens with high light collecting efficiency and lead it to the two-dimensional solid state sensor. Therefore, since it is possible to effectively prevent chemiluminescence emission released from neighboring absorptive regions formed in the substrate of the biochemical analysis unit and to effectively prevent noise caused by the scattering of chemiluminescence emission from being generated in biochemical analysis data, biochemical analysis data having an excellent quantitative characteristic can be produced.

Further, according to this preferred aspect of the present invention, unlike the case where chemiluminescence emission released from the plurality of absorptive regions is led through a single condenser lens to the two-dimensional solid state sensor, since generation of stray light in the condenser lens can be prevented by decreasing a view angle from each of the plurality of absorptive regions into the condenser lens, chemiluminescence emission released from the plurality of absorptive regions can be detected by the two-dimensional solid state sensor with high sensitivity and data, biochemical analysis data having an excellent quantitative characteristic can be produced.

In a further preferred aspect of the present invention, each of the plurality of condenser lenses is constituted as a lens having a great numerical aperture.

In a further preferred aspect of the present invention, the plurality of condenser lenses are mounted on a lens array so that a pitch between neighboring condenser lenses is equal to a distance between neighboring absorptive regions formed in the substrate of the biochemical analysis unit.

In a further preferred aspect of the present invention, the two-dimensional solid state sensor is constituted by a cooled CCD area sensor.

According to this preferred aspect of the present invention, since the two-dimensional solid state sensor is constituted by a cooled CCD area sensor, it is possible to detect chemiluminescence emission released from the plurality of absorptive regions for a long time, biochemical analysis data can be produced with sufficiently high sensitivity by photoelectrically detecting chemiluminescence emission by the cooled CCD area sensor.

In a further preferred aspect of the present invention, the plurality of absorptive regions formed in the substrate of the biochemical analysis unit are selectively labeled with a labeling substance which generates chemiluminescence emission when it contacts a chemiluminescent substrate by spotting a solution containing specific binding substances which can specifically bind with a substance derived from a living organism and whose sequence, base length, composition and the like are known into the plurality of absorptive regions and specifically binding a substance derived from a living body and labeled with a labeling substance which generates chemiluminescence emission when it contacts a chemiluminescent substrate with the specific binding substances contained in the plurality of absorptive regions.

In a further preferred aspect of the present invention, the substrate of the biochemical analysis unit has a property of attenuating light energy.

According to this preferred aspect of the present invention, since the substrate of the biochemical analysis unit has a property of attenuating light energy, it is possible to prevent fluorescence emission or chemiluminescence emission released from the absorptive regions formed in the substrate of the biochemical analysis unit from scattering in the substrate of the biochemical analysis unit and being mixed with each other. Therefore, since only fluorescence emission or chemiluminescence emission released from the absorptive region to be detected can be efficiently collected by and led through the corresponding light guide member to a light detector and be photoelectrically detected by the light detector, it is possible to efficiently prevent noise caused by the scattering of fluorescence emission or chemiluminescence emission from being generated in biochemical analysis data produced by photoelectrically detecting fluorescence emission or chemiluminescence emission and to produce biochemical analysis data having an excellent quantitative characteristic.

Further, according to this preferred aspect of the present invention, since the substrate of the biochemical analysis unit has a property of attenuating light energy, even in the case of forming a plurality of absorptive regions in the substrate of the biochemical analysis unit at a high density, spotting specific binding substances whose sequence, base length, composition and the like are known in the plurality of absorptive regions, specifically binding a substance derived from a living organism and labeled with a labeling substance which generates chemiluminescence emission when it contacts a chemiluminescent substrate with the specific binding substances contained in the plurality of absorptive regions, thereby selectively labeling the plurality of absorptive regions with a labeling substance which generates chemiluminescence emission when it contacts a chemiluminescent substrate, bringing the biochemical analysis unit into contact with a chemiluminescent substrate, thereby causing the plurality of absorptive regions to selectively release chemiluminescence emission and facing the biochemical analysis unit while in a state of releasing chemiluminescence emission toward a stimulable phosphor sheet formed with a plurality of stimulable phosphor layer regions, thereby exposing the plurality of stimulable phosphor layer regions of the stimulable phosphor sheet to chemiluminescence emission, it is possible to effectively prevent chemiluminescence emission released from the individual absorptive regions from scattering in the substrate of the biochemical analysis unit and to effectively prevent the thus scattered chemiluminescence emission from entering a stimulable phosphor layer regions of the stimulable phosphor sheet to be exposed to chemiluminescence emission released from the neighboring absorptive regions. Therefore, it is possible to effectively prevent noise caused by the scattering of chemiluminescence emission from being generated in biochemical analysis data produced by irradiating the stimulable phosphor layer regions exposed to chemiluminescence emission with a stimulating ray.

In a preferred aspect of the present invention, the substrate of the biochemical analysis unit has a property of reducing the energy of light to $1/5$ or less when the light travels in the substrate by a distance equal to that between neighboring absorptive regions.

In a further preferred aspect of the present invention, the substrate of the biochemical analysis unit has a property of reducing the energy of light to $1/10$ or less when the light travels in the substrate by a distance equal to that between neighboring absorptive regions.

In a further preferred aspect of the present invention, the substrate of the biochemical analysis unit has a property of reducing the energy of light to $1/50$ or less when the light travels in the substrate by a distance equal to that between neighboring absorptive regions.

In a further preferred aspect of the present invention, the substrate of the biochemical analysis unit has a property of reducing the energy of light to $1/100$ or less when the light travels in the substrate by a distance equal to that between neighboring absorptive regions.

In a further preferred aspect of the present invention, the substrate of the biochemical analysis unit has a property of reducing the energy of light to $1/500$ or less when the light travels in the substrate by a distance equal to that between neighboring absorptive regions.

In a further preferred aspect of the present invention, the substrate of the biochemical analysis unit has a property of reducing the energy of light to $1/1,000$ or less when the light travels in the substrate by a distance equal to that between neighboring absorptive regions.

In a further preferred aspect of the present invention, the substrate of the biochemical analysis unit has a property of attenuating radiation energy.

According to this preferred aspect of the present invention, since the substrate of the biochemical analysis unit has a property of attenuating radiation energy, even in the case of forming a plurality of absorptive regions in the substrate of the biochemical analysis unit at a high density, spotting specific binding substances whose sequence, base length, composition and the like are known in the plurality of absorptive regions, specifically binding a substance derived from a living organism and labeled with a radioactive labeling substance with the specific binding substances contained in the plurality of absorptive regions, thereby selectively labeling the plurality of absorptive regions with a radioactive labeling substance and facing the biochemical analysis unit toward a stimulable phosphor sheet formed with a plurality of stimulable phosphor layer regions, thereby exposing the plurality of stimulable phosphor layer regions of the stimulable phosphor sheet to a radioactive labeling substance selectively contained in the plurality of absorptive regions formed in the substrate of the biochemical analysis unit, it is possible to effectively prevent electron beams ($\beta$ rays) released from the radioactive labeling substance contained in the individual absorptive regions from scattering in the substrate of the biochemical analysis unit and to effectively prevent the thus scattered electron beams ($\beta$ rays) from entering a stimulable phosphor layer regions of the stimulable phosphor sheet to be exposed to a radioactive labeling substance contained in the neighboring absorptive regions. Therefore, it is possible to effectively prevent noise caused by the scattering of electron beams ($\beta$ rays) from being generated in biochemical analysis data produced by irradiating the stimulable phosphor layer regions exposed to a radioactive labeling substance with a stimulating ray.

In a preferred aspect of the present invention, the substrate of the biochemical analysis unit has a property of reducing the energy of radiation to ⅕ or less when the radiation travels in the substrate by a distance equal to that between neighboring absorptive regions.

In a further preferred aspect of the present invention, the substrate of the biochemical analysis unit has a property of reducing the energy of radiation to ¹⁄₁₀ or less when the radiation travels in the substrate by a distance equal to that between neighboring absorptive regions.

In a further preferred aspect of the present invention, the substrate of the biochemical analysis unit has a property of reducing the energy of radiation to ¹⁄₅₀ or less when the radiation travels in the substrate by a distance equal to that between neighboring absorptive regions.

In a further preferred aspect of the present invention, the substrate of the biochemical analysis unit has a property of reducing the energy of radiation to ¹⁄₁₀₀ or less when the radiation travels in the substrate by a distance equal to that between neighboring absorptive regions.

In a further preferred aspect of the present invention, the substrate of the biochemical analysis unit has a property of reducing the energy of radiation to ¹⁄₅₀₀ or less when the radiation travels in the substrate by a distance equal to that between neighboring absorptive regions.

In a further preferred aspect of the present invention, the substrate of the biochemical analysis unit has a property of reducing the energy of radiation to ¹⁄₁,₀₀₀ or less when the radiation travels in the substrate by a distance equal to that between neighboring absorptive regions.

In the present invention, the material for forming the substrate of the biochemical analysis unit is preferably capable of attenuating light energy and is more preferably capable of attenuating radiation energy but is not particularly limited. The material for forming the substrate of the biochemical analysis unit may be any type of inorganic compound material or organic compound material and the substrate of the biochemical analysis unit can preferably be formed of a metal material, a ceramic material or a plastic material.

Illustrative examples of inorganic compound materials preferably usable for forming the substrate of the biochemical analysis unit in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound can preferably be used as an organic compound material preferably usable for forming the substrate of the biochemical analysis unit. Illustrative examples of high molecular compounds preferably usable for forming the substrate of the biochemical analysis unit in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating light energy generally increases as scattering and/or absorption of light increases, the substrate of the biochemical analysis unit preferably has absorbance of 0.3 per cm (thickness) or more and more preferably has absorbance of 1 per cm (thickness) or more. The absorbance can be determined by placing an integrating sphere immediately behind a plate-like member having a thickness of T cm, measuring an amount A of transmitted light at a wavelength of probe light or emission light used for measurement by a spectrophotometer, and calculating A/T. In the present invention, a light scattering substance or a light absorbing substance may be added to the substrate of the biochemical analysis unit in order to improve the capability of attenuating light energy. Particles of a material different from a material forming the substrate of the biochemical analysis unit may be preferably used as a light scattering substance and a pigment or dye may be preferably used as a light absorbing substance.

Since the capability of attenuating radiation energy generally increases as specific gravity increases, the substrate of the biochemical analysis unit is preferably formed of a compound material or a composite material having specific gravity of 1.0 g/cm³ or more and more preferably formed of a compound material or a composite material having specific gravity of 1.5 g/cm³ to 23 g/cm³.

In a preferred aspect of the present invention, the substrate of the biochemical analysis unit is formed with 10 or more absorptive regions.

In a further preferred aspect of the present invention, the substrate of the biochemical analysis unit is formed with 50 or more absorptive regions.

In a further preferred aspect of the present invention, the substrate of the biochemical analysis unit is formed with 100 or more absorptive regions.

In a further preferred aspect of the present invention, the substrate of the biochemical analysis unit is formed with 500 or more absorptive regions.

In a further preferred aspect of the present invention, the substrate of the biochemical analysis unit is formed with 1,000 or more absorptive regions.

In a further preferred aspect of the present invention, the substrate of the biochemical analysis unit is formed with 5,000 or more absorptive regions.

In a further preferred aspect of the present invention, the substrate of the biochemical analysis unit is formed with 10,000 or more absorptive regions.

In a further preferred aspect of the present invention, the substrate of the biochemical analysis unit is formed with 50,000 or more absorptive regions.

In a further preferred aspect of the present invention, the substrate of the biochemical analysis unit is formed with 100,000 or more absorptive regions.

In a preferred aspect of the present invention, each of the plurality of absorptive regions is formed in the biochemical analysis unit to have a size of less than 5 mm$^2$.

In a further preferred aspect of the present invention, each of the plurality of absorptive regions is formed in the biochemical analysis unit to have a size of less than 1 mm$^2$.

In a further preferred aspect of the present invention, each of the plurality of absorptive regions is formed in the biochemical analysis unit to have a size of less than 0.5 mm$^2$.

In a further preferred aspect of the present invention, each of the plurality of absorptive regions is formed in the biochemical analysis unit to have a size of less than 0.1 mm$^2$.

In a further preferred aspect of the present invention, each of the plurality of absorptive regions is formed in the biochemical analysis unit to have a size of less than 0.05 mm$^2$.

In a further preferred aspect of the present invention, each of the plurality of absorptive regions is formed in the biochemical analysis unit to have a size of less than 0.01 mm$^2$.

In the present invention, the density of the absorptive regions formed in the substrate of the biochemical analysis unit can be determined based upon the material of the substrate, the kind of electron beam released from the radioactive labeling substance and the like.

In a preferred aspect of the present invention, the plurality of absorptive regions are formed in the substrate of the biochemical analysis unit at a density of 10 or more per cm$^2$.

In a further preferred aspect of the present invention, the plurality of absorptive regions are formed in the substrate of the biochemical analysis unit at a density of 50 or more per cm$^2$.

In a further preferred aspect of the present invention, the plurality of absorptive regions are formed in the substrate of the biochemical analysis unit at a density of 100 or more per cm$^2$.

In a further preferred aspect of the present invention, the plurality of absorptive regions are formed in the substrate of the biochemical analysis unit at a density of 500 or more per cm$^2$.

In a further preferred aspect of the present invention, the plurality of absorptive regions are formed in the substrate of the biochemical analysis unit at a density of 1,000 or more per cm$^2$.

In a further preferred aspect of the present invention, the plurality of absorptive regions are formed in the substrate of the biochemical analysis unit at a density of 5,000 or more per cm$^2$.

In a further preferred aspect of the present invention, the plurality of absorptive regions are formed in the substrate of the biochemical analysis unit at a density of 10,000 or more per cm$^2$.

In a further preferred aspect of the present invention, the plurality of absorptive regions are formed in the substrate of the biochemical analysis unit at a density of 50,000 or more per cm$^2$.

In a further preferred aspect of the present invention, the plurality of absorptive regions are formed in the substrate of the biochemical analysis unit at a density of 100,000 or more per cm$^2$.

In a preferred aspect of the present invention, each of the absorptive regions is formed substantially circular in the substrate of the biochemical analysis unit.

In another preferred aspect of the present invention, each of the absorptive regions is formed substantially rectangular in the substrate of the biochemical analysis unit.

In the present invention, a porous material or a fiber material may be preferably used as the absorptive material for forming the absorptive regions of the biochemical analysis unit. The absorptive regions may be formed by combining a porous material and a fiber material.

In the present invention, a porous material for forming the absorptive regions of the biochemical analysis unit may be any type of an organic material or an inorganic material and may be an organic/inorganic composite material.

In the present invention, an organic porous material used for forming the absorptive regions of the biochemical analysis unit is not particularly limited but a carbon porous material such as an activated carbon or a porous material capable of forming a membrane filter is preferably used. Illustrative examples of porous materials capable of forming a membrane filter include nylons such as nylon-6, nylon-6,6, nylon-4,10; cellulose derivatives such as nitrocellulose, acetyl cellulose, butyric-acetyl cellulose; collagen; alginic acids such as alginic acid, calcium alginate, alginic acid/poly-L-lysine polyionic complex; polyolefins such as polyethylene, polypropylene; polyvinyl chloride; polyvinylidene chloride; polyfluoride such as polyvinylidene fluoride, polytetrafluoride; and copolymers or composite materials thereof.

In the present invention, an inorganic porous material used for forming the absorptive regions of the biochemical analysis unit is not particularly limited. Illustrative examples of inorganic porous materials preferably usable in the present invention include metals such as platinum, gold, iron, silver, nickel, aluminum and the like; metal oxides such as alumina, silica, titania, zeolite and the like; metal salts such as hydroxy apatite, calcium sulfate and the like; and composite materials thereof.

In the present invention, a fiber material used for forming the absorptive regions of the biochemical analysis unit is not particularly limited. Illustrative examples of fiber materials preferably usable in the present invention include nylons such as nylon-6, nylon-6,6, nylon-4,10; and cellulose derivatives such as nitrocellulose, acetyl cellulose, butyricacetyl cellulose.

In a preferred aspect of the present invention, the stimulating ray source is constituted as a laser stimulating ray source for emitting a laser beam.

The above and other objects of the present invention can be also accomplished by an apparatus for producing biochemical analysis data comprising a sample stage on which a sample two-dimensionally formed with a plurality of light releasable regions spaced apart from each other and selectively releasing light is to be placed, a light detector for photpelectrically detecting light released from the plurality of light releasable regions formed in the sample placed on the sample stage, and a plurality of light guide members disposed in such a manner that each of them faces one of the light releasable regions formed in the sample placed on the sample stage and leads light released therefrom to the light detector.

According to one application of the present invention, when a plurality of stimulable phosphor layer regions two-dimensionally formed to be spaced apart from each other in the support of the stimulable phosphor sheet are selectively exposed to a radioactive labeling substance, thereby recording radiation data in the plurality of stimulable phosphor layer regions and the radiation data recorded in the plurality of stimulable phosphor layer regions are to be read to produce biochemical analysis data by placing the stimulable phosphor sheet on the sample stage, irradiating the plurality of stimulable phosphor layer regions formed in the support of the stimulable phosphor sheet with a stimulating ray and photoelectrically detecting stimulated emission released from the plurality of stimulable phosphor layer regions by the light detector, since stimulated emission released from the plurality of stimulable phosphor layer regions is collected with high light collecting efficiency by the plurality of light guide members each of which is disposed to face one of the plurality of stimulable phosphor layer regions to lead it to the light detector, it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector with high sensitivity and to read radiation data recorded in the plurality of stimulable phosphor layer regions of the stimulable phosphor sheet, thereby producing biochemical analysis data. Therefore, biochemical analysis data having high quantitative characteristics can be produced with high resolution.

According to another application of the present invention, when a plurality of stimulable phosphor layer regions two-dimensionally formed to be spaced apart from each other in the support of the stimulable phosphor sheet are selectively exposed to chemiluminescence emission, thereby recording chemiluminescence data in the plurality of stimulable phosphor layer regions and the chemiluminescence data recorded in the plurality of stimulable phosphor layer regions are to be read to produce biochemical analysis data by placing the stimulable phosphor sheet on the sample stage, irradiating the plurality of stimulable phosphor layer regions formed in the support of the stimulable phosphor sheet with a stimulating ray and photoelectrically detecting stimulated emission released from the plurality of stimulable phosphor layer regions by the light detector, since stimulated emission released from the plurality of stimulable phosphor layer regions is collected with high light collecting efficiency by the plurality of light guide members each of which is disposed to face one of the plurality of stimulable phosphor layer regions to lead it to the light detector, it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector with high sensitivity and to read chemiluminescence data recorded in the plurality of stimulable phosphor layer regions of the stimulable phosphor sheet, thereby producing biochemical analysis data. Therefore, biochemical analysis data having high quantitative characteristics can be produced with high resolution.

According to a further application of the present invention, when a plurality of spot-like regions two-dimensionally formed to be spaced apart from each other at a high density in a biochemical analysis unit are selectively labeled with a fluorescent substance such as a fluorescent dye, thereby recording fluorescence data in the plurality of spot-like regions and the fluorescence data recorded in the plurality of spot-like regions are to be read to produce biochemical analysis data by placing the biochemical analysis unit on the sample stage, irradiating the plurality of spot-like regions formed in the biochemical analysis unit with a stimulating ray and photoelectrically detecting fluorescence emission released from the plurality of spot-like regions by the light detector, since fluorescence emission released from the plurality of spot-like regions is collected with high light collecting efficiency by the plurality of light guide members each of which is disposed to face one of the plurality of spot-like regions to lead it to the light detector, it is possible to effectively prevent fluorescence emission released from neighboring spot-like regions formed in the biochemical analysis unit from being mixed with each other and to lead only fluorescence emission released from the spot-like region through the corresponding light guide member to the light detector, and to photoelectrically detect the fluorescence emission by the light detector with high sensitivity and to read fluorescence data recorded in the plurality of spot-like regions of the biochemical analysis unit, thereby producing biochemical analysis data. Therefore, biochemical analysis data having high quantitative characteristics can be produced with high resolution.

According to a further application of the present invention, when a plurality of spot-like regions two-dimensionally formed to be spaced apart from each other at a high density in a biochemical analysis unit are selectively labeled with a labeling substance which generates chemiluminescence emission when it contacts a chemiluminescent substrate, thereby recording chemiluminescence data in the plurality of spot-like regions and the chemiluminescence data recorded in the plurality of spot-like regions formed in the biochemical analysis unit are to be read to produce biochemical analysis data by bringing the biochemical analysis unit into contact with a chemiluminescent substrate, thereby causing the plurality of spot-like regions to release chemiluminescence emission, placing the biochemical analysis unit while in a state of releasing chemiluminescence emission on the sample stage, and photoelectrically detecting chemiluminescence emission released from the plurality of spot-like regions by the light detector, since chemiluminescence emission released from the plurality of spot-like regions is collected with high light collecting efficiency by the plurality of light guide members each of which is disposed to face one of the plurality of spot-like regions to lead it to the light detector, it is possible to effectively prevent chemiluminescence emission released from neighboring spot-like regions formed in the biochemical analysis unit from being mixed with each other and to lead only chemiluminescence emission released from the spot-like region through the corresponding light guide member to the light detector, and to photoelectrically detect the chemiluminescence emission by the light detector with high sensitivity and to read chemiluminescence data recorded in the plurality of spot-like regions of the biochemical analysis unit, thereby producing biochemical analysis data. Therefore, biochemical analysis data having high quantitative characteristics can be produced with high resolution.

In a preferred aspect of the present invention, each of the plurality of light guide members includes a light collecting end portion capable of collecting light and the light collecting end portion of each of the plurality of light guide members is disposed to face one of the plurality of light releasable regions formed in the sample placed on the sample stage.

According to one application of this preferred aspect of the present invention, when a plurality of stimulable phosphor layer regions two-dimensionally formed to be spaced apart from each other in the support of the stimulable phosphor sheet are selectively exposed to a radioactive labeling substance, thereby recording radiation data in the plurality of stimulable phosphor layer regions and the radiation data recorded in the plurality of stimulable phosphor layer regions are to be read to produce biochemical analysis data by placing the stimulable phosphor sheet on the sample stage, scanning the plurality of stimulable phosphor layer regions formed in the support of the stimulable phosphor sheet with a stimulating ray and photoelectrically detecting stimulated emission released from the plurality of stimulable phosphor layer regions by the light detector, it is possible for each of the light collecting end portions of the light guide members to effectively collect only stimulated emission released from the corresponding stimulable phosphor layer region by disposing the plurality of light guide members so that each of the light collecting end portions of the light guide members is located sufficiently close to one of the stimulable phosphor layer regions of the stimulable phosphor sheet placed on the sample stage. Therefore, since it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector and to read radiation data recorded in the plurality of stimulable phosphor layer regions of the stimulable phosphor sheet, thereby producing biochemical analysis data, biochemical analysis data having high quantitative characteristics can be produced with high resolution.

According to another application of this preferred aspect of the present invention, when a plurality of stimulable phosphor layer regions two-dimensionally formed to be spaced apart from each other in the support of the stimulable phosphor sheet are selectively exposed to chemiluminescence emission, thereby recording chemiluminescence data in the plurality of stimulable phosphor layer regions and the chemiluminescence data recorded in the plurality of stimulable phosphor layer regions are to be read to produce biochemical analysis data by placing the stimulable phosphor sheet on the sample stage, scanning the plurality of stimulable phosphor layer regions formed in the support of the stimulable phosphor sheet with a stimulating ray and photoelectrically detecting stimulated emission released from the plurality of stimulable phosphor layer regions by the light detector, it is possible for each of the light collecting end portions of the light guide members to effectively collect only stimulated emission released from the corresponding stimulable phosphor layer region by disposing the plurality of light guide members so that each of the light collecting end portions of the light guide members is located sufficiently close to one of the stimulable phosphor layer regions of the stimulable phosphor sheet placed on the sample stage. Therefore, since it is possible to effectively prevent stimulated emission released from neighboring stimulable phosphor layer regions formed in the stimulable phosphor sheet from being mixed with each other and to lead only stimulated emission released from the stimulable phosphor layer region through the corresponding light guide member to the light detector, and to photoelectrically detect the stimulated emission by the light detector and to read chemiluminescence data recorded in the plurality of stimulable phosphor layer regions of the stimulable phosphor sheet, thereby producing biochemical analysis data, biochemical analysis data having high quantitative characteristics can be produced with high resolution.

According to a further application of this preferred aspect of the present invention, when a plurality of spot-like regions two-dimensionally formed to be spaced apart from each other at a high density in a biochemical analysis unit are selectively labeled with a fluorescent substance such as a fluorescent dye, thereby recording fluorescence data in the plurality of spot-like regions and the fluorescence data recorded in the plurality of spot-like regions are to be read to produce biochemical analysis data by placing the biochemical analysis unit on the sample stage, scanning the plurality of spot-like regions formed in the biochemical analysis unit with a stimulating ray and photoelectrically detecting fluorescence emission released from the plurality of spot-like regions by the light detector, it is possible for each of the light collecting end portions of the light guide members to effectively collect only fluorescence emission released from the corresponding spot-like region by disposing the plurality of light guide members so that each of the light collecting end portions of the light guide members is located sufficiently close to one of the spot-like regions of the biochemical analysis unit placed on the sample stage. Therefore, since it is possible to effectively prevent fluorescence emission released from neighboring spot-like regions formed in the biochemical analysis unit from being mixed with each other and to lead only fluorescence emission released from the spot-like region through the corresponding light guide member to the light detector, to photoelectrically detect the fluorescence emission by the light detector and to read fluorescence data recorded in the plurality of spot-like regions of the biochemical analysis unit, thereby producing biochemical analysis data, biochemical analysis data having high quantitative characteristics can be produced with high resolution.

According to a further application of this preferred aspect of the present invention, when a plurality of spot-like regions two-dimensionally formed to be spaced apart from each other at a high density in a biochemical analysis unit are selectively labeled with a labeling substance which generates chemiluminescence emission when it contacts a chemiluminescent substrate, thereby recording chemiluminescence data in the plurality of spot-like regions and the chemiluminescence data recorded in the plurality of spot-like regions formed in the biochemical analysis unit are to be read to produce biochemical analysis data by bringing the biochemical analysis unit into contact with a chemiluminescent substrate, thereby causing the plurality of spot-like regions to release chemiluminescence emission, placing the biochemical analysis unit while in a state of releasing chemiluminescence emission on the sample stage, and photoelectrically detecting chemiluminescence emission released from the plurality of spot-like regions by the light detector, it is possible for each of the light collecting end portions of the light guide members to effectively collect only chemiluminescence emission released from the corresponding spot-like region by disposing the plurality of light guide members so that each of the light collecting end portions of the light guide members is located sufficiently close to one of the spot-like regions of the biochemical analysis unit placed on the sample stage. Therefore, since it is possible to effectively prevent chemiluminescence emission released from neighboring spot-like regions formed in the biochemical analysis unit from being mixed with each other and to lead only chemiluminescence emission released from the spot-like region through the corresponding light guide member to the light detector, to photoelectrically detect the chemiluminescence emission by the light detector and to read chemiluminescence data recorded in the plurality of spot-like regions of the biochemical analysis unit, thereby producing biochemical analysis data, biochemical analysis data having high quantitative characteristics can be produced with high resolution.

In a preferred aspect of the present invention, each of the plurality of light guide members is formed of at least one optical fiber.

In another preferred aspect of the present invention, each of the plurality of light guide members is formed of an optical fiber bundle constituted by a plurality of optical fibers.

In a preferred aspect of the present invention, the plurality of light guide members are disposed in such a manner that each of the plurality of light releasable regions formed in the sample faces one of the light collecting end portions of the plurality of light guide members.

In another preferred aspect of the present invention, the plurality of light guide members are disposed in such a manner that at least some of the plurality of light releasable regions formed in the sample face two or more light collecting end portions of the plurality of light guide members.

According to this preferred aspect of the present invention, since it is not necessary to accurately position the light collecting end portions of the plurality of light guide members and the plurality of light releasable regions formed in the sample, it is possible to markedly lower the cost of manufacturing an apparatus for producing biochemical analysis data.

In a preferred aspect of the present invention, the plurality of light guide members are gathered in the vicinity of end portions opposite to the light collecting end portions.

According to this preferred aspect of the present invention, since the plurality of light guide members are gathered in the vicinity of end portions opposite to the light collecting end portions, in the case where light released from the plurality of light releasable regions of the sample and led through the plurality of light guide members is photoelectrically detected by a two-dimensional sensor, it is possible to employ a two-dimensional sensor having a small light detecting surface, thereby enabling an apparatus for producing biochemical analysis data to be smaller and lowering cost for manufacturing it.

In a preferred aspect of the present invention, the plurality of light guide members are mounted on a fixing head in the vicinity of the light collecting end portions so that each of the light collecting end portions of the plurality of light guide members are disposed to face one of the light releasable regions of the sample placed on the sample stage.

In a preferred aspect of the present invention, the apparatus for producing biochemical analysis data further comprises a stimulating ray source for emitting stimulating ray on a side of the sample stage opposite to the side facing the light collecting end portions of the plurality of light guide members and a stimulating ray cutting filter having a property of cutting light having a wavelength of that of the stimulating ray and transmitting light having a wavelength of that of stimulated emission between the plurality of light guide members and the light detector, the sample being constituted by a stimulable phosphor sheet including a support two-dimensionally formed with a plurality of through-holes to be spaced apart from each other, the plurality of light releasable regions being constituted by a plurality of stimulable phosphor layer regions formed by charging stimulable phosphor in the plurality of through-holes formed in the support and selectively storing radiation energy in the stimulable phosphor regions by exposing them to a radioactive labeling substance, the stimulating ray source being controlled so that the plurality of stimulable phosphor layer regions formed in the support of the stimulable phosphor sheet placed on the sample stage are simultaneously irradiated with the stimulating ray emitted from the stimulating ray source for a predetermined time, the plurality of light guide members being constituted so as to collect stimulated emission released from the plurality of stimulable phosphor layer regions in response to excitation of stimulable phosphor contained therein with the stimulating ray by the light collecting end portions thereof and lead it to the stimulating ray cutting filter, and the light detector being constituted as a two-dimensional solid state sensor.

According to one application of the present invention, when a plurality of stimulable phosphor layer regions two-dimensionally formed to be spaced apart from each other in the support of the stimulable phosphor sheet are selectively exposed to a radioactive labeling substance, thereby recording radiation data in the plurality of stimulable phosphor layer regions and the radiation data recorded in the plurality of stimulable phosphor layer regions formed in the support of the stimulable phosphor sheet are to be read to produce biochemical analysis data by placing the stimulable phosphor sheet on the sample stage, simultaneously irradiating the plurality of stimulable phosphor layer regions of the stimulable phosphor sheet with a stimulating ray from the side opposite to the light collecting end portions of the plurality of light guide members for a predetermined time, thereby exciting stimulable phosphor contained therein and photoelectrically detecting stimulated emission released from the plurality of stimulable phosphor layer regions by the two-dimensional solid state sensor, it is possible for each of the light collecting end portions of the light guide members to collect stimulated emission released from the plurality of stimulable phosphor layer regions with high efficiency by positioning the plurality of light guide members so that each of the light collecting end portions thereof is located sufficiently close to one of the plurality of stimulable phosphor layer regions formed in the support of the stimulable phosphor sheet placed on the sample stage and, therefore, biochemical analysis data having an excellent quantitative characteristic can be produced with high resolution by photoelectrically detecting stimulated emission led through the plurality of light collecting members to the two-dimensional solid state sensor.

Furthermore, according to another application of this preferred aspect of the present invention, when a plurality of stimulable phosphor layer regions two-dimensionally formed to be spaced apart from each other in the support of the stimulable phosphor sheet are selectively exposed to chemiluminescence emission, thereby recording chemiluminescence data in the plurality of stimulable phosphor layer regions and the chemiluminescence data recorded in the plurality of stimulable phosphor layer regions formed in the support of the stimulable phosphor sheet are to be read to produce biochemical analysis data by placing the stimulable phosphor sheet on the sample stage, simultaneously irradiating the plurality of stimulable phosphor layer regions of the stimulable phosphor sheet with a stimulating ray from the side opposite to the light collecting end portions of the plurality of light guide members for a predetermined time, thereby exciting stimulable phosphor contained therein and photoelectrically detecting stimulated emission released from the plurality of stimulable phosphor layer regions by the two-dimensional solid state sensor, it is possible for each of the light collecting end portions of the light guide members to collect stimulated emission released from the plurality of stimulable phosphor layer regions with high efficiency by positioning the plurality of light guide members so that each of the light collecting end portions thereof is located sufficiently close to one of the plurality of stimulable phosphor layer regions formed in the support of the stimulable phosphor sheet placed on the sample stage and, therefore, biochemical analysis data having an excellent quantitative characteristic can be produced with high resolution by photoelectrically detecting stimulated emission led through the plurality of light collecting members to the two-dimensional solid state sensor.

Further, according to this preferred aspect of the present invention, since the stimulating ray is simultaneously projected onto the plurality of stimulable phosphor layer regions formed in the support of the stimulable phosphor sheet from the side opposite to the plurality of light guide members for leading stimulated emission for a predetermined time, thereby exciting stimulable phosphor contained in the plurality of stimulable phosphor layer regions, unlike the case where the surface of a stimulable phosphor layer of a stimulable phosphor sheet is scanned with the stimulating ray at a high density, it is possible to prevent neighboring stimulable phosphor layer regions from being irradiated with the stimulating ray, thereby exciting stimulable phosphor contained therein and being caused to release radiation energy or the energy of chemiluminescence emission stored therein in the form of stimulated emission. Instead, since each of the stimulable phosphor layer regions can be irradiated with the stimulating ray for a sufficiently long time to excite stimulable phosphor contained therein and almost all radiation energy or the energy of chemiluminescence emission stored therein can be released in the form of stimulated emission, biochemical analysis data can be produced with sufficiently high sensitivity by leading stimulated emission through the plurality of light guide members via the stimulating ray cutting filter to the two-dimensional solid state sensor and photoelectrically detecting the stimulated emission.

In a further preferred aspect of the present invention, the two-dimensional solid state sensor is constituted by a cooled CCD area sensor.

According to this preferred aspect of the present invention, since the two-dimensional solid state sensor is constituted by a cooled CCD area sensor, it is possible to irradiate the plurality of stimulable phosphor layer regions formed in the support of the stimulable phosphor sheet with the stimulating ray for a long time, thereby exciting stimulable phosphor contained therein and to cause the plurality of stimulable phosphor layer regions to release radiation energy or the energy of chemiluminescence emission stored therein in the form of stimulated emission, biochemical analysis data can be produced with sufficiently high sensitivity by leading stimulated emission through the plurality of light guide members. Therefore, biochemical analysis data can be produced by collecting stimulated emission by photoelectrically detecting stimulated emission collected by the plurality of light guide members and led thereby to the cooled CCD area sensor with sufficiently high sensitivity by the cooled CCD area sensor.

In another preferred aspect of the present invention, the apparatus for producing biochemical analysis data further comprises a stimulating ray source for emitting stimulating ray on a side of the sample stage opposite to the side facing the light collecting end portions of the plurality of light guide members, a stimulating ray cutting filter having a property of cutting light having a wavelength of that of the stimulating ray and transmitting light having a wavelength of that of stimulated emission between the plurality of light guide members and the light detector and a scanning mechanism for scanning the sample placed on the sample stage with the stimulating ray emitted from the stimulating ray source, the sample being constituted by a stimulable phosphor sheet including a support two-dimensionally formed with a plurality of through-holes to be spaced apart from each other, the plurality of light releasable regions being constituted by a plurality of stimulable phosphor layer regions formed by charging stimulable phosphor in the plurality of through-holes formed in the support and selectively storing radiation energy in the stimulable phosphor regions by exposing them to a radioactive labeling substance, each of the plurality of light guide members being constituted so as to collect stimulated emission released from the corresponding stimulable phosphor layer region in response to excitation of stimulable phosphor contained therein with the stimulating ray by the light collecting end portions thereof and lead it to the stimulating ray cutting filter, and the light detector being constituted as a zero-dimensional solid state sensor.

In the present invention, a zero-dimensional sensor as termed herein means a sensor whose pixel is not divided.

According to one application of the present invention, when a plurality of stimulable phosphor layer regions two-dimensionally formed to be spaced apart from each other in the support of the stimulable phosphor sheet are selectively exposed to a radioactive labeling substance, thereby recording radiation data in the plurality of stimulable phosphor layer regions and the radiation data recorded in the plurality of stimulable phosphor layer regions formed in the support of the stimulable phosphor sheet are to be read to produce biochemical analysis data by placing the stimulable phosphor sheet on the sample stage, scanning the plurality of stimulable phosphor layer regions of the stimulable phosphor sheet with a stimulating ray from the side opposite to the light collecting end portions of the plurality of light guide members, thereby sequentially exciting stimulable phosphor contained therein and photoelectrically detecting stimulated emission released from the plurality of stimulable phosphor layer regions by the zero-dimensional sensor, it is possible for each of the light collecting end portions of the light guide members to collect stimulated emission released from one of the plurality of stimulable phosphor layer regions with high efficiency by positioning the plurality of light guide members so that each of the light collecting end portions thereof is located sufficiently close to one of the plurality of stimulable phosphor layer regions formed in the support of the stimulable phosphor sheet placed on the sample stage and, therefore, biochemical analysis data having an excellent quantitative characteristic can be produced with high resolution by photoelectrically detecting stimulated emission led through the plurality of light collecting members to the zero-dimensional sensor and reading the radiation data recorded in the plurality of stimulable phosphor layer regions formed in the support of the stimulable phosphor sheet.

Furthermore, according to another application of this preferred aspect of the present invention, when a plurality of stimulable phosphor layer regions two-dimensionally formed to be spaced apart from each other in the support of the stimulable phosphor sheet are selectively exposed to chemiluminescence emission, thereby recording chemiluminescence data in the plurality of stimulable phosphor layer regions and the chemiluminescence data recorded in the plurality of stimulable phosphor layer regions formed in the support of the stimulable phosphor sheet are to be read to produce biochemical analysis data by placing the stimulable phosphor sheet on the sample stage, scanning the plurality of stimulable phosphor layer regions of the stimulable phosphor sheet with a stimulating ray from the side opposite to the light collecting end portions of the plurality of light guide members for a predetermined time, thereby sequentially exciting stimulable phosphor contained therein and photoelectrically detecting stimulated emission released from the plurality of stimulable phosphor layer regions by the zero-dimensional sensor, it is possible for each of the light collecting end portions of the light guide members to collect stimulated emission released from one of the plurality of stimulable phosphor layer regions with high efficiency by positioning the plurality of light guide members so that each of the light collecting end portions thereof is located sufficiently close to one of the plurality of stimulable phosphor layer regions formed in the support of the stimulable phosphor sheet placed on the sample stage and, therefore, biochemical analysis data having an excellent quantitative characteristic can be produced with high resolution by photoelectrically detecting stimulated emission led through the plurality of light collecting members to the zero-dimensional sensor and reading the chemiluminescence data recorded in the plurality of stimulable phosphor layer regions formed in the support of the stimulable phosphor sheet.

In a further preferred aspect of the present invention, the scanning mechanism is constituted so as to intermittently move the stimulating ray emitted from the stimulating ray source by a pitch equal to a distance between neighboring stimulable phosphor layer regions formed in the support of the stimulable phosphor sheet, thereby scanning the plurality of stimulable phosphor layer regions formed in the support of the stimulable phosphor sheet placed on the sample stage with the stimulating ray.

In a further preferred aspect of the present invention, the zero-dimensional sensor is constituted as a photomultiplier.

In a preferred aspect of the present invention, the apparatus for producing biochemical analysis data further comprises a stimulating ray source for emitting stimulating ray on a side of the sample stage opposite to the side facing the plurality of light guide members and a stimulating ray cutting filter having a property of cutting light having a wavelength of that of the stimulating ray and transmitting light having a wavelength longer than that of stimulating ray between the plurality of light guide members and the light detector, the sample being constituted by a biochemical analysis unit including a substrate two-dimensionally formed with a plurality of through-holes to be spaced apart from each other, the plurality of light releasable regions being constituted by a plurality of absorptive regions formed by charging an absorptive material in the plurality of through-holes formed in the substrate of the biochemical analysis unit and selectively labeled with a fluorescent substance, the stimulating ray source being controlled so that the plurality of absorptive regions formed in the substrate of the biochemical analysis unit placed on the sample stage are simultaneously irradiated with the stimulating ray emitted from the stimulating ray source for a predetermined time, the plurality of light guide members being constituted so as to collect fluorescence emission released from the plurality of absorptive regions in response to excitation of a fluorescent substance contained therein with the stimulating ray and lead it to the stimulating ray cutting filter, and the light detector being constituted as a two-dimensional solid state sensor.

According to this preferred aspect of the present invention, when a plurality of absorptive regions two-dimensionally formed to be spaced apart from each other at a high density in the substrate of the biochemical analysis unit are selectively labeled with a fluorescent substance such as a fluorescent dye, thereby recording fluorescence data in the plurality of absorptive regions and the fluorescence data recorded in the plurality of absorptive regions formed in the substrate of the biochemical analysis unit are to be read to produce biochemical analysis data by placing the biochemical analysis unit on the sample stage, simultaneously irradiating the plurality of absorptive regions with the stimulating ray from the side opposite to the plurality of light guide members for a predetermined time, thereby exciting a fluorescent substance contained therein, and photoelectrically detecting fluorescence emission released from the plurality of absorptive regions, since fluorescence emission released from the plurality of absorptive regions is collected by the plurality of light guide members each of which is disposed to face one of the plurality of absorptive regions to lead it to the two-dimensional solid state sensor and the fluorescence emission is photoelectrically detected by the two-dimensional solid state sensor, thereby reading fluorescence data recorded in the number of absorptive regions formed in the substrate of the biochemical analysis unit, it is possible to effectively prevent fluorescence emission released from neighboring absorptive regions formed in the substrate of the biochemical analysis unit from being mixed with each other and to lead only fluorescence emission released from the absorptive region through the corresponding light guide member to the two-dimensional solid state sensor, to photoelectrically detect the fluorescence emission by the two-dimensional solid state sensor and to read fluorescence data recorded in the plurality of absorptive regions formed in the substrate of the biochemical analysis unit, thereby producing biochemical analysis data. Therefore, biochemical analysis data having high quantitative characteristics can be produced with high resolution.

Further, according to this preferred aspect of the present invention, since the stimulating ray is simultaneously projected onto the plurality of absorptive regions formed in the substrate of the biochemical analysis unit from the side opposite to the plurality of light guide members for leading fluorescence emission for a predetermined time, thereby exciting a fluorescent substance contained in the plurality of absorptive regions and fluorescence emission released from the plurality of absorptive regions is collected by the plurality of light guide member, it is possible to irradiate the plurality of absorptive regions with the stimulating ray for a sufficiently long time, thereby exciting a fluorescent substance contained in the plurality of absorptive regions and cause the plurality of absorptive regions to release a sufficiently large amount of fluorescence emission. Therefore, since a sufficiently large amount of fluorescence emission can be led via the stimulating ray cutting filter to a two-dimensional solid state sensor, biochemical analysis data having an excellent quantitative characteristic can be produced by photoelectrically detecting fluorescence emission with high sensitivity.

In a preferred aspect of the present invention, each of the plurality of light guide members includes a light collecting end portion capable of collecting light and the light collecting end portion of each of the plurality of light guide members is disposed to face one of the plurality of absorptive regions formed in the substrate of the biochemical analysis unit placed on the sample stage.

According to a further application of this preferred aspect of the present invention, when biochemical analysis data are to be produced by irradiating the plurality of absorptive regions two-dimensionally formed to be spaced apart from each other in the substrate of the biochemical analysis unit and selectively labeled with a fluorescent substance with the stimulating ray to excite fluorescent substance contained in the absorptive regions, photoelectrically detecting fluorescence emission released from the absorptive regions and reading fluorescence data recorded in the plurality of absorptive regions formed in the substrate of the biochemical analysis unit, it is possible for each of the light collecting end portions of the light guide members to effectively collect only fluorescence emission released from the corresponding absorptive region by disposing the plurality of light guide members so that each of the light collecting end portions of the light guide members is located sufficiently close to one of the absorptive regions formed in the substrate of the biochemical analysis unit placed on the sample stage. Therefore, since it is possible to effectively prevent fluorescence emission released from neighboring absorptive regions formed in the substrate of the biochemical analysis unit from being mixed with each other and to lead only fluorescence emission released from the absorptive region through the corresponding light guide member to the light detector, to photoelectrically detect the fluorescence emission by the light detector and to read fluorescence data recorded in the plurality of absorptive regions formed in the substrate of the biochemical analysis unit, thereby producing biochemical analysis data, biochemical analysis data having high quantitative characteristics can be produced with high resolution.

In a preferred aspect of the present invention, each of the plurality of light guide members is formed of at least one optical fiber.

In another preferred aspect of the present invention, each of the plurality of light guide members is formed of an optical fiber bundle constituted by a plurality of optical fibers.

In a preferred aspect of the present invention, the plurality of light guide members are disposed in such a manner that each of the plurality of absorptive regions formed in the substrate of the biochemical analysis unit faces one of the light collecting end portions of the plurality of light guide members.

In another preferred aspect of the present invention, the plurality of light guide members are disposed in such a manner that at least some of the plurality of absorptive regions formed in the substrate of the biochemical analysis unit face the two or more light collecting end portions of the plurality of light guide members.

According to this preferred aspect of the present invention, since it is not necessary to accurately position the light collecting end portions of the plurality of light guide members and the plurality of absorptive regions formed in the substrate of the biochemical analysis unit, it is possible to markedly lower the cost of manufacturing an apparatus for producing biochemical analysis data.

In a preferred aspect of the present invention, the plurality of light guide members are gathered in the vicinity of end portions opposite to the light collecting end portions.

According to this preferred aspect of the present invention, since the plurality of light guide members are gathered in the vicinity of end portions opposite to the light collecting end portions, in the case where fluorescence emission released from the plurality of absorptive regions formed in the substrate of the biochemical analysis unit and led through the plurality of light guide members is photoelectrically detected by a two-dimensional sensor, it is possible to employ a two-dimensional sensor having a small light detecting surface, thereby enabling an apparatus for producing biochemical analysis data to be smaller and lowering cost for manufacturing it.

In a preferred aspect of the present invention, the plurality of light guide members are mounted on a fixing head in the vicinity of the light collecting end portions so that each of the light collecting end portions of the plurality of light guide members are disposed to face one of the absorptive regions formed in the substrate of the biochemical analysis unit placed on the sample stage.

In a preferred aspect of the present invention, each of the plurality of light guiding members is constituted as a condenser lens disposed so as to face one of the plurality of absorptive regions formed in the substrate of the biochemical analysis unit placed on the sample stage so that fluorescence emission released from the plurality of absorptive regions can be led through the plurality of condenser lens to a two-dimensional solid state sensor.

According to this preferred aspect of the present invention, when biochemical analysis data are to be produced by irradiating the plurality of absorptive regions two-dimensionally formed to be spaced apart from each other in the substrate of the biochemical analysis unit and selectively labeled with a fluorescent substance with the stimulating ray to excite fluorescent substance contained in the plurality of absorptive regions, photoelectrically detecting fluorescence emission released from the absorptive regions and reading fluorescence data recorded in the plurality of absorptive regions formed in the substrate of the biochemical analysis unit, it is possible to collect fluorescence emission released from the plurality of absorptive regions by the plurality of condenser lens with high light collecting efficiency and lead it to the two-dimensional solid state sensor. Therefore, since it is possible to effectively prevent fluorescence emission released from neighboring absorptive regions formed in the substrate of the biochemical analysis unit and to effectively prevent noise caused by the scattering of fluorescence emission from being generated in biochemical analysis data, biochemical analysis data having an excellent quantitative characteristic can be produced.

Further, according to this preferred aspect of the present invention, unlike the case where fluorescence emission released from the plurality of absorptive regions is led through a single condenser lens to the two-dimensional solid state sensor, since generation of stray light in the condenser lens can be prevented by decreasing a view angle from each of the plurality of absorptive regions into the condenser lens, fluorescence emission released from the plurality of absorptive regions can be detected by the two-dimensional solid state sensor with high sensitivity and data, biochemical analysis data having an excellent quantitative characteristic can be produced.

In a further preferred aspect of the present invention, each of the plurality of condenser lenses is constituted as a lens having a great numerical aperture.

In a further preferred aspect of the present invention, the plurality of condenser lenses are mounted on a lens array so that a pitch between neighboring condenser lenses is equal to a distance between neighboring absorptive regions formed in the substrate of the biochemical analysis unit.

In a further preferred aspect of the present invention, the two-dimensional solid state sensor is constituted by a cooled CCD area sensor.

According to this preferred aspect of the present invention, since the two-dimensional solid state sensor is constituted by a cooled CCD area sensor, it is possible to irradiate the plurality of absorptive regions formed in the substrate of the biochemical analysis unit with the stimulating ray for a long time, thereby exciting a fluorescent substance contained therein and to detect fluorescence emission released from the plurality of absorptive regions, biochemical analysis data can be produced with sufficiently high sensitivity by photoelectrically detecting fluorescence emission by the cooled CCD area sensor.

In another preferred aspect of the present invention, the apparatus for producing biochemical analysis data further comprises a stimulating ray source emitting a stimulating ray on a side of the sample stage opposite to the side facing the light collecting end portions of the plurality of light guide members, a stimulating ray cutting filter having a property of cutting light having a wavelength of that of the stimulating ray and transmitting light having a wavelength longer than that of stimulating ray between the plurality of light guide members and the light detector and a scanning mechanism for scanning the sample placed on the sample stage with the stimulating ray emitted from the stimulating ray source, the sample being constituted by a biochemical analysis unit including a substrate two-dimensionally formed with a plurality of through-holes to be spaced apart from each other, the plurality of light releasable regions being constituted by a plurality of absorptive regions formed by charging an absorptive material in the plurality of through-holes formed in the substrate of the biochemical analysis unit and selectively labeled with a fluorescent substance, the plurality of light guide members being constituted so as to collect fluorescence emission released from the plurality of absorptive regions in response to excitation of a fluorescent substance contained therein with the stimulating ray by the light collecting end portions thereof and lead it to the stimulating ray cutting filter, and the light detector being constituted as a zero-dimensional sensor.

According to this preferred aspect of the present invention, when biochemical analysis data are to be produced by scanning the plurality of absorptive regions two-dimensionally formed to be spaced apart from each other in the substrate of the biochemical analysis unit and selectively labeled with a fluorescent substance with the stimulating ray emitted from the stimulating ray source from the side opposite to the light collecting end portions of the light guide members, thereby sequentially exciting fluorescent substance contained in the absorptive regions, photoelectrically detecting fluorescence emission released from the absorptive regions by the zero-dimensional sensor and reading fluorescence data recorded in the plurality of absorptive regions formed in the substrate of the biochemical analysis unit, it is possible for each of the light collecting end portions of the light guide members to collect fluorescence emission released from one of the plurality of absorptive regions with high efficiency by positioning the plurality of light guide members so that each of the light collecting end portions thereof is located sufficiently close to one of the plurality of absorptive regions formed in the substrate of the biochemical analysis unit placed on the sample stage and, therefore, biochemical analysis data having an excellent quantitative characteristic can be produced with high resolution by photoelectrically detecting fluorescence emission led through the plurality of light collecting members to the zero-dimensional sensor.

In a further preferred aspect of the present invention, the scanning mechanism is constituted so as to intermittently move the stimulating ray emitted from the stimulating ray source by a pitch equal to a distance between neighboring absorptive regions formed in the substrate of the biochemical analysis unit, thereby scanning the plurality of absorptive regions formed in the substrate of the biochemical analysis unit placed on the sample stage with the stimulating ray.

In a further preferred aspect of the present invention, the zero-dimensional sensor is constituted as a photomultiplier.

In a preferred aspect of the present invention, the sample is constituted by a biochemical analysis unit including a substrate two-dimensionally formed with a plurality of through-holes to be spaced apart from each other, the plurality of light releasable regions are constituted by a plurality of absorptive regions formed by charging an absorptive material in the plurality of through-holes formed in the substrate of the biochemical analysis unit and selectively labeled with a labeling substance which generates chemiluminescence emission when it contacts a chemiluminescent substrate, each of the plurality of light guide members includes a light collecting end portion capable of collecting light and the light collecting end portion of each of the plurality of light guide members is disposed to face one of the plurality of absorptive regions formed in the substrate of the biochemical analysis unit placed on the sample stage.

According to this preferred aspect of the present invention, when a plurality of absorptive regions two-dimensionally formed to be spaced apart from each other in the substrate of the biochemical analysis unit are selectively labeled with a labeling substance which generates chemiluminescence emission when it contacts a chemiluminescent substrate, thereby recording chemiluminescence data in the plurality of absorptive regions formed in the substrate of the biochemical analysis unit and biochemical analysis data are to be produced by bringing the biochemical analysis unit into contact with a chemiluminescent substrate, thereby causing the plurality of absorptive regions to release chemiluminescence emission, placing the biochemical analysis unit releasing chemiluminescence emission on the sample stage, photoelectrically detecting chemiluminescence emission released from the plurality of absorptive regions by a light detector and reading chemiluminescence data recorded in the plurality of absorptive regions formed in the substrate of the biochemical analysis unit, it is possible to effectively prevent chemiluminescence emission released from neighboring absorptive regions formed in the substrate of the biochemical analysis unit from being mixed with each other and to lead only chemiluminescence emission released from the absorptive region through the corresponding light guide member to the light detector by disposing the plurality of light guide members so that each of the light collecting end portions of the light guide members is located sufficiently close to one of the absorptive regions formed in the substrate of the biochemical analysis unit placed on the sample stage and collecting chemiluminescence emission released from each of the plurality of absorptive regions by the light collecting end portion of the corresponding light guide member, thereby leading it to the light detector. Therefore, since it is possible for each of the light guide members to collect and lead chemiluminescence emission released from only the corresponding absorptive region to the light detector and to read chemiluminescence data recorded in the plurality of absorptive regions formed in the substrate of the biochemical analysis unit by photoelectrically detecting chemiluminescence emission, biochemical analysis data having an excellent quantitative characteristic can be produced with high resolution.

In a preferred aspect of the present invention, each of the plurality of light guide members is formed of at least one optical fiber.

In another preferred aspect of the present invention, each of the plurality of light guide members is formed of an optical fiber bundle constituted by a plurality of optical fibers.

In a preferred aspect of the present invention, the plurality of light guide members are disposed in such a manner that each of the plurality of absorptive regions formed in the substrate of the biochemical analysis unit faces one of the light collecting end portions of the plurality of light guide members.

In another preferred aspect of the present invention, the plurality of light guide members are disposed in such a manner that at least some of the plurality of absorptive regions formed in the substrate of the biochemical analysis unit face the two or more light collecting end portions of the plurality of light guide members.

According to this preferred aspect of the present invention, since it is not necessary to accurately position the light collecting end portions of the plurality of light guide members and the plurality of absorptive regions formed in the substrate of the biochemical analysis unit, it is possible to markedly lower the cost of manufacturing an apparatus for producing biochemical analysis data.

In a preferred aspect of the present invention, the plurality of light guide members are gathered in the vicinity of end portions opposite to the light collecting end portions.

According to this preferred aspect of the present invention, since the plurality of light guide members are gathered in the vicinity of end portions opposite to the light collecting end portions, in the case where chemiluminescence emission released from the plurality of absorptive regions formed in the substrate of the biochemical analysis unit and led through the plurality of light guide members is photoelectrically detected by a two-dimensional sensor, it is possible to employ a two-dimensional sensor having a small light detecting surface, thereby enabling an apparatus for producing biochemical analysis data to be smaller and lowering cost for manufacturing it.

In a preferred aspect of the present invention, the plurality of light guide members are mounted on a fixing head in the vicinity of the light collecting end portions so that each of the light collecting end portions of the plurality of light guide members are disposed to face one of the absorptive regions formed in the substrate of the biochemical analysis unit placed on the sample stage.

In a preferred aspect of the present invention, the light detector is constituted as a two-dimensional solid state sensor.

In a preferred aspect of the present invention, the sample is constituted by a biochemical analysis unit including a substrate two-dimensionally formed with a plurality of through-holes to be spaced apart from each other, the plurality of light releasable regions are constituted by a plurality of absorptive regions formed by charging an absorptive material in the plurality of through-holes formed in the substrate of the biochemical analysis unit and selectively labeled with a labeling substance which generates chemiluminescence emission when it contacts a chemiluminescent substrate and each of the plurality of light guiding members is constituted as a condenser lens disposed so as to face one of the plurality of absorptive regions formed in the substrate of the biochemical analysis unit placed on the sample stage so that chemiluminescence emission released from the plurality of absorptive regions can be led through the plurality of condenser lens to a two-dimensional solid state sensor.

According to this preferred aspect of the present invention, when a plurality of absorptive regions two-dimensionally formed to be spaced apart from each other in the substrate of the biochemical analysis unit are selectively labeled with a labeling substance which generates chemiluminescence emission when it contacts a chemiluminescent substrate, thereby recording chemiluminescence data in the plurality of absorptive regions formed in the substrate of the biochemical analysis unit and biochemical analysis data are to be produced by bringing the biochemical analysis unit into contact with a chemiluminescent substrate, thereby causing the plurality of absorptive regions to release chemiluminescence emission, placing the biochemical analysis unit releasing chemiluminescence emission on the sample stage, photoelectrically detecting chemiluminescence emission released from the plurality of absorptive regions by a light detector and reading chemiluminescence data recorded in the plurality of absorptive regions formed in the substrate of the biochemical analysis unit, it is possible to collect chemiluminescence emission released from the plurality of absorptive regions by the plurality of condenser lens with high light collecting efficiency and lead it to the two-dimensional solid state sensor. Therefore, since it is possible to effectively prevent chemiluminescence emission released from neighboring absorptive regions formed in the substrate of the biochemical analysis unit and to effectively prevent noise caused by the scattering of chemiluminescence emission from being generated in biochemical analysis data, biochemical analysis data having an excellent quantitative characteristic can be produced.

Further, according to this preferred aspect of the present invention, unlike the case where chemiluminescence emission released from the plurality of absorptive regions is led through a single condenser lens to the two-dimensional solid state sensor, since generation of stray light in the condenser lens can be prevented by decreasing a view angle from each of the plurality of absorptive regions into the condenser lens, chemiluminescence emission released from the plurality of absorptive regions can be detected by the two-dimensional solid state sensor with high sensitivity and data, biochemical analysis data having an excellent quantitative characteristic can be produced.

In a further preferred aspect of the present invention, each of the plurality of condenser lenses is constituted as a lens having a great numerical aperture.

In a further preferred aspect of the present invention, the plurality of condenser lenses are mounted on a lens array so that a pitch between neighboring condenser lenses is equal to a distance between neighboring absorptive regions formed in the substrate of the biochemical analysis unit.

In a further preferred aspect of the present invention, the two-dimensional solid state sensor is constituted by a cooled CCD area sensor.

According to this preferred aspect of the present invention, since the two-dimensional solid state sensor is constituted by a cooled CCD area sensor, it is possible to detect chemiluminescence emission released from the plurality of absorptive regions for a long time, biochemical analysis data can be produced with sufficiently high sensitivity by photoelectrically detecting chemiluminescence emission by the cooled CCD area sensor.

In a preferred aspect of the present invention, the stimulating ray source is constituted as a laser stimulating ray source for emitting a laser beam.

The above and other objects and features of the present invention will become apparent from the following description made with reference to the accompanying drawings.

DESCRIPTION OF THE PREFERRED EMBODIMENTS

Figure 1:
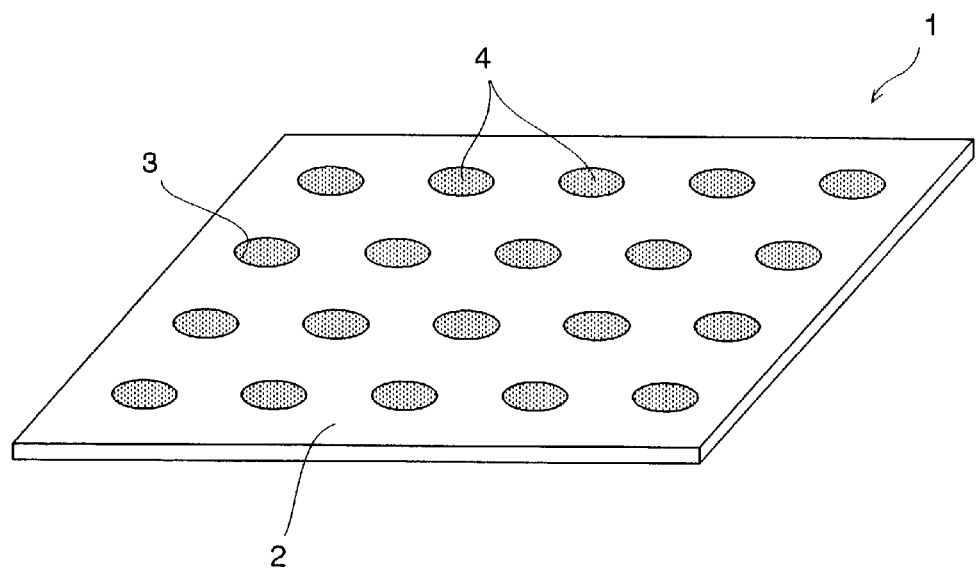
FIG. 1 is a schematic perspective view showing a biochemical analysis unit used in a method for producing biochemical analysis data which is a preferred embodiment of the present invention.

FIG. 1 is a schematic perspective view showing a biochemical analysis unit used in a method for producing biochemical analysis data which is a preferred embodiment of the present invention.

As shown in FIG. 1, a biochemical analysis unit 1 according to this embodiment includes a substrate 2 formed of stainless steel and formed with a number of substantially circular through-holes 3 at a high density, and a number of absorptive regions 4 are dot-like formed by charging nylon-6 in the through-holes 3.

Although not accurately shown in FIG. 1, in this embodiment, about 10,000 through-holes 3 having a size of about 0.01 mm$^2$ are regularly formed at a density of about 5,000 per cm$^2$ in the substrate 2.

A number of absorptive regions 4 are formed by charging nylon-6 in the through-holes 3 formed in the substrate in such a manner that the surfaces of the absorptive regions 4 are located at the same height level as that of the substrate 2.

Figure 2:
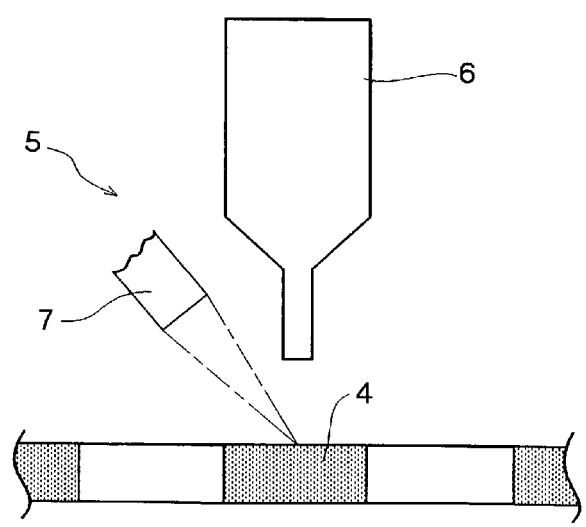
FIG. 2 is a schematic front view showing a spotting device.

FIG. 2 is a schematic front view showing a spotting device.

As shown in FIG. 2, when biochemical analysis is performed, a solution containing specific binding substances such as a plurality of cDNAs whose sequences are known but differ from each other are spotted using a spotting device 5 onto a number of the absorptive regions 4 of the biochemical analysis unit 1 and the specific binding substances are fixed therein.

As shown in FIG. 2, the spotting device 5 includes an injector 6 for ejecting a solution of specific binding substances toward the biochemical analysis unit 1 and a CCD camera 7 and is constituted so that the solution of specific binding substances such as cDNAs are spotted from the injector 6 when the tip end portion of the injector 6 and the center of the absorptive region 4 into which the solution containing specific binding substances is to be spotted are determined to coincide with each other as a result of viewing them using the CCD camera, thereby ensuring that the solution of specific binding substances can be accurately spotted into a number of the absorptive regions 4 of the biochemical analysis unit 1.

Figure 3:
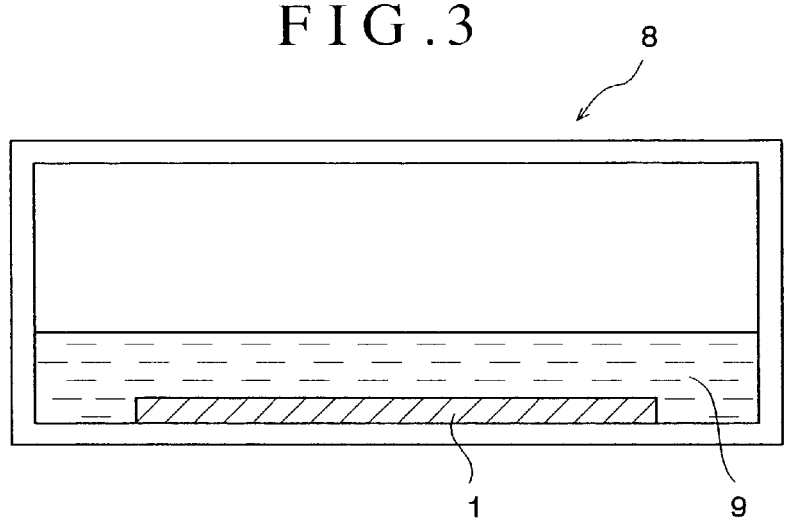
FIG. 3 is a schematic longitudinal cross sectional view showing a hybridization reaction vessel.

FIG. 3 is a schematic longitudinal cross sectional view showing a hybridization reaction vessel.

As shown in FIG. 3, a hybridization reaction vessel 8 is formed to have a substantially rectangular cross section and accommodates a hybridization solution 9 containing a substance derived from a living organism labeled with a labeling substance as a probe therein.

In the case where a specific binding substance such as cDNA is to be labeled with a radioactive labeling substance, a hybridization solution 9 containing a substance derived from a living organism and labeled with a radioactive labeling substance as a probe is prepared and is accommodated in the hybridization reaction vessel 8.

On the other hand, in the case where a specific binding substance such as cDNA is to be labeled with a labeling substance which generates chemiluminescence emission when it contacts a chemiluminescent substrate, a hybridization solution 9 containing a substance derived from a living organism and labeled with a labeling substance which generates chemiluminescence emission when it contacts a chemiluminescent substrate as a probe is prepared and is accommodated in the hybridization reaction vessel 8.

Further, in the case where a specific binding substance such as cDNA is to be labeled with a fluorescent substance such as a fluorescent dye, a hybridization solution 9 containing a substance derived from a living organism and labeled with a fluorescent substance such as a fluorescent dye as a probe is prepared and is accommodated in the hybridization reaction vessel 8.

It is possible to prepare a hybridization reaction solution 9 containing two or more substances derived from a living organism among a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye and accommodate it in the hybridization vessel 8. In this embodiment, a hybridization reaction solution 9 containing a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye is prepared and accommodated in the hybridization reaction vessel 8.

When hybridization is to be performed, the biochemical analysis unit 1 containing specific binding substances such as a plurality of cDNAs spotted into a number of absorptive regions 4 is accommodated in the hybridization reaction vessel 8.

As a result, specific binding substances spotted in a number of the absorptive regions 4 of the biochemical analysis unit 1 can be selectively hybridized with a substance derived from a living organism, labeled with a radioactive labeling substance and contained in the hybridization reaction solution 9, a substance derived from a living organism, labeled with a labeling substance which generates chemiluminescence emission when it contacts a chemiluminescent substrate and contained in the hybridization reaction solution 9 and a substance derived from a living organism, labeled with a fluorescent substance such as a fluorescent dye and contained in the hybridization reaction solution 9.

In this manner, radiation data of a radioactive labeling substance, chemiluminescence data of a labeling substance which generates chemiluminescence emission when it contacts a chemiluminescent substrate and fluorescence data of a fluorescent substance such as a fluorescent dye are recorded in a number of absorptive regions 4 formed in the biochemical analysis unit 1.

Fluorescence data recorded in a number of absorptive regions 4 formed in the biochemical analysis unit 1 are read by an apparatus for producing biochemical analysis data described later, thereby producing biochemical analysis data.

On the other hand, radiation data of the radioactive labeling substance recorded in a number of absorptive regions 4 formed in the biochemical analysis unit 1 are transferred onto a stimulable phosphor sheet and read by the apparatus for producing biochemical analysis data described later, thereby producing biochemical analysis data.

Further, chemiluminescence data recorded in a number of absorptive regions 4 formed in the biochemical analysis unit 1 are read by the apparatus for producing biochemical analysis data described later or transferred onto a stimulable phosphor sheet described later and transferred chemiluminescence data are read by another apparatus for producing biochemical analysis data described later, thereby producing biochemical analysis data.

Figure 4:
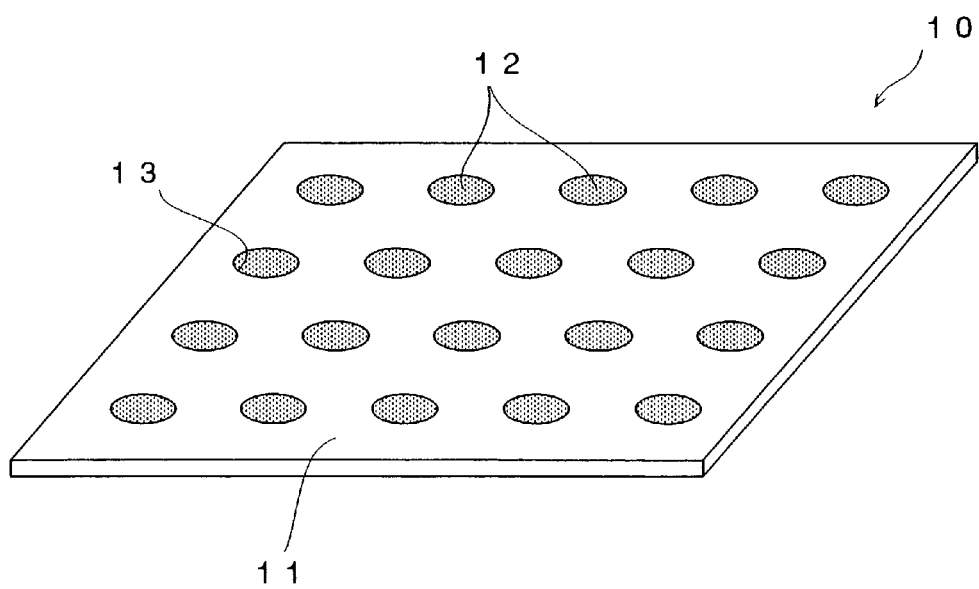
FIG. 4 is a schematic perspective view showing a stimulable phosphor sheet on which radiation data are to be transferred, used in a method for producing biochemical analysis data which is a preferred embodiment of the present invention.

FIG. 4 is a schematic perspective view showing a stimulable phosphor sheet on which radiation data are to be transferred, used in a method for producing biochemical analysis data which is a preferred embodiment of the present invention.

As shown in FIG. 4, a stimulable phosphor sheet 10 according to this embodiment includes a support 11 made of stainless steel and regularly formed with a number of substantially circular through-holes 13 and a number of stimulable phosphor layer regions 12 are dot-like formed by charging BaFX system stimulable phosphor (where X is at least one halogen atom selected from the group consisting of Cl, Br and I) capable of absorbing and storing radiation energy in the through-holes 13.

A number of the through-holes 13 are formed in the support 11 in the same pattern as that of a number of the absorptive regions 4 formed in the substrate 2 of the biochemical analysis unit 1 and each of them has the same size as that of the absorptive region 4 formed in the substrate 2 of the biochemical analysis unit 1.

Therefore, although not accurately shown in FIG. 4, in this embodiment, about 10,000 substantially circular stimulable phosphor layer regions 12 having a size of about 0.01 $mm^2$ are dot-like formed in a regular pattern at a density of about 5,000 per $cm^2$ in the support 11 of the stimulable phosphor sheet 10.

In this embodiment, stimulable phosphor is charged in a number of the through-holes 13 formed in the support 11 in such a manner that the surfaces of the stimulable phosphor layer regions 12 lie at the same height level of that of the surface of the support 11.

Figure 5:
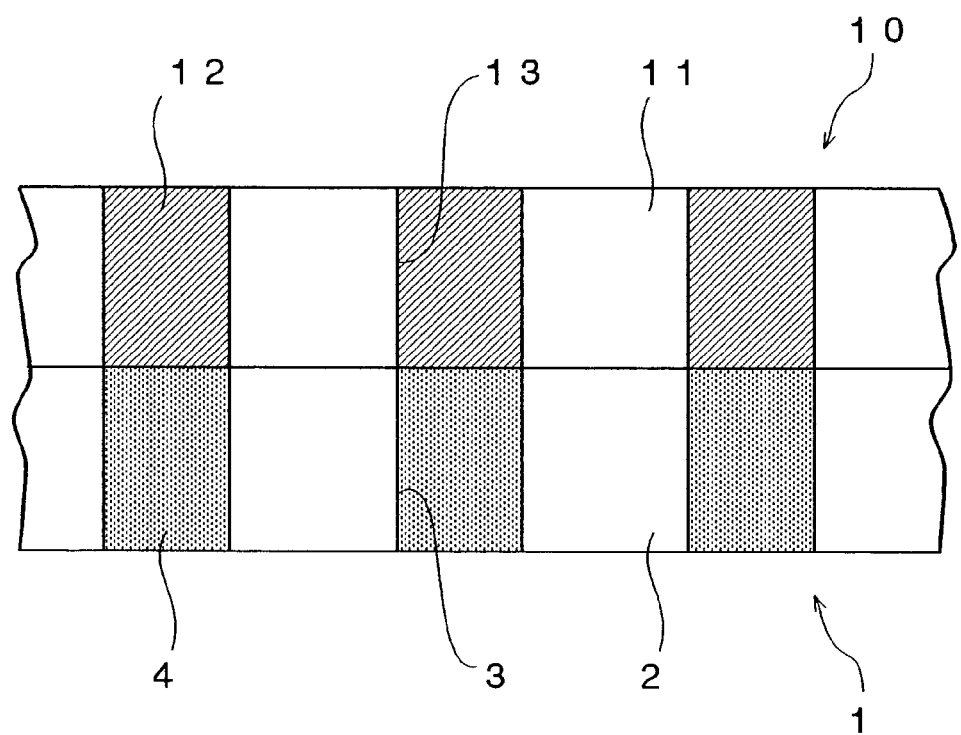
FIG. 5 is a schematic cross-sectional view showing a method for exposing a number of stimulable phosphor layer regions formed in a stimulable phosphor sheet by a radioactive labeling substance contained in a number of absorptive regions formed in a biochemical analysis unit.

FIG. 5 is a schematic cross-sectional view showing a method for exposing a number of the stimulable phosphor layer regions 12 formed in the stimulable phosphor sheet 10 by a radioactive labeling substance contained in a number of the absorptive regions 4 formed in the biochemical analysis unit 1.

As shown in FIG. 5, when the stimulable phosphor layer regions 12 of a stimulable phosphor sheet 10 are to be exposed, the stimulable phosphor sheet 10 is superposed on the biochemical analysis unit 1 in such a manner that each of the stimulable phosphor layer regions 12 formed in the support 11 of the stimulable phosphor sheet 10 faces the corresponding absorptive regions 4 formed in the substrate 2 of the biochemical analysis unit 1.

In this embodiment, since the biochemical analysis unit 1 is formed by charging nylon-6 in a number of the through-holes 3 formed in the substrate 2 made of stainless steel, the biochemical analysis unit 1 does not stretch or shrink even when it is subjected to liquid processing such as hybridization and, therefore, it is possible to easily and accurately superpose the stimulable phosphor sheet 10 on the biochemical analysis unit 1 so that each of the stimulable phosphor layer regions 12 formed in the support 11 of the stimulable phosphor sheet 10 accurately faces the corresponding absorptive region 4 formed in the substrate 2 of the biochemical analysis unit 1, thereby exposing the stimulable phosphor layer regions 12.

In this manner, each of the stimulable phosphor layer regions 12 formed in the support 11 of the stimulable phosphor sheet 10 is kept to face the corresponding absorptive region 4 formed in the substrate 2 of the biochemical analysis unit 1 for a predetermined time period, whereby a number of the stimulable phosphor layer regions 12 formed in the support 11 of the stimulable phosphor sheet 10 are exposed to the radioactive labeling substance contained in a number of the absorptive regions 4 formed in the substrate 2 of the biochemical analysis unit 1.

During the exposure operation, electron beams ($\beta$ rays) are released from the radioactive labeling substance contained in the absorptive regions 4 of the biochemical analysis unit 1. However, since a number of the absorptive regions 4 of the biochemical analysis unit 1 are formed spaced apart from each other in the substrate 2 made of stainless steel and the substrate 2 made of stainless steel capable of attenuating radiation energy is present around each of the absorptive regions 4, electron beams ($\beta$ rays) released from the radioactive labeling substance contained in the absorptive regions 4 of the biochemical analysis unit 1 can be efficiently prevented from scattering in the substrate 2 of the biochemical analysis unit 1. Further, since a number of the stimulable phosphor layer regions 12 of the stimulable phosphor sheet 10 are formed by charging stimulable phosphor in a number of the through-holes 13 formed in the support 11 made of stainless steel capable of attenuating radiation energy and the support 11 made of stainless steel is present around each of the stimulable phosphor layer regions 12, electron beams ($\beta$ rays) released from the radioactive labeling substance contained in the absorptive regions 4 of the biochemical analysis unit 1 can be efficiently prevented from scattering in the support 11 of the stimulable phosphor sheet 10. Therefore, it is possible to cause all electron beams ($\beta$ rays) released from the radioactive labeling substance contained in the absorptive region 4 to enter the stimulable phosphor layer region 12 the absorptive region 4 faces and to effectively prevent electron beams (E rays) released from the absorptive region 4 from entering stimulable phosphor layer regions 12 to be exposed to electron beams ($\beta$ rays) released from neighboring absorptive regions 4.

In this manner, a number of the stimulable phosphor layer regions 12 formed in the support 11 of the stimulable phosphor sheet 10 are be selectively exposed to a radioactive labeling substance contained in the corresponding absorptive region 4 of the biochemical analysis unit 1.

Thus, radiation data of a radioactive labeling substance are recorded in a number of the stimulable phosphor layer regions 12 formed in the support 11 of the stimulable phosphor sheet 10.

Figure 6:
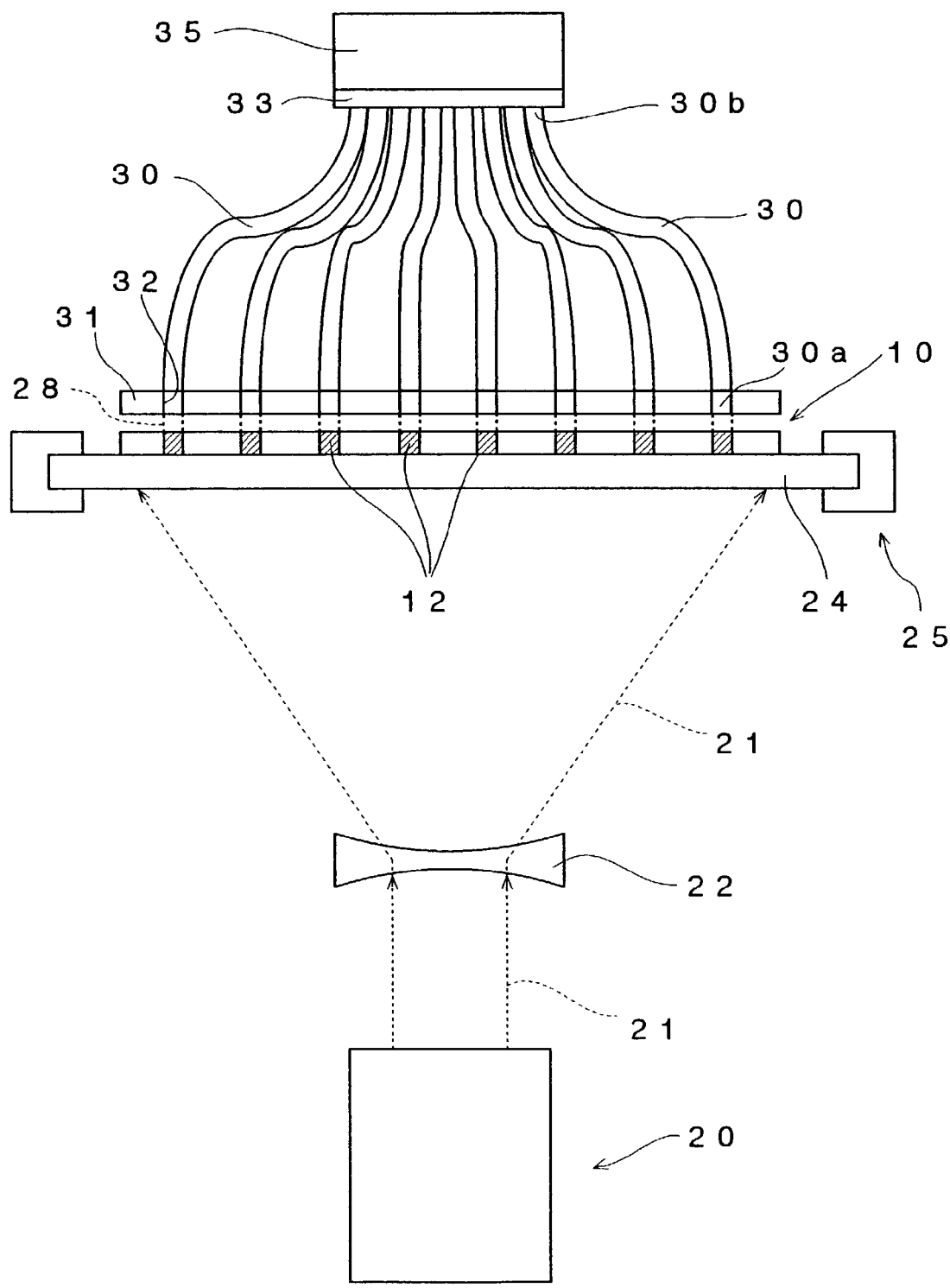
FIG. 6 is a schematic view showing an apparatus for producing biochemical analysis data which is a preferred embodiment of the present invention.

FIG. 6 is a schematic view showing an apparatus for producing biochemical analysis data which is a preferred embodiment of the present invention.

An apparatus for producing biochemical analysis data according to this embodiment is constituted so as to read radiation data recorded in a number of the stimulable phosphor layer regions 12 formed in the support 11 of the stimulable phosphor sheet 10.

As shown in FIG. 6, the apparatus for producing biochemical analysis data according to this embodiment is provided with a laser stimulating ray source 20 for emitting a laser beam 21 having a wavelength of 640 nm. In this embodiment, the laser stimulating ray source 20 constituted by a semiconductor laser beam source.

A laser beam 21 having a wavelength of 640 nm and emitted from the laser stimulating ray source 20 passes through a concave lens 22, thereby being made a divergent beam 21 and impinges onto the stimulable phosphor sheet 10 placed on a transparent glass plate 24 of a sample stage 25.

As a result, stimulable phosphor contained in a number of the stimulable phosphor layer regions 12 formed in the support 11 of the stimulable phosphor sheet 10 is stimulated to release stimulated emission 28.

As shown in FIG. 6, in this embodiment, the apparatus for producing biochemical analysis data includes a number of optical fiber members 30 each of which has a light collecting end portion 30a facing one of a number of the stimulable phosphor layer regions 12 formed in the support 11 of the stimulable phosphor sheet 10 and being located in the vicinity thereof.

In this embodiment, each of the optical fiber members 30 is constituted as a plurality of optical fibers and secured into a through-hole 32 formed in a fixing head 31 in the vicinity of the light collecting end portion 30a so that the light collecting end portion 30a of each of the optical fiber members 30 is positioned in a desired manner.

Further, as shown in FIG. 6, the optical fiber members 30 are gathered in the vicinity of end portions 30b opposite to the light collecting end portions 30a.

As shown in FIG. 6, each of the optical fiber members 30 is disposed so that end portion 30b thereof opposite to the light collecting end portion 30a faces a stimulating ray cutting filter 33. The stimulating ray cutting filter 33 has a property of transmitting light having a wavelength of that of stimulated emission 28 and cutting light having a wavelength of 640 nm.

The apparatus for producing biochemical analysis data includes a cooled CCD area sensor 35 disposed so as to face the surface of the stimulating ray cutting filter 33 opposite to the optical fiber members 30.

Figure 7:
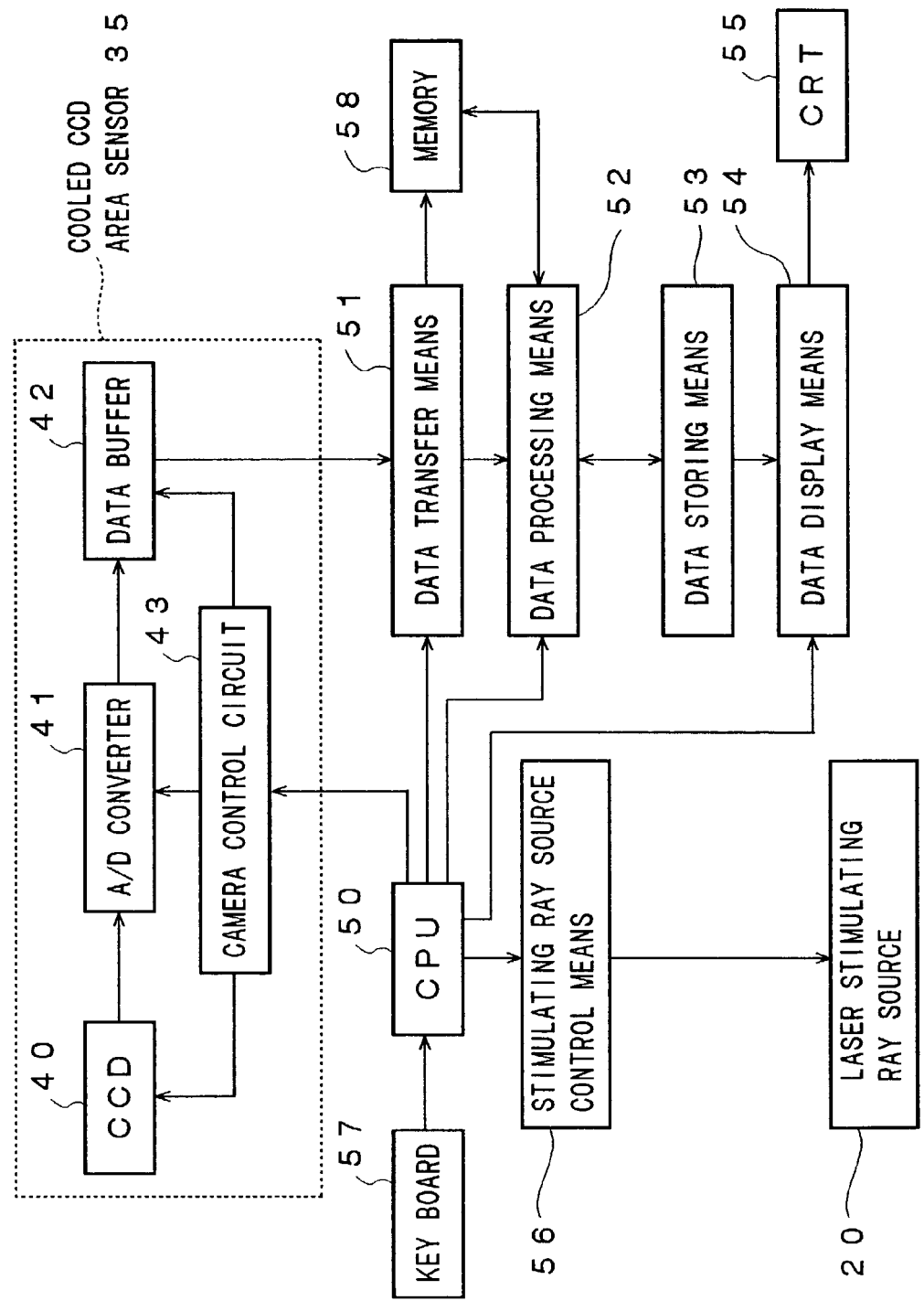
FIG. 7 is a block diagram of a control system, a detection system and a memory system of a cooled CCD area sensor and a control system, a memory system, a display system and an input system of an apparatus for producing biochemical analysis data, which is a preferred embodiment of the present invention.

FIG. 7 is a block diagram of a control system, a detection system and a memory system of the cooled CCD area sensor 35 and a control system, a memory system, a display system and an input system of the apparatus for producing biochemical analysis data according to this embodiment.

As shown in FIG. 7, the cooled CCD area sensor 35 includes a CCD 40, an A/D converter 41 for digitizing analog data produced by the CCD 40 in the form of electric charge, a data buffer 42 for temporarily storing biochemical analysis data produced by digitizing analog data by the A/D converter 41 and a camera control circuit 43 for controlling the overall operation of the cooled CCD area sensor 35.

As shown in FIG. 7, the apparatus for producing biochemical analysis data according to this embodiment includes a CPU 50 for controlling the overall operation of the cooled CCD area sensor 35, a data transfer means 51 for reading biochemical analysis data produced by the cooled CCD area sensor 35 from the data buffer 42, a data processing means 52 for effecting data processing on biochemical analysis data read by the data transfer means 51, a data storing means 53 for biochemical analysis data subjected to data processing by the data processing means 52, a data display means 54 for producing quantitative data based on biochemical analysis data stored in the data storing means 53 and displaying the quantitative data on the screen of a CRT 55, a stimulating ray source control means 56 for controlling the laser stimulating ray source 20 and an LED light source of a position data production optical system described later, a keyboard 57 which can be operated by a user and through which various instruction signals can be input, and a memory 58.

Based on instruction signals input through the keyboard 57, the CPU 50 is adapted for controlling the stimulating ray source control means 56 and outputting various signals to the camera control circuit 43 of the cooled CCD area sensor 35.

In this embodiment, since a number of the optical fiber members 30 are gathered in the vicinity of the end portions 30b opposite to the light collecting end portions 30a, what region on the photo-electric detecting surface of the CCD 40 of the cooled CCD area sensor 35 stimulated emission 28 released from each of the stimulable phosphor layer regions 12 formed in the support 11 of the stimulable phosphor sheet 10 is led to and what region on the photo-electric detecting surface of the CCD 40 of the cooled CCD area sensor 35 the stimulated emission 28 is received by depend upon how the optical fiber members 30 are gathered in the vicinity of the end portions 30b opposite to the light collecting end portions 30a and are not obvious.

Therefore, in this embodiment, it is detected in advance what region on the photo-electric detecting surface of the CCD 40 stimulated emission 28 released from each of the stimulable phosphor layer regions 12 formed in the support 11 of the stimulable phosphor sheet 10 is led to by the optical fiber member 30 and what region on the photo-electric detecting surface of the CCD 40 the stimulated emission 28 is received by and position data are produced and stored in the memory 58.

When position data are to be produced, the laser stimulating ray source 20 and the concave lens 22 are removed from the apparatus for producing biochemical analysis data and a position data production optical system is installed.

Figure 8:
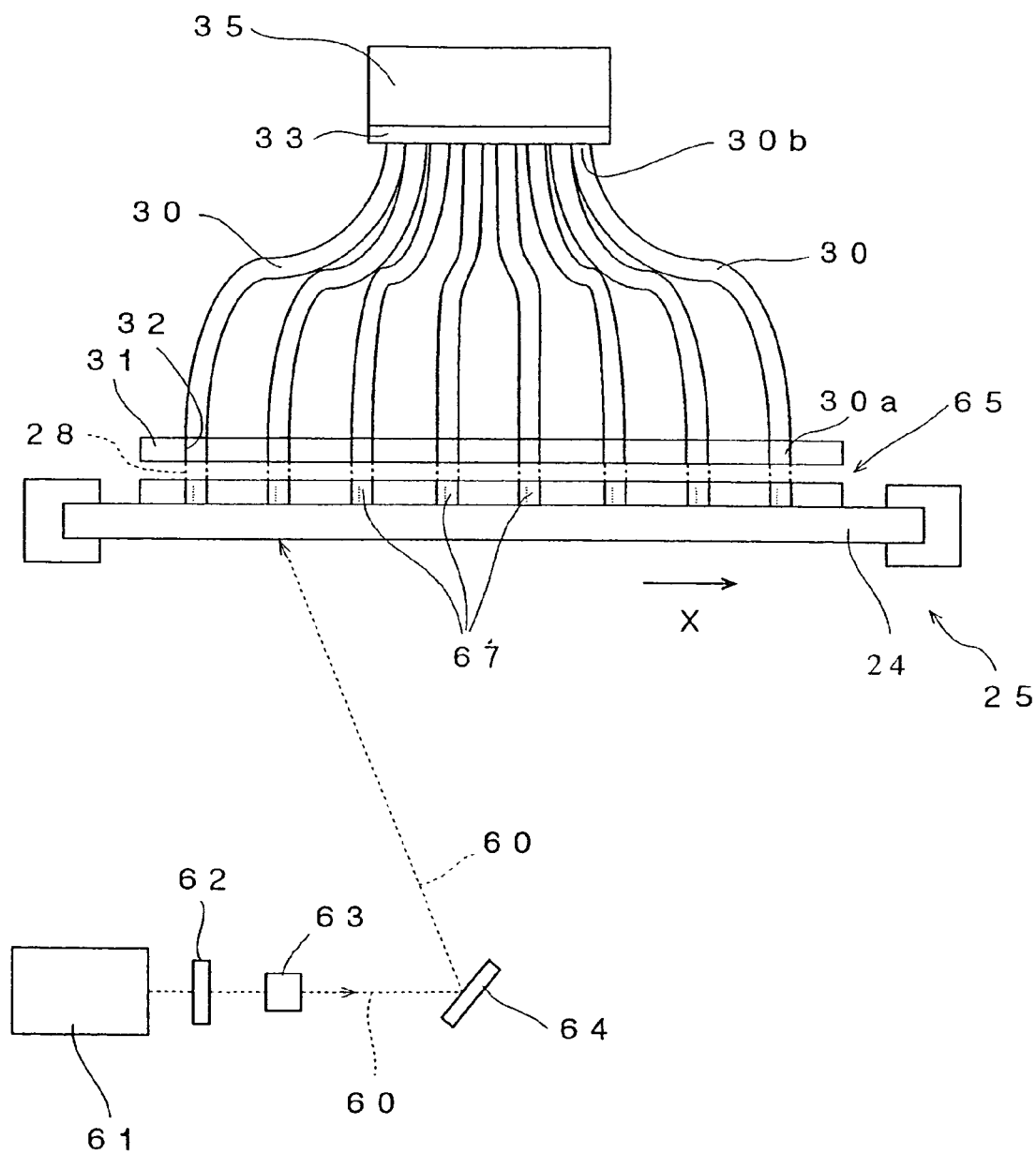
FIG. 8 is a schematic cross sectional view showing an apparatus for producing biochemical analysis data in which a position data production optical system is installed.

FIG. 8 is a schematic cross-sectional view showing the apparatus for producing biochemical analysis data in which the position data production optical system is installed.

As shown in FIG. 8, the position data production optical system includes an LED light source 61 for emitting a light beam 60 having a wavelength of that of stimulated emission 28 released from BaFX system stimulable phosphor, a collimator lens 62, a beam expander 63 and a reflection mirror 64.

The reflection mirror 64 is controlled to be intermittently rotated by a main scanning stepping motor (not shown) in a main scanning direction indicated by an arrow X in FIG. 8, and the sample stage 25, the fixing head 31, a number of the optical fiber members 30, the stimulating ray cutting filter 33 and the cooled CCD area sensor 35 are constituted so as to be moved by a sub-scanning pulse motor in a sub-scanning direction perpendicular to the main scanning direction indicated by the arrow X in FIG. 8.

When position data are to be produced, drive pulses determined in accordance with the rotation position of the reflection mirror 64 and to be output to the main scanning stepping motor are input through the keyboard 57 and stored in the memory 58 and a position data producing unit is placed on the transparent glass plate 24 of the sample stage 25.

Figure 9:
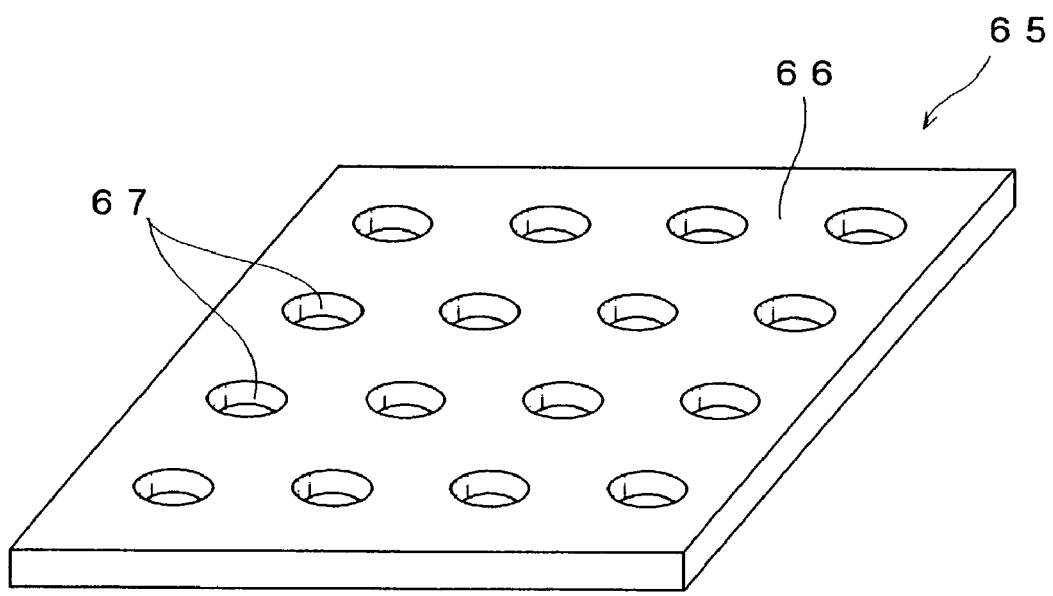
FIG. 9 is a schematic perspective view showing a position data producing unit.

FIG. 9 is a schematic perspective view showing a position data producing unit.

As shown in FIG. 9, the position data producing unit 65 includes a substrate 66 made of aluminum and the substrate 66 is formed with a number of substantially circular through-holes 67.

A number of the through-holes 67 are formed in the substrate 66 of the position data producing unit 65 in the same regular pattern as that of a number of the absorptive regions 4 formed in the substrate 2 of the biochemical analysis unit 1, namely, in the same regular pattern as that of a number of the stimulable phosphor layer regions 12 formed in the support 11 of the stimulable phosphor sheet 10.

Therefore, although not accurately shown in FIG. 9, in this embodiment, about 10,000 substantially circular through-holes 67 having a size of about 0.01 mm² are dot-like formed in a regular pattern at a density of about 5,000 per cm² in the substrate 66 of the position data producing unit 65.

In this embodiment, guide members (not shown) are provided in the sample stage 25 for ensuring that the position data producing unit 65 is placed on the sample stage 25 so that a number of the through-holes 67 formed in the substrate 66 of the position data producing unit 65 accurately face the corresponding light collecting end portions 30a of the corresponding optical fiber members 30.

A position data production signal is then input through the keyboard 57.

The position data production signal is output to the CPU 50 and when the CPU 50 receives the position data production signal, it outputs a drive signal to the LED light source 61, thereby turning it on.

A light beam 60 emitted from the LED light source 61 passes through a collimator lens 62, thereby being made a parallel beam and enters a beam expander 63.

The light beam 60 passes through the beam expander 63, whereby the beam diameter thereof is accurately adjusted and impinges onto a reflection mirror 64, thereby being reflected by the reflection mirror 64.

The light beam 60 reflected by the reflection mirror 64 enters a first through-hole 67 formed in the substrate 66 of the position data producing unit 65 placed on the transparent glass plate 24 of the sample stage 25.

In this embodiment, the reflection mirror 64 is constituted so as to be rotated by the main scanning stepping motor so that the position data producing unit 65 is scanned with the light beam 60 reflected by the reflection mirror 64 in the main scanning direction indicated by the arrow X in FIG. 8 at a pitch equal to the distance between neighboring through-holes 67.

The light beam 60 entering the first through-hole 67 formed in the substrate 66 of the position data producing unit 65 is collected by the light collecting end portion 30a of the optical fiber member 30 disposed so as to face the first through-hole 67 and guided by the optical fiber member 30 to impinge upon a region of the stimulating ray cutting filter 33 facing the end portion 30b opposite to the light collecting end portion 30a of the optical fiber member 30.

Since the stimulating ray cutting filter 33 has a property of transmitting light having a wavelength of that of stimulated emission 28 and cutting light having a wavelength of 640 nm, the light beam 60 emitted from the LED light source 61 and transmitted through the first through-hole 67 of the position data producing unit 65 passes through the stimulating ray cutting filter 33 and impinges onto the photo-electric detecting surface of the CCD 40, thereby forming an image thereon. The CCD 40 receives light of the thus formed image and accumulates it in the form of electric charges therein.

When a predetermined time has passed, the CPU 50 outputs an exposure completion signal to the camera control circuit 43 of the cooled CCD area sensor 35 and the stimulating ray source control means 56 and when stimulating ray source control means 56 receives the exposure completion signal from the CPU 50, it turns off the LED light source 61.

The CPU 50 further outputs a drive signal to the main scanning stepping motor based on drive pulses determined in accordance with the rotation position of the reflecting mirror 64 and stored in the memory 58, thereby rotating the reflection mirror 64 to a position where a second through-hole 67 of the position data producing unit 65 next to the first through-hole 67 can be irradiated with the light beam 60 emitted from the LED light source 61.

On the other hand, when the camera control circuit 43 receives the exposure completion signal from the CPU 50, it transfers analog data accumulated in the CCD 40 in the form of electric charge to the A/D converter 41 to cause the A/D converter 41 to digitize the data, thereby producing position data of the first through-hole 67 of the position data producing unit 65 and to temporarily store the thus produced position data in the data buffer 42.

At the same time, the CPU 50 outputs a data transfer signal to the data transfer means 51 to cause it to read out the position data of the first through-hole 67 of the position data producing unit 65 from the data buffer 42 of the cooled CCD area sensor 35 and to store them to the memory 58.

In this manner, the position data are produced by collecting the light beam 60 emitted from the LED light source 61 transmitted through the first through-hole 67 by the light collecting end portion 30a of the optical fiber member 30 facing the first through-hole 67, leading it to the photo-electric detecting surface of the CCD 40 and photoelectrically detecting it and so-produced position data are stored in the memory 58. These position data correspond to position data of stimulated emission 28 released from a stimulable phosphor layer region 12 corresponding to the first through-hole 67 of the position data producing unit 65 among a number of the stimulable phosphor layer regions 12 formed in the support 11 of the stimulable phosphor sheet 10.

When the position data of the first through-hole 67 of the position data producing unit 65 have been stored in the memory 58, the CPU 50 outputs a drive signal to the LED light source 61, thereby turning it on.

A light beam 60 emitted from the LED light source 61 passes through the collimator lens 62, thereby being made a parallel beam and enters the beam expander 63.

The light beam 60 passes through the beam expander 63, whereby the beam diameter thereof is accurately adjusted and impinges onto the reflection mirror 64, thereby being reflected by the reflection mirror 64.

The light beam 60 reflected by the reflection mirror 64 enters the second through-hole 67 formed in the substrate 66 of the position data producing unit 65 next to the first through-hole 67 placed on the transparent glass plate 24 of the sample stage 25.

The light beam 60 entering the second through-hole 67 formed in the substrate 66 of the position data producing unit 65 is collected by the light collecting end portion 30a of the optical fiber member 30 disposed so as to face the second through-hole 67 and guided by the optical fiber member 30 to impinge upon a region of the stimulating ray cutting filter 33 facing the end portion 30b opposite to the light collecting end portion 30a of the optical fiber member 30. The light beam 60 then passes through the stimulating ray cutting filter 33 and impinges onto the photo-electric detecting surface of the CCD 40, thereby forming an image thereon. The CCD 40 receives light of the thus formed image and accumulates it in the form of electric charges therein.

When a predetermined time has passed, the CPU 50 outputs an exposure completion signal to the camera control circuit 43 of the cooled CCD area sensor 35 and the stimulating ray source control means 56 and when stimulating ray source control means 56 receives the exposure completion signal from the CPU 50, it turns off the LED light source 61.

The CPU 50 further outputs a drive signal to the main scanning stepping motor based on drive pulses determined in accordance with the rotation position of the reflecting mirror 64 and stored in the memory 58, thereby rotating the reflection mirror 64 to a position where a third through-hole 67 of the position data producing unit 65 next to the second through-hole 67 can be irradiated with the light beam 60 emitted from the LED light source 61.

On the other hand, when the camera control circuit 43 receives the exposure completion signal from the CPU 50, it transfers analog data accumulated in the CCD 40 in the form of electric charge to the A/D converter 41 to cause the A/D converter 41 to digitize the data, thereby producing position data of the second through-hole 67 of the position data producing unit 65 and to temporarily store the thus produced position data in the data buffer 42.

At the same time, the CPU 50 outputs a data transfer signal to the data transfer means 51 to cause it to read out the position data of the second through-hole 67 of the position data producing unit 65 from the data buffer 42 of the cooled CCD area sensor 35 and to store them to the memory 58.

In this manner, the position data are produced by collecting the light beam 60 emitted from the LED light source 61 transmitted through the second through-hole 67 by the light collecting end portion 30a of the optical fiber member 30, leading it to the photo-electric detecting surface of the CCD 40 and photoelectrically detecting it and the so-produced position data are stored in the memory 58. These position data correspond to position data of stimulated emission 28 released from a stimulable phosphor layer region 12 corresponding to the second through-hole 67 of the position data producing unit 65 among a number of the stimulable phosphor layer regions 12 formed in the support 11 of the stimulable phosphor sheet 10.

The CPU 50 further outputs a drive signal to the LED light source 61, thereby turning it on and produces position data of the third through-hole 67 of the position data producing unit 65 to store them in the memory 58.

When position data of all of the through-holes 67 formed in the substrate 66 of the position data producing unit 65 have been produced by the cooled CCD area sensor 35 and stored in the memory 58 similarly to the above, the production of the positional data is completed.

When the position data of a number of the through-holes 67 formed in the substrate 66 of the position data producing unit 65 have been stored in the memory 58 in this manner, the apparatus for producing biochemical analysis data according to this embodiment reads radiation data recorded in a number of the stimulable phosphor layer regions 12 formed in the support 11 of the stimulable phosphor sheet 10 in the following manner.

A stimulable phosphor sheet 10 formed with a number of the stimulable phosphor layer regions 12 in which radiation data are recorded is first set on a transparent glass plate 24 of the sample stage 25 by a user.

In this embodiment, guide members (not shown) are provided in the sample stage 25 for ensuring that the stimulable phosphor sheet 10 is placed on the sample stage 25 so that a number of the stimulable phosphor layer regions 12 accurately face the corresponding light collecting end portions 30a of the corresponding optical fiber members 30.

A data production start signal is then input through the keyboard 57 by the user and the data production start signal is input to the CPU 50.

When the CPU 50 receives the data production start signal, it outputs the data production start signal to the laser stimulating ray source 20, thereby activating it and outputs an exposure start signal to the camera control circuit 43 of the cooled CCD area sensor 35, thereby causing the cooled CCD area sensor 35 to start detecting stimulated emission 28.

A laser beam 21 having a wavelength of 640 nm and emitted from the laser stimulating ray source 20 passes through a concave lens 22, thereby being diverged and the whole surface of the stimulable phosphor sheet 10 placed on the transparent glass plate 24 of the sample stage 25 is simultaneously irradiated with the diverged laser beam 21.

When each of the stimulable phosphor layer regions 12 formed in the support 11 of the stimulable phosphor sheet 10 is irradiated with the laser beam 21, stimulable phosphor contained therein is excited, thereby releasing stimulated emission 28.

Stimulated emission 28 released from each of the stimulable phosphor layer regions 12 is collected by the light collecting end portion 30a of the corresponding optical fiber member 30 disposed so as to face the stimulable phosphor layer region 12.

In this embodiment, since each of a number of the optical fiber members 30 is secured into the through-hole 32 formed in the fixing head 31 in the vicinity of the light collecting end portion 30a so that the light collecting end portion 30a of each of the optical fiber members 30 faces one of the stimulable phosphor layer regions 12 of the stimulable phosphor sheet 10 placed on the transparent glass plate 24 of the sample stage 25, stimulated emission 28 released from each of the stimulable phosphor layer regions 12 is reliably collected by the light collecting end portion 30a of the corresponding optical fiber member 30.

Further, in this embodiment, since the support 11 of the stimulable phosphor sheet 10 is made of stainless steel and has a property of attenuating the energy of light, stimulated emission 28 released from neighboring stimulable phosphor layer regions 12 can be effectively prevented from scattering in the support 11 of the stimulable phosphor sheet 10 and being mixed with each other.

Stimulated emission 28 collected by the light collecting end portion 30a of a particular optical fiber member 30 is guided by the optical fiber member 30 and impinges onto a corresponding region of the stimulating ray cutting filter 33.

In this embodiment, since the optical fiber members 30 are gathered in the vicinity of the end portions 30b opposite to the light collecting end portions 30a, even in the case where a number of the optical fiber members 30 are provided correspondingly to a number of the stimulable phosphor layer regions 12 formed in the support 11 of the stimulable phosphor sheet 10, it is possible to employ a stimulating ray source cutting filter 33 having a small area and a cooled CCD area sensor 35 provided with a photo-electric detecting surface having a small area. Therefore, it is possible to make the apparatus for producing biochemical analysis data smaller and to lower cost for manufacturing the apparatus for producing biochemical analysis data.

Further, in this embodiment, since the position data indicating the positional relationship between the position of each of the stimulable phosphor layer regions 12 which is to release stimulated emission 28 and the position of the photo-electric detecting surface of the CCD 40 by which stimulated emission 28 led by the optical fiber member 30 is to be received are produced in advance and stored in the memory 58, it is not necessary to dispose the end portions 30b of the optical fiber members 30 in the same pattern as that of the light collecting end portions 30a thereof.

Since the stimulating ray source cutting filter 33 has a property of transmitting only light having a wavelength of that of stimulated emission 28 released from the stimulable phosphor layer regions 12 formed in the support 11 of the stimulable phosphor sheet 10 and cutting light having a wavelength of 640 nm, light having a wavelength of 640 nm is cut off by the stimulating ray source cutting filter 33 and only stimulated emission 28 released from the stimulable phosphor layer regions 12 is transmitted therethrough and impinges onto the photo-electric detecting surface of the CCD 40, thereby forming an image on the photo-electric detecting surface of the CCD 40. The CCD 40 receives light of the thus formed image and accumulates it in the form of electric charges therein.

When a predetermined time has passed, the CPU 50 outputs an exposure completion signal to the camera control circuit 43 of the cooled CCD area sensor 35 and outputs a data production completion signal to the stimulating ray source control means 56.

When the stimulating ray source control means 56 receives the data production completion signal from the CPU 50, it turns off the laser stimulating ray source 20.

On the other hand, when the camera control circuit 43 receives the exposure completion signal from the CPU 50, it transfers analog data accumulated in the CCD 40 in the form of electric charge to the A/D converter 41 to cause the A/D converter 41 to digitize the data, thereby producing biochemical analysis data and to temporarily store the thus produced biochemical analysis data in the data buffer 42.

At the same time, the CPU 50 outputs a data transfer signal to the data transfer means 51 to cause it to read out the biochemical analysis data from the data buffer 42 of the cooled CCD area sensor 35 and to input them to the data processing means 52.

The data processing means 52 effects necessary data processing on the biochemical analysis data in accordance with the user's instructions, reads the position data stored in the memory 58 and stores the biochemical analysis data of each of the stimulable phosphor layer regions 12 formed in the support 11 of the stimulable phosphor sheet 10 in a corresponding memory area in the data storing means 53.

When the user inputs a data display signal through the keyboard 57, the CPU 50 outputs the data display signal to the data display means 54, thereby causing the data display means 54 to produce quantitative analysis data based on the biochemical analysis data stored in the data storing means 53 and to display them on the screen of the CRT 55.

According to this embodiment, since each of a number of the optical fiber members 30 is secured into the through-hole 32 formed in the fixing head 31 in the vicinity of the light collecting end portion 30a so that the light collecting end portion 30a of each of the optical fiber members 30 faces one of the stimulable phosphor layer regions 12 of the stimulable phosphor sheet 10 placed on the transparent glass plate 24 of the sample stage 25, stimulated emission 28 released from each of the stimulable phosphor layer regions 12 is reliably collected by the light collecting end portion 30a of the corresponding optical fiber member 30. Therefore, since the efficiency for collecting stimulated emission 28 can be markedly improved, biochemical analysis data having an excellent quantitative characteristic can be produced by photoelectrically detecting stimulated emission 28 with high sensitivity Further, according to this embodiment, since each of the stimulable phosphor layer regions 12 formed in the support 11 of the stimulable phosphor sheet 10 can be irradiated with the laser beam 21 for a sufficiently long time, thereby exciting stimulable phosphor contained therein to cause the stimulable phosphor to release radiation energy stored therein in the form of stimulated emission 28, it is possible to produce biochemical analysis data by photoelectrically detecting stimulated emission 28 by the cooled CCD area sensor 35 with high sensitivity.

Furthermore, according to this embodiment, since the support 11 of the stimulable phosphor sheet 10 is made of stainless steel and has a property of attenuating the energy of light, stimulated emission 28 released from neighboring stimulable phosphor layer regions 12 formed in the support 11 of the stimulable phosphor sheet 10 can be effectively prevented from scattering in the support 11 of the stimulable phosphor sheet 10 and being mixed with each other. Therefore, it is possible to effectively prevent noise caused by the scattering of stimulated emission 28 from being generated in biochemical analysis data produced by reading radiation data recorded in a number of the stimulable phosphor layer regions 12 formed in the support 11 of the stimulable phosphor sheet 10.

Moreover, according to this embodiment, since the position data indicating the positional relationship between the position of each of the stimulable phosphor layer regions 12 which is to release stimulated emission 28 and the position of the photo-electric detecting surface of the CCD 40 by which stimulated emission 28 led by the optical fiber member 30 is to be received are produced in advance and stored in the memory 58, it is possible to gather a number of the optical fiber members 30 in the vicinity of the end portions 30b opposite to the light collecting end portions 30a in arbitrary arrangement. Therefore, even when a number of the optical fiber members 30 are provided correspondingly to a number of the stimulable phosphor layer regions 12 formed in the support 11 of the stimulable phosphor sheet 10, it is possible to employ a stimulating ray source cutting filter 33 having a small area and a cooled CCD area sensor 35 provided with a photo-electric detecting surface having a small area. Therefore, it is possible to make the apparatus for producing biochemical analysis data smaller and to lower the cost of manufacturing the apparatus for producing biochemical analysis data.

On the other hand, fluorescence data recorded in a number of the absorptive regions 4 formed in the substrate 2 of the biochemical analysis unit 1 are read by another apparatus for producing biochemical analysis data, thereby producing biochemical analysis data.

Figure 10:
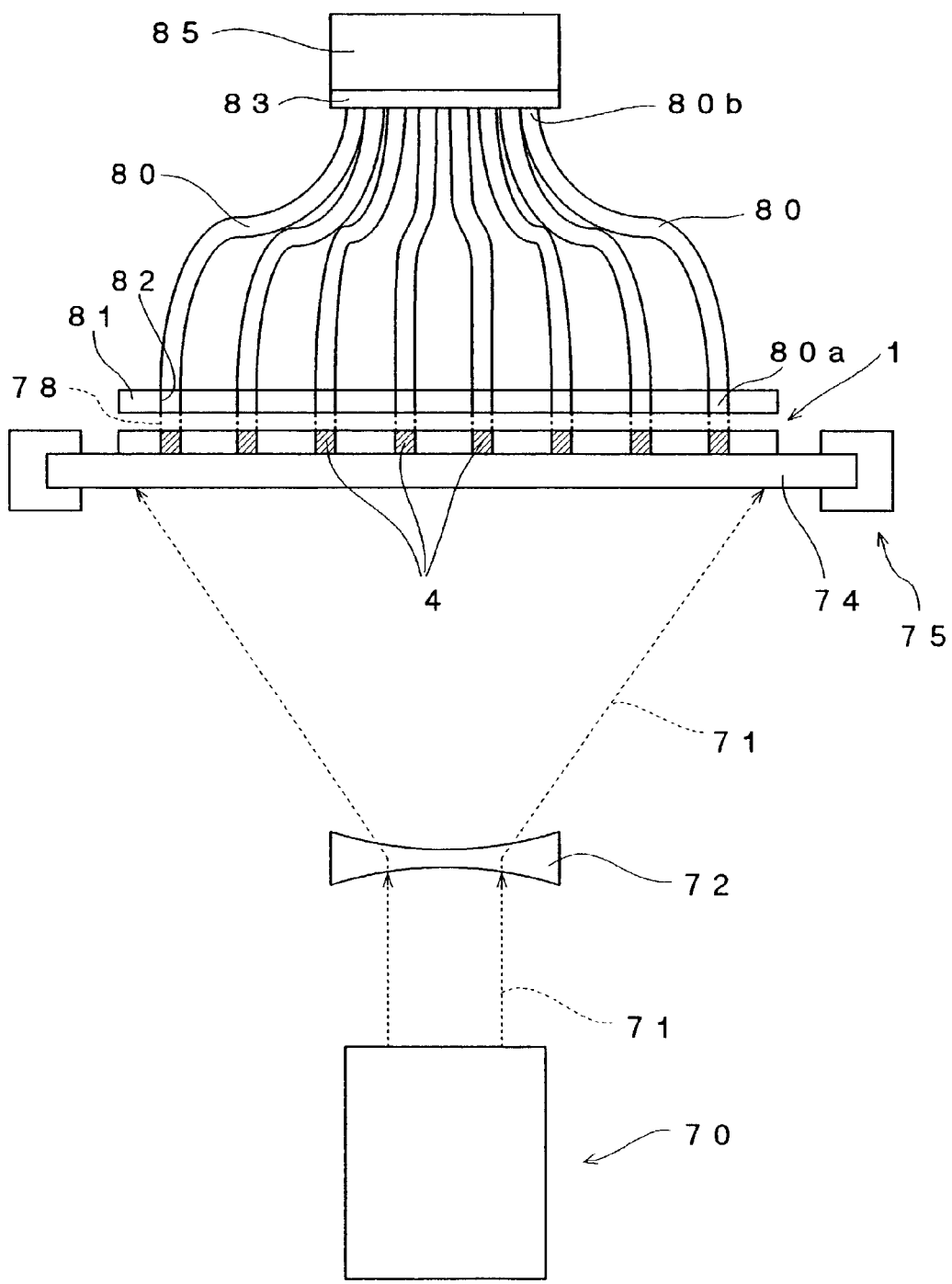
FIG. 10 is a schematic view showing an apparatus for producing biochemical analysis data for reading fluorescence data recorded in a number of absorptive regions formed in a substrate of a biochemical analysis unit, thereby producing biochemical analysis data, which is another preferred embodiment of the present invention.

FIG. 10 is a schematic view showing an apparatus of producing biochemical analysis data for reading fluorescence data recorded in a number of the absorptive regions 4 formed in the substrate 2 of the biochemical analysis unit 1, thereby producing biochemical analysis data.

An apparatus of producing biochemical analysis data according to this embodiment is constituted so as to read fluorescence data of a fluorescent substance effectively stimulable by a laser beam having a wavelength of 473 nm, for example, Cy3 (registered trademark), to produce biochemical analysis data and includes a laser stimulating ray source 70 for emitting a laser beam 71 having a wavelength of 473 nm. In this embodiment, the laser stimulating ray source 70 is constituted by a second harmonic generation element.

As shown in FIG. 10, a laser beam 71 having a wavelength of 473 nm and emitted from the laser stimulating ray source 70 passes through a concave lens 72, thereby being made a divergent beam 71 and impinges onto the biochemical analysis unit 1 placed on a transparent glass plate 74 of a sample stage 75.

As a result, a fluorescent substance contained in a number of the absorptive regions 4 formed in the substrate 2 of the biochemical analysis unit 1 is stimulated to release fluorescence emission 78.

As shown in FIG. 10, in this embodiment, the apparatus for producing biochemical analysis data includes a number of optical fiber members 80 each of which has a light collecting end portion 80*a* facing one of a number of the absorptive regions 4 formed in the substrate 2 of the biochemical analysis unit 1 and being located in the vicinity thereof.

In this embodiment, each of the optical fiber members 80 is constituted as a plurality of optical fibers and secured into a through-hole 82 formed in a fixing head 81 in the vicinity of the light collecting end portion 80*a* so that the light collecting end portion 80*a* of each of the optical fiber members 80 is positioned in a desired manner.

Further, as shown in FIG. 10, the optical fiber members 80 are gathered in the vicinity of end portions 80*b* opposite to the light collecting end portions 80*a*.

As shown in FIG. 10, each of the optical fiber members 80 is disposed so that end portion 80*b* thereof opposite to the light collecting end portion 80*a* faces a stimulating ray cutting filter 83. The stimulating ray cutting filter 83 has a property of cutting light having a wavelength of 473 nm equal to a wavelength of the laser beam 71 and transmitting light having a wavelength longer than 473 nm.

The apparatus for producing biochemical analysis data includes a cooled CCD area sensor 85 disposed so as to face the surface of the stimulating ray cutting filter 83 opposite to the optical fiber members 80.

Figure 11:
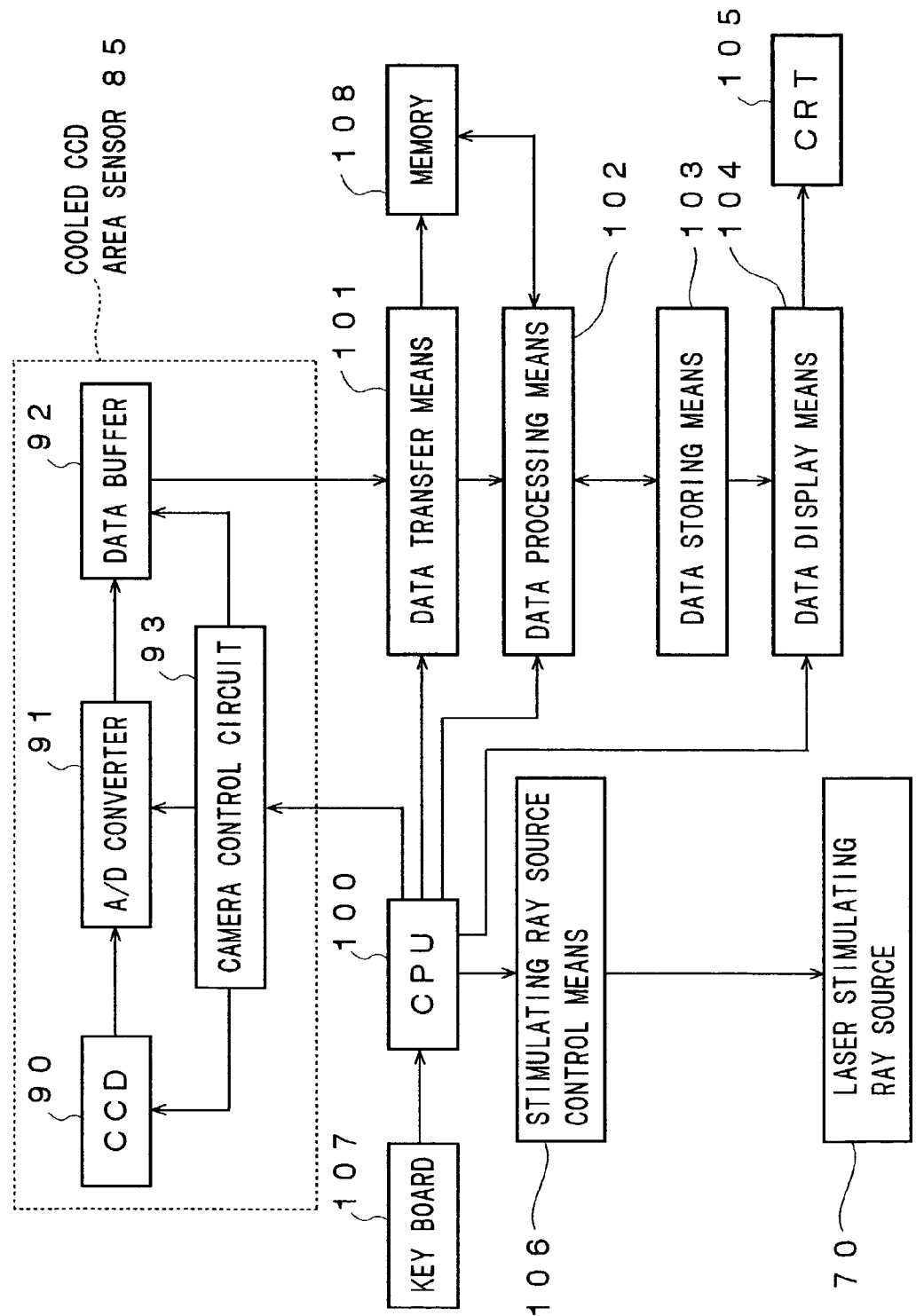
FIG. 11 is a block diagram of a control system, a detection system and a memory system of a cooled CCD area sensor and a control system, a memory system, a display system and an input system of an apparatus for producing biochemical analysis data, which is another preferred embodiment of the present invention.

FIG. 11 is a block diagram of a control system, a detection system and a memory system of the cooled CCD area sensor 85 and a control system, a memory system, a display system and an input system of the apparatus for producing biochemical analysis data according to this embodiment.

As shown in FIG. 11, the cooled CCD area sensor 85 includes a CCD 90, an A/D converter 91 for digitizing analog data produced by the CCD 90 in the form of electric charge, a data buffer 92 for temporarily storing biochemical analysis data produced by digitizing analog data by the A/D converter 91 and a camera control circuit 93 for controlling the overall operation of the cooled CCD area sensor 85.

As shown in FIG. 11, the apparatus for producing biochemical analysis data according to this embodiment includes a CPU 100 for controlling the overall operation of the cooled CCD area sensor 85, a data transfer means 101 for reading biochemical analysis data produced by the cooled CCD area sensor 85 from the data buffer 92, a data processing means 102 for effecting data processing on biochemical analysis data read by the data transfer means 101, a data storing means 103 for biochemical analysis data subjected to data processing by the data processing means 102, a data display means 104 for producing quantitative data based on biochemical analysis data stored in the data storing means 103 and displaying the quantitative data on the screen of a CRT 105, a stimulating ray source control means 106 for controlling the laser stimulating ray source 70 and the position data production optical system shown in FIG. 8, a keyboard 107 which can be operated by a user and through which various instruction signals can be input, and a memory 108.

Based on instruction signals input through the keyboard 107, the CPU 100 is adapted for controlling the stimulating ray source control means 106 and outputting various signals to the camera control circuit 93 of the cooled CCD area sensor 85.

In this embodiment, since a number of the optical fiber members 80 are gathered in the vicinity of the end portions 80*b* opposite to the light collecting end portions 80*a*, what region on the photo-electric detecting surface of the CCD 90 of the cooled CCD area sensor 85 fluorescence emission 78 released from each of the absorptive layer regions 4 formed in the substrate 2 of the biochemical analysis unit 1 is led to and what region on the photo-electric detecting surface of the CCD 90 of the cooled CCD area sensor 35 the fluorescence emission 78 is received by depend upon how the optical fiber members 80 are gathered in the vicinity of the end portions 80*b* opposite to the light collecting end portions 80*a* and are not obvious.

Therefore, in this embodiment, it is detected in advance what region on the photo-electric detecting surface of the CCD 90 fluorescence emission 78 released from each of the absorptive layer regions 4 formed in the substrate 2 of the biochemical analysis unit 1 is led to by the optical fiber member 80 and what region on the photo-electric detecting surface of the CCD 90 the fluorescence emission 78 is received by and position data are produced and stored in the memory 108.

When position data are to be produced, the laser stimulating ray source 70 and the concave lens 72 are removed from the apparatus for producing biochemical analysis data and the position data production optical system is installed. The position data producing unit 65 shown in FIG. 9 is placed on the transparent glass plate 74 of the sample stage 75.

Position data are produced and stored in the memory 108 in the same way as in the foregoing embodiment except that an LED light source 61 for emitting a light beam 60 having a wavelength longer than 473 nm is employed.

When the position data have been stored in the memory 108 in this manner, the apparatus for producing biochemical analysis data according to this embodiment reads fluorescence data recorded in a number of the absorptive regions 4 formed in the substrate 2 of the biochemical analysis unit 1 in the following manner.

A biochemical analysis unit 1 formed with a number of the absorptive regions 4 in which fluorescence data are recorded is first set on a transparent glass plate 74 of the sample stage 75 by a user.

In this embodiment, guide members (not shown) are provided in the sample stage 75 for ensuring that the biochemical analysis unit 1 is placed on the sample stage 75 so that a number of the absorptive regions 4 accurately face the corresponding light collecting end portions 80*a* of the corresponding optical fiber members 80.

A data production start signal is then input through the keyboard 107 by the user and the data production start signal is input to the CPU 100.

When the CPU 100 receives the data production start signal, it outputs the data production start signal to the laser stimulating ray source 70, thereby activating it and outputs an exposure start signal to the camera control circuit 93 of the cooled CCD area sensor 85, thereby causing the cooled CCD area sensor 85 to start detecting fluorescence emission 78.

A laser beam 71 having a wavelength of 473 nm and emitted from the laser stimulating ray source 70 passes through a concave lens 72, thereby being diverged and the whole surface of the biochemical analysis unit 1 placed on the transparent glass plate 74 of the sample stage 75 is simultaneously irradiated with the diverged laser beam 71.

When a number of the absorptive regions 4 formed in the substrate 2 of the biochemical analysis unit 1 are irradiated with the laser beam 71, a fluorescent substance, for example, Cy3, contained therein is excited, thereby releasing fluorescence emission 78.

Fluorescence emission 78 released from each of the absorptive regions 4 is collected by the light collecting end portion 80a of the corresponding optical fiber member 80 disposed so as to face the absorptive region 4.

In this embodiment, since each of a number of the optical fiber members 80 is secured into the through-hole 82 formed in the fixing head 81 in the vicinity of the light collecting end portion 80a so that the light collecting end portion 80a of each of the optical fiber members 80 faces one of the absorptive region 4 of the biochemical analysis unit 1 placed on the transparent glass plate 74 of the sample stage 75, fluorescence emission 78 released from each of the absorptive regions 4 is reliably collected by the light collecting end portion 80a of the corresponding optical fiber member 80.

Further, in this embodiment, since the substrate 2 of the biochemical analysis unit 1 is made of stainless steel and has a property of attenuating the energy of light, fluorescence emission 78 released from neighboring absorptive region 4 can be effectively prevented from scattering in the substrate 2 of the biochemical analysis unit 1 and being mixed with each other.

Fluorescence emission 78 collected by the light collecting end portion 80a of a particular optical fiber member 80 is guided by the optical fiber member 80 and impinges onto a corresponding region of the stimulating ray cutting filter 83.

In this embodiment, since the optical fiber members 80 are gathered in the vicinity of the end portions 80b opposite to the light collecting end portions 80a, even in the case where a number of the optical fiber members 80 are provided correspondingly to a number of the absorptive region 4 formed in the substrate 2 of the biochemical analysis unit 1, it is possible to employ a stimulating ray source cutting filter 83 having a small area and a cooled CCD area sensor 85 provided with a photo-electric detecting surface having a small area. Therefore, it is possible to make an apparatus for producing biochemical analysis data smaller and to lower cost for manufacturing an apparatus for producing biochemical analysis data.

Further, in this embodiment, since the position data indicating the positional relationship between the position of each of the absorptive regions 4 which is to release fluorescence emission 78 and the position of the photo-electric detecting surface of the CCD 90 by which fluorescence emission 78 led by the optical fiber member 80 is to be received are produced in advance and stored in the memory 108, it is not necessary to dispose the end portions 80b of the optical fiber members 80 in the same pattern as that of the light collecting end portions 80a thereof.

Since the stimulating ray source cutting filter 83 has a property of cutting off light having a wavelength of 473 nm equal to that of the laser beam 71 and transmitting light having a wavelength longer than 473 nm, light having a wavelength of 473 nm is cut off by the stimulating ray source cutting filter 83 and only fluorescence emission 78 released from the absorptive regions 4 is transmitted therethrough and impinges onto the photo-electric detecting surface of the CCD 90, thereby forming an image on the photo-electric detecting surface of the CCD 90. The CCD 90 receives light of the thus formed image and accumulates it in the form of electric charges therein.

When a predetermined time has passed, the CPU 100 outputs an exposure completion signal to the camera control circuit 93 of the cooled CCD area sensor 85 and outputs a data production completion signal to the stimulating ray source control means 106.

When the stimulating ray source control means 106 receives the data production completion signal from the CPU 100, it turns off the laser stimulating ray source 70.

On the other hand, when the camera control circuit 93 receives the exposure completion signal from the CPU 100, it transfers analog data accumulated in the CCD 90 in the form of electric charge to the A/D converter 91 to cause the A/D converter 91 to digitize the data, thereby producing biochemical analysis data and to temporarily store the thus produced biochemical analysis data in the data buffer 92.

At the same time, the CPU 100 outputs a data transfer signal to the data transfer means 101 to cause it to read out the biochemical analysis data from the data buffer 92 of the cooled CCD area sensor 85 and to input them to the data processing means 102.

The data processing means 102 effects necessary data processing on the biochemical analysis data in accordance with the user's instructions, reads the position data stored in the memory 108 and stores the biochemical analysis data of each of the absorptive regions 4 formed in the substrate 2 of the biochemical analysis unit 1 in a corresponding memory area in the data storing means 103.

When the user inputs a data display signal through the keyboard 107, the CPU 100 outputs the data display signal to the data display means 104, thereby causing the data display means 104 to produce quantitative analysis data based on the biochemical analysis data stored in the data storing means 103 and to display them on the screen of the CRT 105.

According to this embodiment, since each of a number of the optical fiber members 80 is secured into the through-hole 82 formed in the fixing head 81 in the vicinity of the light collecting end portion 80a so that the light collecting end portion 80a of each of the optical fiber members 80 faces one of the absorptive regions 4 of the biochemical analysis unit 1 placed on the transparent glass plate 74 of the sample stage 75, fluorescence emission 78 released from each of the absorptive regions 4 is reliably collected by the light collecting end portion 80a of the corresponding optical fiber member 80. Therefore, since the efficiency for collecting fluorescence emission 78 can be markedly improved, biochemical analysis data having an excellent quantitative characteristic can be produced by photoelectrically detecting fluorescence emission 78 with high sensitivity.

Further, according to this embodiment, since each of the absorptive regions 4 formed in the substrate 2 of the biochemical analysis unit 1 can be irradiated with the laser beam 71 for a sufficiently long time, thereby exciting a fluorescent substance contained therein to cause the fluorescent substance to release fluorescence emission 78, it is possible to produce biochemical analysis data by photoelectrically detecting fluorescence emission 78 by the cooled CCD area sensor 85 with high sensitivity.

Moreover, according to this embodiment, since the position data indicating the positional relationship between the position of each of the absorptive regions 4 which is to release fluorescence emission 78 and the position of the photo-electric detecting surface of the CCD 90 by which fluorescence emission 78 led by the optical fiber member 80 is to be received are produced in advance and stored in the memory 108, it is possible to gather a number of the optical fiber members 80 in the vicinity of the end portions 80b opposite to the light collecting end portions 80a in arbitrary arrangement. Therefore, even when a number of the optical fiber members 80 are provided correspondingly to a number of the absorptive regions 4 formed in the substrate 2 of the biochemical analysis unit 1, it is possible to employ a stimulating ray source cutting filter 83 having a small area and a cooled CCD area sensor 85 provided with a photoelectric detecting surface having a small area. Therefore, it is possible to make the apparatus for producing biochemical analysis data smaller and to lower the cost of manufacturing the apparatus for producing biochemical analysis data.

Furthermore, according to this embodiment, since the substrate 2 of the biochemical analysis unit 1 is made of stainless steel and has a property of attenuating the energy of light, fluorescence emission 78 released from neighboring absorptive regions 4 formed in the substrate 2 of the biochemical analysis unit 1 can be effectively prevented from scattering in the substrate 2 of the biochemical analysis unit 1 and being mixed with each other. Therefore, it is possible to effectively prevent noise caused by the scattering of fluorescence emission 78 from being generated in biochemical analysis data produced by reading fluorescence data recorded in a number of the absorptive regions 4 formed in the substrate 2 of the biochemical analysis unit 1.

To the contrary, chemiluminescence data recorded in a number of the absorptive regions 4 formed in the substrate 2 of the biochemical analysis unit 1 are read by a further different apparatus for producing biochemical analysis data to produce biochemical analysis data.

Figure 12:
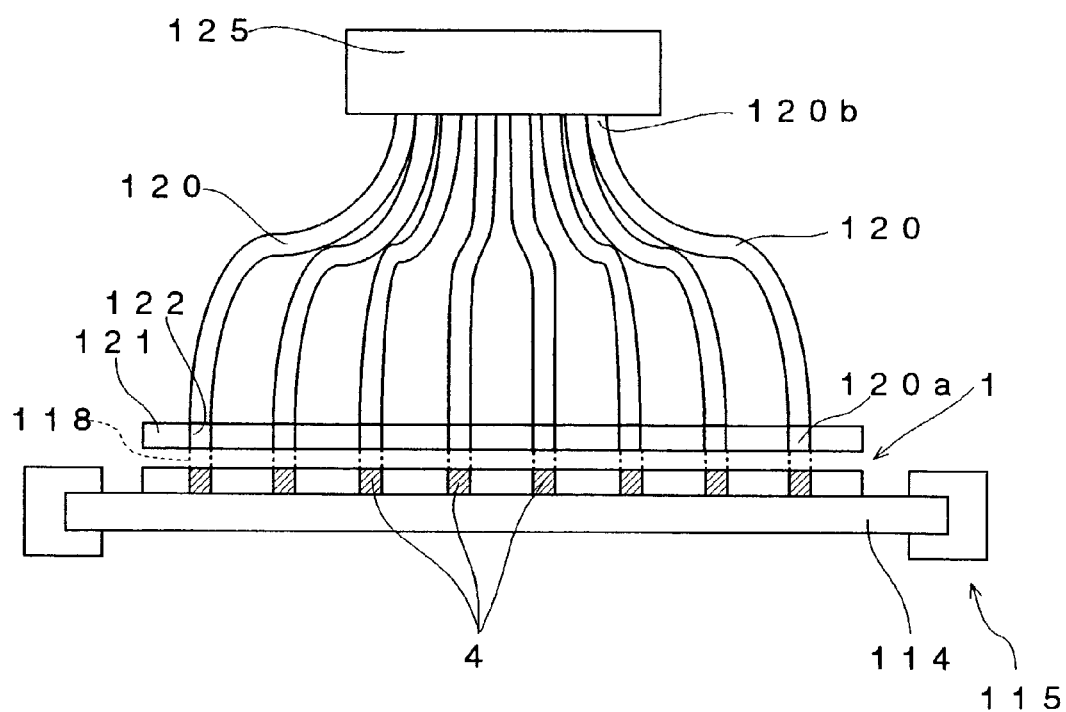
FIG. 12 is a schematic view showing an apparatus for producing biochemical analysis data for reading chemiluminescence data recorded in a number of absorptive regions formed in a substrate of a biochemical analysis unit, thereby producing biochemical analysis data, which is a further preferred embodiment of the present invention.

FIG. 12 is a schematic view showing an apparatus for producing biochemical analysis data for reading chemiluminescence data recorded in a number of the absorptive regions 4 formed in the substrate 2 of the biochemical analysis unit 1, thereby producing biochemical analysis data.

The apparatus for producing biochemical analysis data shown in FIG. 12 is not provided with any laser stimulating ray source or any stimulating ray cutting filter.

As shown in FIG. 12, the apparatus for producing biochemical analysis data includes a cooled CCD area sensor 125, a sample stage 115 provided with a transparent glass plate 114 on which the biochemical analysis unit 1 formed with a number of the absorptive regions 4 in which chemiluminescence data are recorded is to be placed, and a number of optical fiber members 120 having light collecting end portions 120a each of which is located in the vicinity of one the absorptive regions 4 formed in the substrate 2 of the biochemical analysis unit 1 placed on the sample stage 115 so as to face it.

In this embodiment, each of the optical fiber members 120 is constituted as a plurality of optical fibers and secured into a through-hole 122 formed in a fixing head 121 in the vicinity of the light collecting end portion 120a so that the light collecting end portion 120a of each of the optical fiber members 120 is positioned in a desired manner.

Further, as shown in FIG. 12, the optical fiber members 120 are gathered in the vicinity of end portions 120b opposite to the light collecting end portions 120a.

As shown in FIG. 12, each of the optical fiber members 120 is disposed so that end portion 120b thereof opposite to the light collecting end portion 120a faces the photo-electric detecting surface of a cooled CCD area sensor 125.

Figure 13:
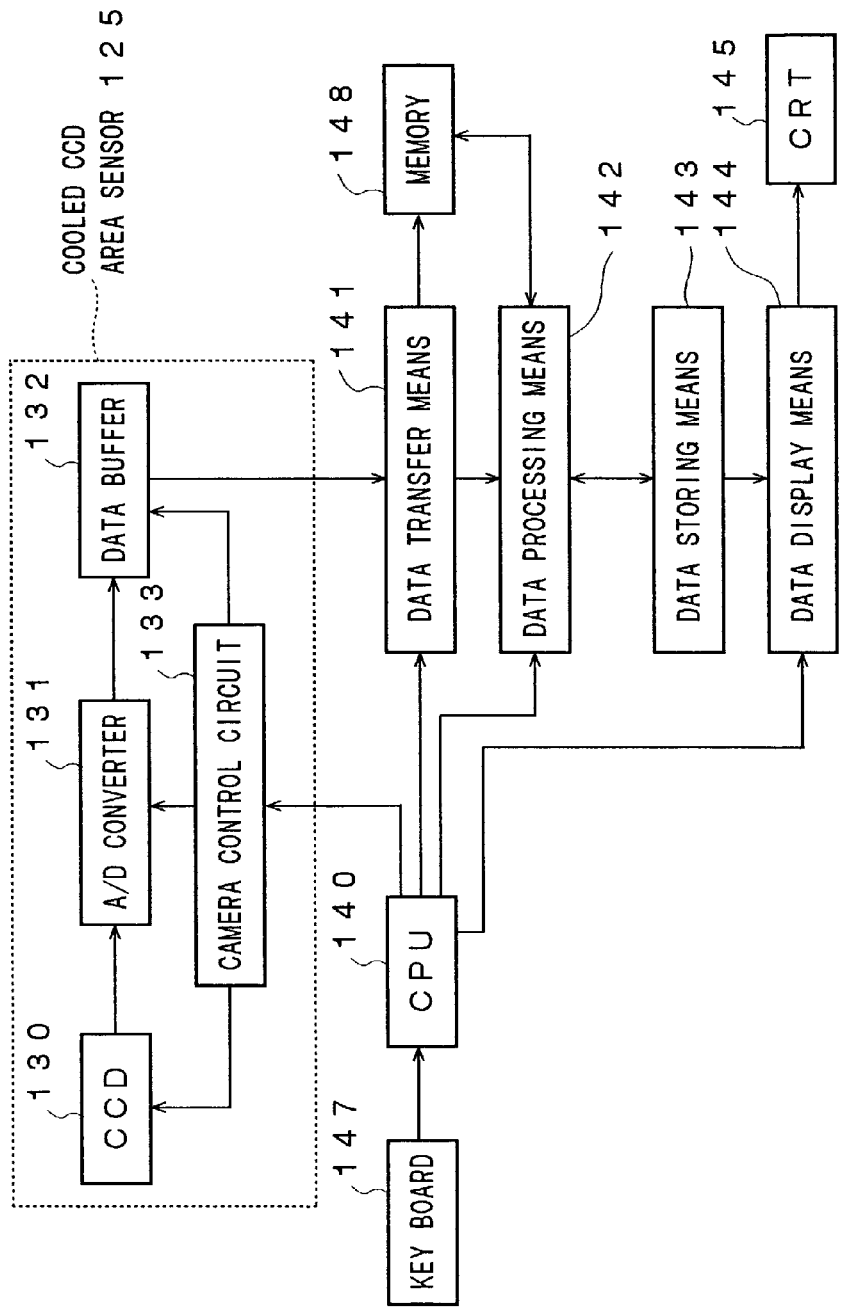
FIG. 13 is a block diagram of a control system, a detection system and a memory system of a cooled CCD area sensor and a control system, a memory system, a display system and an input system of an apparatus for producing biochemical analysis data, which is a further preferred embodiment of the present invention.

FIG. 13 is a block diagram of a control system, a detection system and a memory system of the cooled CCD area sensor 125 and a control system, a memory system, a display system and an input system of the apparatus for producing biochemical analysis data according to this embodiment.

As shown in FIG. 13, the cooled CCD area sensor 125 includes a CCD 130, an A/D converter 131 for digitizing analog data produced by the CCD 130 in the form of electric charge, a data buffer 132 for temporarily storing biochemical analysis data produced by digitizing analog data by the A/D converter 131 and a camera control circuit 133 for controlling the overall operation of the cooled CCD area sensor 125.

As shown in FIG. 13, the apparatus for producing biochemical analysis data according to this embodiment includes a CPU 140 for controlling the overall operation of the cooled CCD area sensor 125, a data transfer means 141 for reading biochemical analysis data produced by the cooled CCD area sensor 125 from the data buffer 132, a data processing means 142 for effecting data processing on biochemical analysis data read by the data transfer means 141, a data storing means 143 for storing biochemical analysis data subjected to data processing by the data processing means 142, a data display means 144 for producing quantitative data based on biochemical analysis data stored in the data storing means 143 and displaying the quantitative data on the screen of a CRT 145, a keyboard 147 which can be operated by a user and through which various instruction signals can be input, and a memory 148.

The CPU 140 is constituted so as to output various signals to the camera control circuit 123 of the cooled CCD area sensor 125 based on instruction signals input through the keyboard 147.

In this embodiment, since a number of the optical fiber members 120 are gathered in the vicinity of the end portions 120b opposite to the light collecting end portions 120a, what region on the photo-electric detecting surface of the CCD 130 of the cooled CCD area sensor 125 chemiluminescence emission 118 released from each of the absorptive layer regions 4 formed in the substrate 2 of the biochemical analysis unit 1 is led to and what region on the photo-electric detecting surface of the CCD 130 of the cooled CCD area sensor 125 the chemiluminescence emission 118 is received by depend upon how the optical fiber members 120 are gathered in the vicinity of the end portions 120b opposite to the light collecting end portions 120a and are not obvious.

Therefore, in this embodiment, it is detected in advance what region on the photo-electric detecting surface of the CCD 130 chemiluminescence emission 118 released from each of the absorptive layer regions 4 formed in the substrate 2 of the biochemical analysis unit 1 is led to by the optical fiber member 120 and what region on the photo-electric detecting surface of the CCD 130 the chemiluminescence emission 118 is received by and position data are produced and stored in the memory 148.

When position data are to be produced, similarly to the previous embodiments, the position data production optical system shown in FIG. 8 is installed and the position data producing unit 65 shown in FIG. 9 is placed on the transparent glass plate 114 of the sample stage 115.

Position data are produced and stored in the memory 148 in the same way as in the foregoing embodiments except that an LED light source 61 for emitting a light beam 60 having an arbitrary wavelength is employed,.

When the position data have been stored in the memory 148 in this manner, the apparatus for producing biochemical analysis data according to this embodiment reads chemiluminescence data recorded in a number of the absorptive regions 4 formed in the substrate 2 of the biochemical analysis unit 1 in the following manner.

The biochemical analysis unit 1 is first placed by a user on the transparent glass plate 114 of the sample stage 115, while in a state of releasing chemiluminescence emission as a result of contact of a labeling substance contained in the absorptive layers 4 formed in the substrate 2 of the biochemical analysis unit 1 and a chemiluminescent substrate.

In this embodiment, guide members (not shown) are provided in the sample stage 115 for ensuring that the biochemical analysis unit 1 is placed on the sample stage 115 so that a number of the absorptive regions 4 face the light collecting end portions 120a of the corresponding optical fiber members 120.

A data production start signal is then input through the keyboard 147 by the user and the data production start signal is input to the CPU 140.

When the CPU 130 receives the data production start signal, it outputs an exposure start signal to the camera control circuit 133 of the cooled CCD area sensor 125, thereby causing the cooled CCD area sensor 125 to start detecting chemiluminescence emission 118.

Chemiluminescence emission 118 released from each of the absorptive regions 4 is collected by the light collecting end portion 120a of the corresponding optical fiber member 120 disposed so as to face the absorptive region 4.

In this embodiment, since each of a number of the optical fiber members 120 is secured into the through-hole 122 formed in the fixing head 121 in the vicinity of the light collecting end portion 120a so that the light collecting end portion 120a of each of the optical fiber members 120 faces one of the absorptive region 4 of the biochemical analysis unit 1 placed on the transparent glass plate 114 of the sample stage 115, chemiluminescence emission 118 released from each of the absorptive regions 4 is reliably collected by the light collecting end portion 120a of the corresponding optical fiber member 120.

Chemiluminescence emission 118 collected by the light collecting end portion 120a of a particular optical fiber member 120 is guided by the optical fiber member 110 and impinges onto the photo-electric detecting surface of the cooled CCD area sensor 125, thereby forming an image on the photo-electric detecting surface of the CCD 130. The CCD 130 receives light of the thus formed image and accumulates it in the form of electric charges therein.

In this embodiment, since the substrate 2 of the biochemical analysis unit 1 is made of stainless steel and has a property of attenuating the energy of light, chemiluminescence emission 118 released from neighboring absorptive region 4 can be effectively prevented from scattering in the substrate 2 of the biochemical analysis unit 1 and being mixed with each other.

Further, in this embodiment, since the optical fiber members 120 are gathered in the vicinity of the end portions 120b opposite to the light collecting end portions 120a, even in the case where a number of the optical fiber members 120 are provided correspondingly to a number of the absorptive region 4 formed in the substrate 2 of the biochemical analysis unit 1, it is possible to employ a cooled CCD area sensor 125 provided with a photo-electric detecting surface having a small area. Therefore, it is possible to make an apparatus for producing biochemical analysis data smaller and to lower cost for manufacturing an apparatus for producing biochemical analysis data.

Further, in this embodiment, since the position data indicating the positional relationship between the position of each of the absorptive regions 4 which is to release chemiluminescence emission 118 and the position of the photo-electric detecting surface of the CCD 130 by which chemiluminescence emission led by the optical fiber member 120 is to be received are produced in advance and stored in the memory 148, it is not necessary to dispose the end portions 120b of the optical fiber members 120 in the same pattern as that of the light collecting end portions 120a thereof When a predetermined time has passed, the CPU 140 outputs an exposure completion signal to the camera control circuit 133 of the cooled CCD area sensor 125.

When the camera control circuit 133 receives the exposure completion signal from the CPU 140, it transfers analog data accumulated in the CCD 130 in the form of electric charge to the A/D converter 131 to cause the A/D converter 131 to digitize the data, thereby producing biochemical analysis data and to temporarily store the thus produced biochemical analysis data in the data buffer 132.

At the same time, the CPU 140 outputs a data transfer signal to the data transfer means 141 to cause it to read out the biochemical analysis data from the data buffer 132 of the cooled CCD area sensor 125 and to input them to the data processing means 142.

The data processing means 142 effects necessary data processing on the biochemical analysis data in accordance with the user's instructions, reads the position data stored in the memory 148 and stores the biochemical analysis data of each of the absorptive regions 4 formed in the substrate 2 of the biochemical analysis unit 1 in a corresponding memory area in the data storing means 143.

When the user inputs a data display signal through the keyboard 147, the CPU 140 outputs the data display signal to the data display means 144, thereby causing the data display means 144 to produce quantitative analysis data based on the biochemical analysis data stored in the data storing means 143 and to display them on the screen of the CRT 145.

According to this embodiment, since each of a number of the optical fiber members 120 is secured into the through-hole 122 formed in the fixing head 121 in the vicinity of the light collecting end portion 120a so that the light collecting end portion 120a of each of the optical fiber members 120 faces one of the absorptive regions 4 of the biochemical analysis unit 1 placed on the transparent glass plate 114 of the sample stage 115, chemiluminescence emission 118 released from each of the absorptive regions 4 is reliably collected by the light collecting end portion 120a of the corresponding optical fiber member 120. Therefore, since the efficiency for collecting chemiluminescence emission 118 can be markedly improved, biochemical analysis data having an excellent quantitative characteristic can be produced by photoelectrically detecting chemiluminescence emission 118 with high sensitivity.

Further, according to this embodiment, since chemiluminescence emission 118 released from a number of the absorptive regions 4 formed in the substrate 2 of the biochemical analysis unit 1 can be detected by the cooled CCD area sensor 125 for a sufficiently long time, even when chemiluminescence emission 118 is very weak, it is possible to produce biochemical analysis data having an excellent quantitative characteristic by photoelectrically detecting chemiluminescence emission 118 by the cooled CCD area sensor 125 with high sensitivity.

Moreover, according to this embodiment, since the position data indicating the positional relationship between the position of each of the absorptive regions 4 which is to release chemiluminescence emission 118 and the position of the photo-electric detecting surface of the CCD 130 by which chemiluminescence emission led by the optical fiber member 120 is to be received are produced in advance and stored in the memory 148, it is possible to gather a number of the optical fiber members 120 in the vicinity of the end portions 120b opposite to the light collecting end portions 120a in arbitrary arrangement. Therefore, even when a number of the optical fiber members 120 are provided correspondingly to a number of the absorptive regions 4 formed in the substrate 2 of the biochemical analysis unit 1, it is possible to employ a cooled CCD area sensor 125 provided with a photo-electric detecting surface having a small area. Therefore, it is possible to make the apparatus for producing biochemical analysis data smaller and to lower the cost of manufacturing the apparatus for producing biochemical analysis data.

Furthermore, according to this embodiment, since the substrate 2 of the biochemical analysis unit 1 is made of stainless steel and has a property of attenuating the energy of light, chemiluminescence emission 118 released from neighboring absorptive regions 4 formed in the substrate 2 of the biochemical analysis unit 1 can be effectively prevented from scattering in the substrate 2 of the biochemical analysis unit 1 and being mixed with each other. Therefore, it is possible to effectively prevent noise caused by the scattering of chemiluminescence emission 118 from being generated in biochemical analysis data produced by reading chemiluminescence data recorded in a number of the absorptive regions 4 formed in the substrate 2 of the biochemical analysis unit 1.

In this embodiment, it is possible to transfer chemiluminescence data recorded in a number of the absorptive regions 4 formed in the substrate 2 of the biochemical analysis unit 1 onto a stimulable phosphor sheet and read chemiluminescence data transferred onto the stimulable phosphor sheet to produce biochemical analysis data.

Figure 14:
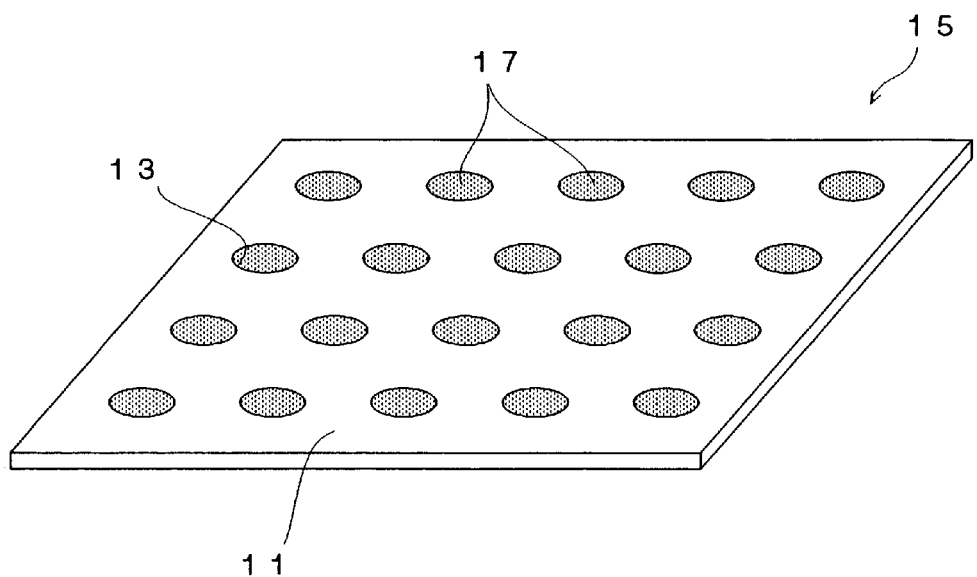
FIG. 14 is a schematic perspective view showing a stimulable phosphor sheet onto which chemiluminescence data recorded in a number of absorptive regions formed in a substrate of a biochemical analysis unit are to be transferred.

FIG. 14 is a schematic perspective view showing a stimulable phosphor sheet onto which chemiluminescence data recorded in a number of the absorptive regions 4 formed in the substrate 2 of the biochemical analysis unit 1 are to be transferred.

A stimulable phosphor sheet 15 shown in FIG. 14 has the same configuration as that of the stimulable phosphor sheet 10 shown in FIG. 4 except that a number of stimulable phosphor layer regions 17 are dot-like formed by charging SrS system stimulable phosphor capable of absorbing and storing light energy and a binder in a number of through-holes 13 formed in a support 11 made of stainless steel.

Chemiluminescence data recorded in a number of the absorptive regions 4 formed in the substrate 2 of the biochemical analysis unit 1 are transferred onto a number of the stimulable phosphor layer regions 17 of the stimulable phosphor sheet 15 shown in FIG. 14.

When chemiluminescence data recorded in a number of the absorptive regions 4 formed in the substrate 2 of the biochemical analysis unit 1 are to be transferred onto a number of the stimulable phosphor layer regions 17 formed in the support 11 of the stimulable phosphor sheet 15, a number of the absorptive regions 4 formed in the substrate 2 of the biochemical analysis unit 1 are first brought into contact with a chemiluminescent substrate.

As a result, chemiluminescence emission in a wavelength of visible light is selectively released from a number of the absorptive regions 4 formed in the substrate 2 of the biochemical analysis unit 1.

Figure 15:
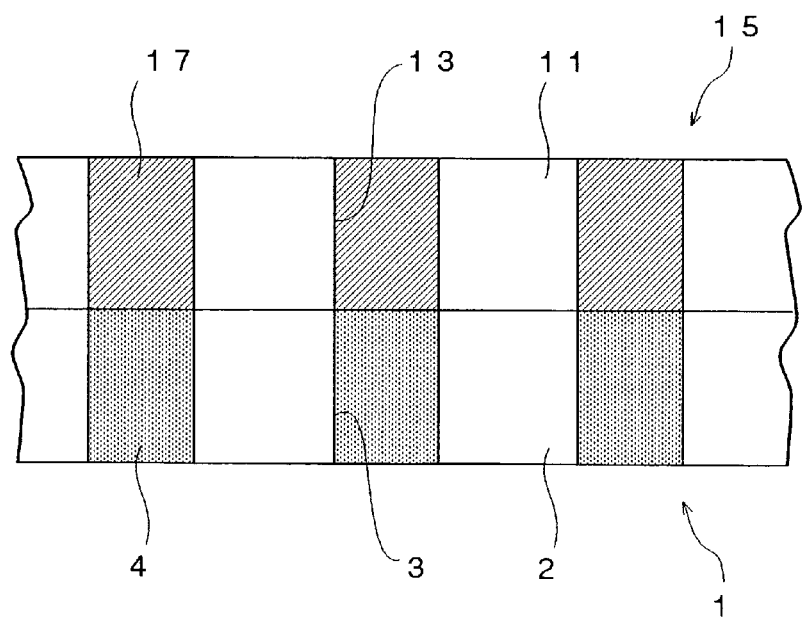
FIG. 15 is a schematic cross-sectional view showing a method for exposing a number of stimulable phosphor layer regions formed in a stimulable phosphor sheet to chemiluminescence emission released from a number of absorptive regions formed in a biochemical analysis unit.

As shown in FIG. 15, the stimulable phosphor sheet 15 is then superposed on the biochemical analysis unit 1 formed with a number of the absorptive regions 4 selectively releasing chemiluminescence emission in such a manner that a number of the stimulable phosphor layer regions 17 formed in the support 11 of the stimulable phosphor sheet 15 face the corresponding absorptive regions 4 formed in the substrate 2 of the biochemical analysis unit 1.

In this manner, each of the stimulable phosphor layer regions 17 formed in the support 11 of the stimulable phosphor sheet 15 is kept to face the corresponding absorptive region 4 formed in the substrate 2 of the biochemical analysis unit 1 for a predetermined time period, whereby a number of the stimulable phosphor layer regions 17 formed in the support 11 of the stimulable phosphor sheet 15 are exposed to chemiluminescence emission released from a number of the absorptive regions 4 formed in the substrate 2 of the biochemical analysis unit 1.

In this embodiment, since a number of the absorptive regions 4 of the biochemical analysis unit 1 are formed spaced apart from each other in the substrate 2 made of stainless steel and the substrate 2 made of stainless steel capable of attenuating light energy is present around each of the absorptive regions 4, chemiluminescence emission released from the absorptive regions 4 of the biochemical analysis unit 1 during the exposure operation can be efficiently prevented from scattering in the substrate 2 of the biochemical analysis unit 1. Further, since a number of the stimulable phosphor layer regions 17 of the stimulable phosphor sheet 15 are formed by charging stimulable phosphor in a number of the through-holes 13 formed in the support 11 made of stainless steel and the support 11 made of stainless steel capable of attenuating light energy is present around each of the stimulable phosphor layer regions 17, chemiluminescence emission released from the absorptive regions 4 of the biochemical analysis unit 1 during the exposure operation can be efficiently prevented from scattering in the support 11 of the stimulable phosphor sheet 15. Therefore, it is possible to selectively expose only the stimulable phosphor layer region 17 each of the absorptive regions 4 faces to the chemiluminescence emission released from the absorptive regions 4 of the biochemical analysis unit 1.

In this manner, chemiluminescence data are recorded in a number of the stimulable phosphor layer regions 17 formed in the support 11 of the stimulable phosphor sheet 15.

Figure 16:
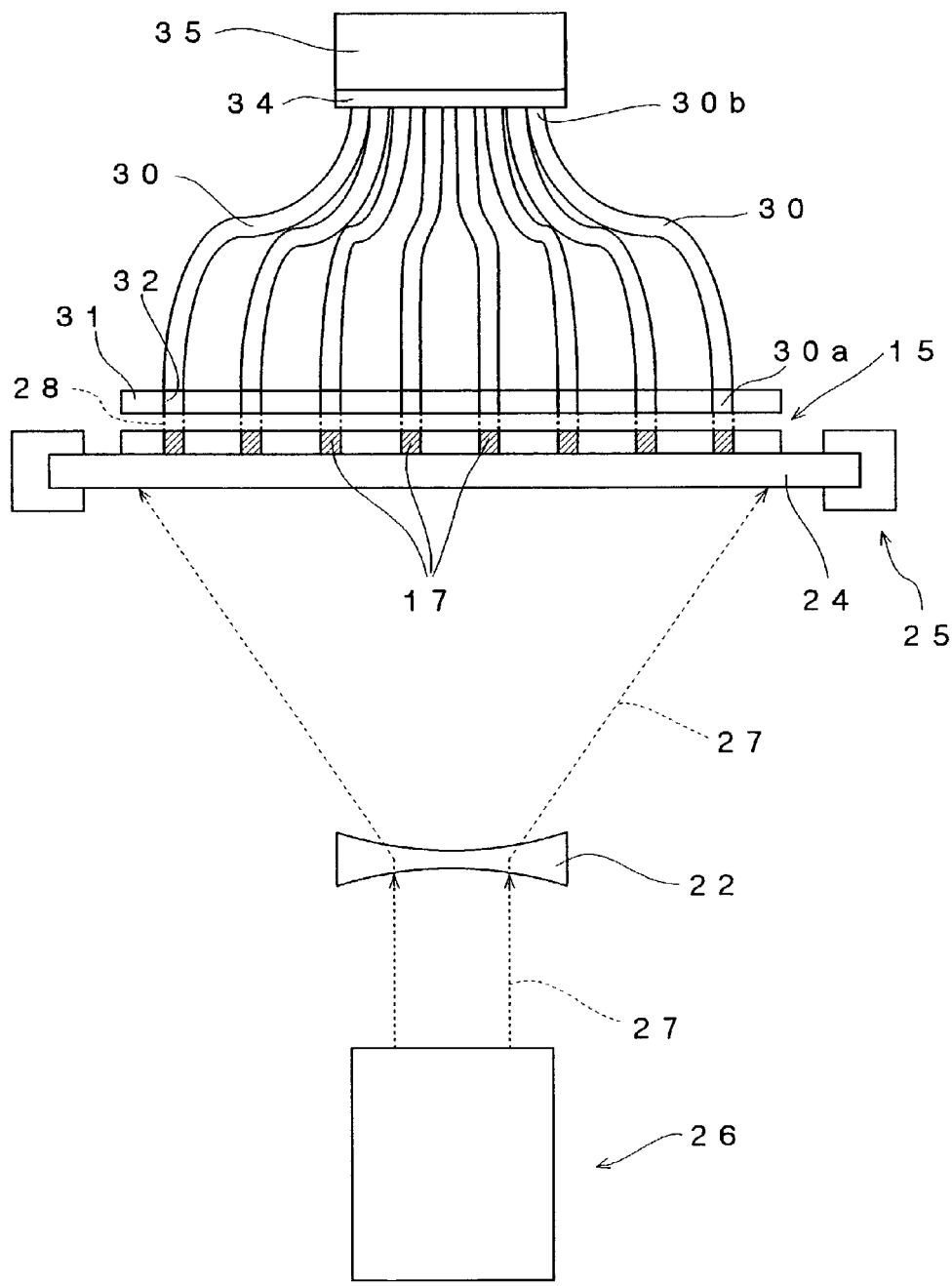
FIG. 16 is a schematic view showing an apparatus for producing biochemical analysis data by reading chemiluminescence data recorded in a number of stimulable phosphor layer regions formed in a support of a stimulable phosphor sheet shown in FIG. 14, thereby producing biochemical analysis data, which is a further preferred embodiment of the present invention.

FIG. 16 is a schematic view showing an apparatus for producing biochemical analysis data by reading chemiluminescence data recorded in a number of the stimulable phosphor layer regions 17 formed in the support 11 of the stimulable phosphor sheet 15 shown in FIG. 14, thereby producing biochemical analysis data.

The apparatus for producing biochemical analysis data shown in FIG. 16 has the same configuration as that of the apparatus for producing biochemical analysis data shown in FIG. 6 except that a laser stimulating ray source 26 for emitting a laser beam 27 having a wavelength of 980 nm effectively excitable SrS system stimulable phosphor is provided instead of the laser stimulating ray source 20 for emitting a laser beam 21 having a wavelength of 640 nm and that a stimulating ray cutting filter 34 having a property of cutting off light having a wavelength of that of the laser beam 27 emitted from the laser stimulating ray source 26 and transmitting only light having a wavelength of that of stimulated emission 28 released from a number of the stimulable phosphor layer regions 17 formed in the support 11 of the stimulable phosphor sheet 15 is provided instead of the stimulating ray cutting filter 33 having a property of cutting off light having a wavelength of that of the laser beam 21 emitted from the laser stimulating ray source 20 and transmitting only light having a wavelength of that of stimulated emission 28 released from a number of the stimulable phosphor layer regions 12 formed in the support 11 of the stimulable phosphor sheet 10.

Figure 17:
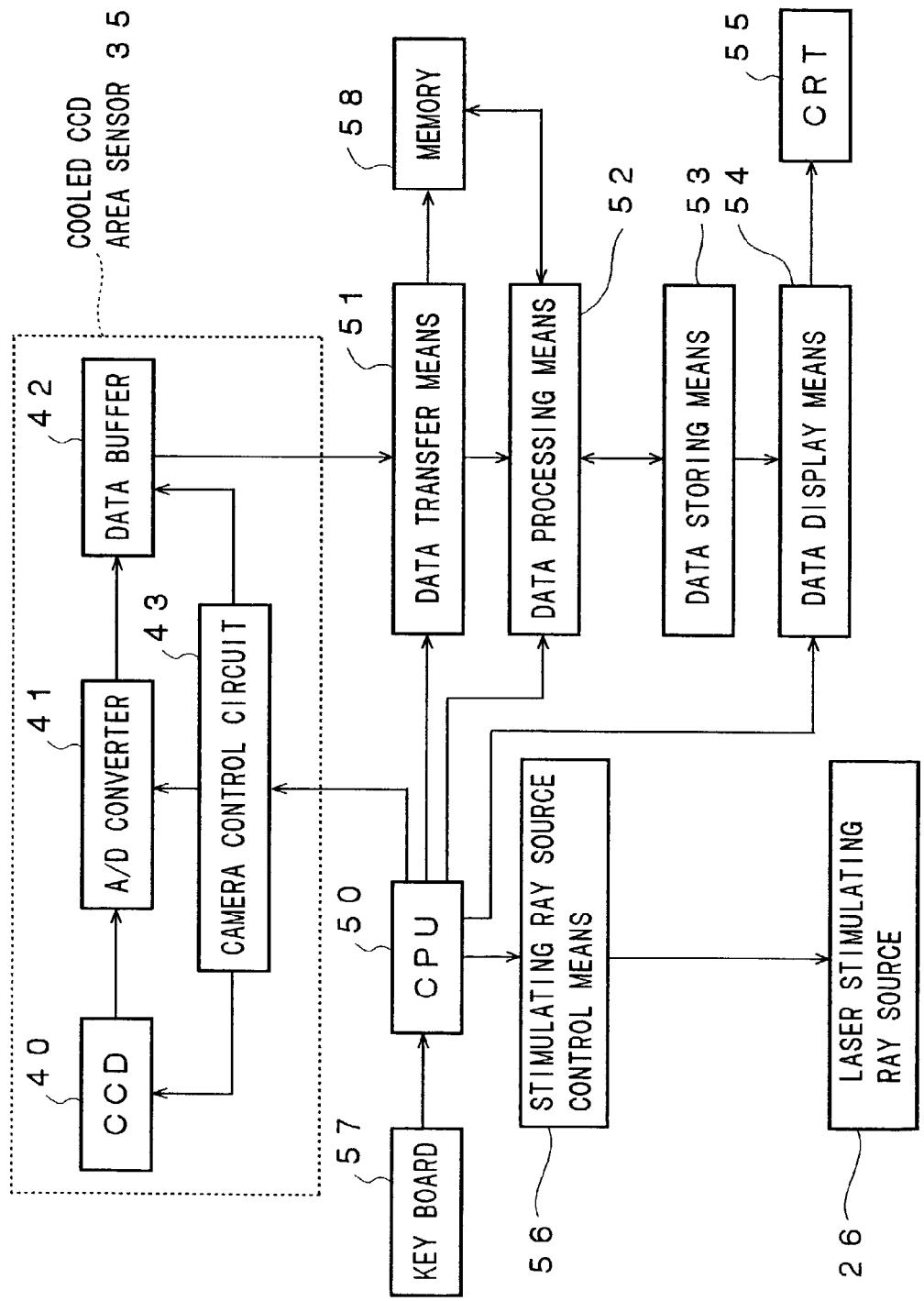
FIG. 17 is a block diagram of a control system, a detection system and a memory system of a cooled CCD area sensor and a control system, a memory system, a display system and an input system of an apparatus for producing biochemical analysis data, which is a further preferred embodiment of the present invention.

FIG. 17 is a block diagram of a control system, a detection system and a memory system of the cooled CCD area sensor 35 and a control system, a memory system, a display system and an input system of the apparatus for producing biochemical analysis data according to this embodiment.

As shown in FIG. 17, the control system, the detection system and the memory system of the cooled CCD area sensor 35 have exactly the same configurations as those of the cooled CCD area sensor 35 shown in FIG. 7 and the control system, the memory system, the display system and the input system of the apparatus for producing biochemical analysis data have the same configurations as those of the apparatus for producing biochemical analysis data shown in FIG. 7 except that the stimulating ray source control means 56 is constituted so as to control the laser stimulating ray source 26 for emitting a laser beam 27 having a wavelength of 980 nm.

In this embodiment, it is detected in advance what region on the photo-electric detecting surface of the CCD 40 of the cooled CCD area sensor 35 stimulated emission 28 released from each of the stimulable phosphor layer regions 17 formed in the support 11 of the stimulable phosphor sheet 15 is led to by the optical fiber member 30 and what region on the photo-electric detecting surface of the CCD 40 of the stimulated emission 28 is received by and position data are produced and stored in the memory 58.

When position data are to be produced, similarly to the above described embodiments, the laser stimulating ray source 26 and the concave lens 22 are removed from the apparatus for producing biochemical analysis data and the position data production optical system shown in FIG. 8 is installed. The position data producing unit 65 is then placed on the transparent glass plate 24 of the sample stage 25.

Position data are produced and stored in the memory 58 in the same way as in the above described embodiments except that an LED light source 61 for emitting a light beam 60 having a wavelength of that of stimulated emission released from SrS system stimulable phosphor is employed.

When the position data have been stored in the memory in this manner, the apparatus for producing biochemical analysis data according to this embodiment reads chemiluminescence data recorded in a number of the stimulable phosphor layer regions 17 formed in the support 11 of the stimulable phosphor sheet 15 in the following manner.

A stimulable phosphor sheet 15 formed with a number of the stimulable phosphor layer regions 17 in which chemiluminescence data are recorded is first set on the transparent glass plate 24 of the sample stage 25 by a user.

In this embodiment, guide members (not shown) are provided in the sample stage 25 for ensuring that the stimulable phosphor sheet 15 is placed on the sample stage 25 so that a number of the stimulable phosphor layer regions 17 face the light collecting end portions 30a of the corresponding optical fiber members 30.

A data production start signal is then input through the keyboard 57 by the user and the data production start signal is input to the CPU 50.

When the CPU 50 receives the data production start signal, it outputs the data production start signal to the laser stimulating ray source 26, thereby activating it and outputs an exposure start signal to the camera control circuit 43 of the cooled CCD area sensor 35, thereby causing the cooled CCD area sensor 35 to start detecting stimulated emssion 28.

A laser beam 27 having a wavelength of 980 nm emitted from the laser stimulating ray source 26 passes through a concave lens 22, thereby being diverged and the whole surface of the stimulable phosphor sheet 15 placed on the transparent glass plate 24 of the sample stage 25 is simultaneously irradiated with the diverged laser beam 27.

When each of the stimulable phosphor layer regions 17 formed in the support 11 of the stimulable phosphor sheet 15 is irradiated with the laser beam 27, stimulable phosphor contained therein is excited, thereby releasing stimulated emission 28.

Stimulated emission 28 released from each of the stimulable phosphor layer regions 17 is collected by the light collecting end portion 30a of the corresponding optical fiber member 30 disposed so as to face the stimulable phosphor layer region 17.

In this embodiment, since each of a number of the optical fiber members 30 is secured into the through-hole 32 formed in the fixing head 31 in the vicinity of the light collecting end portion 30a so that the light collecting end portion 30a of each of the optical fiber members 30 faces one of the stimulable phosphor layer regions 17 of the stimulable phosphor sheet 15 placed on the transparent glass plate 24 of the sample stage 25, stimulated emission 28 released from each of the stimulable phosphor layer regions 17 is reliably collected by the light collecting end portion 30a of the corresponding optical fiber member 30.

Further, in this embodiment, since the support 11 of the stimulable phosphor sheet 15 is made of stainless steel and has a property of attenuating the energy of light, stimulated emission 28 released from neighboring stimulable phosphor layer regions 17 can be effectively prevented from scattering in the support 11 of the stimulable phosphor sheet 15 and being mixed with each other.

Stimulated emission 28 collected by the light collecting end portion 30a of a particular optical fiber member 30 is guided by the optical fiber member 30 and impinges onto a corresponding region of the stimulating ray cutting filter 34.

In this embodiment, since the optical fiber members 30 are gathered in the vicinity of the end portions 30b opposite to the light collecting end portions 30a, even in the case where a number of the optical fiber members 30 are provided correspondingly to a number of the stimulable phosphor layer regions 17 formed in the support 11 of the stimulable phosphor sheet 15, it is possible to employ a stimulating ray source cutting filter 34 having a small area and a cooled CCD area sensor 35 provided with a photo-electric detecting surface having a small area. Therefore, it is possible to make an apparatus for producing biochemical analysis data smaller and to lower cost for manufacturing an apparatus for producing biochemical analysis data.

Further, in this embodiment, since the position data indicating the positional relationship between the position of each of the stimulable phosphor layer regions 17 which is to release stimulated emission 28 and the position of the photo-electric detecting surface of the CCD 40 by which stimulated emission 28 led by the optical fiber member 30 is to be received are produced in advance and stored in the memory 58, it is not necessary to dispose the end portions 30b of the optical fiber members 30 in the same pattern as that of the light collecting end portions 30a thereof.

Since the stimulating ray source cutting filter 34 has a property of transmitting only light having a wavelength of that of stimulated emission 28 released from the stimulable phosphor layer regions 17 formed in the support 11 of the stimulable phosphor sheet 15 and cutting light having a wavelength of 980 nm, light having a wavelength of 980 nm is cut off by the stimulating ray source cutting filter 34 and only stimulated emission 28 released from the stimulable phosphor layer regions 17 is transmitted therethrough and impinges onto the photo-electric detecting surface of the CCD 40, thereby forming an image on the photo-electric detecting surface of the CCD 40. The CCD 40 receives light of the thus formed image and accumulates it in the form of electric charges therein.

When a predetermined time has passed, the CPU 50 outputs an exposure completion signal to the camera control circuit 43 of the cooled CCD area sensor 35 and outputs a data production completion signal to the stimulating ray source control means 56.

When the stimulating ray source control means 56 receives the data production completion signal from the CPU 50, it turns off the laser stimulating ray source 26.

On the other hand, when the camera control circuit 43 receives the exposure completion signal from the CPU 50, it transfers analog data accumulated in the CCD 40 in the form of electric charge to the A/D converter 41 to cause the A/D converter 41 to digitize the data, thereby producing biochemical analysis data and to temporarily store the thus produced biochemical analysis data in the data buffer 42.

At the same time, the CPU 50 outputs a data transfer signal to the data transfer means 51 to cause it to read out the biochemical analysis data from the data buffer 42 of the cooled CCD area sensor 35 and to input them to the data processing means 52.

The data processing means 52 effects necessary data processing on the biochemical analysis data in accordance with the user's instructions, reads the position data stored in the memory 58 and stores the biochemical analysis data of each of the stimulable phosphor layer regions 17 formed in the support 11 of the stimulable phosphor sheet 15 in a corresponding memory area in the data storing means 53.

When the user inputs a data display signal through the keyboard 57, the CPU 50 outputs the data display signal to the data display means 54, thereby causing the data display means 54 to produce quantitative analysis data based on the biochemical analysis data stored in the data storing means 53 and to display them on the screen of the CRT 55.

According to this embodiment, since each of a number of the optical fiber members 30 is secured into the through-hole 32 formed in the fixing head 31 in the vicinity of the light collecting end portion 30a so that the light collecting end portion 30a of each of the optical fiber members 30 faces one of the stimulable phosphor layer regions 17 of the stimulable phosphor sheet 15 placed on the transparent glass plate 24 of the sample stage 25, stimulated emission 28 released from each of the stimulable phosphor layer regions 17 is reliably collected by the light collecting end portion 30a of the corresponding optical fiber member 30. Therefore, since the efficiency for collecting stimulated emission 28 can be markedly improved, biochemical analysis data having an excellent quantitative characteristic can be produced by photoelectrically detecting stimulated emission 28 with high sensitivity.

Further, according to this embodiment, since each of the stimulable phosphor layer regions 17 formed in the support 11 of the stimulable phosphor sheet 15 can be irradiated with the laser beam 27 for a sufficiently long time, thereby exciting stimulable phosphor contained therein to cause the stimulable phosphor to release the energy of chemiluminescence emission stored therein in the form of stimulated emission 28, it is possible to produce biochemical analysis data by photoelectrically detecting stimulated emission 28 by the cooled CCD area sensor 35 with high sensitivity.

Moreover, according to this embodiment, since the position data indicating the positional relationship between the position of each of the stimulable phosphor layer regions 17 which is to release stimulated emission 28 and the position of the photo-electric detecting surface of the CCD 40 by which stimulated emission 28 led by the optical fiber member 30 is to be received are produced in advance and stored in the memory 58, it is possible to gather a number of optical fiber members 30 in the vicinity of the end portions 30b opposite to the light collecting end portions 30a in arbitrary arrangement. Therefore, even when a number of the optical fiber members 30 are provided correspondingly to a number of the stimulable phosphor layer regions 17 formed in the support 11 of the stimulable phosphor sheet 15, it is possible to employ a stimulating ray source cutting filter 33 having a small area and a cooled CCD area sensor 35 provided with a photo-electric detecting surface having a small area. Therefore, it is possible to make the apparatus for producing biochemical analysis data smaller and to lower the cost of manufacturing the apparatus for producing biochemical analysis data.

Furthermore, according to this embodiment, since the support 11 of the stimulable phosphor sheet 15 is made of stainless steel and has a property of attenuating the energy of light, stimulated emission 28 released from neighboring stimulable phosphor layer regions 17 formed in the support 11 of the stimulable phosphor sheet 15 can be effectively prevented from scattering in the support 11 of the stimulable phosphor sheet 15 and being mixed with each other. Therefore, it is possible to effectively prevent noise caused by the scattering of stimulated emission 28 from being generated in biochemical analysis data produced by reading chemiluminescence data recorded in a number of the stimulable phosphor layer regions 17 formed in the support 11 of the stimulable phosphor sheet 15.

Figure 18:
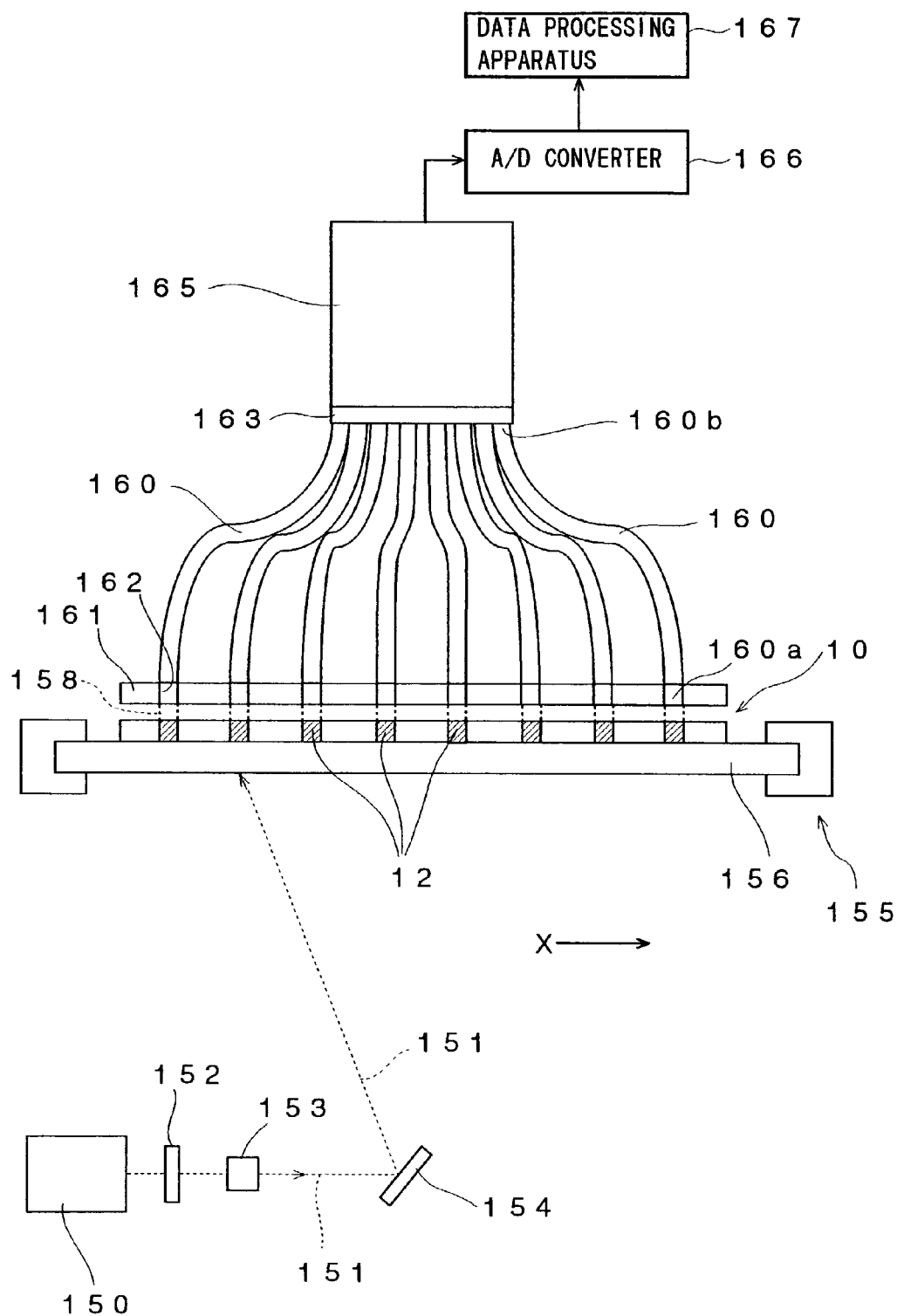
FIG. 18 is a schematic view showing an apparatus for producing biochemical analysis data which is a further preferred embodiment of the present invention.

FIG. 18 is a schematic view showing an apparatus for producing biochemical analysis data which is a further preferred embodiment of the present invention.

An apparatus for producing biochemical analysis data according to this embodiment is constituted so as to read radiation data recorded in a number of the stimulable phosphor layer regions 12 formed in the support 11 of the stimulable phosphor sheet 10 to produce biochemical analysis data and is provided with a laser stimulating ray source 150 for emitting a laser beam 151 having a wavelength of 640 nm. In this embodiment, the laser stimulating ray source 150 constituted by a semiconductor laser beam source.

A laser beam 151 having a wavelength of 640 nm and emitted from the laser stimulating ray source 150 passes through a collimator lens 152, thereby being made a parallel beam and enters a beam expander 153.

The laser beam 151 passes through the beam expander 153, whereby the beam diameter thereof is accurately adjusted and impinges onto a reflection mirror 154, thereby being reflected by the reflection mirror 154.

The laser beam 151 reflected by the reflection mirror 154 impinges onto one of the stimulable phosphor layer regions 12 formed in the support 11 of the stimulable phosphor sheet 10 placed on a transparent glass plate 156 of a sample stage 155.

In this embodiment, the reflection mirror 154 is controlled to be rotated by a motor (not shown) so that the stimulable phosphor sheet 10 is scanned with the laser beam 151 reflected by the reflection mirror 154 in a main scanning direction indicated by an arrow X in FIG. 18 at a pitch equal to the distance between neighboring stimulable phosphor layer regions 12.

As shown in FIG. 18, in this embodiment, the apparatus for producing biochemical analysis data includes a number of optical fiber members 160 each of which has a light collecting end portion 160a facing one of a number of the stimulable phosphor layer regions 12 formed in the support 11 of the stimulable phosphor sheet 10 and being located in the vicinity thereof.

In this embodiment, each of the optical fiber members 160 is constituted as a plurality of optical fibers and secured into a through-hole 162 formed in a fixing head 161 in the vicinity of the light collecting end portion 160*a* so that the light collecting end portion 160*a* of each of the optical fiber members 160 is positioned in a desired manner.

Further, as shown in FIG. 18, the optical fiber members 160 are gathered in the vicinity of end portions 160*b* opposite to the light collecting end portions 160*a*.

As shown in FIG. 18, each of the optical fiber members 160 is disposed so that end portion 160*b* thereof opposite to the light collecting end portion 160*a* faces a stimulating ray cutting filter 163. The stimulating ray cutting filter 163 has a property of transmitting light having a wavelength of that of stimulated emission 158 and cutting light having a wavelength of 640 nm.

The apparatus for producing biochemical analysis data according to this embodiment includes a photomultiplier 165 disposed so as to face the surface of the stimulating ray cutting filter 163 opposite to the optical fiber members 160. Analog data produced by photoelectrically detecting stimulated emission 158 by the photomultiplier 165 are output to an A/D converter 166 and converted by the A/D converter 166 to digital data and the thus produced digital data are forwarded to a data processing apparatus 167.

In this embodiment, the sample stage 155, the fixing head 161, a number of the optical fiber members 160, the stimulating ray cutting filter 163 and the photomultiplier 165 are moved by a scanning mechanism (not shown) in a sub-scanning direction perpendicular to the main scanning direction indicated by the arrow X in FIG. 18.

Figure 19:
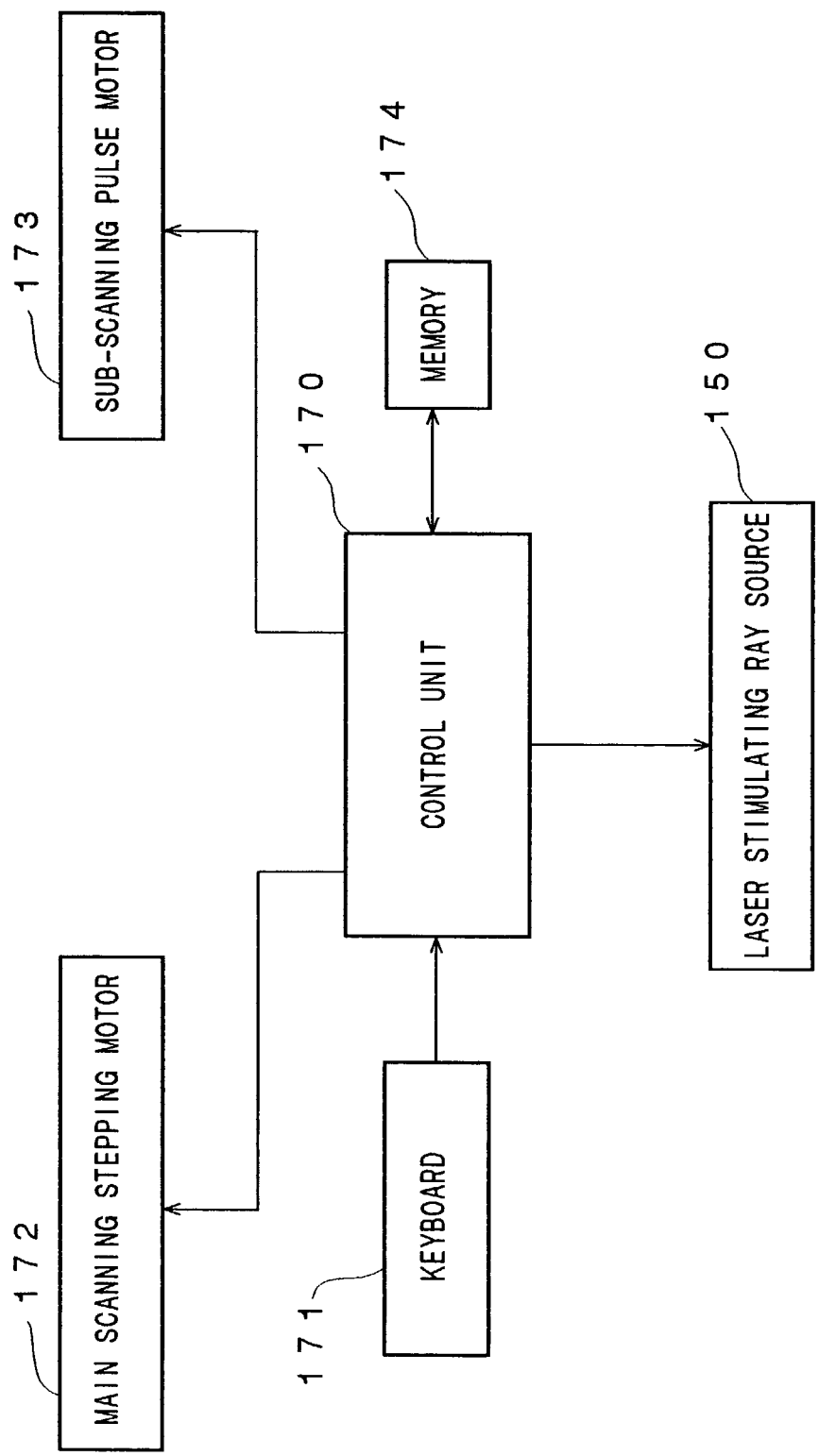
FIG. 19 is a block diagram of a control system, an input system, a drive system, a detection system and a memory system of the apparatus for producing biochemical analysis data shown in FIG. 18.

FIG. 19 is a block diagram of a control system, an input system, a drive system, a detection system and a memory system of the apparatus for producing biochemical analysis data shown in FIG. 18.

As shown in FIG. 19, the control system of the apparatus for producing biochemical analysis data includes a control unit 170 for controlling the overall operation of the apparatus for producing biochemical analysis data and the input system of the apparatus for producing biochemical analysis data includes a keyboard 171 which can be operated by a user and through which various instruction signals can be input.

As shown in FIG. 19, the drive system of the apparatus for producing biochemical analysis data includes a main scanning stepping motor 172 for intermittently rotating the reflection mirror 154 so that the stimulable phosphor sheet 10 is scanned with the laser beam 151 reflected by the reflection mirror 154 in a main scanning direction indicated by the arrow X in FIG. 18 at a pitch equal to the distance between neighboring stimulable phosphor layer regions 12, and a sub-scanning pulse motor 173 for intermittently moving the sample stage 155, the fixing head 161, a number of the optical fiber members 160, the stimulating ray cutting filter 163 and the photomultiplier 165 in the sub-scanning direction perpendicular to the main scanning direction indicated by the arrow X in FIG. 18. The detection system of the apparatus for producing biochemical analysis data includes the photomultiplier 165.

As shown in FIG. 19, the memory system of the apparatus for producing biochemical analysis data includes a memory 174 for storing drive pulses to be output to the main scanning stepping motor 172 in accordance with the rotational position of the reflecting mirror 154.

The control unit 170 is constituted so as to output a drive signal and a drive stop signal to the laser stimulating ray source 150, thereby on and off controlling the laser stimulating ray source 150.

The thus constituted apparatus for producing biochemical analysis data according to this embodiment reads radiation data recorded in a number of the stimulable phosphor layer regions 12 formed in the support 11 of the stimulable phosphor sheet 10 in the following manner.

A stimulable phosphor sheet 10 formed with a number of the stimulable phosphor layer regions 12 in which radiation data are recorded is first set on the transparent glass plate 156 of the sample stage 155 by a user.

A data production start signal is then input through the keyboard 171 by the user and the data production start signal is input to the control unit 170.

When the control unit 170 receives the data production start signal, it produces a drive signal based on the drive pulses in accordance with the rotational position of the reflecting mirror 154 stored in the memory 174 and outputs it to the main scanning stepping motor 172, thereby causing the main scanning stepping motor 172 to rotate the reflection mirror 154. When the control unit 170 determines that the reflection mirror 154 has been rotated to a position where the laser beam 151 can be projected onto a first stimulable phosphor layer region 12 among a number of the stimulable phosphor layer regions 12 formed in the support 11 of the stimulable phosphor sheet 10, it outputs a drive stop signal to the main scanning stepping motor 172 and a drive signal to the laser stimulating ray source 150, thereby actuating it to emit a laser beam 151 having a wavelength of 640 nm.

The laser beam 151 having a wavelength of 640 nm and emitted from the laser stimulating ray source 150 passes through a collimator lens 152, thereby being made a parallel beam and enters a beam expander 153.

The laser beam 151 passes through the beam expander 153, whereby the beam diameter thereof is accurately adjusted and impinges onto a reflection mirror 154, thereby being reflected by the reflection mirror 154.

The laser beam 151 reflected by the reflection mirror 154 impinges onto the first stimulable phosphor layer regions 12 formed in the support 11 of the stimulable phosphor sheet 10 placed on the transparent glass plate 156 of the sample stage 155.

As a result, stimulable phosphor contained in the first stimulable phosphor layer regions 12 is excited by the laser beam 151, thereby releasing stimulated emission 158 from the first stimulable phosphor layer region 12.

Stimulated emission 158 released from the first stimulable phosphor layer region 12 is collected by the light collecting end portion 160*a* of the corresponding optical fiber member 160 disposed so as to face the first stimulable phosphor layer region 12.

In this embodiment, since each of a number of the optical fiber members 160 is secured into the through-hole 162 formed in the fixing head 161 in the vicinity of the light collecting end portion 160*a* so that the light collecting end portion 160*a* of each of the optical fiber members 160 faces one of the stimulable phosphor layer regions 12 of the stimulable phosphor sheet 10 placed on the transparent glass plate 156 of the sample stage 155, stimulated emission 158 released from the first stimulable phosphor layer regions 12 is reliably collected by the light collecting end portion 160*a* of the corresponding optical fiber member 160.

Further, in this embodiment, since the support 11 of the stimulable phosphor sheet 10 is made of stainless steel and has a property of attenuating the energy of light, stimulated emission 158 released from neighboring stimulable phosphor layer regions 12 can be effectively prevented from scattering in the support 11 of the stimulable phosphor sheet 10 and being mixed with each other.

Stimulated emission 158 collected by the light collecting end portion 160a of the optical fiber member 160 corresponding to the first stimulable phosphor layer region 12 is guided by the optical fiber member 160 and impinges onto a corresponding region of the stimulating ray cutting filter 163.

In this embodiment, since the optical fiber members 160 are gathered in the vicinity of the end portions 160b opposite to the light collecting end portions 160a, even in the case where a number of the optical fiber members 160 are provided correspondingly to a number of the stimulable phosphor layer regions 12 formed in the support 11 of the stimulable phosphor sheet 10, it is possible to employ a stimulating ray source cutting filter 163 having a small area and a photomultiplier 165 provided with a photo-electric detecting surface having a small area.

Therefore, it is possible to make an apparatus for producing biochemical analysis data smaller and to lower cost for manufacturing an apparatus for producing biochemical analysis data.

Further, since the apparatus for producing biochemical analysis data according to this embodiment is constituted so as to produce biochemical analysis data by scanning a number of the stimulable phosphor layer regions 12 formed in the support 11 of the stimulable phosphor sheet 10 with the laser beam 151, successively exciting stimulable phosphor contained in a number of the stimulable phosphor layer regions 12, and photoelectrically detecting stimulated emission 158 released from the stimulable phosphor layer regions 12 with the photomultiplier 165, it is not necessary to dispose the end portions 160b of the optical fiber members 160 in the same pattern as that of the light collecting end portions 160a thereof.

Since the stimulating ray source cutting filter 163 has a property of transmitting only light having a wavelength of that of stimulated emission 158 released from the stimulable phosphor layer regions 12 formed in the support 11 of the stimulable phosphor sheet 10 and cutting light having a wavelength of 640 nm, light having a wavelength of 640 nm is cut off by the stimulating ray source cutting filter 163 and only stimulated emission 158 released from the stimulable phosphor layer regions 12 is transmitted therethrough and photoelectrically detected by the photomultiplier 165.

Analog data produced by photoelectrically detecting stimulated emission 158 with the photomultiplier 165 are converted by the A/D converter 166 into digital data and the digital data are fed to the data processing apparatus 167.

When a predetermined time has passed after the laser stimulating ray source 150 was turned on, the control unit 170 outputs a drive stop signal to the laser stimulating ray source 150, thereby turning it off. At the same time, the control unit 170 produces a drive signal based on the drive pulses in accordance with the rotational position of the reflecting mirror 154 stored in the memory 174 and outputs it to the main scanning stepping motor 172, thereby causing the main scanning stepping motor 172 to rotate the reflection mirror 154 to a position where a laser beam 151 can be projected onto a second stimulable phosphor layer region 12 next to the first stimulable phosphor layer region 12 formed in the support 11 of the stimulable phosphor sheet 10.

When the control unit 170 determines that the reflection mirror 154 has been rotated to a position where a laser beam 151 can be projected onto a second stimulable phosphor layer region 12 next to the first stimulable phosphor layer region 12 formed in the support 11 of the stimulable phosphor sheet 10, it outputs a drive signal to the laser stimulating ray source 150 to turn it on, thereby causing the laser beam 151 to excite stimulable phosphor contained in the second stimulable phosphor layer region 12 formed in the support 11 of the stimulable phosphor sheet 10.

Similarly to the above, the second stimulable phosphor layer region 12 formed in the support 11 of the stimulable phosphor sheet 10 is irradiated with the laser beam 151 for a predetermined time and when stimulated emission 158 released from the second stimulable phosphor layer region 12 has been collected by the corresponding optical fiber member 160 and photoelectrically detected by the photomultiplier 165 via the stimulating ray cutting filter 163, the control unit 170 outputs a drive stop signal to the laser stimulating ray source 150, thereby turning it off. At the same time, the control unit 170 produces a drive signal based on the drive pulses in accordance with the rotational position of the reflecting mirror 154 stored in the memory 174 and outputs it to the main scanning stepping motor 172, thereby causing the main scanning stepping motor 172 to rotate the reflection mirror 154 to a position where a laser beam 151 can be projected onto a third stimulable phosphor layer region 12 next to the second stimulable phosphor layer region 12 formed in the support 11 of the stimulable phosphor sheet 10.

In this manner, the on and off operation of the laser stimulating ray source 150 is repeated in synchronism with the intermittent rotation of the reflection mirror 154 and when the control unit 170 determines that the stimulable phosphor layer regions 12 included in a first line of the stimulable phosphor layer regions 12 formed in the support 11 of the stimulable phosphor sheet 10 have been scanned with the laser beam 151, it outputs a drive signal to the main scanning stepping motor 172, thereby returning the reflection mirror 154 to its original position and outputs a drive signal to the sub-scanning pulse motor 173, thereby causing it to move the sample stage 155, the fixing head 161, a number of the optical fiber members 160, the stimulating ray cutting filter 163 and the photomultiplier 165 by one scanning line in the sub-scanning direction.

When the control unit 170 determines that the reflection mirror 154 has been returned to its original position and determines that the sample stage 155, the fixing head 161, a number of the optical fiber members 160, the stimulating ray cutting filter 163 and the photomultiplier 165 have been moved by one scanning line in the sub-scanning direction, similarly to the manner in which the stimulable phosphor layer regions 12 included in the first line of the stimulable phosphor layer regions 12 formed in the support 11 of the stimulable phosphor sheet 10 were sequentially irradiated with the laser beam 151 emitted from the laser stimulating ray source 150, the stimulable phosphor layer regions 12 included in a second line of the stimulable phosphor layer regions 12 formed in the support 11 of the stimulable phosphor sheet 10 are sequentially irradiated with the laser beam 151 emitted from the laser stimulating ray source 150, thereby exciting stimulable phosphor contained in the stimulable phosphor layer regions 12 included in the second line and stimulated emission 158 released from the stimulable phosphor layer regions 12 in the second line is sequentially and photoelectrically detected by the photomultiplier 165.

Analog data produced by photoelectrically detecting stimulated emission 158 with the photomultiplier 165 are converted by the A/D converter 166 into digital data and the digital data are fed to the data processing apparatus 167.

When all of the stimulable phosphor layer regions 12 formed in the support 11 of the stimulable phosphor sheet 10 have been scanned with the laser beam 151 to excite stimulable phosphor contained in the stimulable phosphor layer regions 12 and digital data produced by collecting stimulated emission 158 released from the stimulable phosphor layer regions 12 by the corresponding optical fiber members 160, leading the stimulated emission 158 to the photomultiplier 165 via the stimulating ray cutting filter 163, photoelectrically detecting the stimulated emission 158 by the photomultiplier 165 to produce analog data and digitizing the analog data by the A/D converter 166 have been forwarded to the data processing apparatus 167, the control unit 170 outputs a drive stop signal to the laser stimulating ray source 150 thereby turning it off.

As described above, radiation data recorded in a number of the stimulable phosphor layer regions 12 formed in the support 11 of the stimulable phosphor sheet 10 are read to produce biochemical analysis data.

According to this embodiment, since each of a number of the optical fiber members 160 is secured into the through-hole 162 formed in the fixing head 161 in the vicinity of the light collecting end portion 160a so that the light collecting end portion 160a of each of the optical fiber members 160 faces one of the stimulable phosphor layer regions 12 of the stimulable phosphor sheet 10 placed on the transparent glass plate 156 of the sample stage 155, stimulated emission 158 released from each of the stimulable phosphor layer regions 12 can be reliably collected by the light collecting end portion 160a of the corresponding optical fiber member 160. Therefore, since the efficiency for collecting stimulated emission 158 can be markedly improved, biochemical analysis data having an excellent quantitative characteristic can be produced by photoelectrically detecting stimulated emission 158 with high sensitivity.

Furthermore, according to this embodiment, since the support 11 of the stimulable phosphor sheet 10 is made of stainless steel and has a property of attenuating the energy of light, stimulated emission 158 released from neighboring stimulable phosphor layer regions 12 formed in the support 11 of the stimulable phosphor sheet 10 can be effectively prevented from scattering in the support 11 of the stimulable phosphor sheet 10 and being mixed with each other. Therefore, it is possible to effectively prevent noise caused by the scattering of stimulated emission 158 from being generated in biochemical analysis data produced by reading radiation data recorded in a number of the stimulable phosphor layer regions 12 formed in the support 11 of the stimulable phosphor sheet 10.

Figure 20:
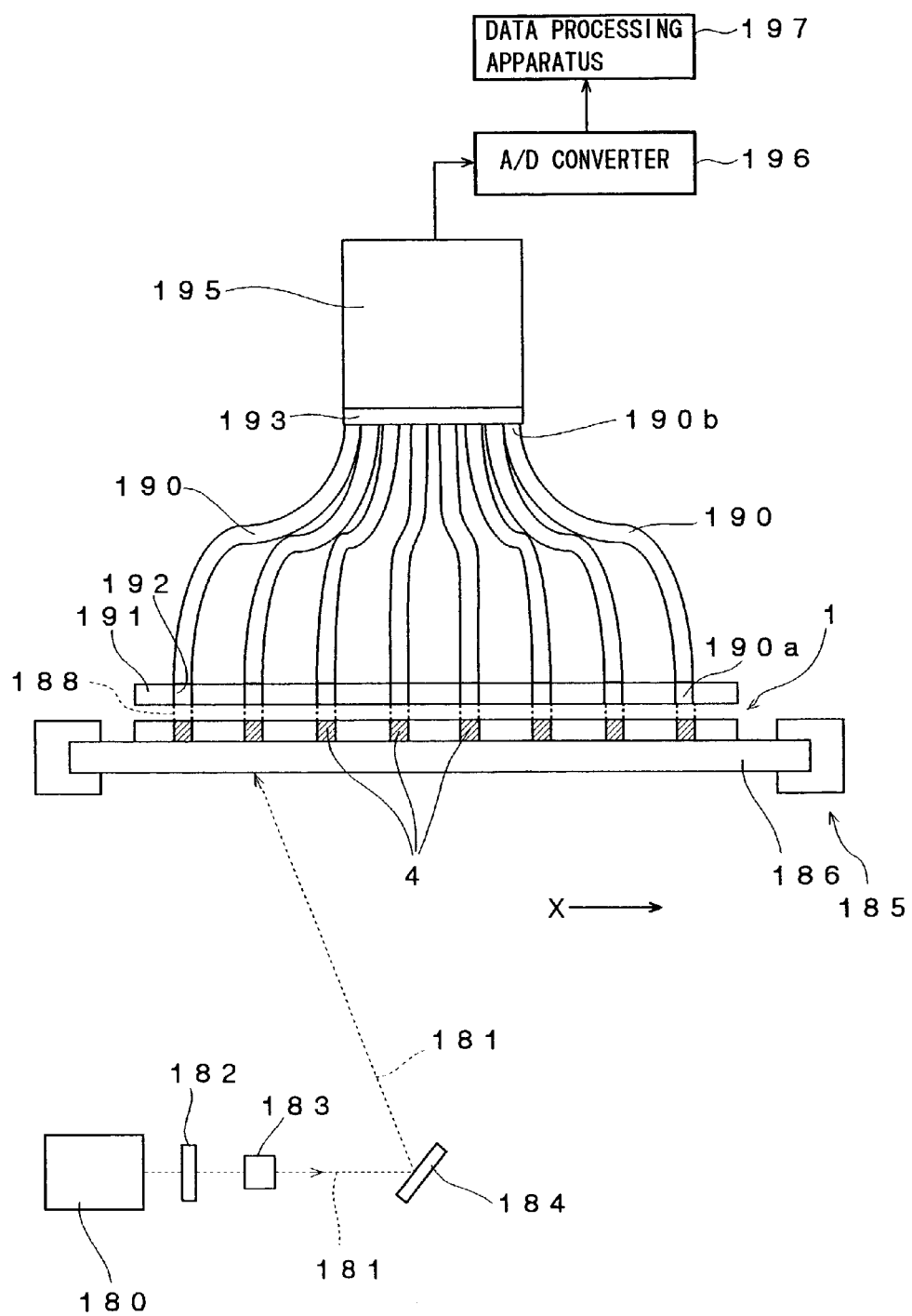
FIG. 20 is a schematic view showing an apparatus for producing biochemical analysis data which is a further preferred embodiment of the present invention.

FIG. 20 is a schematic view showing an apparatus for producing biochemical analysis data which is a further preferred embodiment of the present invention.

An apparatus of producing biochemical analysis data according to this embodiment is constituted so as to read fluorescence data of a fluorescent substance effectively stimulable by a laser beam having a wavelength of 473 nm, for example, Cy3 (registered trademark) to produce biochemical analysis data and includes a laser stimulating ray source 180 for emitting a laser beam 181 having a wavelength of 473 nm. In this embodiment, the laser stimulating ray source 180 is constituted by a second harmonic generation element.

A laser beam 181 having a wavelength of 473 nm and emitted from the laser stimulating ray source 180 passes through a collimator lens 182, thereby being made a parallel beam and enters a beam expander 183.

The laser beam 181 passes through the beam expander 183, whereby the beam diameter thereof is accurately adjusted and impinges onto a reflection mirror 184, thereby being reflected by the reflection mirror 184.

The laser beam 181 reflected by the reflection mirror 184 impinges onto one of the absorptive regions 4 formed in the substrate 2 of the biochemical analysis unit 1 placed on a transparent glass plate 186 of a sample stage 185.

In this embodiment, the reflection mirror 184 is controlled to be rotated by a motor (not shown) so that the biochemical analysis unit 1 is scanned with the laser beam 181 reflected by the reflection mirror 184 in a main scanning direction indicated by an arrow X in FIG. 20 at a pitch equal to the distance between neighboring absorptive regions 4.

As shown in FIG. 20, in this embodiment, the apparatus for producing biochemical analysis data includes a number of optical fiber members 190 each of which has a light collecting end portion 190a facing one of a number of the absorptive regions 4 formed in the substrate 2 of the biochemical analysis unit 1 and being located in the vicinity thereof In this embodiment, each of the optical fiber members 190 is constituted as a plurality of optical fibers and secured into a through-hole 192 formed in a fixing head 191 in the vicinity of the light collecting end portion 190a so that the light collecting end portion 190a of each of the optical fiber members 190 is positioned in a desired manner.

Further, as shown in FIG. 20, the optical fiber members 190 are gathered in the vicinity of end portions 190b opposite to the light collecting end portions 190a.

As shown in FIG. 20, each of the optical fiber members 190 is disposed so that end portion 190b thereof opposite to the light collecting end portion 190a faces a stimulating ray cutting filter 193. The stimulating ray cutting filter 193 has a property of cutting off light having a wavelength equal to 473 nm which is a wavelength of the laser beam 181 as a stimulating ray and transmitting light having a wavelength longer than 473 nm.

The apparatus for producing biochemical analysis data according to this embodiment includes a photomultiplier 195 disposed so as to face the surface of the stimulating ray cutting filter 193 opposite to the optical fiber members 190. Analog data produced by photoelectrically detecting fluorescence emission 188 by the photomultiplier 195 are output to an A/D converter 196 and converted by the A/D converter 196 to digital data and the thus produced digital data are forwarded to a data processing apparatus 197.

In this embodiment, the sample stage 185, the fixing head 191, a number of the optical fiber members 190, the stimulating ray cutting filter 193 and the photomultiplier 195 are moved by a scanning mechanism (not shown) in a sub-scanning direction perpendicular to the main scanning direction indicated by the arrow X in FIG. 20.

Figure 21:
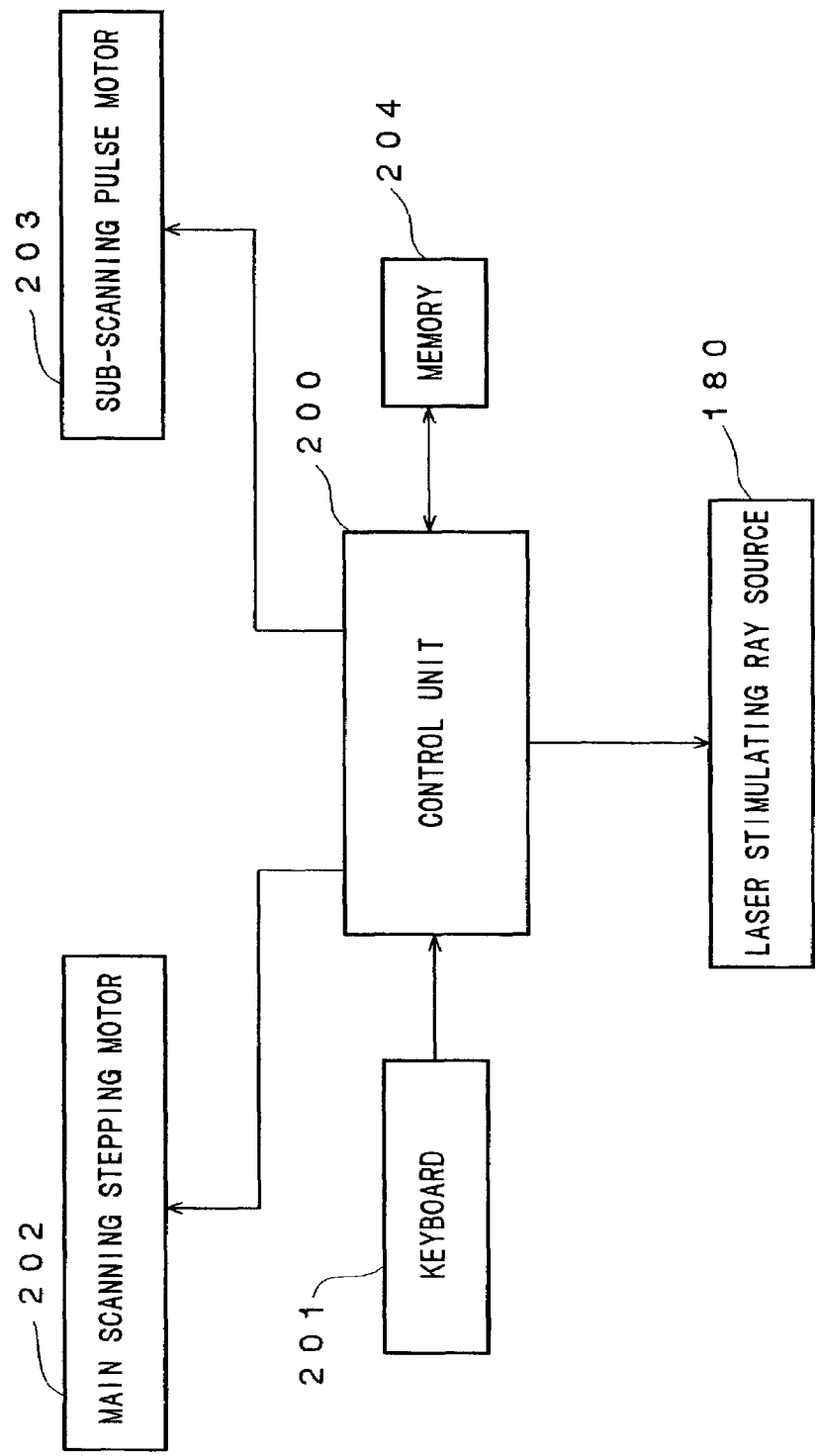
FIG. 21 is a block diagram of a control system, an input system, a drive system, a detection system and a memory system of the apparatus for producing biochemical analysis data shown in FIG. 20.

FIG. 21 is a block diagram of a control system, an input system, a drive system, a detection system and a memory system of the apparatus for producing biochemical analysis data shown in FIG. 20.

As shown in FIG. 21, the control system of the apparatus for producing biochemical analysis data includes a control unit 200 for controlling the overall operation of the apparatus for producing biochemical analysis data and the input system of the apparatus for producing biochemical analysis data includes a keyboard 201 which can be operated by a user and through which various instruction signals can be input.

As shown in FIG. 21, the drive system of the apparatus for producing biochemical analysis data includes a main scanning stepping motor 202 for intermittently rotating the reflection mirror 184 so that the biochemical analysis unit 1 is scanned with the laser beam 181 reflected by the reflection mirror 184 in a main scanning direction indicated by the arrow X in FIG. 20 at a pitch equal to a distance between neighboring absorptive regions 4, and a sub-scanning pulse motor 203 for intermittently moving the sample stage 185, the fixing head 191, a number of the optical fiber members 190, the stimulating ray cutting filter 193 and the photomultiplier 195 in the sub-scanning direction perpendicular to the main scanning direction indicated by the arrow X in FIG. 20. The detection system of the apparatus for producing biochemical analysis data includes the photomultiplier 195.

As shown in FIG. 21, the memory system of the apparatus for producing biochemical analysis data includes a memory 204 for storing drive pulses to be output to the main scanning stepping motor 202 in accordance with the rotational position of the reflecting mirror 184.

The control unit 200 is constituted so as to output a drive signal and a drive stop signal to the laser stimulating ray source 180, thereby on and off controlling the laser stimulating ray source 180.

The thus constituted apparatus for producing biochemical analysis data according to this embodiment reads fluorescence data recorded in a number of the absorptive regions 4 formed in the substrate 2 of the biochemical analysis unit 1 in the following manner.

A biochemical analysis unit 1 formed with a number of the absorptive regions 4 in which fluorescence data are recorded is first set on the transparent glass plate 186 of the sample stage 185 by a user.

A data production start signal is then input through the keyboard 201 by the user and the data production start signal is input to the control unit 190.

When the control unit 200 receives the data production start signal, it produces a drive signal based on the drive pulses in accordance with the rotational position of the reflecting mirror 184 stored in the memory 204 and outputs it to the main scanning stepping motor 202, thereby causing the main scanning stepping motor 202 to rotate the reflection mirror 184. When the control unit 200 determines that the reflection mirror 184 has been rotated to a position where a laser beam 181 can be projected onto a first absorptive region 4 among a number of the absorptive regions 4 formed in the substrate 2 of the biochemical analysis unit 1, it outputs a drive stop signal to the main scanning stepping motor 202 and a drive signal to the laser stimulating ray source 180, thereby actuating it to emit a laser beam 181 having a wavelength of 473 nm.

The laser beam 181 having a wavelength of 473 nm and emitted from the laser stimulating ray source 180 passes through a collimator lens 182, thereby being made a parallel beam and enters a beam expander 183.

The laser beam 181 passes through the beam expander 183, whereby the beam diameter thereof is accurately adjusted and impinges onto a reflection mirror 184, thereby being reflected by the reflection mirror 184.

The laser beam 181 reflected by the reflection mirror 184 impinges onto the first absorptive regions 4 formed in the substrate 2 of the biochemical analysis unit 1 placed on the transparent glass plate 186 of the sample stage 185.

As a result, a fluorescent substance contained in the first absorptive regions 4 is excited by the laser beam 181, thereby releasing fluorescence emission 188 from the first absorptive region 4.

Fluorescence emission 188 released from the first absorptive region 4 is collected by the light collecting end portion 190*a* of the corresponding optical fiber member 190 disposed so as to face the first absorptive region 4.

In this embodiment, since each of a number of the optical fiber members 190 is secured into the through-hole 192 formed in the fixing head 191 in the vicinity of the light collecting end portion 190*a* so that the light collecting end portion 190*a* of each of the optical fiber members 190 faces one of the absorptive regions 4 formed in the substrate 2 of the biochemical analysis unit 1 placed on the transparent glass plate 186 of the sample stage 185, fluorescence emission 168 released from the first absorptive regions 4 is reliably collected by the light collecting end portion 190*a* of the corresponding optical fiber member 190.

Further, in this embodiment, since the substrate 2 of the biochemical analysis unit 1 is made of stainless steel and has a property of attenuating the energy of light, fluorescence emission 168 released from neighboring absorptive regions 4 can be effectively prevented from scattering in the substrate 2 of the biochemical analysis unit 1 and being mixed with each other.

Fluorescence emission 168 collected by the light collecting end portion 190*a* of the optical fiber member 190 corresponding to the first absorptive region 4 is guided by the optical fiber member 190 and impinges onto a corresponding region of the stimulating ray cutting filter 193.

In this embodiment, since the optical fiber members 190 are gathered in the vicinity of the end portions 190*b* opposite to the light collecting end portions 190*a,* even in the case where a number of the optical fiber members 190 are provided correspondingly to a number of the absorptive regions 4 formed in the substrate 2 of the biochemical analysis unit 1, it is possible to employ a stimulating ray source cutting filter 193 having a small area and a photomultiplier 195 provided with a photo-electric detecting surface having a small area. Therefore, it is possible to make an apparatus for producing biochemical analysis data smaller and to lower cost for manufacturing an apparatus for producing biochemical analysis data.

Further, since the apparatus for producing biochemical analysis data according to this embodiment is constituted so as to produce biochemical analysis data by scanning a number of the absorptive regions 4 formed in the substrate 2 of the biochemical analysis unit 1 with the laser beam 181, successively exciting a fluorescent substance contained in a number of the absorptive regions 4, and photoelectrically detecting fluorescence emission 188 released from the absorptive regions 4 with the photomultiplier 195, it is not necessary to dispose the end portions 190*b* of the optical fiber members 190 in the same pattern as that of the light collecting end portions 190*a* thereof.

Since the stimulating ray source cutting filter 193 has a property of cutting off light having a wavelength of 473 nm which is a wavelength of the laser beam 181 as the stimulating ray and transmitting light having a wavelength longer than 473 nm and fluorescence emission 188 has a wavelength longer than 473 nm, light having a wavelength of 473 nm is cut off by the stimulating ray source cutting filter 193 and only fluorescence emission 188 released from the absorptive regions 4 is transmitted therethrough and photoelectrically detected by the photomultiplier 195.

Analog data produced by photoelectrically detecting fluorescence emission 188 with the photomultiplier 195 are converted by the A/D converter 196 into digital data and the digital data are fed to the data processing apparatus 197.

When a predetermined time has passed after the laser stimulating ray source 180 was turned on, the control unit 200 outputs a drive stop signal to the laser stimulating ray source 180, thereby turning it off. At the same time, the control unit 200 produces a drive signal based on the drive pulses in accordance with the rotational position of the reflecting mirror 184 stored in the memory 204 and outputs it to the main scanning stepping motor 202, thereby causing the main scanning stepping motor 202 to rotate the reflection mirror 184 to a position where a laser beam 181 can be projected onto a second absorptive region 4 next to the first absorptive region 4 formed in the substrate 2 of the biochemical analysis unit 1.

When the control unit 200 determines that the reflection mirror 184 has been rotated to a position where a laser beam 181 can be projected onto the second absorptive region 4 next to the first absorptive region 4 formed in the substrate 2 of the biochemical analysis unit 1, it outputs a drive signal to the laser stimulating ray source 180 to turn it on, thereby causing the laser beam 181 to excite a fluorescent substance contained in the second absorptive region 4 next to the first absorptive region 4 formed in the substrate 2 of the biochemical analysis unit 1.

Similarly to the above, the second absorptive region 4 formed in the substrate 2 of the biochemical analysis unit 1 is irradiated with the laser beam 181 for a predetermined time and when fluorescence emission 168 released from the second absorptive region 4 has been collected by the corresponding optical fiber member 190 and photoelectrically detected by the photomultiplier 195 via the stimulating ray cutting filter 193, the control unit 200 outputs a drive stop signal to the laser stimulating ray source 180, thereby turning it off. At the same time, the control unit 200 produces a drive signal based on the drive pulses in accordance with the rotational position of the reflecting mirror 184 stored in the memory 204 and outputs it to the main scanning stepping motor 202, thereby causing the main scanning stepping motor 202 to rotate the reflection mirror 184 to a position where a laser beam 181 can be projected onto a third absorptive region 4 next to the second absorptive region 4 formed in the substrate 2 of the biochemical analysis unit 1.

In this manner, the on and off operation of the laser stimulating ray source 180 is repeated in synchronism with the intermittent rotation of the reflection mirror 184 and when the control unit 200 determines that the absorptive regions 4 included in a first line of the absorptive regions 4 formed in the substrate 2 of the biochemical analysis unit 1 have been scanned with the laser beam 181, it outputs a drive signal to the main scanning stepping motor 202, thereby returning the reflection mirror 184 to its original position and outputs a drive signal to the sub-scanning pulse motor 203, thereby causing it to move the sample stage 185, the fixing head 191, a number of the optical fiber members 190, the stimulating ray cutting filter 193 and the photomultiplier 195 by one scanning line in the sub-scanning direction.

When the control unit 200 determines that the reflection mirror 184 has been returned to its original position and determines that the sample stage 185, the fixing head 191, a number of the optical fiber members 190, the stimulating ray cutting filter 193 and the photomultiplier 195 have been moved by one scanning line in the sub-scanning direction, similarly to the manner in which the absorptive regions 4 included in the first line of the absorptive regions 4 formed in the substrate 2 of the biochemical analysis unit 1 were sequentially irradiated with the laser beam 181 emitted from the laser stimulating ray source 180, the absorptive regions 4 included in a second line of the absorptive regions 4 formed in the substrate 2 of the biochemical analysis unit 1 are sequentially irradiated with the laser beam 181 emitted from the laser stimulating ray source 180, thereby exciting a fluorescent substance contained in the absorptive regions 4 included in the second line and fluorescence emission 188 released from the absorptive regions 4 in the second line is sequentially and photoelectrically detected by the photomultiplier 195.

Analog data produced by photoelectrically detecting fluorescence emission 188 with the photomultiplier 195 are converted by the A/D converter 196 into digital data and the digital data are fed to the data processing apparatus 197.

When all of the absorptive regions 4 formed in the substrate 2 of the biochemical analysis unit 1 have been scanned with the laser beam 181 to excite a fluorescent substance contained in the absorptive regions 4 and digital data produced by collecting fluorescence emission 188 released from the absorptive regions 4 by the corresponding optical fiber members 190, leading the fluorescence emission 188 to the photomultiplier 195 via the stimulating ray cutting filter 193, photoelectrically detecting the fluorescence emission 188 by the photomultiplier 195 to produce analog data and digitizing the analog data by the A/D converter 196 have been forwarded to the data processing apparatus 197, the control unit 190 outputs a drive stop signal to the laser stimulating ray source 180 thereby turning it off.

As described above, fluorescence data recorded in a number of the absorptive regions 4 formed in the substrate 2 of the biochemical analysis unit 1 are read to produce biochemical analysis data.

According to this embodiment, since each of a number of the optical fiber members 190 is secured into the through-hole 192 formed in the fixing head 191 in the vicinity of the light collecting end portion 190a so that the light collecting end portion 190a of each of the optical fiber members 190 faces one of the absorptive regions 4 of the biochemical analysis unit 1 placed on the transparent glass plate 186 of the sample stage 185, fluorescence emission 188 released from each of the absorptive regions 4 can be reliably collected by the light collecting end portion 190a of the corresponding optical fiber member 190. Therefore, since the efficiency for collecting fluorescence emission 188 can be markedly improved, biochemical analysis data having an excellent quantitative characteristic can be produced by photoelectrically detecting fluorescence emission 188 with high sensitivity.

Furthermore, according to this embodiment, since the substrate 2 of the biochemical analysis unit 1 is made of stainless steel and has a property of attenuating the energy of light, fluorescence emission 188 released from neighboring absorptive regions 4 formed in the substrate 2 of the biochemical analysis unit 1 can be effectively prevented from scattering in the substrate 2 of the biochemical analysis unit 1 and being mixed with each other. Therefore, it is possible to effectively prevent noise caused by the scattering of fluorescence emission 188 from being generated in biochemical analysis data produced by reading fluorescence data recorded in a number of the absorptive regions 4 formed in the substrate 2 of the biochemical analysis unit 1.

Figure 22:
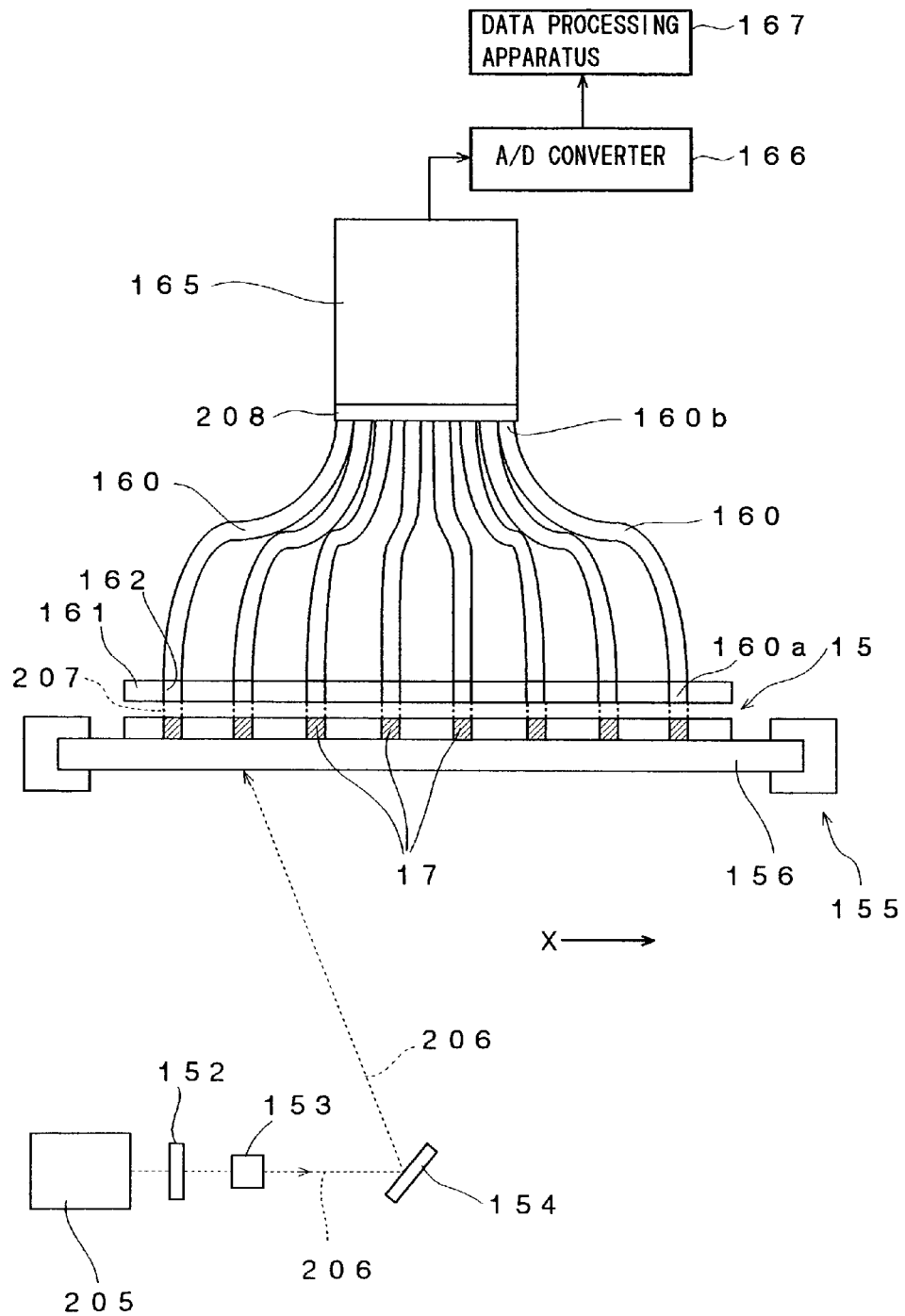
FIG. 22 is a schematic view showing an apparatus for producing biochemical analysis data which is a further preferred embodiment of the present invention.

FIG. 22 is a schematic view showing an apparatus for producing biochemical analysis data which is a further preferred embodiment of the present invention, The apparatus for producing biochemical analysis data shown in FIG. 22 is constituted so as to read chemiluminescence data recorded in a number of the stimulable phosphor layer regions 17 formed in the support 11 of the stimulable phosphor sheet 15 shown in FIG. 14 to produce biochemical analysis data and has the same configuration as that of the apparatus for producing biochemical analysis data shown in FIG. 18 except that a laser stimulating ray source 205 for emitting a laser beam 206 having a wavelength of 980 nm effectively excitable SrS system stimulable phosphor is provided instead of the laser stimulating ray source 150 for emitting a laser beam 151 having a wavelength of 640 nm and that a stimulating ray cutting filter 208 having a property of cutting off light having a wavelength of that of the laser beam 206 emitted from the laser stimulating ray source 205 and transmitting only light having a wavelength of that of stimulated emission 207 released from a number of the stimulable phosphor layer regions 17 formed in the support 11 of the stimulable phosphor sheet 15 is provided instead of the stimulating ray cutting filter 163 having a property of cutting off light having a wavelength of that of the laser beam 151 emitted from the laser stimulating ray source 150 and transmitting only light having a wavelength of that of stimulated emission 158 released from a number of the stimulable phosphor layer regions 12 formed in the support 11 of the stimulable phosphor sheet 10.

Figure 23:
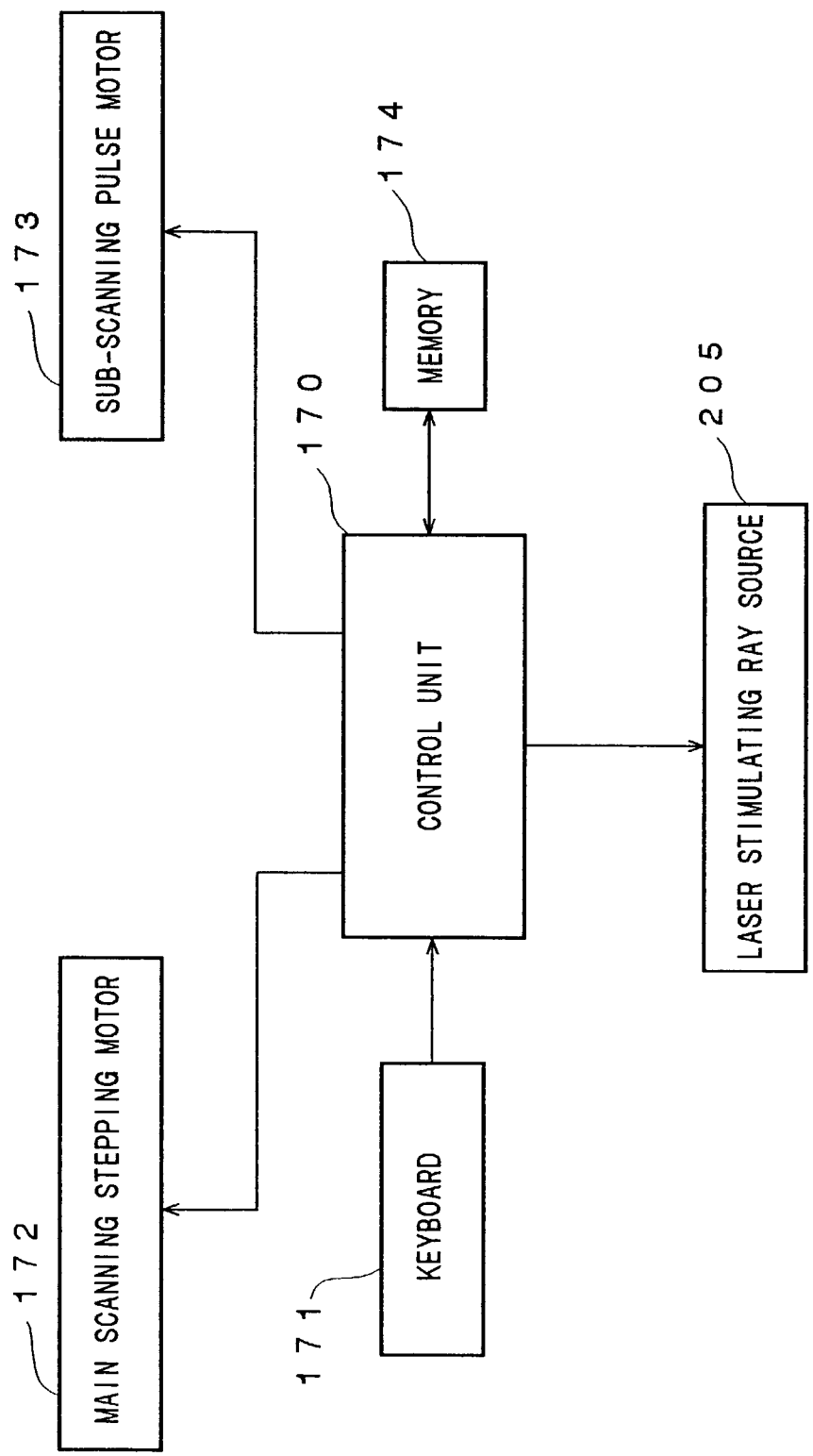
FIG. 23 is a block diagram of a control system, an input system, a drive system, a detection system and a memory system of the apparatus for producing biochemical analysis data shown in FIG. 22.

FIG. 23 is a block diagram of a control system, an input system, a drive system, a detection system and a memory system of the apparatus for producing biochemical analysis data according to this embodiment.

As shown in FIG. 23, the control system, the input system, the drive system, the detection system and the memory system of the apparatus for producing biochemical analysis data according to this embodiment have the same configurations as those of the apparatus for producing biochemical analysis data shown in FIG. 19 except that the control unit 160 is is constituted so as to control the laser stimulating ray source 205 for emitting a laser beam 206 having a wavelength of 980 nm.

The thus constituted apparatus for producing biochemical analysis data according to this embodiment reads chemiluminescence data recorded in a number of the stimulable phosphor layer regions 17 formed in the support 11 of the stimulable phosphor sheet 15 in the following manner.

A stimulable phosphor sheet 15 formed with a number of the stimulable phosphor layer regions 17 in which chemiluminescence data are recorded is first set on the transparent glass plate 156 of the sample stage 155 by a user.

A data production start signal is then input through the keyboard 171 by the user and the data production start signal is input to the control unit 160.

When the control unit 160 receives the data production start signal, it produces a drive signal based on the drive pulses in accordance with the rotational position of the reflecting mirror 154 stored in the memory 174 and outputs it to the main scanning stepping motor 172, thereby causing the main scanning stepping motor 172 to rotate the reflection mirror 154. When the control unit 160 determines that the reflection mirror 154 has been rotated to a position where a laser beam 206 can be projected onto a first stimulable phosphor layer region 17 among a number of the stimulable phosphor layer regions 17 formed in the support 11 of the stimulable phosphor sheet 15, it outputs a drive stop signal to the main scanning stepping motor 172 and a drive signal to the laser stimulating ray source 205, thereby actuating it to emit a laser beam 206 having a wavelength of 980 nm.

The laser beam 206 having a wavelength of 980 nm and emitted from the laser stimulating ray source 205 passes through a collimator lens 152, thereby being made a parallel beam and enters a beam expander 153.

The laser beam 206 passes through the beam expander 153, whereby the beam diameter thereof is accurately adjusted and impinges onto a reflection mirror 154, thereby being reflected by the reflection mirror 154.

The laser beam 206 reflected by the reflection mirror 154 impinges onto the first stimulable phosphor layer regions 17 formed in the support 11 of the stimulable phosphor sheet 15 placed on the transparent glass plate 156 of the sample stage 155.

As a result, stimulable phosphor contained in the first stimulable phosphor layer regions 17 is excited by the laser beam 206, thereby releasing stimulated emission 207 from the first stimulable phosphor layer region 17.

Stimulated emission 207 released from the first stimulable phosphor layer region 17 is collected by the light collecting end portion 160a of the corresponding optical fiber member 160 disposed so as to face the first stimulable phosphor layer region 17.

In this embodiment, since each of a number of the optical fiber members 160 is secured into the through-hole 162 formed in the fixing head 161 in the vicinity of the light collecting end portion 160a so that the light collecting end portion 160a of each of the optical fiber members 160 faces one of the stimulable phosphor layer regions 17 of the stimulable phosphor sheet 15 placed on the transparent glass plate 156 of the sample stage 155, stimulated emission 207 released from the first stimulable phosphor layer regions 17 is reliably collected by the light collecting end portion 160a of the corresponding optical fiber member 160.

Further, in this embodiment, since the support 11 of the stimulable phosphor sheet 15 is made of stainless steel and has a property of attenuating the energy of light, stimulated emission 207 released from neighboring stimulable phosphor layer regions 17 can be effectively prevented from scattering in the support 11 of the stimulable phosphor sheet 15 and being mixed with each other.

Stimulated emission 207 collected by the light collecting end portion 160a of the optical fiber member 160 corresponding to the first stimulable phosphor layer region 17 is guided by the optical fiber member 160 and impinges onto a corresponding region of the stimulating ray cutting filter 208.

In this embodiment, since the optical fiber members 160 are gathered in the vicinity of the end portions 160b opposite to the light collecting end portions 160a, even in the case where a number of the optical fiber members 160 are provided correspondingly to a number of the stimulable phosphor layer regions 17 formed in the support 11 of the stimulable phosphor sheet 15, it is possible to employ a stimulating ray source cutting filter 208 having a small area and a photomultiplier 165 provided with a photo-electric detecting surface having a small area. Therefore, it is possible to make an apparatus for producing biochemical analysis data smaller and to lower cost for manufacturing an apparatus for producing biochemical analysis data.

Further, since the apparatus for producing biochemical analysis data according to this embodiment is constituted so as to produce biochemical analysis data by scanning a number of the stimulable phosphor layer regions 17 formed in the support 11 of the stimulable phosphor sheet 15 with the laser beam 206, successively exciting stimulable phosphor contained in a number of the stimulable phosphor layer regions 17, and photoelectrically detecting stimulated emission 207 released from the stimulable phosphor layer regions 17 with the photomultiplier 165, it is not necessary to dispose the end portions 160b of the optical fiber members 160 in the same pattern as that of the light collecting end portions 160a thereof.

Since the stimulating ray source cutting filter 208 has a property of transmitting only light having a wavelength of that of stimulated emission 208 released from the stimulable phosphor layer regions 17 formed in the support 11 of the stimulable phosphor sheet 15 and cutting light having a wavelength of 980 nm, light having a wavelength of 980 nm is cut off by the stimulating ray source cutting filter 208 and only stimulated emission 207 released from the stimulable phosphor layer regions 17 is transmitted therethrough and photoelectrically detected by the photomultiplier 165.

Analog data produced by photoelectrically detecting stimulated emission 207 with the photomultiplier 165 are converted by the A/D converter 166 into digital data and the digital data are fed to the data processing apparatus 167.

When a predetermined time has passed after the laser stimulating ray source 205 was turned on, the control unit 160 outputs a drive stop signal to the laser stimulating ray source 205, thereby turning it off. At the same time, the control unit 160 produces a drive signal based on the drive pulses in accordance with the rotational position of the reflecting mirror 154 stored in the memory 174 and outputs it to the main scanning stepping motor 172, thereby causing the main scanning stepping motor 172 to rotate the reflection mirror 154 to a position where a laser beam 206 can be projected onto a second stimulable phosphor layer region 17 next to the first stimulable phosphor layer region 17 formed in the support 11 of the stimulable phosphor sheet 15.

When the control unit 160 determines that the reflection mirror 154 has been rotated to a position where a laser beam 206 can be projected onto a second stimulable phosphor layer region 17 next to the first stimulable phosphor layer region 17 formed in the support 11 of the stimulable phosphor sheet 15, it outputs a drive signal to the laser stimulating ray source 205 to turn it on, thereby causing the laser beam 206 to excite stimulable phosphor contained in the second stimulable phosphor layer region 17 formed in the support 11 of the stimulable phosphor sheet 15.

Similarly to the above, the second stimulable phosphor layer region 17 formed in the support 11 of the stimulable phosphor sheet 15 is irradiated with the laser beam 206 for a predetermined time and when stimulated emission 207 released from the second stimulable phosphor layer region 17 has been collected by the corresponding optical fiber member 160 and photoelectrically detected by the photomultiplier 165 via the stimulating ray cutting filter 208, the control unit 160 outputs a drive stop signal to the laser stimulating ray source 205, thereby turning it off. At the same time, the control unit 160 produces a drive signal based on the drive pulses in accordance with the rotational position of the reflecting mirror 154 stored in the memory 174 and outputs it to the main scanning stepping motor 172, thereby causing the main scanning stepping motor 172 to rotate the reflection mirror 154 to a position where a laser beam 206 can be projected onto a third stimulable phosphor layer region 17 next to the second stimulable phosphor layer region 17 formed in the support 11 of the stimulable phosphor sheet 15.

In this manner, the on and off operation of the laser stimulating ray source 205 is repeated in synchronism with the intermittent rotation of the reflection mirror 154 and when the control unit 160 determines that the stimulable phosphor layer regions 17 included in a first line of the stimulable phosphor layer regions 17 formed in the support 11 of the stimulable phosphor sheet 15 have been scanned with the laser beam 206, it outputs a drive signal to the main scanning stepping motor 172, thereby returning the reflection mirror 154 to its original position and outputs a drive signal to the sub-scanning pulse motor 173, thereby causing it to move the sample stage 155, the fixing head 161, a number of the optical fiber members 160, the stimulating ray cutting filter 208 and the photomultiplier 165 by one scanning line in the sub-scanning direction.

When the control unit 160 determines that the reflection mirror 154 has been returned to its original position and determines that the sample stage 155, the fixing head 161, a number of the optical fiber members 160, the stimulating ray cutting filter 208 and the photomultiplier 165 have been moved by one scanning line in the sub-scanning direction, similarly to the manner in which the stimulable phosphor layer regions 17 included in the first line of the stimulable phosphor layer regions 17 formed in the support 11 of the stimulable phosphor sheet 15 were sequentially irradiated with the laser beam 206 emitted from the laser stimulating ray source 205, the stimulable phosphor layer regions 17 included in a second line of the stimulable phosphor layer regions 17 formed in the support 11 of the stimulable phosphor sheet 15 are sequentially irradiated with the laser beam 206 emitted from the laser stimulating ray source 205, thereby exciting stimulable phosphor contained in the stimulable phosphor layer regions 17 included in the second line and stimulated emission 207 released from the stimulable phosphor layer regions 17 in the second line is sequentially and photoelectrically detected by the photomultiplier 165.

Analog data produced by photoelectrically detecting stimulated emission 207 with the photomultiplier 165 are converted by the A/D converter 166 into digital data and the digital data are fed to the data processing apparatus 167.

When all of the stimulable phosphor layer regions 17 formed in the support 11 of the stimulable phosphor sheet 15 have been scanned with the laser beam 206 to excite stimulable phosphor contained in the stimulable phosphor layer regions 17 and digital data produced by collecting stimulated emission 207 released from the stimulable phosphor layer regions 17 by the corresponding optical fiber members 160, leading the stimulated emission 207 to the photomultiplier 165 via the stimulating ray cutting filter 208, photoelectrically detecting the stimulated emission 207 by the photomultiplier 165 to produce analog data and digitizing the analog data by the A/D converter 166 have been forwarded to the data processing apparatus 167, the control unit 160 outputs a drive stop signal to the laser stimulating ray source 205 thereby turning it off.

As described above, chemiluminescence data recorded in a number of the stimulable phosphor layer regions 17 formed in the support 11 of the stimulable phosphor sheet 15 are read to produce biochemical analysis data.

According to this embodiment, since each of a number of the optical fiber members 160 is secured into the through-hole 162 formed in the fixing head 161 in the vicinity of the light collecting end portion 160a so that the light collecting end portion 160a of each of the optical fiber members 160 faces one of the stimulable phosphor layer regions 17 of the stimulable phosphor sheet 15 placed on the transparent glass plate 156 of the sample stage 155, stimulated emission 207 released from each of the stimulable phosphor layer regions 17 can be reliably collected by the light collecting end portion 160a of the corresponding optical fiber member 160. Therefore, since the efficiency for collecting stimulated emission 207 can be markedly improved, biochemical analysis data having an excellent quantitative characteristic can be produced by photoelectrically detecting stimulated emission 207 with high sensitivity.

Furthermore, according to this embodiment, since the support 11 of the stimulable phosphor sheet 15 is made of stainless steel and has a property of attenuating the energy of light, stimulated emission 207 released from neighboring stimulable phosphor layer regions 17 formed in the support 11 of the stimulable phosphor sheet 15 can be effectively prevented from scattering in the support 11 of the stimulable phosphor sheet 15 and being mixed with each other. Therefore, it is possible to effectively prevent noise caused by the scattering of stimulated emission 207 from being generated in biochemical analysis data produced by reading chemiluminescence data recorded in a number of the stimulable phosphor layer regions 17 formed in the support 11 of the stimulable phosphor sheet 15.

Figure 24:
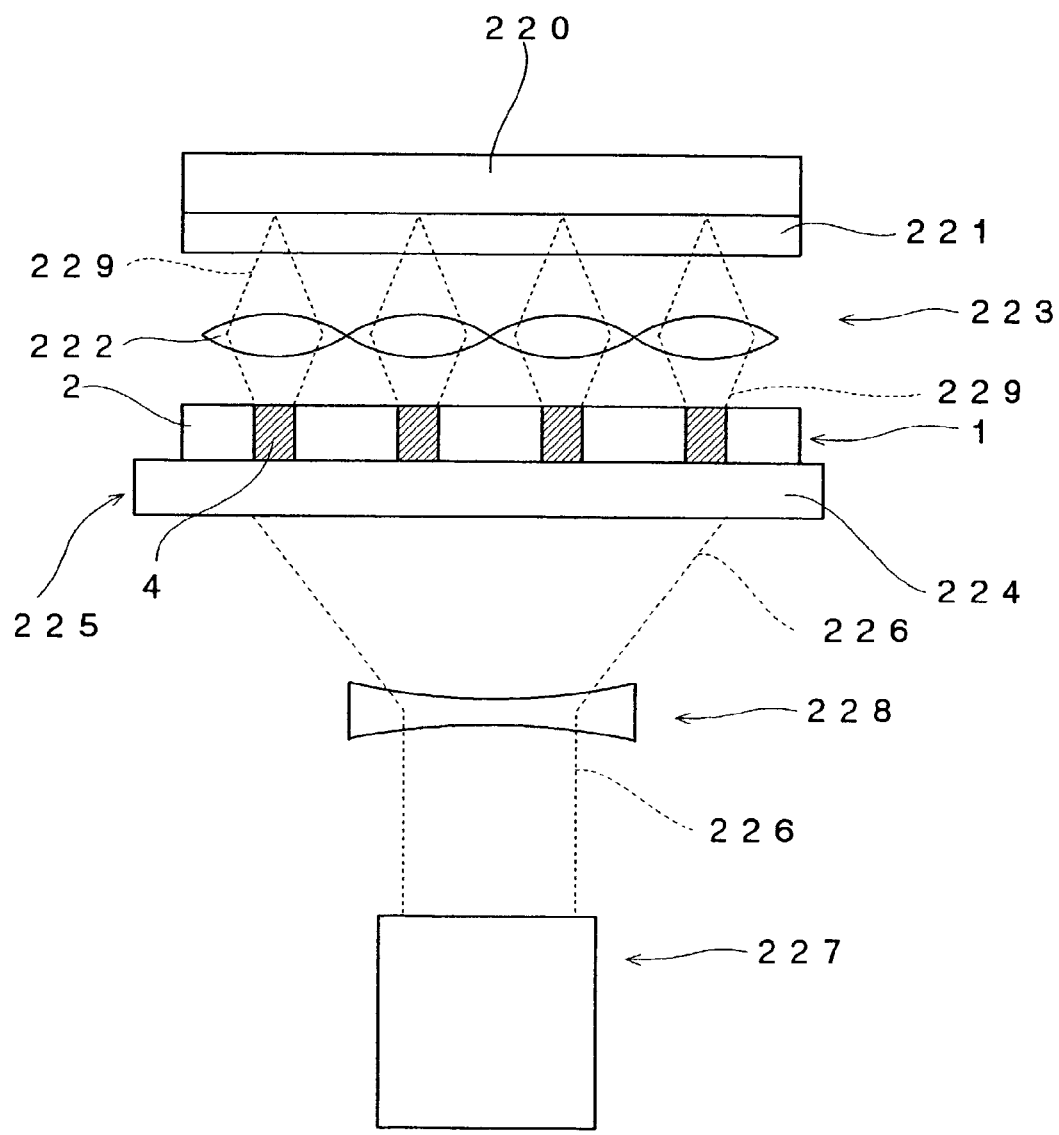
FIG. 24 is a schematic view showing an apparatus for producing biochemical analysis data which is a further preferred embodiment of the present invention.

FIG. 24 is a schematic view showing an apparatus for producing biochemical analysis data which is a further preferred embodiment of the present invention.

An apparatus for producing biochemical analysis data according to this embodiment is constituted so as to read fluorescence data recorded in a number of the absorptive regions 4 formed in the substrate 2 of the biochemical analysis unit 1 and as shown in FIG. 24, it includes a cooled CCD area sensor 220, a stimulating ray cutting filter 221 disposed in front of the cooled CCD area sensor 220, a sample stage 225 provided with a transparent glass plate 224 on which the biochemical analysis unit 1 is to be placed, a lens array 223 disposed close to the sample stage 225 and provided with a number of convex lenses 222 so that each of them is disposed at a position corresponding to one of a number of the absorptive regions 4 formed in the substrate 2 of the biochemical analysis unit 1 to be placed on the sample stage 225, a laser stimulating ray source 227 for emitting a laser beam 226, and a concave lens 228 for diverging a laser beam 226 emitted from the laser stimulating ray source 227 to impinge it onto the biochemical analysis unit 1 placed on the transparent glass plate 224 of the sample stage 225.

As the laser stimulating ray source 227 is selected a laser beam source that emits a laser beam 226 capable of effectively stimulating a fluorescent substance contained in a number of the absorptive regions 4 formed in the substrate 2 of the biochemical analysis unit 1. In this embodiment, a number of the absorptive regions 4 of the biochemical analysis unit 1 are selectively labeled with a fluorescent substance effectively stimulable by a laser beam of a wavelength of 473 nm, for example, Cy3 (registered trademark), and, therefore, the laser stimulating ray source 227 emits a laser beam 226 having a wavelength of 473 nm.

Accordingly, the stimulating ray cutting filter 221 has a property of cutting light having a wavelength of 473 nm equal to that of the laser beam 226 emitted from the laser stimulating ray source 227 and transmitting light having a wavelength longer than 473 nm.

Figure 25:
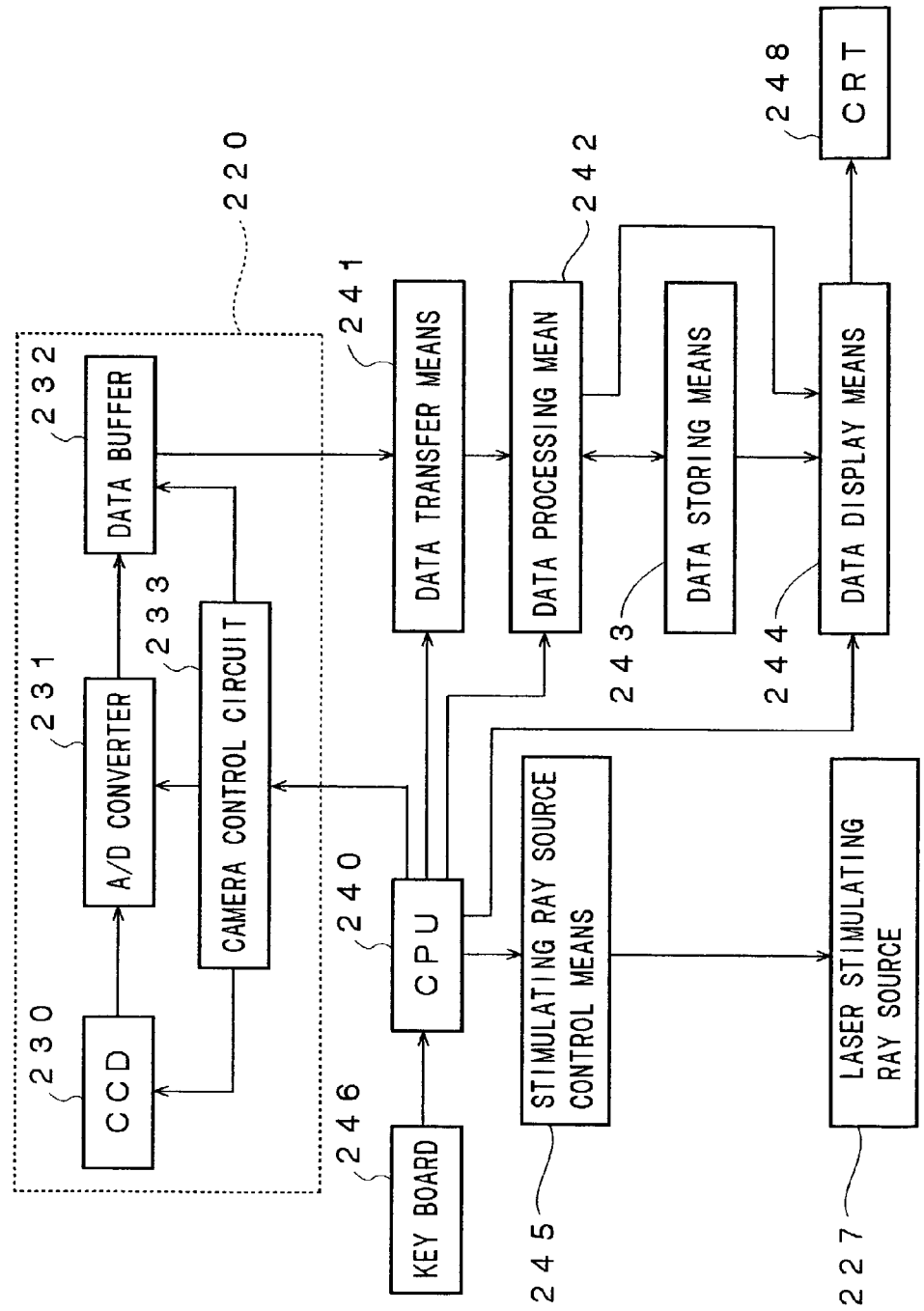
FIG. 25 is a block diagram of a control system, a detection system and a memory system of a cooled CCD area sensor and a control system, a memory system, a display system and an input system of an apparatus for producing biochemical analysis data shown in FIG. 24.

FIG. 25 is a block diagram of a control system, a detection system and a memory system of the cooled CCD area sensor 220 and a control system, a memory system, a display system and an input system of an apparatus for producing biochemical analysis data according to this embodiment.

As shown in FIG. 25, the cooled CCD area sensor 220 includes a CCD 230, an A/D converter 231 for digitizing analog data produced by the CCD 230 in the form of electric charge, a data buffer 232 for temporarily storing biochemical analysis data produced by digitizing analog data by the A/D converter 231 and a camera control circuit 233 for controlling the overall operation of the cooled CCD area sensor 220.

As shown in FIG. 25, the apparatus for producing biochemical analysis data according to this embodiment includes a CPU 240 for controlling the overall operation of the cooled CCD area sensor 220, a data transfer means 241 for reading biochemical analysis data produced by the cooled CCD area sensor 220 from the data buffer 232, a data processing means 242 for effecting data processing on biochemical analysis data read by the data transfer means 241, a data storing means 243 for biochemical analysis data subjected to data processing by the data processing means 242, a data display means 244 for producing quantitative data based on biochemical analysis data stored in the data storing means 243 and displaying the quantitative data on the screen of a CRT 248, a stimulating ray source control means 245 for controlling the laser stimulating ray source 227, and a keyboard 246 which can be operated by a user and through which various instruction signals can be input.

Based on instruction signals input through the keyboard 246, the CPU 240 is adapted for controlling the stimulating ray source control means 245 and outputting various signals to the camera control circuit 233 of the cooled CCD area sensor 220.

The thus constituted apparatus for producing biochemical analysis data according to this embodiment reads fluorescence data recorded in a number of the absorptive regions 4 formed in the substrate 2 of the biochemical analysis unit 1 in the following manner.

A biochemical analysis unit 1 formed with a number of the absorptive regions 4 in which fluorescence data are recorded is first set on the transparent glass plate 224 of the sample stage 225 by the user.

In this embodiment, guide members (not shown) are provided in the sample stage 225 for ensuring that the biochemical analysis unit 1 is placed on the sample stage 225 so that a number of the absorptive regions 4 accurately face the corresponding convex lenses 222 mounted on the lens array 223.

A data production start signal is then input through the keyboard 246 by the user and the data production start signal is input to the CPU 240.

When the CPU 240 receives the data production start signal, it outputs the data production start signal to the laser stimulating ray source 227, thereby activating it and outputs an exposure start signal to the camera control circuit 233 of the cooled CCD area sensor 220, thereby causing the cooled CCD area sensor 220 to start detecting fluorescence emission 229.

A laser beam 226 having a wavelength of 473 nm and emitted from the laser stimulating ray source 227 passes through the concave lens 226, thereby being diverged and the whole surface of the biochemical analysis unit 1 placed on the transparent glass plate 224 of the sample stage 225 is simultaneously irradiated, with the diverged laser beam 226.

When a number of the absorptive regions 4 formed in the substrate 2 of the biochemical analysis unit 1 are irradiated with the laser beam 226, a fluorescent substance, for example, Cy3, contained therein is excited, thereby releasing fluorescence emission 229.

Fluorescence emission 229 released from a number of the absorptive regions 4 of the biochemical analysis unit 1 is collected by the corresponding convex lens 222 disposed so as to face and be close to the absorptive region 4 and is condensed onto the corresponding region of the stimulating ray cutting filter 221.

Since the stimulating ray cutting filter 221 has a property of cutting light having a wavelength of 473 nm equal to that of the laser beam 226 emitted from the laser stimulating ray source 227 and transmitting light having a wavelength longer than 473 nm and the wavelength of fluorescence emission 229 released from a fluorescent substance in response to the excitation with a stimulating ray is longer than the wavelength of the stimulating ray, light having a wavelength of 473 nm is cut off by the stimulating ray cutting filter 221 and only fluorescence emission 229 released from a fluorescent substance contained in the absorptive regions 4 of the biochemical analysis unit 1 is transmitted through the stimulating ray cutting filter 221 and impinges onto the photo-electric detecting surface of the CCD 230, thereby forming an image on the photo-electric detecting surface of the CCD 230.

The CCD 230 of the CCD area sensor 220 receives light of the thus formed image and accumulates it in the form of electric charges therein.

When a predetermined time has passed, the CPU 240 outputs an exposure completion signal to the camera control circuit 233 of the cooled CCD area sensor 220 and outputs a data production completion signal to the stimulating ray source control means 245.

When the stimulating ray source control means 245 receives the data production completion signal from the CPU 240, it turns off the laser stimulating ray source 227.

On the other hand, when the camera control circuit 233 receives the exposure completion signal from the CPU 240, it transfers analog data accumulated in the CCD 230 in the form of electric charge to the A/D converter 231 to cause the A/D converter 231 to digitize the data, thereby producing biochemical analysis data and to temporarily store the thus produced biochemical analysis data in the data buffer 232.

At the same time, the CPU 240 outputs a data transfer signal to the data transfer means 241 to cause it to read out the biochemical analysis data from the data buffer 232 of the cooled CCD area sensor 220 and to input them to the data processing means 242.

The data processing means 242 effects necessary data processing on the biochemical analysis data in accordance with the user's instructions and stores the biochemical analysis data in the data storing means 243.

When the user inputs a data display signal through the keyboard 246, the CPU 240 outputs the data display signal to the data display means 244, thereby causing the data display means 244 to produce quantitative analysis data based on the biochemical analysis data stored in the data storing means 243 and to display them on the screen of the CRT 248.

In this embodiment, the laser beam 226 emitted from the laser stimulating ray source 227 is diverged by the concave lens 228 and the diverged laser beam 226 is simultaneously projected onto the whole surface of the biochemical analysis unit 1 placed on the transparent glass plate 224 of the sample stage 225 to excite a fluorescent substance contained in a number of the absorptive regions 4 formed in the substrate 2 of the biochemical analysis unit 1, whereby fluorescence emission 229 is released from the absorptive regions 4.

Since the lens array 223 is disposed to be close to the biochemical analysis unit 1 placed on the sample stage 225 and is provided with the convex lens so that each of them accurately faces one of the absorptive regions 4 formed in the substrate 2 of the biochemical analysis unit 1, fluorescence emission 229 released from the absorptive regions 4 of the biochemical analysis unit 1 is reliably collected by the corresponding convex lenses 222 of the lens array 223 and led to the corresponding regions of the stimulating ray cutting filter 221.

As a result, light having a wavelength of 473 nm is cut off by the stimulating ray cutting filter 221 and only fluorescence emission 229 released from the absorptive regions 4 of the biochemical analysis unit 1 is transmitted through the stimulating ray cutting filter 221 and is photoelectrically detected by the CCD 230 of cooled CCD area sensor 220.

Analog data produced by photoelectrically detecting fluorescence emission 229 with the CCD 230 of the cooled CCD area sensor 220 are digitized by the A/D converter 241, thereby producing biochemical analysis data.

Therefore, according to this embodiment, even in the case where the absorptive regions 4 are formed in the substrate 2 of the biochemical analysis unit 1 at a high density, since only fluorescence emission 229 released from the absorptive regions 4 of the biochemical analysis unit 1 is collected by the corresponding convex lenses 222 and led to the CCD 230 of the cooled CCD area sensor 220 via the stimulating ray cutting filter 221, it is possible to detect fluorescence emission 229 with high sensitivity, thereby producing biochemical analysis data.

Figure 26:
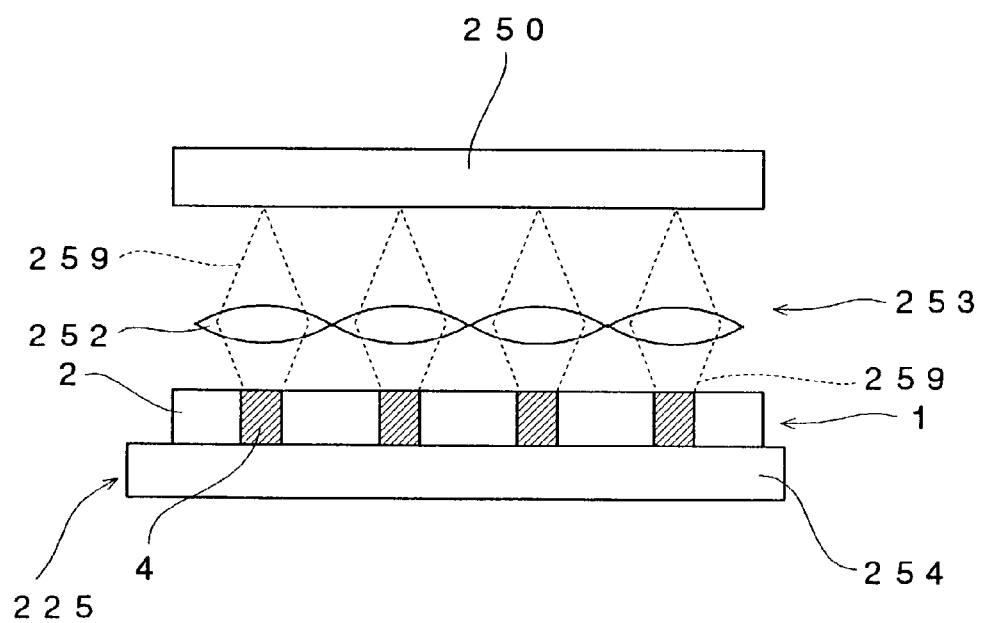
FIG. 26 is a schematic view of an apparatus for producing biochemical analysis data which is a further preferred embodiment of the present invention.

FIG. 26 is a schematic view of an apparatus for producing biochemical analysis data which is a further preferred embodiment of the present invention.

An apparatus for producing biochemical analysis data according to this embodiment is constituted so as to read chemiluminescence data recorded in a number of the absorptive regions 4 formed in the substrate 2 of the biochemical analysis unit 1 and as shown in FIG. 26, it includes a cooled CCD area sensor 250, a sample stage 255 provided with a transparent glass plate 254 on which the biochemical analysis unit 1 formed with a number of the absorptive regions 4 in which chemiluminescence data are recorded is to be placed, and a lens array 253 disposed close to the sample stage 255 and provided with a number of convex lenses 252 so that each of them is disposed at a position corresponding to one of a number of the absorptive regions 4 formed in the substrate 2 of the biochemical analysis unit 1 to be placed on the sample stage 255.

Figure 27:
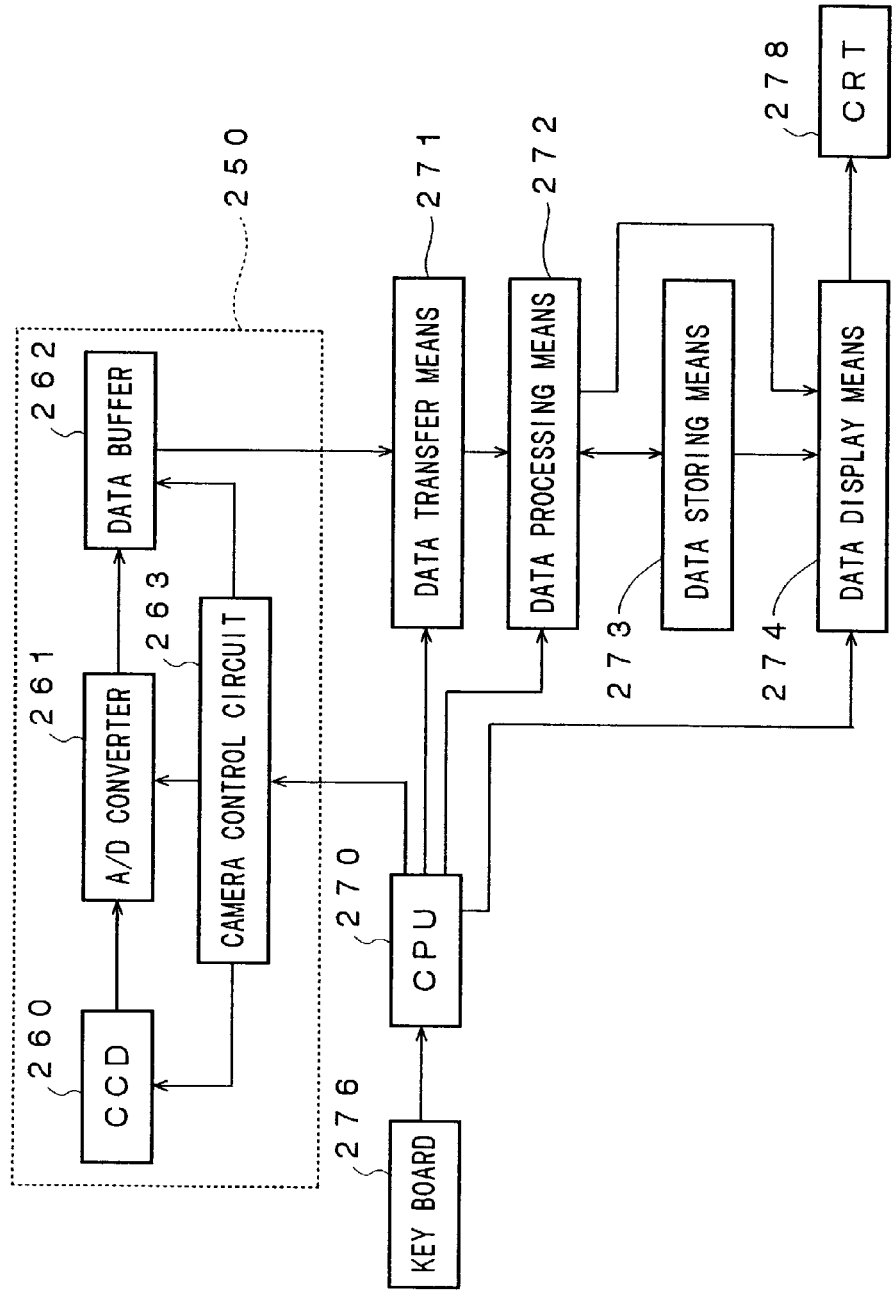
FIG. 27 is a block diagram of a control system, a detection system and a memory system of a cooled CCD area sensor and a control system, a memory system, a display system and an input system of an apparatus for producing biochemical analysis data shown in FIG. 26.

FIG. 27 is a block diagram of a control system, a detection system and a memory system of the cooled CCD area sensor 250 and a control system, a memory system, a display system and an input system of an apparatus for producing biochemical analysis data according to this embodiment.

As shown in FIG. 27, the cooled CCD area sensor 250 includes a CCD 260, an A/D converter 261 for digitizing analog data produced by the CCD 260 in the form of electric charge, a data buffer 262 for temporarily storing biochemical analysis data produced by digitizing analog data by the A/D converter 261 and a camera control circuit 263 for controlling the overall operation of the cooled CCD area sensor 250.

As shown in FIG. 27, the apparatus for producing biochemical analysis data according to this embodiment includes a CPU 270 for controlling the overall operation of the cooled CCD area sensor 250, a data transfer means 271 for reading biochemical analysis data produced by the cooled CCD area sensor 250 from the data buffer 262, a data processing means 272 for effecting data processing on biochemical analysis data read by the data transfer means 271, a data storing means 273 for biochemical analysis data subjected to data processing by the data processing means 272, a data display means 274 for producing quantitative data based on biochemical analysis data stored in the data storing means 263 and displaying the quantitative data on the screen of a CRT 278, and a keyboard 276 which can be operated by a user and through which various instruction signals can be input.

The CPU 270 is adapted for outputting various signals to the camera control circuit 263 of the cooled CCD area sensor 250 based on instruction signals input through the keyboard 276.

The thus constituted apparatus for producing biochemical analysis data according to this embodiment reads chemiluminescence data recorded in a number of the absorptive regions 4 formed in the substrate 2 of the biochemical analysis unit 1 in the following manner.

The biochemical analysis unit 1 is first placed by the user on the transparent glass plate 254 of the sample stage 255, while in a state of releasing chemiluminescence emission as a result of contact of a labeling substance contained in the absorptive layers 4 formed in the substrate 2 of the biochemical analysis unit 1 and a chemiluminescent substrate.

In this embodiment, guide members (not shown) are provided in the sample stage 255 for ensuring that the biochemical analysis unit 1 is placed on the sample stage 255 so that a number of the absorptive regions 4 accurately face the corresponding convex lenses 252 mounted on the lens array 253.

A data production start signal is then input through the keyboard 276 by the user and the data production start signal is input to the CPU 270.

When the CPU 270 receives the data production start signal, it outputs an exposure start signal to the camera control circuit 263 of the cooled CCD area sensor 250, thereby causing the cooled CCD area sensor 220 to start detecting chemiluminescence emission 259 released from a number of the absorptive regions 4 formed in the substrate 2 of the biochemical analysis unit 1.

Chemiluminescence emission 259 released from a number of the absorptive regions 4 of the biochemical analysis unit 1 is collected by the corresponding convex lens 252 disposed so as to face and be close to the absorptive region 4 and impinges onto the photo-electric detecting surface of the CCD 260 of the cooled CCD area sensor 250, thereby forming an image on the photo-electric detecting surface of the CCD 260.

The CCD 260 of the CCD area sensor 250 receives light of the thus formed image and accumulates it in the form of electric charges therein.

When a predetermined time has passed, the CPU 270 outputs an exposure completion signal to the camera control circuit 263 of the cooled CCD area sensor 250.

When the camera control circuit 263 receives the exposure completion signal from the CPU 270, it transfers analog data accumulated in the CCD 260 in the form of electric charge to the A/D converter 261 to cause the A/D converter 261 to digitize the data, thereby producing biochemical analysis data and to temporarily store the thus produced biochemical analysis data in the data buffer 262.

At the same time, the CPU 270 outputs a data transfer signal to the data transfer means 271 to cause it to read out the biochemical analysis data from the data buffer 262 of the cooled CCD area sensor 250 and to input them to the data processing means 272.

The data processing means 272 effects necessary data processing on the biochemical analysis data in accordance with the user's instructions and stores the biochemical analysis data in the data storing means 273.

When the user inputs a data display signal through the keyboard 276, the CPU 270 outputs the data display signal to the data display means 274, thereby causing the data display means 274 to produce quantitative analysis data based on the biochemical analysis data stored in the data storing means 273 and to display them on the screen of the CRT 278.

According to this embodiment, even in the case where the absorptive regions 4 are formed in the substrate 2 of the biochemical analysis unit 1 at a high density, since the lens array 253 provided with a number of the convex lenses 252 is provided to be close to the biochemical analysis unit 1 placed on the sample stage 255 in such a manner that each of the convex lenses 252 accurately faces one of the absorptive regions 4 formed in the substrate 2 of the biochemical analysis unit 1, only chemiluminescence emission 259 released from the absorptive regions 4 of the biochemical analysis unit 1 can be collected by the corresponding convex lenses 252 and led to the CCD 260 of the cooled CCD area sensor 250. Therefore, it is possible to detect chemiluminescence emission 259 with high sensitivity, thereby producing biochemical analysis data.

Figure 28:
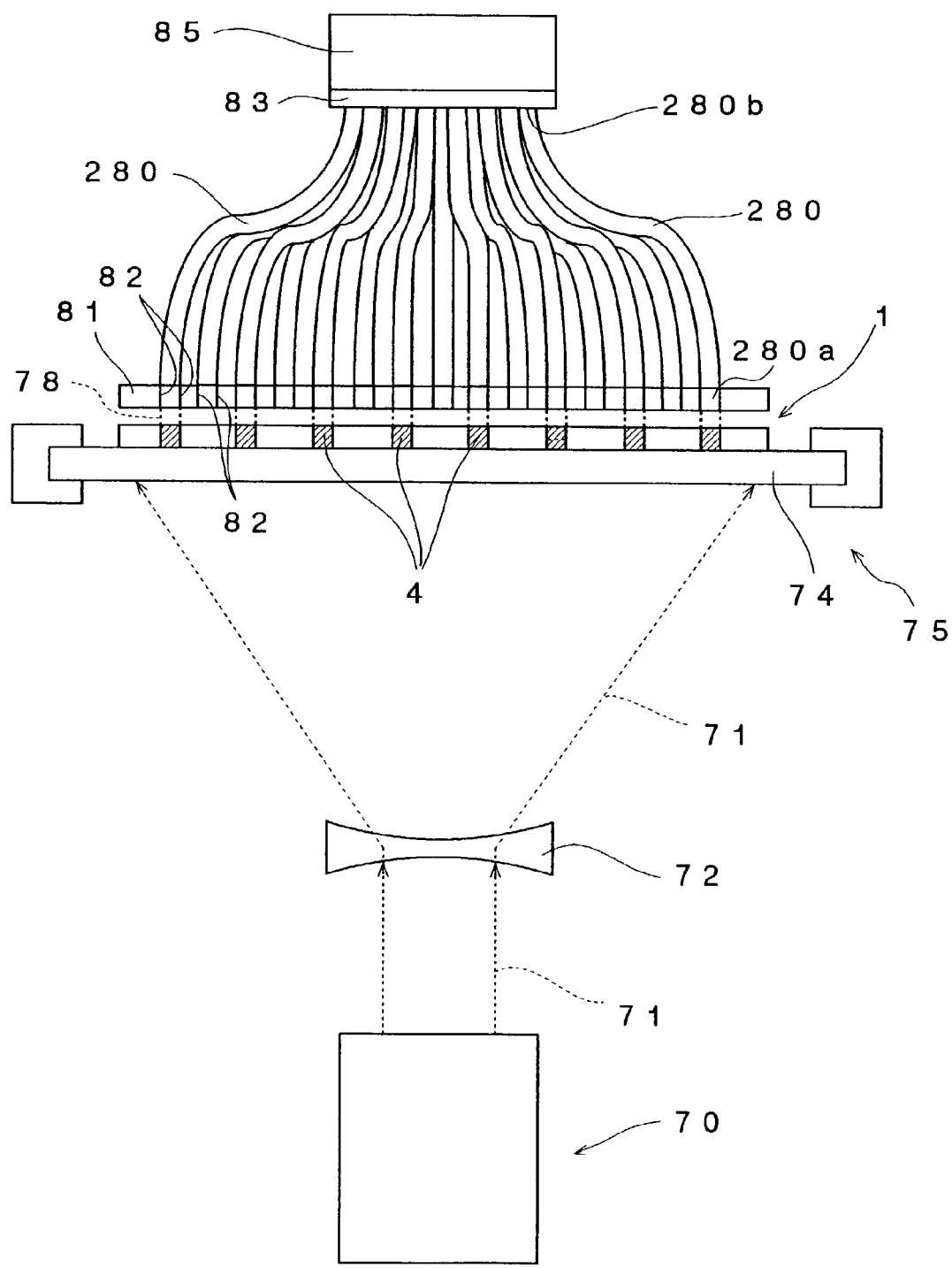
FIG. 28 is a schematic cross sectional view showing an apparatus for producing biochemical analysis data which is a further preferred embodiment of the present invention.

FIG. 28 is a schematic cross-sectional view showing an apparatus for producing biochemical analysis data which is a further preferred embodiment of the present invention.

Similarly to the apparatus for producing biochemical analysis data shown in FIG. 10, the apparatus for producing biochemical analysis data according to this embodiment is constituted so as to read fluorescence data of a fluorescent substance effectively stimulable by a laser beam having a wavelength of 473 nm, for example, Cy3 (registered trademark), to produce biochemical analysis data.

As shown in FIG. 28, the apparatus for producing biochemical analysis data according to this embodiment has the same configuration as that of the apparatus for producing biochemical analysis data shown in FIG. 10 except that a number of optical fiber members 280 disposed at a high density so that adjacent light collecting end portions 280*a* are in contact with each other are provided instead of a number of the optical fiber members 80 formed with the light collecting end portions 80*a* at positions facing the individual absorptive regions 4 formed in the substrate 2 of the biochemical analysis unit 1.

Therefore, since fluorescence emission 78 released from a fluorescent substance contained in each of the absorptive regions 4 of the biochemical analysis unit 1 in response to the excitation with the laser beam 71 is collected by light collecting end portions 280*a* of the two or more optical fiber members 280, led to a corresponding region of the stimulating ray cutting filter 83 by the optical fiber members 280, transmitted through the stimulating ray cutting filter 83 and received by the photo-electric detecting surface of the CCD 90 of the CCD area sensor 85, what region on the photo-electric detecting surface of the CCD 90 of the cooled CCD area sensor 85 fluorescence emission 78 released from each of the absorptive regions 4 formed in the substrate 2 of the biochemical analysis unit 1 is led to and what region on the photo-electric detecting surface of the CCD 90 of the cooled CCD area sensor 85 the fluorescence emission 78 is received by depend upon how the optical fiber members 280 are gathered in the vicinity of the end portions 280*b* opposite to the light collecting end portions 280*a* and are not obvious.

Therefore, in this embodiment, it is detected in advance what region on the photo-electric detecting surface of the CCD 90 fluorescence emission 78 released from each of the absorptive regions 4 formed in the substrate 2 of the biochemical analysis unit 1 is led to by two or more optical fiber members 280 and what region on the photo-electric detecting surface of the CCD 90 the fluorescence emission 78 is received by and position data are produced and stored in the memory 108.

When position data are to be produced, the laser stimulating ray source 70 and the concave lens 72 are removed from the apparatus for producing biochemical analysis data and the position data production optical system shown in FIG. 8 is installed.

Then, the position data producing unit 65 shown in FIG. 9 is placed on the transparent glass plate 74 of the sample stage 75 and a position data production signal is input through the keyboard 107.

The position data production signal is output to the CPU 100 and when the CPU 100 receives the position data production signal, it outputs a drive signal to the LED light source 61, thereby activating it.

A light beam 60 emitted from the LED light source 61 passes through a collimator lens 62, thereby being made a parallel beam and enters a beam expander 63.

The light beam 60 passes through the beam expander 63, whereby the beam diameter thereof is accurately adjusted and impinges onto the reflection mirror 64, thereby being reflected by the reflection mirror 64.

The light beam 60 reflected by the reflection mirror 64 enters a first through-hole 67 formed in the substrate 66 of the position data producing unit 65 placed on the transparent glass plate 74 of the sample stage 75.

In this embodiment, the reflection mirror 64 is constituted so as to be rotated by a motor (not shown) so that the position data producing unit 65 is scanned with the light beam 60 reflected by the reflection mirror 64 in the main scanning direction indicated by the arrow X in FIG. 8 at a pitch equal to the distance between neighboring through-holes 67.

The light beam 60 entering the first through-hole 67 formed in the substrate 66 of the position data producing unit 65 is collected by the light collecting end portions 280a of the two or more optical fiber members 280 disposed so as to face the first through-hole 67 and guided by the optical fiber members 280 to impinge upon a region of the stimulating ray cutting filter 83 facing the end portions 280b opposite to the light collecting end portions 280a of the optical fiber members 280.

Since the stimulating ray cutting filter 83 has a property of cutting light having a wavelength of 473 nm equal to a wavelength of the laser beam 71 and transmitting light having a wavelength longer than 473 nm, the light beam 60 emitted from the LED light source 61 and transmitted through the first through-hole 67 of the position data producing unit 65 passes through the stimulating ray cutting filter 83 and impinges onto the photo-electric detecting surface of the CCD 90, thereby forming an image thereon. The CCD 90 receives light of the thus formed image and accumulates it in the form of electric charges therein.

When a predetermined time has passed, the CPU 100 outputs an exposure completion signal to the camera control circuit 93 of the cooled CCD area sensor 85 and the stimulating ray source control means 106 and when stimulating ray source control means 106 receives the exposure completion signal from the CPU 100, it turns off the LED light source 61.

The CPU 100 further outputs a drive signal to the main scanning stepping motor based on drive pulses determined in accordance with the rotation position of the reflecting mirror 64 and stored in the memory 108, thereby rotating the reflection mirror 64 to a position where a second through-hole 67 of the position data producing unit 65 next to the first through-hole 67 can be irradiated with the light beam 60 emitted from the LED light source 61.

On the other hand, when the camera control circuit 93 receives the exposure completion signal from the CPU 100, it transfers analog data accumulated in the CCD 90 in the form of electric charge to the A/D converter 91 to cause the A/D converter 91 to digitize the data, thereby producing position data of the first through-hole 67 of the position data producing unit 65 and to temporarily store the thus produced position data in the data buffer 92.

At the same time, the CPU 100 outputs a data transfer signal to the data transfer means 101 to cause it to read out the position data of the first through-hole 67 of the position data producing unit 65 from the data buffer 92 of the cooled CCD area sensor 85 and to store them to the memory 108.

In this manner, the position data are produced by collecting the light beam 60 emitted from the LED light source 61 transmitted through the first through-hole 67 by the light collecting end portions 280a of the two or more optical fiber members 280, leading it to the photo-electric detecting surface of the CCD 90 and photoelectrically detecting it and the so-produced position data are stored in the memory 108. These position data correspond to position data of fluorescence emission 78 released from an absorptive region 4 corresponding to the first through-hole 67 of the position data producing unit 65 among a number of the absorptive regions 4 formed in the substrate 2 of the biochemical analysis unit 1.

When the position data of the first through-hole 67 of the position data producing unit 65 have been stored in the memory 108, the CPU 100 outputs a drive signal to the LED light source 61, thereby turning it on.

A light beam 60 emitted from the LED light source 61 passes through a collimator lens 62, thereby being made a parallel beam and enters a beam expander 63.

The light beam 60 passes through the beam expander 63, whereby the beam diameter thereof is accurately adjusted and impinges onto a reflection mirror 64, thereby being reflected by the reflection mirror 64.

The light beam 60 reflected by the reflection mirror 64 enters the second through-hole 67 formed in the substrate 66 of the position data producing unit 65 next to the first through-hole 67 placed on the transparent glass plate 74 of the sample stage 75.

The light beam 60 entering the second through-hole 67 formed in the substrate 66 of the position data producing unit 65 is collected by the light collecting end portions 280a of the two or more optical fiber members 280 disposed so as to face the second through-hole 67 and guided by the optical fiber members 280 to impinge upon a region of the stimulating ray cutting filter 83 facing the end portions 280b opposite to the light collecting end portions 280a of the optical fiber members 280. The light beam 60 then passes through the stimulating ray cutting filter 83 and impinges onto the photo-electric detecting surface of the CCD 90, thereby forming an image thereon. The CCD 90 receives light of the thus formed image and accumulates it in the form of electric charges therein.

When a predetermined time has passed, the CPU 100 outputs an exposure completion signal to the camera control circuit 93 of the cooled CCD area sensor 85 and the stimulating ray source control means 106 and when stimulating ray source control means 106 receives the exposure completion signal from the CPU 100, it turns off the LED light source 61.

The CPU 100 further outputs a drive signal to the main scanning stepping motor based on drive pulses determined in accordance with the rotation position of the reflecting mirror 64 and stored in the memory 108, thereby rotating the reflection mirror 64 to a position where a third through-hole 67 of the position data producing unit 65 next to the second through-hole 67 can be irradiated with the light beam 60 emitted from the LED light source 61.

On the other hand, when the camera control circuit 93 receives the exposure completion signal from the CPU 100, it transfers analog data accumulated in the CCD 90 in the form of electric charge to the A/D converter 91 to cause the A/D converter 91 to digitize the data, thereby producing position data of the second through-hole 67 of the position data producing unit 65 and to temporarily store the thus produced position data in the data buffer 92.

At the same time, the CPU 100 outputs a data transfer signal to the data transfer means 101 to cause it to read out the position data of the second through-hole 67 of the position data producing unit 65 from the data buffer 92 of the cooled CCD area sensor 85 and to store them to the memory 108.

In this manner, the position data are produced by collecting the light beam 60 emitted from the LED light source 61 transmitted through the second through-hole 67 by the light collecting end portions 280a of the two or more optical fiber members 280, leading it to the photo-electric detecting surface of the CCD 90 and photoelectrically detecting it and the so-produced position data are stored in the memory 108. These position data correspond to position data of fluorescence emission 78 released from an absorptive region 4 corresponding to the second through-hole 67 of the position data producing unit 65 among a number of the absorptive regions 4 formed in the substrate 2 of the biochemical analysis unit 1.

The CPU 100 further outputs a drive signal to the LED light source 61, thereby turning it on and produces position data of the third through-hole 67 of the position data producing unit 65 to store them in the memory 108.

When position data of all of the through-holes 67 formed in the substrate 66 of the position data producing unit 65 have been produced by the cooled CCD area sensor 85 and stored in the memory 108 similarly to the above, the production of the positional data is completed.

When the position data of a number of the through-holes 67 formed in the substrate 66 of the position data producing unit 65 have been stored in the memory 108 in this manner, the apparatus for producing biochemical analysis data according to this embodiment reads fluorescence data recorded in a number of the absorptive regions 4 formed in the substrate 2 of the biochemical analysis unit 1 to produce biochemical analysis data in the following manner.

A biochemical analysis unit 1 formed with a number of the absorptive regions 4 in which fluorescence data are recorded is first set on a transparent glass plate 74 of the sample stage 75 by a user.

A data production start signal is then input through the keyboard 107 by the user and the data production start signal is input to the CPU 100.

When the CPU 100 receives the data production start signal, it outputs the data production start signal to the laser stimulating ray source 70, thereby activating it.

A laser beam 71 having a wavelength of 473 nm and emitted from the laser stimulating ray source 70 passes through a concave lens 72, thereby being diverged and the whole surface of the biochemical analysis unit 1 placed on the transparent glass plate 74 of the sample stage 75 is simultaneously irradiated with the diverged laser beam 71.

When a number of the absorptive regions 4 formed in the substrate 2 of the biochemical analysis unit 1 are irradiated with the laser beam 71, a fluorescent substance, for example, Cy3, contained therein is excited, thereby releasing fluorescence emission 78.

Fluorescence emission 78 released from each of the absorptive regions 4 formed in the substrate 2 of the biochemical analysis unit 1 is collected by the light collecting end portions 280a of the two or more optical fiber members 280 disposed at positions facing each of the absorptive regions 4.

In this embodiment, since each of a number of the optical fiber members 280 is secured into the through-hole 82 formed in the fixing head 81 in the vicinity of the light collecting end portion 280a so that the adjacent light collecting end portions 280a of the optical fiber members 280 are in contact with each other and disposed at a high density to be close to the individual absorptive regions 4 of the biochemical analysis unit 1 placed on the transparent glass plate 74 of the sample stage 75, fluorescence emission 78 released from each of the absorptive regions 4 is reliably collected by the light collecting end portions 280a of the two or more optical fiber members 280.

Fluorescence emission 78 released from each of the absorptive regions 4 of the biochemical analysis unit 1 and collected by the light collecting end portions 280a of a particular set of the two or more optical fiber members 280 is guided by the two or more optical fiber members 280 and impinges onto a corresponding region of the stimulating ray cutting filter 83.

In this embodiment, since the optical fiber members 280 are gathered in the vicinity of the end portions 280b opposite to the light collecting end portions 280a, even in the case where a number of the optical fiber members 280 are provided at a high density so that the adjacent light collecting end portions 280a are in contact with each other, it is possible to employ a stimulating ray source cutting filter 83 having a small area and a cooled CCD area sensor 85 provided with a photo-electric detecting surface having a small area. Therefore, it is possible to make an apparatus for producing biochemical analysis data smaller and to lower the cost of manufacturing an apparatus for producing biochemical analysis data.

Further, in this embodiment, since the position data indicating the positional relationship between the position of each of the absorptive regions 4 which are to release fluorescence emission 78 and the position of the photo-electric detecting surface of the CCD 90 where fluorescence emission 78 led by the two or more optical fiber members 280 is to be detected are produced in advance and stored in the memory 108, it is not necessary to dispose the end portions 280b of the optical fiber members 280 in the same pattern as that of the light collecting end portions 280a thereof.

Since the stimulating ray source cutting filter 83 has a property of cutting off light having a wavelength of 473 nm equal to that of the laser beam 71 and transmitting light having a wavelength longer than 473 nm, light having a wavelength of 473 nm is cut off by the stimulating ray source cutting filter 83 and only fluorescence emission 78 released from the absorptive regions 4 is transmitted therethrough and impinges onto the photo-electric detecting surface of the CCD 90, thereby forming an image on the photo-electric detecting surface of the CCD 90. The CCD 90 receives light of the thus formed image and accumulates it in the form of electric charges therein.

When a predetermined time has passed, the CPU 100 outputs an exposure completion signal to the camera control circuit 93 of the cooled CCD area sensor 85 and outputs a data production completion signal to the stimulating ray source control means 106.

When the stimulating ray source control means 106 receives the data production completion signal from the CPU 100, it turns off the laser stimulating ray source 70.

On the other hand, when the camera control circuit 93 receives the exposure completion signal from the CPU 100, it transfers analog data accumulated in the CCD 90 in the form of electric charge to the A/D converter 91 to cause the A/D converter 91 to digitize the data, thereby producing biochemical analysis data and to temporarily store the thus produced biochemical analysis data in the data buffer 92.

At the same time, the CPU 100 outputs a data transfer signal to the data transfer means 101 to cause it to read out the biochemical analysis data from the data buffer 92 of the cooled CCD area sensor 85 and to input them to the data processing means 102.

The data processing means 102 effects necessary data processing on the biochemical analysis data in accordance with the user's instructions, reads the position data stored in the memory 108 and stores the biochemical analysis data of each of the absorptive regions 4 formed in the substrate 2 of the biochemical analysis unit 1 in a corresponding memory area in the data storing means 103.

When the user inputs a data display signal through the keyboard 107, the CPU 100 outputs the data display signal to the data display means 104, thereby causing the data display means 104 to produce quantitative analysis data based on the biochemical analysis data stored in the data storing means 103 and to display them on the screen of the CRT 105.

According to this embodiment, since the position data indicating the positional relationship between the position of each of the absorptive regions 4 which are to release fluorescence emission 78 and the position of the photo-electric detecting surface of the CCD 90 where fluorescence emission 78 led by the two or more optical fiber members 280 is to be detected are produced in advance and stored in the memory 108, it is not necessary to dispose a number of the optical fiber members 280 so that each of them faces one of the absorptive regions 4 formed in the substrate 2 of the biochemical analysis unit 1 and biochemical analysis data can be produced by disposing a number of the optical fiber members 280 at a high density so that adjacent light collecting end portions 280a of the optical fiber members 280 are in contact with each other, leading fluorescence emission 78 released from a number of the absorptive regions 4 of the biochemical analysis unit 1 by the optical fiber members 280 to the photo-electric detecting surface of the CCD 90 of the cooled CCD area sensor 85 and photoelectrically detecting the fluorescence emission 78. Therefore, it is possible to markedly lower the cost of manufacturing an apparatus for producing biochemical analysis data and produce biochemical analysis data having an excellent quantitative characteristic by photoelectrically detecting fluorescence emission 78 with high resolution.

Further, according to this embodiment, since the position data indicating the positional relationship between the position of each of the absorptive regions 4 which are to release fluorescence emission 78 and the position of the photo-electric detecting surface of the CCD 90 where fluorescence emission 78 led by the two or more optical fiber members 280 is to be detected are produced in advance and stored in the memory 108, a number of the optical fiber members 280 can be gathered in the vicinity of the end portions 280b opposite to the light collecting end portions 280a and even in the case where a number of the optical fiber members 280 are disposed at a high density so that the adjacent light collecting end portions 280a are in contact with each other and fluorescence emission 78 released from a number of the absorptive regions 4 of the biochemical analysis unit 1 is led by the optical fiber members 280 to the photo-electric detecting surface of the CCD 90 of the cooled CCD area sensor 85, it is possible to employ a stimulating ray source cutting filter 83 having a small area and a cooled CCD area sensor 85 provided with a photo-electric detecting surface having a small area. Therefore, it is possible to make an apparatus for producing biochemical analysis data smaller and to lower the cost of manufacturing an apparatus for producing biochemical analysis data.

Figure 29:
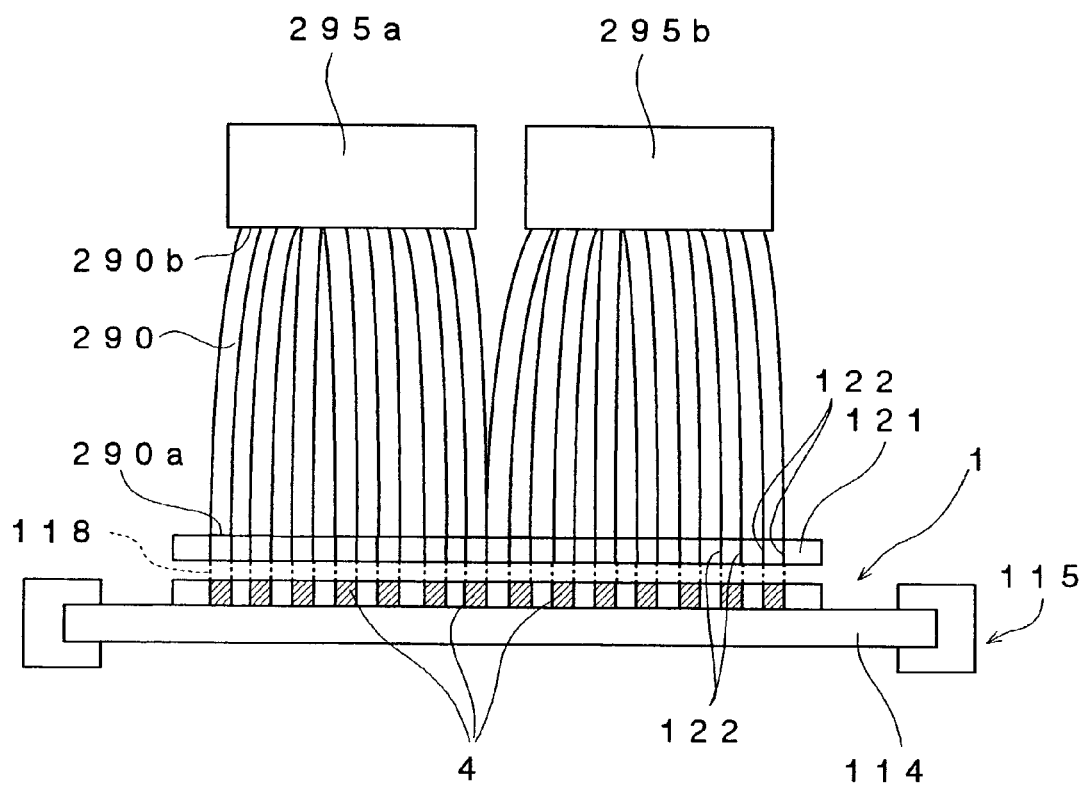
FIG. 29 is a schematic cross sectional view showing an apparatus for producing biochemical analysis data which is a further preferred embodiment of the present invention.

FIG. 29 is a schematic cross-sectional view showing an apparatus for producing biochemical analysis data which is a further preferred embodiment of the present invention.

Similarly to the apparatus for producing biochemical analysis data shown in FIG. 12, the apparatus for producing biochemical analysis data according to this embodiment is constituted so as to read chemiluminescence data recorded in a number of the absorptive regions 4 of the biochemical analysis unit 1 to produce biochemical analysis data.

As shown in FIG. 29, the apparatus for producing biochemical analysis data according to this embodiment has the same configuration as that of the apparatus for producing biochemical analysis data shown in FIG. 12 except that two cooled CCD area sensor 295a and 295b are provided and that a number of optical fiber members 290 disposed at a high density so that adjacent light collecting end portions 290a are in contact with each other are provided instead of a number of the optical fiber members 120 formed with the light collecting end portions 120a at positions facing the individual absorptive regions 4 formed in the substrate 2 of the biochemical analysis unit 1.

Figure 30:
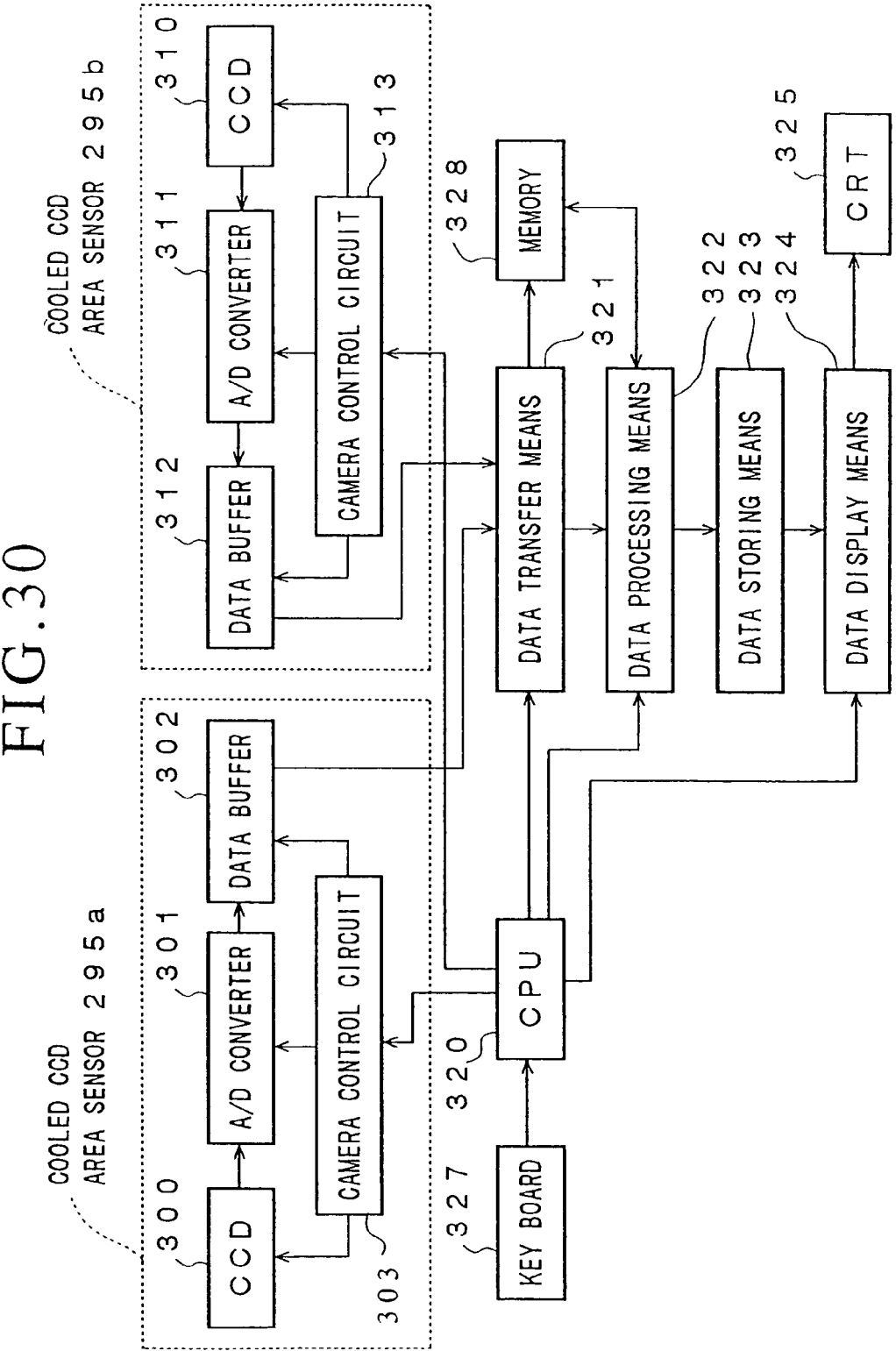
FIG. 30 is a block diagram of a control system, a detection system and a memory system of the cooled CCD area sensors and a control system, a memory system, a display system and an input system of the apparatus for producing biochemical analysis data shown in FIG. 29.

FIG. 30 is a block diagram of a control system, a detection system and a memory system of the cooled CCD area sensors 295a and 295b and a control system, a memory system, a display system and an input system of the apparatus for producing biochemical analysis data according to this embodiment.

As shown in FIG. 30, the cooled CCD area sensor 295a includes a CCD 300, an A/D converter 301 for digitizing analog data produced by the CCD 300 in the form of electric charge, a data buffer 302 for temporarily storing biochemical analysis data produced by digitizing analog data by the A/D converter 301 and a camera control circuit 303 for controlling the overall operation of the cooled CCD area sensor 295a.

Similarly, as shown in FIG. 30, the cooled CCD area sensor 295b includes a CCD 310, an A/D converter 311 for digitizing analog data produced by the CCD 310 in the form of electric charge, a data buffer 312 for temporarily storing biochemical analysis data produced by digitizing analog data by the A/D converter 311 and a camera control circuit 313 for controlling the overall operation of the cooled CCD area sensor 295b.

As shown in FIG. 30, the apparatus for producing biochemical analysis data according to this embodiment includes a CPU 320 for controlling the overall operation of the cooled CCD area sensor 295a and the overall operation of the cooled CCD area sensor 295b, a data transfer means 321 for reading biochemical analysis data produced by the cooled CCD area sensor 295a from the data buffer 302 and reading biochemical analysis data produced by the cooled CCD area sensor 295b from the data buffer 312, a data processing means 322 for effecting data processing on biochemical analysis data read by the data transfer means 321, a data storing means 323 for storing biochemical analysis data subjected to data processing by the data processing means 322, a data display means 324 for producing quantitative data based on biochemical analysis data stored in the data storing means 323 and displaying the quantitative data on the screen of a CRT 325, a keyboard 327 which can be operated by a user and through which various instruction signals can be input and a memory 328.

The CPU 320 is constituted so as to output various signals to the camera control circuit 303 of the cooled CCD area sensor 295a and the camera control circuit 313 of the cooled CCD area sensor 295b based on instruction signals input through the keyboard 327.

In the apparatus for producing biochemical analysis data according to this embodiment, a number of the optical fiber members 290 are disposed at a high density so that adjacent light collecting end portions 290a thereof are in contact with each other and chemiluminescence emission 118 is selectively led by a number of the optical fiber members 290 to one of the cooled CCD area sensor 295a and the cooled CCD area sensor 295b, thereby being photoelectrically detected. Therefore, since chemiluminescence emission 118 released from each of the absorptive regions 4 formed in the substrate 2 of the biochemical analysis unit 1 is collected by the light collecting end portions 290a of the two or more optical fiber members 290 and guided and led by the two or more optical fiber members 290 to the photo-electric detecting surface of the CCD 300 of the cooled CCD area sensor 295a or the photo-electric detecting surface of the CCD 310 of the cooled CCD area sensor 295b to be received thereby, what region on the photo-electric detecting surface of the CCD 300 of the cooled CCD area sensor 295a or the photo-electric detecting surface of the CCD 310 of the cooled CCD area sensor 295b chemiluminescence emission 118 released from each of the absorptive regions 4 formed in the substrate 2 of the biochemical analysis unit 1 is led to and what region on the photo-electric detecting surface of the CCD 300 of the cooled CCD area sensor 295a or the photo-electric detecting surface of the CCD 310 of the cooled CCD area sensor 295b the chemiluminescence emission 118 is received by depend upon the positional relationship between the end portions 290b opposite to the light collecting end portions 290a of a number of the optical fiber members 290, the photo-electric detecting surface of the CCD 300 of the cooled CCD area sensor 295a and the photo-electric detecting surface of the CCD 310 of the cooled CCD area sensor 295b, and how the optical fiber members 290 are gathered in the vicinity of the end portions 290b opposite to the light collecting end portions 290a and are not obvious.

Therefore, in this embodiment, it is detected in advance what region on the photo-electric detecting surface of the CCD 300 of the cooled CCD area sensor 295a or the photo-electric detecting surface of the CCD 310 of the cooled CCD area sensor 295b chemiluminescence emission 118 released from each of the absorptive regions 4 formed in the substrate 2 of the biochemical analysis unit 1 is led to by two or more optical fiber members 290 and what region on the photo-electric detecting surface of the CCD 300 of the cooled CCD area sensor 295a or the photo-electric detecting surface of the CCD 310 of the cooled CCD area sensor 295b the chemiluminescence emission 118 is received by and position data are produced and stored in the memory 328.

When position data are to be produced, the position data production optical system shown in FIG. 8 is installed.

Then, the position data producing unit 65 shown in FIG. 9 is placed on the transparent glass plate 114 of the sample stage 115 and a position data production signal is input through the keyboard 327. In this embodiment, an LED light source 61 for emitting a light beam 60 having an arbitrary wavelength can be employed.

The position data production start signal is input to the CPU 320 and when the CPU 320 receives the position data production start signal, it outputs a drive signal to the LED light source 61, thereby turning it on.

A light beam 60 emitted from the LED light source 61 passes through the collimator lens 62, thereby being made a parallel beam and enters the beam expander 63.

The light beam 60 passes through the beam expander 63, whereby the beam diameter thereof is accurately adjusted and impinges onto the reflection mirror 64, thereby being reflected by the reflection mirror 64.

The light beam 60 reflected by the reflection mirror 64 enters a first through-hole 67 formed in the substrate 66 of the position data producing unit 65 placed on the transparent glass plate 114 of the sample stage 115.

In this embodiment, the reflection mirror 64 is constituted so as to be rotated by a motor (not shown) so that the position data producing unit 65 is scanned with the light beam 60 reflected by the reflection mirror 64 in the main scanning direction indicated by the arrow X in FIG. 8 at a pitch equal to the distance between neighboring through-holes 67.

The light beam 60 entering the first through-hole 67 formed in the substrate 66 of the position data producing unit 65 is collected by the light collecting end portions 290a of the two or more optical fiber members 290 disposed so as to face the first through-hole 67 and guided by the optical fiber members 290 to be led onto the photo-electric detecting surface of the CCD 300 of the cooled CCD area sensor 295a or the photo-electric detecting surface of the CCD 310 of the cooled CCD area sensor 295b, thereby forming an image thereon.

The CCD 300 of the cooled CCD area sensor 295a or the CCD 310 of the cooled CCD area sensor 295b receives light of the thus formed image and accumulates it in the form of electric charges therein.

When a predetermined time has passed, the CPU 320 outputs an exposure completion signal to the camera control circuit 303 of the cooled CCD area sensor 295a and the camera control circuit 313 of the cooled CCD area sensor 295b, and outputs a drive stop signal to the LED light source 61, thereby turning it off.

The CPU 320 further outputs a drive signal to the main scanning stepping motor based on drive pulses determined in accordance with the rotation position of the reflecting mirror 64 and stored in the memory 328, thereby rotating the reflection mirror 64 to a position where a second through-hole 67 of the position data producing unit 65 next to the first through-hole 67 can be irradiated with the light beam 60 emitted from the LED light source 61.

Further, in the case where the light beam 60 has been received by the CCD 300 of the cooled CCD area sensor 295a, when the camera control circuit 303 of the cooled CCD area sensor 295a receives the exposure completion signal from the CPU 320, it transfers analog data accumulated in the CCD 300 in the form of electric charge to the A/D converter 301 to cause the A/D converter 301 to digitize the data, thereby producing position data of the first through-hole 67 of the position data producing unit 65 and to temporarily store the thus produced position data in the data buffer 302.

On the other hand, in the case where the light beam 60 has been received by the CCD 310 of the cooled CCD area sensor 295b, when the camera control circuit 313 of the cooled CCD area sensor 295b receives the exposure completion signal from the CPU 320, it transfers analog data accumulated in the CCD 310 in the form of electric charge to the A/D converter 311 to cause the A/D converter 311 to digitize the data, thereby producing position data of the first through-hole 67 of the position data producing unit 65 and to temporarily store the thus produced position data in the data buffer 312.

At the same time, the CPU 320 outputs a data transfer signal to the data transfer means 321 to cause it to read out the position data of the first through-hole 67 of the position data producing unit 65 from the data buffer 302 of the cooled CCD area sensor 295a or the data buffer 312 of the cooled CCD area sensor 295b and to store them to the memory 328.

In this manner, the position data are produced by collecting the light beam 60 emitted from the LED light source 61 transmitted through the first through-hole 67 by the light collecting end portions 290a of the two or more optical fiber members 290, leading it to the photo-electric detecting surface of the CCD 300 of the cooled CCD area sensor 295a and photoelectrically detecting it or by collecting the light beam 60 emitted from the LED light source 61 transmitted through the first through-hole 67 by the light collecting end portions 290a of the two or more optical fiber members 290, leading it to the photo-electric detecting surface of the CCD 310 of the cooled CCD area sensor 295b and photoelectrically detecting it, and are stored in the memory 328. These position data correspond to position data of chemiluminescence emission 118 released from an absorptive region 4 corresponding to the first through-hole 67 of the position data producing unit 65 among a number of the absorptive regions 4 formed in the substrate 2 of the biochemical analysis unit 1.

When the position data of the first through-hole 67 of the position data producing unit 65 have been stored in the memory 328, the CPU 320 outputs a drive signal to the LED light source 61, thereby turning it on.

A light beam 60 emitted from the LED light source 61 passes through the collimator lens 62, thereby being made a parallel beam and enters the beam expander 63.

The light beam 60 passes through the beam expander 63, whereby the beam diameter thereof is accurately adjusted and impinges onto the reflection mirror 64, thereby being reflected by the reflection mirror 64.

The light beam 60 reflected by the reflection mirror 64 enters the second through-hole 67 formed in the substrate 66 of the position data producing unit 65 next to the first through-hole 67 placed on the transparent glass plate 114 of the sample stage 115.

The light beam 60 entering the second through-hole 67 formed in the substrate 66 of the position data producing unit 65 is collected by the light collecting end portions 290a of the two or more optical fiber members 290 disposed so as to face the second through-hole 67 and guided by the optical fiber members 290 to be led onto the photo-electric detecting surface of the CCD 300 of the cooled CCD area sensor 295a or the photo-electric detecting surface of the CCD 310 of the cooled CCD area sensor 295b, thereby forming an image thereon.

The CCD 300 of the cooled CCD area sensor 295a or the CCD 310 of the cooled CCD area sensor 295b receives light of the thus formed image and accumulates it in the form of electric charges therein.

When a predetermined time has passed, the CPU 320 outputs an exposure completion signal to the camera control circuit 303 of the cooled CCD area sensor 295a and the camera control circuit 313 of the cooled CCD area sensor 295b, and outputs a drive stop signal to the LED light source 61, thereby turning it off.

The CPU 320 further outputs a drive signal to the main scanning stepping motor based on drive pulses determined in accordance with the rotation position of the reflecting mirror 64 and stored in the memory 328, thereby rotating the reflection mirror 64 to a position where a third through-hole 67 of the position data producing unit 65 next to the second through-hole 67 can be irradiated with the light beam 60 emitted from the LED light source 61.

Further, in the case where the light beam 60 has been received by the CCD 300 of the cooled CCD area sensor 295a, when the camera control circuit 303 of the cooled CCD area sensor 295a receives the exposure completion signal from the CPU 320, it transfers analog data accumulated in the CCD 300 in the form of electric charge to the A/D converter 301 to cause the A/D converter 301 to digitize the data, thereby producing position data of the second through-hole 67 of the position data producing unit 65 and to temporarily store the thus produced position data in the data buffer 302.

On the other hand, in the case where the light beam 60 has been received by the CCD 310 of the cooled CCD area sensor 295b, when the camera control circuit 313 of the cooled CCD area sensor 295b receives the exposure completion signal from the CPU 320, it transfers analog data accumulated in the CCD 310 in the form of electric charge to the A/D converter 311 to cause the A/D converter 311 to digitize the data, thereby producing position data of the second through-hole 67 of the position data producing unit 65 and to temporarily store the thus produced position analysis data in the data buffer 312.

At the same time, the CPU 320 outputs a data transfer signal to the data transfer means 321 to cause it to read out the position data of the second through-hole 67 of the position data producing unit 65 from the data buffer 302 of the cooled CCD area sensor 295a or the data buffer 312 of the cooled CCD area sensor 295b and to store them to the memory 328.

In this manner, the position data are produced by collecting the light beam 60 emitted from the LED light source 61 transmitted through the second through-hole 67 by the light collecting end portions 290a of the two or more optical fiber members 290, leading it to the photo-electric detecting surface of the CCD 300 of the cooled CCD area sensor 295a and photoelectrically detecting it or by collecting the light beam 60 emitted from the LED light source 61 transmitted through the second through-hole 67 by the light collecting end portions 290a of the two or more optical fiber members 290, leading it to the photo-electric detecting surface of the CCD 310 of the cooled CCD area sensor 295b and photoelectrically detecting it, and are stored in the memory 328. These position data correspond to position data of chemiluminescence emission 118 released from an absorptive region 4 corresponding to the second through-hole 67 of the position data producing unit 65 among a number of the absorptive regions 4 formed in the substrate 2 of the biochemical analysis unit 1.

The CPU 320 further outputs a drive signal to the LED light source 61, thereby turning it on and produces position data of the third through-hole 67 of the position data producing unit 65 to store them in the memory 328.

When position data of all of the through-holes 67 formed in the substrate 66 of the position data producing unit 65 have been produced by the cooled CCD area sensor 295a or the cooled CCD area sensor 295b and stored in the memory 328 similarly to the above, the production of the positional data is completed.

When the position data of a number of the through-holes 67 formed in the substrate 66 of the position data producing unit 65 have been stored in the memory 328 in this manner, the apparatus for producing biochemical analysis data according to this embodiment reads chemiluminescence data recorded in a number of the absorptive regions 4 formed in the substrate 2 of the biochemical analysis unit 1 to produce biochemical analysis data in the following manner.

The biochemical analysis unit 1 is first placed by a user on the transparent glass plate 114 of the sample stage 115, while in a state of releasing chemiluminescence emission as a result of contact of a labeling substance contained in the absorptive layers 4 formed in the substrate 2 of the biochemical analysis unit 1 and a chemiluminescent substrate.

A data production start signal is then input through the keyboard 327 by the user and the data production start signal is input to the CPU 320.

When the CPU 140 receives the data production start signal, it outputs an exposure start signal to the camera control circuit 303 of the cooled CCD area sensor 295a or the camera control circuit 313 of the cooled CCD area sensor 295b, thereby causing the cooled CCD area sensor 295a or the cooled CCD area sensor 295b to start detecting chemiluminescence emission 118.

Chemiluminescence emission 118 released from each of the absorptive regions 4 is collected by the light collecting end portions 290a of the two or more optical fiber members 290 disposed so as to face the absorptive region 4.

In this embodiment, since each of a number of the optical fiber members 290 is secured into the through-hole 122 formed in the fixing head 121 in the vicinity of the light collecting end portion 290a so that the adjacent light collecting end portions 290a of the optical fiber members 290 are in contact with each other and disposed at a high density to be close to the individual absorptive regions 4 of the biochemical analysis unit 1 placed on the transparent glass plate 114 of the sample stage 115, chemiluminescence emission 118 released from each of the absorptive regions 4 is reliably collected by the light collecting end portions 290a of the two or more optical fiber members 290.

Chemiluminescence emission 118 released from each of the absorptive regions 4 of the biochemical analysis unit 1 and collected by the light collecting end portions 290a of a particular set of the two or more optical fiber members 290 is guided by the two or more optical fiber members 290 and led to the photo-electric detecting surface of the CCD 300 of the cooled CCD area sensor 295a or the photo-electric detecting surface of the CCD 310 of the cooled CCD area sensor 295b, thereby forming an image thereon.

The CCD 300 of the cooled CCD area sensor 295a or the CCD 310 of the cooled CCD area sensor 295b receives light of the thus formed image and accumulates it in the form of electric charges therein.

In this embodiment, since the optical fiber members 290 are gathered in the vicinity of the end portions 290b opposite to the light collecting end portions 290a, even in the case where a number of the optical fiber members 290 are provided at a high density so that the adjacent light collecting end portions 290a are in contact with each other, it is possible to employ a cooled CCD area sensor 295a, 295b provided with a photo-electric detecting surface having a small area. Therefore, it is possible to make an apparatus for producing biochemical analysis data smaller and to lower the cost of manufacturing an apparatus for producing biochemical analysis data.

Further, in this embodiment, since the position data indicating the positional relationship between the position of each of the absorptive regions 4 which are to release chemiluminescence emission 118 and the positions of the photo-electric detecting surface of the CCD 300 of the cooled CCD area sensor 295a and the photo-electric detecting surface of the CCD 310 of the cooled CCD area sensor 295b where chemiluminescence emission 118 led by the two or more optical fiber members 290 is to be detected are produced in advance and stored in the memory 328, it is not necessary to dispose the end portions 290b of the optical fiber members 290 in the same pattern as that of the light collecting end portions 290a thereof.

When a predetermined time has passed, the CPU 320 outputs an exposure completion signal to the camera control circuit 303 of the cooled CCD area sensor 295a and the camera control circuit 313 of the cooled CCD area sensor 295b.

When the camera control circuit 303 of the cooled CCD area sensor 295a receives the exposure completion signal from the CPU 320, it transfers analog data accumulated in the CCD 300 in the form of electric charge to the A/D converter 301 to cause the A/D converter 301 to digitize the data, thereby producing biochemical analysis data and to temporarily store the thus produced biochemical analysis data in the data buffer 302.

On the other hand, when the camera control circuit 313 of the cooled CCD area sensor 295b receives the exposure completion signal from the CPU 320, it transfers analog data accumulated in the CCD 310 in the form of electric charge to the A/D converter 311 to cause the A/D converter 311 to digitize the data, thereby producing biochemical analysis data and to temporarily store the thus produced biochemical analysis data in the data buffer 312.

The CPU 320 further outputs a data transfer signal to the data transfer means 321, thereby causing it to read biochemical analysis data from the data buffer 302 of the cooled CCD area sensor 295a and to output them to the data processing means 322 and causing it to read biochemical analysis data from the data buffer 312 of the cooled CCD area sensor 295b and to output them to the data processing means 322.

The data processing means 322 effects necessary data processing on the biochemical analysis data in accordance with the user's instructions, reads the position data stored in the memory 328 and stores the biochemical analysis data of each of the absorptive regions 4 formed in the substrate 2 of the biochemical analysis unit 1 in a corresponding memory area in the data storing means 323.

When the user inputs a data display signal through the keyboard 327, the CPU 320 outputs the data display signal to the data display means 324, thereby causing the data display means 324 to produce quantitative analysis data based on the biochemical analysis data stored in the data storing means 323 and to display them on the screen of the CRT 325.

According to this embodiment, since the position data indicating the positional relationship between the position of each of the absorptive regions 4 which are to release chemiluminescence emission 118 and the positions of the photo-electric detecting surface of the CCD 300 of the cooled CCD area sensor 295a and the photo-electric detecting surface of the CCD 310 of the cooled CCD area sensor 295b where chemiluminescence emission 118 led by the two or more optical fiber members 290 is to be detected are produced in advance and stored in the memory 328, it is not necessary to dispose a number of the optical fiber members 290 so that each of them faces one of the absorptive regions 4 formed in the substrate 2 of the biochemical analysis unit 1 and biochemical analysis data can be produced by disposing a number of the optical fiber members 290 at a high density so that adjacent light collecting end portions 290a of the optical fiber members 290 are in contact with each other, leading chemiluminescence emission 118 released from a number of the absorptive regions 4 of the biochemical analysis unit 1 by the optical fiber members 290 to the photo-electric detecting surface of the CCD 300 of the cooled CCD area sensor 295a or the photo-electric detecting surface of the CCD 310 of the cooled CCD area sensor 295b and photoelectrically detecting the chemiluminescence emission 118. Therefore, it is possible to markedly lower the cost of manufacturing an apparatus for producing biochemical analysis data and produce biochemical analysis data having an excellent quantitative characteristic by photoelectrically detecting chemiluminescence emission 118 with high resolution.

Further, according to this embodiment, since the position data indicating the positional relationship between the position of each of the absorptive regions 4 which are to release chemiluminescence emission 118 and the positions of the photo-electric detecting surface of the CCD 300 of the cooled CCD area sensor 295a and the photo-electric detecting surface of the CCD 310 of the cooled CCD area sensor 295b where chemiluminescence emission 118 led by the two or more optical fiber members 290 is to be detected are produced in advance and stored in the memory 328, a number of the optical fiber members 290 can be gathered in the vicinity of the end portions 290b opposite to the light collecting end portions 290a and even in the case where a number of the optical fiber members 290 are disposed at a high density so that the adjacent light collecting end portions 290a are in contact with each other and chemiluminescence emission 118 released from a number of the absorptive regions 4 of the biochemical analysis unit 1 is led by the optical fiber members 290 to the photo-electric detecting surface of the CCD 300 of the cooled CCD area sensor 295a or the photo-electric detecting surface of the CCD 310 of the cooled CCD area sensor 295b, it is possible to employ a cooled CCD area sensor 295a, 295b provided with a photo-electric detecting surface having a small area. Therefore, it is possible to make an apparatus for producing biochemical analysis data smaller and to lower the cost of manufacturing an apparatus for producing biochemical analysis data.

Figure 31:
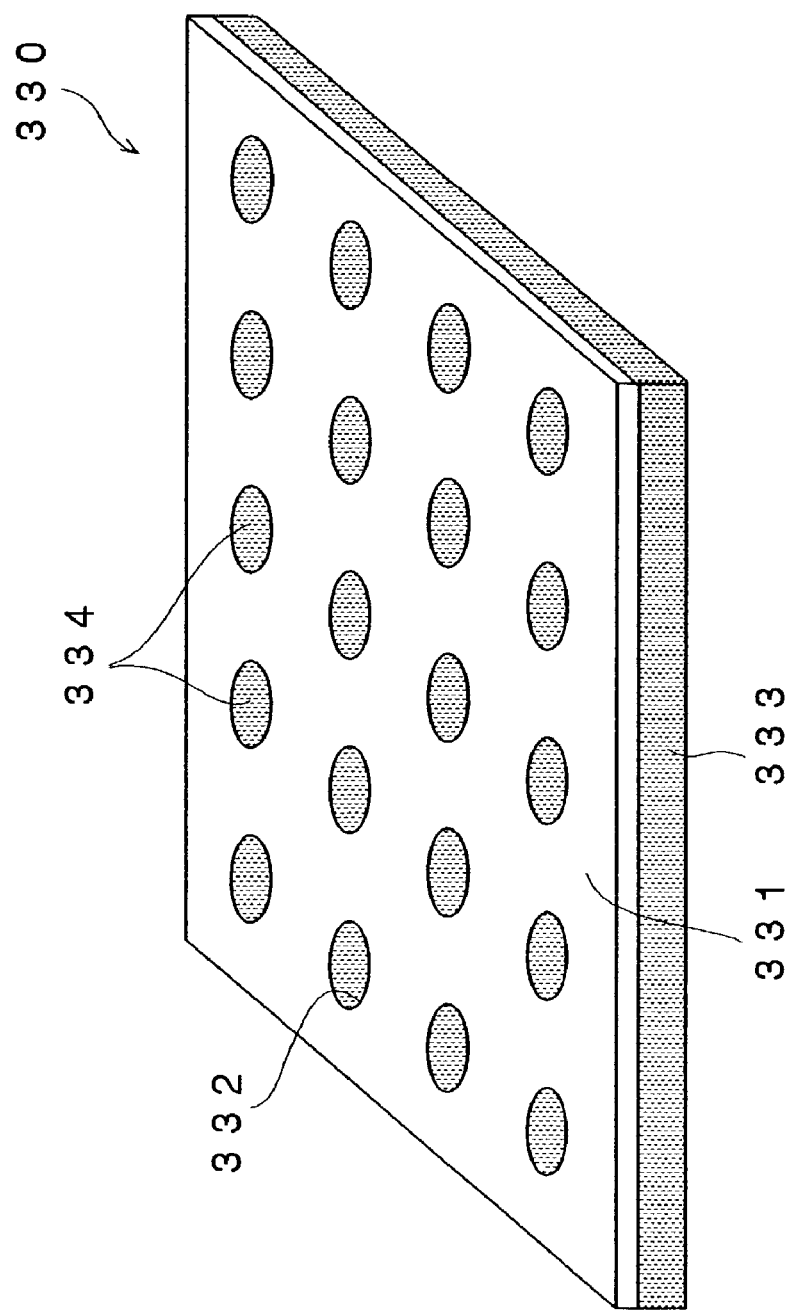
FIG. 31 is a schematic perspective view showing a biochemical analysis unit used in a method for producing biochemical analysis data which a further preferred embodiment of the present invention.

FIG. 31 is a schematic perspective view showing a biochemical analysis unit used in a method for producing biochemical analysis data which a further preferred embodiment of the present invention.

As shown in FIG. 31, a biochemical analysis unit 330 according to this embodiment includes a substrate 331 made of stainless steel and formed with a number of substantially circular through-holes 332 and a number of absorptive regions 334 are dot-like formed in a regular pattern by pressing an absorptive membrane 333 formed of nylon-6 into a number of the through-holes 332 formed in the substrate 331 using a calender processing apparatus (not shown).

Although not accurately shown in FIG. 31, in this embodiment, about 10,000 substantially circular absorptive regions 334 having a size of about 0.01 mm$^2$ are regularly formed at a density of about 5,000 per cm$^2$ in the biochemical analysis unit 330.

In this embodiment, a number of absorptive regions 334 are formed by pressing the absorptive membrane 333 into a number of the through-holes 332 formed in the substrate 331 in such a manner that the surfaces of the absorptive regions 334 are located at the same height level as that of the substrate 331.

In this embodiment, similarly to the foregoing embodiments, a solution containing specific binding substances such as a plurality of cDNAs is spotted onto a number of the absorptive regions 334 formed in the substrate 331 of the biochemical analysis unit 330 and the specific binding substances are absorbed in a number of the absorptive regions 334.

Further, a hybridization solution 9 containing a substance derived from a living organism and labeled with a labeling substance which generates chemiluminescence emission when it contacts a chemiluminescent substrate and a substance derived from a living organism and labeled with a fluorescent substance is prepared and accommodated in the hybridization reaction vessel 8 shown in FIG. 3.

The biochemical analysis unit 330 is then set in the hybridization reaction vessel 8 and a substance derived from a living organism, labeled with a labeling substance which generates chemiluminescence emission when it contacts a chemiluminescent substrate and contained in the hybridization reaction solution 9 and a substance derived from a living organism, labeled with a fluorescent substance and contained in the hybridization reaction solution 9 are selectively hybridized with the specific binding substances such as cDNAs absorbed in a number of the absorptive regions 334 of the biochemical analysis unit 330.

In this manner, chemiluminescence data and fluorescence data are recorded in a number of the absorptive regions 334 formed in the substrate 331 of the biochemical analysis unit 330.

Fluorescence data recorded in a number of the absorptive regions 334 formed in the substrate 331 of the biochemical analysis unit 330 are read by the apparatus for producing biochemical analysis data shown in FIGS. 10 and 11, the apparatus for producing biochemical analysis data shown in FIGS. 20 and 21, the apparatus for producing biochemical analysis data shown in FIGS. 24 and 25 or the apparatus for producing biochemical analysis data shown in FIG. 28, thereby producing biochemical analysis data.

On the other hand, chemiluminescence data recorded in a number of the absorptive regions 334 formed in the substrate 331 of the biochemical analysis unit 330 are read by the apparatus for producing biochemical analysis data shown in FIGS. 12 and 13, the apparatus for producing biochemical analysis data shown in FIGS. 26 and 27 or the apparatus for producing biochemical analysis data shown in FIGS. 29 and 30, or are transferred onto a number of the stimulable phosphor layer regions 17 of the stimulable phosphor sheet 15 shown in FIG. 14 and read by the apparatus for producing biochemical analysis data shown in FIGS. 16 and 17 or the apparatus for producing biochemical analysis data shown in FIGS. 22 and 23, thereby producing biochemical analysis data.

The present invention has thus been shown and described with reference to specific embodiments. However, it should be noted that the present invention is in no way limited to the details of the described arrangements but changes and modifications may be made without departing from the scope of the appended claims.

For example, in the above described embodiments, as specific binding substances, cDNAs each of which has a known base sequence and is different from the others are used. However, specific binding substances usable in the present invention are not limited to cDNAs but all specific binding substances capable of specifically binding with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, can be employed in the present invention as a specific binding substance.

Further, a number of the absorptive regions 4 of the biochemical analysis unit 1 according to the embodiment shown in FIG. 1 are formed by charging nylon-6 in a number of the through-holes formed in the substrate made of stainless steel and a number of the absorptive regions 334 of the biochemical analysis unit 330 according to the embodiment shown in FIG. 31 are formed by pressing the absorptive membrane 283 formed of nylon-6 into a number of the through-holes formed in the substrate 331 made of stainless steel. However, it is not absolutely necessary to form a number of the absorptive regions 4, 334 of the biochemical analysis unit 1, 330 of nylon-6 but a number of the absorptive regions 4, 334 of the biochemical analysis unit 1, 330 may be formed of other absorptive material. A porous material or a fiber material may be preferably used as the absorptive material for forming a number of the absorptive regions 4, 334 of the biochemical analysis unit 1, 330 and a number of the absorptive regions 4, 334 of the biochemical analysis unit 1, 330 may be formed by combining a porous material and a fiber material. A porous material for forming a number of the absorptive regions 4, 334 of the biochemical analysis unit 1, 330 may be any type of an organic material or an inorganic material and may be an organic/inorganic composite material. An organic porous material used for forming a number of the absorptive regions 4, 334 of the biochemical analysis unit 1, 330 is not particularly limited but a carbon porous material such as an activated carbon or a porous material capable of forming a membrane filter can be preferably used. Illustrative examples of porous materials capable of forming a membrane filter include nylons such as nylon-6, nylon-6,6, nylon-4,10; cellulose derivatives such as nitrocellulose, acetyl cellulose, butyric-acetyl cellulose; collagen; alginic acids such as alginic acid, calcium alginate, alginic acid/poly-L-lysine polyionic complex; polyolefins such as polyethylene, polypropylene;

polyvinyl chloride; polyvinylidene chloride; polyfluoride such as polyvinylidene fluoride, polytetrafluoride; and copolymers or composite materials thereof An inorganic porous material used for forming a number of the absorptive regions 4, 334 of the biochemical analysis unit 1, 330 is not particularly limited. Illustrative examples of inorganic porous materials preferably usable in the present invention include metals such as platinum, gold, iron, silver, nickel, aluminum and the like; metal oxides such as alumina, silica, titania, zeolite and the like; metal salts such as hydroxy apatite, calcium sulfate and the like; and composite materials thereof. A fiber material used for forming a number of the absorptive regions 4, 334 of the biochemical analysis unit 1, 330 is not particularly limited. Illustrative examples of fiber materials preferably usable in the present invention include nylons such as nylon-6, nylon-6,6, nylon-4,10; and cellulose derivatives such as nitrocellulose, acetyl cellulose, butyric-acetyl cellulose.

Furthermore, in the above described embodiments, although the substrate 2, 331 of the biochemical analysis unit 1, 330 is made of stainless steel, it is not absolutely necessary to make the substrate 2, 331 of the biochemical analysis unit 1, 330 of stainless steel but the substrate 2, 331 of the biochemical analysis unit 1, 330 may be made of other kinds of material. It is preferable to make the substrate 2, 331 of the biochemical analysis unit 1, 330 of a material capable of attenuating light energy and radiation energy but a material for forming the substrate 2, 331 of the biochemical analysis unit 1, 330 is not particularly limited. The substrate 2, 331 of the biochemical analysis unit 1, 330 can be formed of either inorganic compound material or organic compound material and is preferably formed of a metal material, a ceramic material or a plastic material. Illustrative examples of inorganic compound materials usable for forming the substrate 2, 331 of the biochemical analysis unit 1, 330 and capable of attenuating light energy and radiation energy include metals such as gold, silver, copper, zinc, aluminum, titanium, tantalum, chromium, steel, nickel, cobalt, lead, tin, selenium and the like; alloys such as brass, stainless, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. High molecular compounds are preferably used as organic compound material for forming the substrate 2, 331 of the biochemical analysis unit 1, 330 and capable of attenuating light energy and radiation energy and illustrative examples thereof include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Moreover, in the above described embodiments, although a number of the absorptive regions 4 of the biochemical analysis unit 1 are formed by charging nylon-6 in a number of the through-holes 3 formed in the substrate 2 in the embodiment shown in FIG. 1 and a number of the absorptive regions 334 of the biochemical analysis unit 330 are formed by pressing the absorptive membrane 333 into a number of the through-holes 332 formed in the substrate 331 in the embodiment shown in FIG. 31, a number of absorptive regions may be formed to be spaced apart from each other by closely contacting a perforated plate formed with a number of through-holes onto one surface of an absorptive substrate.

Further, the stimulable phosphor sheet 10 includes a number of the stimulable phosphor layer regions 12 formed by charging stimulable phosphor in a number of the through-holes 13 formed in the support 11 made of stainless steel in the embodiment shown in FIG. 4 and the stimulable phosphor sheet 15 includes a number of the stimulable phosphor layer regions 17 formed by charging stimulable phosphor in a number of the through-holes 13 formed in the support 11 made of stainless steel in the embodiment shown in FIG. 14. However, it is not absolutely necessary to form a number of the stimulable phosphor layer regions 12, 17 of the stimulable phosphor sheet 10, 15 by charging stimulable phosphor in a number of the through-holes 13 formed in the support 11 made of stainless steel but a number of stimulable phosphor layer regions may be formed by pressing a stimulable phosphor membrane containing stimulable phosphor into a number of the through-holes 13 formed in the support 11 made of stainless steel.

Moreover, in the above described embodiments, although the support 11 of the stimulable phosphor sheet 10, 15 is made of stainless steel, it is not absolutely necessary to make the support 11 of the stimulable phosphor sheet 10, 15 of stainless steel but the support 11 of the stimulable phosphor sheet 10, 15 may be formed of other kinds of material. It is preferable to make the support 11 of the stimulable phosphor sheet 10, 15 of a material capable of attenuating radiation energy and light energy but a material for forming the support 11 of the stimulable phosphor sheet 10, 15 is not particularly limited. The support 11 of the stimulable phosphor sheet 10, 15 can be can be formed of either inorganic compound material or organic compound material and is preferably formed of a metal material, a ceramic material or a plastic material. Illustrative examples of inorganic compound materials usable for forming the support 11 of the stimulable phosphor sheet 10, 15 and capable of attenuating radiation energy and/or light energy include metals such as gold, silver, copper, zinc, aluminum, titanium, tantalum, chromium, steel, nickel, cobalt, lead, tin, selenium and the like; alloys such as brass, stainless, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. High molecular compounds are preferably used as organic compound material usable for forming the support 11 of the stimulable phosphor sheet 10, 15 and capable of attenuating radiation energy and/or light energy and illustrative examples thereof include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Further, in the above described embodiments, although about 10,000 substantially circular absorptive regions 4, 334 having a size of about 0.01 mm$^2$ are formed in a regular pattern at a density of about 5,000 per cm$^2$ in the biochemical analysis unit 1, 330, the shape of each of the absorptive regions 4, 334 is not limited to substantially a circular shape but may be formed in an arbitrary shape, for example, a rectangular shape.

Furthermore, in the above described embodiments, although about 10,000 substantially circular absorptive regions 4, 334 having a size of about 0.01 mm$^2$ are formed in a regular pattern at a density of about 5,000 per cm$^2$ in the biochemical analysis unit 1, 330, the number or size of the absorptive regions 4, 284 may be arbitrarily selected in accordance with the purpose. Preferably, 10 or more of the absorptive regions 4, 334 having a size of 5 cm$^2$ or less are formed in the biochemical analysis unit 1, 330 at a density of 10/cm$^2$ or greater.

Moreover, in the above described embodiments, although about 10,000 substantially circular absorptive regions 4, 334 having a size of about 0.01 mm$^2$ are formed in a regular pattern at a density of about 5,000 per cm$^2$ in the biochemical analysis unit 1, 330, it is not absolutely necessary to form a number of the absorptive regions 4, 334 in a regular pattern in the biochemical analysis unit 1, 330.

Further, in the above described embodiments, although correspondingly to the absorptive regions 4 formed in the biochemical analysis unit 1, about 10,000 substantially circular stimulable phosphor layer regions 12, 17 having a size of about 0.01 mm$^2$ are dot-like formed in a regular pattern at a density of about 5,000 per cm$^2$ in the stimulable phosphor sheet 10, 15, the shape of each of the stimulable phosphor layer regions 12, 17 is not limited to substantially a circular shape but may be formed in an arbitrary shape, for example, a rectangular shape.

Furthermore, in the above described embodiments, although correspondingly to the absorptive regions 4 formed in the biochemical analysis unit 1, about 10,000 substantially circular stimulable phosphor layer regions 12, 17 having a size of about 0.01 mm$^2$ are dot-like formed in a regular pattern at a density of about 5,000 per cm$^2$ in the stimulable phosphor sheet 10, 15, the number or size of the stimulable phosphor layer regions 12, 17 may be arbitrarily selected in accordance with the purpose. Preferably, 10 or more of the stimulable phosphor layer regions 12, 17 having a size of 5 cm$^2$ or less are formed in the stimulable phosphor sheet 10, 15 at a density of 10/cm$^2$ or greater.

Moreover, in the above described embodiments, although correspondingly to the absorptive regions 4 formed in the biochemical analysis unit 1, about 10,000 substantially circular stimulable phosphor layer regions 12, 17 having a size of about 0.01 mm$^2$ are dot-like formed in a regular pattern at a density of about 5,000 per cm$^2$ in the stimulable phosphor sheet 10, 15, it is not absolutely necessary to form the absorptive regions 4 in a regular pattern in the biochemical analysis unit 1 and, therefore, it is not necessary to form the stimulable phosphor layer regions 12, 17 in a regular pattern in the stimulable phosphor sheet 10, 15. It is sufficient for the stimulable phosphor layer regions 12, 17 to be formed in the stimulable phosphor sheet 10, 15 in the same pattern as that of the absorptive regions 4 formed in the biochemical analysis unit 1.

Further, in the above described embodiments, although the stimulable phosphor layer regions 12, 17 of the stimulable phosphor sheet 10, 15 are formed so that each of them has the same size as that of each of the absorptive regions 4 formed in the biochemical analysis unit 1, it is not absolutely necessary to form each of the stimulable phosphor layer regions 12, 17 so as to have the same size as that of each of the absorptive regions 4 formed in the biochemical analysis unit 1 and the size of each of the stimulable phosphor layer regions 12, 17 may be arbitrarily selected in accordance with the purpose. Preferably, each of the stimulable phosphor layer regions 12, 17 is formed in the stimulable phosphor sheet 10, 15 so as to be equal to or larger than the size of each of the absorptive regions 4 formed in the biochemical analysis unit 1.

Furthermore, in the embodiments shown in FIGS. 1 to 21 and the embodiments shown in FIGS. 22 to 25, a hybridization reaction solution 9 containing a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye is prepared. However, it is not absolutely necessary for the hybridization reaction solution 9 to contain a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye but it is sufficient for the hybridization reaction solution 9 to contain at least one kind of a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye.

Moreover, in the above described embodiments, specific binding substances are hybridized with substances derived from a living organism and labeled with a radioactive labeling substance, a substance derived from a living organism and labeled with a labeling substance which generates chemiluminescence emission when it contacts a chemiluminescent substrate and a fluorescent substance. However, it is not absolutely necessary to hybridize substances derived from a living organism with specific binding substances and substances derived from a living organism may be specifically bound with specific binding substances by means of antigen-antibody reaction, receptor-ligand reaction or the like instead of hybridization.

Further, in the embodiment shown in FIGS. 6 and 7, the embodiment shown in FIGS. 16 and 17, the embodiment shown in FIGS. 10 and 11, the embodiment shown in FIGS. 12 and 13, the embodiment shown in FIG. 28 and the embodiment shown in FIGS. 29 and 30, although position data are produced using the position data producing unit 65, it is possible to produce position data by placing the biochemical analysis unit 1 including the substrate 2 regularly formed with a number of the absorptive regions 4 on the sample stage 75 and scanning a number of the absorptive regions 4 of the biochemical analysis unit 1 with the light beam 60.

Furthermore, in the embodiment shown in FIGS. 6 and 7, the embodiment shown in FIGS. 16 and 17, the embodiment shown in FIGS. 10 and 11, the embodiment shown in FIGS. 12 and 13, the embodiment shown in FIG. 28 and the embodiment shown in FIGS. 29 and 30, the optical fiber members 30, 80, 120, 30, 280, 290 are gathered in the vicinity of the end portions 30*b*, 80*b*, 120*b*, 30*b*, 280*b*, 290*b* opposite to the light collecting end portions 30*a*, 80*a*, 120*a*, 30*a*, 280*a*, 290*a*. However, it is not absolutely necessary to gather the optical fiber members 30, 80, 120, 30, 280, 290 in the vicinity of the end portions 30*b*, 80*b*, 120*b*, 30*b*, 280*b*, 290*b* opposite to the light collecting end portions 30*a*, 80*a*, 120*a*, 30*a*, 280*a*, 290*a* and in the case where the optical fiber members 30, 80, 120, 30, 280, 290 are not gathered in the vicinity of the end portions 30*b*, 80*b*, 120*b*, 30*b*, 280*b*, 290*b* opposite to the light collecting end portions 30*a*, 80*a*, 120*a*, 30*a*, 280*a*, 290*a*, it is unnecessary to produce position data and store them in the memory 58, 108, 148, 328.

Further, in the embodiment shown in FIGS. 6 and 7, the embodiment shown in FIGS. 16 and 17, the embodiment shown in FIGS. 10 and 11, the embodiment shown in FIGS. 12 and 13, the embodiment shown in FIG. 28 and the embodiment shown in FIGS. 29 and 30, stimulated emission 28 released from the stimulable phosphor sheet 10, 15, fluorescence emission 78 released from the biochemical analysis unit 1 or chemiluminescence emission 118 released from the biochemical analysis unit 1 is collected by a number of the optical fiber members 30, 80, 120, 280, 290 each being constituted by a plurality of optical fibers to lead it to the cooled CCD area sensor 35, 85, 125, 295*a*, 295*b*. However, it is possible to collect stimulated emission 28 released from the stimulable phosphor sheet 10, 15, fluorescence emission 78 released from the biochemical analysis unit 1 or chemiluminescence emission 118 released from the biochemical analysis unit 1 to lead it to the cooled CCD area sensor 35, 85, 125, 295*a*, 295*b* using optical fiber members each being constituted by a single optical fiber instead of the optical fiber members 30, 80, 120, 280, 290 each being constituted by a plurality of optical fibers.

Furthermore, in the embodiment shown in FIGS. 18 and 19, the embodiment shown in FIGS. 22 and 23 and the embodiment shown in FIGS. 20 and 21, stimulated emission 158, 207 released from the stimulable phosphor sheet 10, 15 or fluorescence emission 188 released from the biochemical analysis unit 1 is collected by a number of the optical fiber members 160, 190 each being constituted by a plurality of optical fibers to lead it to the photomultiplier 165, 195. However, it is possible to collect stimulated emission 158, 207 released from the stimulable phosphor sheet 10, 15 or fluorescence emission 188 released from the biochemical analysis unit 1 to lead it to the photomultiplier 165, 195 using optical fiber members each being constituted by a single optical fiber instead of the optical fiber members 160, 190 each being constituted by a plurality of optical fibers.

Moreover, in the embodiment shown in FIGS. 18 and 19 and the embodiment shown in FIGS. 22 and 23, the laser beam 151, 206 is intermittently moved at a pitch equal to the distance between neighboring stimulable phosphor layer regions 12, 17 formed in the support 11 of the stimulable phosphor sheet 10, 15 by intermittently rotating the reflection mirror 154 and the laser stimulating ray source 150, 205 is on and off controlled, while in the embodiment shown in FIGS. 20 and 21, the laser beam 181 is intermittently moved at a pitch equal to the distance between neighboring absorptive regions 4 formed in the substrate 2 of the biochemical analysis unit 1 by intermittently rotating the reflection mirror 184 and the laser stimulating ray source 180 is on and off controlled. However, it is not absolutely necessary to intermittently move the laser beam 151, 181, 206 and on and off control the laser stimulating ray source 150, 180, 205. In particular, in the case where the support 11 of the stimulable phosphor sheet 10, 15 and the substrate 2 of the biochemical analysis unit 1 are made of a material capable of attenuating light energy, the laser beam 151, 181, 206 can be continuously moved, while the laser stimulating ray source 150, 180, 205 is kept on.

Further, in the embodiment shown in FIGS. 6 and 7, embodiment shown in FIGS. 16 and 17, the embodiment shown in FIGS. 10 and 11, the embodiment shown in FIGS. 24 and 25, the embodiment shown in FIG. 28, the embodiment shown in FIGS. 12 and 13, the embodiment shown in FIGS. 26 and 27 and the embodiment shown in FIGS. 29 and 30, although stimulated emission 28, 28, fluorescence emission 78, 229, 78 or chemiluminescence emission 118, 259 is photoelectrically detected using the cooled CCD area sensor 35, 35, 85, 220, 85, 125, 220, 250, 295a, 295b, thereby producing biochemical analysis data, biochemical analysis data may be produced by photoelectrically detecting stimulated emission 28, 28, fluorescence emission 78, 229, 78 or chemiluminescence emission 118, 259 using a CCD area sensor provided with no cooling means. Moreover, instead of the CCD area sensor, another type of solid state sensor such as a CID (charge injection device), a PDA (photodiode array), a MOS type imaging device and the like may be used.

Furthermore, in the embodiment shown in FIGS. 18 and 19, the embodiment shown in FIGS. 22 and 23 and the embodiment shown in FIGS. 20 and 21, although the photomultiplier 165, 165, 195 is employed as a light detector, instead of the photomultiplier 165, 165, 195, any other zero dimensional sensor whose pixel is not divided such as a photodiode, an avalanche photodiode or the like may be employed as a light detector.

Further, in the embodiment shown in FIGS. 10 and 11, the embodiment shown in FIGS. 20 and 21, the embodiment shown in FIGS. 24 and 25 and the embodiment shown in FIG. 28, the laser stimulating ray source 70, 180, 227, 70 for emitting a laser beam 71, 181, 226, 71 having a wavelength of 473 nm is employed and, therefore, the stimulating ray cutting filter 83, 193, 221, 83 having a property of cutting of light having a wavelength of 473 nm and transmitting light having a wavelength longer than 473 nm is employed. However, depending upon the kind of a fluorescent substance labeling a substance derived from a living organism, it is possible to employ a laser stimulating ray source for emitting a laser beam capable of effectively stimulating the fluorescent substance and instead of the laser stimulating ray source 70, 180, 227, 70 for emitting a laser beam 71, 181, 226, 71 having a wavelength of 473 nm, a second harmonic generation element for emitting a laser beam having a wavelength of 532 nm or a semiconductor laser stimulating ray source for emitting a laser beam having a wavelength of 640 nm.

Furthermore, in the embodiment shown in FIGS. 6 and 7, the embodiment shown in FIGS. 10 and 11, the embodiment shown in FIGS. 16 and 17, the embodiment shown in FIGS. 18 and 19, the embodiment shown in FIGS. 20 and 21, the embodiment shown in FIGS. 22 and 23, the embodiment shown in FIGS. 24 and 25 and the embodiment shown in FIG. 28, although the laser stimulating ray source 20, 70, 150, 180, 205, 227, 70 is employed as a stimulating ray source, it is not absolutely necessary to employ the laser stimulating ray source 20, 70, 150, 180, 205, 227, 70 as a stimulating ray source and an LED (light emitting diode) light source may be employed as a stimulating ray source instead of a laser stimulating ray source 20, 70, 150, 180, 205, 227, 70. Further, it is possible to employ a halogen lamp as a stimulating ray source and to provide a spectral filter to cut wavelength components which cannot contribute to the excitation.

Moreover, in the embodiment shown in FIGS. 6 and 7, the embodiment shown in FIGS. 10 and 11, the embodiment shown in FIGS. 16 and 17, the embodiment shown in FIGS. 24 and 25 and the embodiment shown in FIG. 28, the laser beam 21, 71, 27, 226, 71 emitted from the laser stimulating ray source 20, 70, 26, 227, 70 is diverged using the concave lens 22, 72, 228, 72, thereby simultaneously irradiating the whole surface of the stimulable phosphor sheet 10, 15 or the whole surface of biochemical analysis unit 1 with the laser beam 21, 71, 27, 226, 71. However, it is not absolutely necessary to diverge the laser beam 21, 71, 27, 226, 71 using the concave lens 22, 62, 228, 72 and it is possible to diverge the laser beam 21, 71, 27, 226, 71 using an arbitrary means instead of the concave lens 22, 62, 228, 72, thereby simultaneously irradiating the whole surface of the stimulable phosphor sheet 10, 15 or the whole surface of biochemical analysis unit 1 with the laser beam 21, 71, 27, 226, 71.

Furthermore, in the embodiment shown in FIG. 28, biochemical analysis data are produced by leading fluorescence emission 78 released from a number of the absorptive regions 4 of the biochemical analysis unit 1 to the CCD area sensor 85 by a number of the optical fibers disposed at a high density and reading fluorescence data recorded in a number of the absorptive regions. However, it is instead possible to read radiation data recorded in a number of the stimulable phosphor layer regions 12 of the stimulable phosphor sheet 10 or chemiluminescence data recorded in a number of the stimulable phosphor layer regions 17 of the stimulable phosphor sheet 15 to produce biochemical analysis data by providing the laser stimulating ray source 20 for emitting a laser beam 24 having a wavelength of 640 nm or the laser stimulating ray source 26 for emitting a laser beam 24 having a wavelength of 980 nm and the stimulating ray cutting filter 33 having a property of transmitting light having a wavelength of that of stimulated emission 28 and cutting light having a wavelength of 640 nm or the stimulating ray cutting filter 34 having a property of transmitting light having a wavelength of that of stimulated emission 28 and cutting light having a wavelength of 980 nm.

Further, in the above described embodiments, a solution containing specific binding substances such as cDNAs are spotted using the spotting device 5 including an injector 6 and a CCD camera 7 so that when the tip end portion of the injector 6 and the center of the absorptive region 4 into which a solution containing specific binding substances is to be spotted are determined to coincide with each other as a result of viewing them using the CCD camera 7, the solution containing the specific binding substances such as cDNA is ejected from the injector 6.

However, the solution containing specific binding substances such as cDNAs can be spotted by detecting the positional relationship between a number of the absorptive regions 4 formed in the biochemical analysis unit 1 and the tip end portion of the injector 6 in advance and two-dimensionally moving the biochemical analysis unit 1 or the tip end portion of the injector 6 so that the tip end portion of the injector 6 coincides with each of the absorptive regions 4.

According to the present invention, it is possible to provide a method for producing biochemical analysis data and an apparatus used therefor which can produce biochemical analysis data having high quantitative characteristics by photoelectrically detecting light emitted from a plurality of spot-like regions even in the case where the plurality of spot-like regions labeled with a labeling substance are formed in a biochemical analysis unit at a high density.

The invention claimed is:

1. A method for producing biochemical analysis data comprising:
    collecting light selectively released from a plurality of light releasable regions two-dimensionally formed to be spaced apart from each other in a sample placed on a sample stage by a plurality of light guide member each of which is disposed to face one of the plurality of light releasable regions,
    leading the thus collected light to a light detector and photoelectrically detecting the light by the light detector, wherein the sample is constituted by a stimulable phosphor sheet including a support two-dimensionally formed with a plurality of through-holes to be spaced apart from each other and the plurality of light releasable regions are constituted by a plurality of stimulable phosphor layer regions formed by charging stimulable phosphor in the plurality of through-holes formed in the support and selectively storing radiation energy or the energy of chemiluminescence in the stimulable phosphor regions, the radiation energy or the energy of chemiluminescence being selectively stored in the stimulable phosphor layer regions by providing a biochemical analysis unit including a substrate two-dimensionally formed with a plurality of through-holes to be spaced apart from each other in the same pattern as that of the through-holes formed in the support of the stimulable phosphor sheet and a plurality of absorptive regions formed by charging an absorptive material in the plurality of through-holes formed in the substrate of the biochemical analysis unit, and selectively labeled with a radioactive labeling substance or a labeling substance which generates chemiluminescence emission when it contacts a chemiluminescent substrate and superposing the stimulable phosphor sheet and the biochemical analysis unit so that each of the stimulable phosphor layer regions formed in the support of the stimulable phosphor sheet faces a corresponding absorptive region formed in the substrate of the biochemical analysis unit, thereby selectively exposing the stimulable phosphor layer regions of the stimulable phosphor sheet to the radioactive labeling substance or the labeling substance which generates chemiluminescence emission when it contacts a chemiluminescent substrate.

2. A method for producing biochemical analysis data in accordance with claim 1, wherein each of the plurality of light guide members includes a light collecting end portion capable of collecting light and the light collecting end portion of each of the plurality of light guide members is disposed to face one of the plurality of stimulable phosphor layer regions formed in the stimulable phosphor sheet placed on the sample stage.

3. A method for producing biochemical analysis data in accordance with claim 2, further comprising:
   simultaneously irradiating the plurality of stimulable phosphor layer regions formed in the support of the stimulable phosphor sheet with a stimulating ray emitted from a stimulating ray source for a predetermined time from a side of the stimulable phosphor sheet opposite to the side facing the light collecting end portion of the plurality of light guide members,
   exciting stimulable phosphor contained in the plurality of stimulable phosphor layer regions,
   collecting stimulated emission released from the plurality of stimulable phosphor layer regions by the light collecting end portions of the plurality of light guide members,
   leading the thus collected stimulated emission through the plurality of light guide members to a stimulating ray cutting filter having a property of cutting light having a wavelength of that of the stimulating ray and transmitting light having a wavelength of that of stimulated emission, thereby cutting the stimulating ray, further leading stimulated emission transmitted through the stimulating ray cutting filter to a two-dimensional solid state sensor, and
   photoelectrically detecting stimulated emission by the two-dimensional solid state sensor to produce biochemical analysis data.

4. A method for producing biochemical analysis data in accordance with claim 3, wherein the two-dimensional solid state sensor is constituted by a cooled CCD area sensor.

5. A method for producing biochemical analysis data in accordance with claim 2, further comprising:
   sequentially irradiating the plurality of stimulable phosphor layer regions formed in the support of the stimulable phosphor sheet placed on the sample stage with a stimulating ray emitted from a stimulating ray source from a side of the stimulable phosphor sheet opposite to the side facing the light collecting end portion of the plurality of light guide members,
   exciting stimulable phosphor contained in the plurality of stimulable phosphor layer regions,
   collecting stimulated emission released from each of the plurality of stimulable phosphor layer regions by the light collecting end portion of the corresponding light guide member among the plurality of light guide members,
   leading stimulated emission collected by the corresponding light guide member to a stimulating ray cutting filter having a property of cutting light having a wavelength of that of the stimulating ray and transmitting light having a wavelength of that of stimulated emission, thereby cutting the stimulating ray,
   further leading stimulated emission transmitted through the stimulating ray cutting filter to a zero-dimensional sensor, and
   photoelectrically detecting stimulated emission by the zero-dimensional sensor to produce biochemical analysis data.

6. A method for producing biochemical analysis data in accordance with claim 5, wherein the stimulating ray emitted from the stimulating ray source is intermittently moved by a pitch equal to a distance between neighboring stimulable phosphor layer regions formed in the support of the stimulable phosphor, thereby scanning the plurality of stimulable phosphor layer regions formed in the support of the stimulable phosphor sheet placed on the sample stage with the stimulating ray.

7. A method for producing biochemical analysis data in accordance with claim 5, wherein the zero-dimensional sensor is constituted as a photomultiplier.

8. A method for producing biochemical analysis data in accordance with claim 2, further comprising:
   exciting stimulable phosphor contained in the plurality of stimulable phosphor layer regions,
   collecting stimulated emission released from the plurality of stimulable phosphor layer regions by the light collecting end portions of the plurality of light guide members,
   leading the thus collected stimulated emission through the plurality of light guide members to a stimulating ray cutting filter having a property of cutting light having a wavelength of that of the stimulating ray and transmitting light having a wavelength of that of stimulated emission, thereby cutting the stimulating ray, further leading stimulated emission transmitted through the stimulating ray cutting filter to a two-dimensional solid state sensor, and
   photoelectrically detecting stimulated emission by the two-dimensional solid state sensor to produce biochemical analysis data wherein the stimulating ray emitted from the stimulating ray source is intermittently moved by a pitch equal to a distance between neighboring stimulable phosphor layer regions formed in the support of the stimulable phosphor, thereby scanning the plurality of stimulable phosphor layer regions formed in the support of the stimulable phosphor sheet placed on the sample stage with the stimulating ray.

9. A method for producing biochemical analysis data in accordance with claim 2, wherein each of the plurality of light guide members is formed of at least one optical fiber.

10. A method for producing biochemical analysis data in accordance with claim 2, wherein the plurality of light guide members are gathered in the vicinity of end portions opposite to the light collecting end portions.

11. A method for producing biochemical analysis data in accordance with claim 2, wherein the plurality of light guide members are mounted on a fixing head in the vicinity of the light collecting end portions so that each of the light collecting end portions of the plurality of light guide members is disposed to face one of the light releasable regions of the sample placed on the sample stage.

12. A method for producing biochemical analysis data in accordance with claim 1, wherein the support of the stimulable phosphor sheet has a property of attenuating light energy and/or radiation energy.

13. A method for producing biochemical analysis data in accordance with claim 12, wherein the support of the stimulable phosphor sheet has a property of reducing the energy of light and/or the energy of radiation to ⅕ or less when the light and/or radiation travels in the support by a distance equal to that between neighboring stimulable phosphor layer regions.

14. A method for producing biochemical analysis data in accordance with claim 13, wherein the support of the stimulable phosphor sheet is made of a material selected from a group consisting of a metal material, a ceramic material and a plastic material.

15. A method for producing biochemical analysis data in accordance with claim 1, wherein the support of the stimulable phospor sheet is formed with 10 or more stimulable phospor layer regions.

16. A method for producing biochemical analysis data in accordance with claim 1, wherein each of the plurality of stimulable phospor layer regions is formed in the stimulable phospor sheet to have a size of less than 5 $mm^2$.

17. A method for producing biochemical analysis data in accordance with claim 1, wherein the plurality of stimulable phospor layer regions are formed in the support of the stimulable phospor sheet at a density of 10 or more per $cm^2$.

18. A method for producing biochemical analysis data comprising:
collecting light selectively released from a plurality of light releasable regions two-dimensionally formed to be spaced apart from each other in a sample placed on a sample stage by a plurality of light guide member each of which is disposed to face one of the plurality of light releasable regions,
leading the thus collected light to a light detector and photoelectrically detecting the light by the light detector,
wherein the sample is constituted by a biochemical analysis unit including a substrate two-dimensionally formed with a plurality of through-holes to be spaced apart from each other and the plurality of light releasable regions are constituted by a plurality of absorptive regions formed by charging an absorptive material in the plurality of through-holes formed in the substrate of the biochemical analysis unit and selectively labeled with a labeling substance which generates chemiluminescence emission when it contacts a chemiluminescent substrate,
wherein the plurality of light guide members are gathered in a vicinity of end portions opposite to the light collecting end portions and,
the light detector is constituted by a two-dimensional solid state sensor,
wherein each of the plurality of light guide members includes a light collecting end portion capable of collecting light and the light collecting end portion of each of the plurality of light guide members is disposed to face one of the plurality of absorptive regions formed in the biochemical analysis unit placed on the sample stage
the method further comprising steps of:
placing a position data producing unit including a second substrate formed with a plurality of through-holes in a same pattern as that of the plurality of absorptive regions formed in the biochemical analysis unit on the sample stage;
installing a position data producing optical system,
scanning the position data producing unit with light emitted from the position data producing optical system,
collecting light passing through the plurality of through holes of the position data producing unit by the plurality of light guide members,
leading the thus collected light to the two-dimensional solid state sensor and photoelectrically detecting light by the two dimensional solid state sensor thereby detecting what region on a photo-electric detecting surface of the two dimensional solid state sensor receives light released from the plurality of absorptive regions and
producing biochemical analysis data based on the position data by photoelectrically detecting light released from the plurality of absorptive regions using the two-dimensional solid state sensor.

19. A method for producing biochemical analysis data in accordance with claim 18, further comprising:
collecting chemiluminescence emission released from the plurality of absorptive regions by the light collecting end portion of the plurality of light guide members,
leading the thus collected chemiluminescence emission through the plurality of light guide members to a two-dimensional solid state sensor, and
photoelectrically detecting chemiluminescence emission by the two-dimensional solid state sensor to produce biochemical analysis data.

20. A method for producing biochemical analysis data in accordance with claim 19, wherein the two-dimensional solid state sensor is constituted by a cooled CCD area sensor.

21. A method for producing biochemical analysis data in accordance with claim 18 further comprising:
collecting chemiluminescence emission released from the plurality of absorptive regions by the light collecting end portion of the plurality of light guide members,
leading the thus collected chemiluminescence emission through the plurality of light guide members to a two-dimensional solid state sensor, and
photoelectrically detecting chemiluminescence emission by the two-dimensional solid state sensor to produce biochemical analysis data.

22. A method for producing biochemical analysis data in accordance with claim 18, wherein the substrate of the biochemical analysis unit has a property of attenuating light energy and/or radiation energy.

23. A method for producing biochemical analysis data in accordance with claim 22, wherein the substrate of the biochemical analysis unit has a property of reducing the energy of light and/or the energy of radiation to $\frac{1}{5}$ or less when the light and/or radiation travels in the substrate by a distance equal to that between neighboring absorptive regions.

24. A method for producing biochemical analysis data in accordance with claim 23, wherein the substrate of the biochemical analysis unit is made of a material selected from a group consisting of a metal material, a ceramic material and a plastic material.

25. A method for producing biochemical analysis data in accordance with claim 18, wherein the substrate of the biochemical analysis unit is formed with 10 or more absorptive regions.

26. A method for producing biochemical analysis data in accordance with claim 18, wherein each of the plurality of absorptive regions is formed in the biochemical analysis unit to have a size of less than 5 mm$^2$.

27. A method for producing biochemical analysis data in accordance with claim 18, wherein the plurality of absorptive regions are formed in the substrate of the biochemical analysis unit at a density of 10 or more per cm$^2$.

28. A method for producing biochemical analysis data in accordance with claim 18, wherein each of the absorptive regions of the biochemical analysis unit is formed of a porous material.

29. A method for producing biochemical analysis data in accordance with claim 28, wherein the porous material includes a carbon material and a material capable of forming a membrane filter.

30. A method for producing biochemical analysis data in accordance with claim 18, wherein each of the absorptive regions of the biochemical analysis unit is formed of a bundle of fibers.

31. A method for producing biochemical analysis data in accordance with claim 18, wherein each of the plurality of light guide members is formed of at least one optical fiber.

32. A method for producing biochemical analysis data in accordance with claim 18, wherein the plurality of light guide members are mounted on a fixing head in the vicinity of the light collecting end portions so that each of the light collecting end portions of the plurality of light guide members is disposed to face one of the light releasable regions of the sample placed on the sample stage.

33. A method for producing biochemical analysis data comprising:

collecting light selectively released from a plurality of light releasable regions two-dimensionally formed to be spaced apart from each other in a sample placed on a sample stage by a plurality of light guide member disposed so that adjacent light collecting end portions are in contact with each other, selectively leading the thus collected light to one of a pair of two-dimensional solid state sensors and photoelectrically detecting the light by the pair of two-dimensional solid state sensors, wherein the sample is constituted by a biochemical analysis unit including a substrate two-dimensionally formed with a plurality of through-holes to be spaced apart from each other and the plurality of light releasable regions are constituted by a plurality of absorptive regions formed by charging an absorptive material in the plurality of through-holes formed in the substrate of the biochemical analysis unit and selectively labeled with a labeling substance which generates chemiluminescence emission when it contacts a chemiluminescent substrate, wherein the plurality of light guide members are gathered in a vicinity of end portions opposite to the light collecting end portions, the method further comprising steps of:

placing a position data producing unit including a second substrate formed with a plurality of through-holes in a same pattern as that of the plurality of absorptive regions formed in the biochemical analysis unit on the sample stage;

installing a position data producing optical system, scanning the position data producing unit with light emitted from the position data producing optical system, collecting light passing through the plurality of through holes of the position data producing unit by the plurality of light guide members, leading the thus collected light to the two-dimensional solid state sensor and photoelectrically detecting light by the two dimensional solid state sensor thereby detecting what region on a photo-electric detecting surface of each of the pair of two-dimensional solid state sensors receives light released from the plurality of absorptive regions and producing biochemical analysis data based on the position data by photoelectrically detecting light released from the plurality of absorptive regions using the pair of two-dimensional solid state sensors.

* * * * *